(12) United States Patent
Szczepanski et al.

(10) Patent No.: US 6,288,071 B1
(45) Date of Patent: Sep. 11, 2001

(54) 1-ETHYLENE-2-ALKYLENE-1,4-CYCLOHEXADIENE PESTICIDES

(75) Inventors: Henry Szczepanski, Wallbach; Martin Zeller, Baden, both of (CH); Ottmar Franz Hüter, Lörrach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/202,264

(22) PCT Filed: Jun. 4, 1997

(86) PCT No.: PCT/EP97/02889

§ 371 Date: Dec. 10, 1998

§ 102(e) Date: Dec. 10, 1998

(87) PCT Pub. No.: WO97/47592

PCT Pub. Date: Dec. 18, 1997

(30) Foreign Application Priority Data

Jun. 12, 1996 (CH) .................................................. 1476/96

(51) Int. Cl.[7] .......................... A01N 33/24; A01N 37/18; A01N 43/54; C07C 69/74; C07C 233/01; C07C 251/32

(52) U.S. Cl. .......................... 514/269; 514/270; 514/274; 514/307; 514/317; 514/327; 514/329; 514/330; 514/331; 514/341; 514/355; 514/357; 514/364; 514/365; 514/369; 514/378; 514/383; 514/386; 514/389; 514/419; 514/452; 514/456; 514/463; 514/464; 514/465; 514/466; 514/472; 514/436; 514/532; 514/534; 514/538; 514/613; 514/617; 514/618; 514/620; 514/640; 544/299; 544/301; 544/302; 544/315; 544/318; 546/145; 546/149; 546/192; 546/216; 546/223; 546/225; 546/232; 546/270.7; 546/329; 546/330; 546/335; 548/126; 548/182; 548/186; 548/202; 548/203; 548/205; 548/247; 548/249; 548/267.1; 548/317.1; 548/319.1; 548/320.1; 548/335.1; 548/336.1; 548/337.1; 548/341.1; 548/346.1; 549/22; 549/362; 549/404; 549/407; 549/434; 549/437; 549/442; 549/443; 549/449; 549/467; 549/473; 549/491; 560/17; 560/35; 560/42; 560/128; 564/164; 564/181; 564/253; 564/265

(58) Field of Search .................................... 514/256, 364, 514/365, 399, 427, 529, 640, 641; 544/242; 546/314; 548/131, 200, 236, 336.1, 561; 564/254, 271; 560/128

(56) References Cited

U.S. PATENT DOCUMENTS 5,342,837 * 8/1994 Clough et al. ..................... 514/427
5,371,084 * 12/1994 De Fraine et al. ................. 514/241

FOREIGN PATENT DOCUMENTS 0 421 102 A2 * 4/1991 (EP) .
0 438 726 A1 * 7/1991 (EP) .
WO 94/26700 * 11/1994 (WO) .
WO 95/18789 * 7/1995 (WO) .

OTHER PUBLICATIONS

Gaudemer et al., "Oxidation of Allyl– and allenylcobaloximes by Manganese (III) Acetate. A New Route to Dimethylglyoxime Monoethers," Tetrahedron Letters, vol. 21, pp. 1445–1447, 1980.*

* cited by examiner

Primary Examiner—Jane C. Oswecki
(74) Attorney, Agent, or Firm—Joseph C. Gil; Jackie Ann Zurcher

(57) ABSTRACT

Pesticidally active cyclohexadienyl derivative compounds of the formula I that are esters, oximes or amides are claimed. These compounds may be used as fungicides, acaricides and insecticides in plant protection.

31 Claims, No Drawings

1-ETHYLENE-2-ALKYLENE-1,4-CYCLOHEXADIENE PESTICIDES

This application is a 371 of PCT/EP97/02889 filed Jun. 4, 1997.

The invention relates to novel pesticidally active compounds of formula I

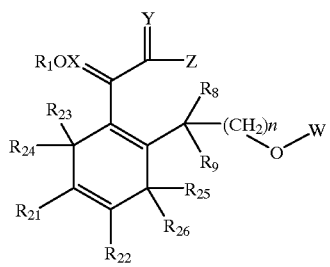

wherein:

X is CH or N;

Y is O, S, S=O or $NR_5$;

Z is $OR_2$, $SR_2$ or $N(R_3)R_4$;

n is 0, 1, 2, 3, 4 or 5; or

Y and Z together form a 5- to 7-membered ring containing 2 or 3 hetero atoms O and/or N that is unsubstituted or mono- or poly-substituted by $C_1$–$C_4$alkyl, halo-$C_1$–$C_4$alkyl, halogen, =O or by cyclopropyl;

W is an aldimino or ketimino group;

$R_1$ is cyclopropyl, $C_1$–$C_6$alkyl or halo-$C_1$–$C_6$-alkyl;

$R_2$ and $R_3$ are each independently of the other $C_1$–$C_6$alkyl or halo-$C_1$–$C_6$alkyl;

$R_4$ and $R_5$ are each independently of the other hydrogen, $C_1$–$C_6$alkyl or $C_1$–$C_6$alkoxy;

$R_8$ and $R_9$ are each independently of the other hydrogen or $C_1$–$C_3$alkyl; or $R_8$ and $R_9$ together are $C_2$–$C_6$alkenyl or $C_3$–$C_6$cycloalkyl;

$R_{21}$ and $R_{22}$ are each independently of the other hydrogen, halogen, $C_1$–$C_8$alkyl, $C_1$–$C_8$alkoxy or $C_1$–$C_8$alkylthio; and $R_{23}$, $R_{24}$, $R_{25}$ and $R_{26}$ are each independently of the others hydrogen, halogen, $C_1$–$C_8$alkyl or $C_1$–$C_8$alkoxy.

Formula I includes all stereoisomeric forms and also mixtures thereof, such as racemic and diastereoisomeric mixtures, for example E/Z mixtures.

The compounds of the invention have fungicidal, acaricidal and insecticidal properties and are suitable for use as active ingredients in agriculture, horticulture and in the hygiene sector.

The invention relates also to the preparation of those compounds, to agrochemical compositions that comprise at least one of those compounds as active ingredient, and to the use of the active ingredients or compositions in the protection of plants against attack by harmful microorganisms as well as in the control of insects.

2-Alkoximino-2-phenylacetic acid derivatives and 2-alkoxymethylene-2-phenylacetic acid derivatives are known as pesticides, for example, from WO 94/26700 and WO 95/18789. Corresponding pesticidal compounds in which a cyclohexenyl group stands in place of the phenyl group are described in EP-A-421 102, and those in which the phenyl group has been replaced by a cyclohexyl group are described in EP-A-438 726. In addition, the phytofungicidal action of 1,4-cyclohexadiene-1-alanine is described in J. of Antibiotics, Vol. XXIII, No.11, p. 537–541 (1970).

The general terms used hereinbefore and hereinafter have the meanings given below unless specified otherwise:

Hydrocarbon radicals may be saturated or unsaturated, open-chained or cyclic, or a mixture of open-chained and cyclic such as, for example, cyclopropylmethyl or benzyl.

Alkyl groups are straight-chain or branched, depending on the number of carbon atoms, and are, for example, methyl, ethyl, n-propyl, isopropyl, n-butyl, sec-butyl, isobutyl, tert-butyl, sec-amyl, tert-amyl, 1-hexyl or 3-hexyl.

Unsaturated hydrocarbon radicals are alkenyl, alkynyl or alkenynyl groups having a maximum of 3 multiple bonds, such as, for example, butadienyl, hexatrienyl or 2-penten-4-ynyl.

Alkenyl is to be understood as meaning straight-chain or branched alkenyl, such as, for example, allyl, methallyl, 1-methylvinyl or but-2-en-1-yl. Alkenyl radicals having a chain length of 3 or 4 carbon atoms are preferred.

Alkynyl may similarly, depending on the number of carbon atoms, be straight-chain or branched, such as, for example, ethynyl, propargyl, but-1-yn-1-yl or but-1-yn-3-yl. Propargyl is preferred.

Cyclic unsaturated hydrocarbon radicals may be aromatic, such as, for example, phenyl and naphthyl, or non-aromatic, such as, for example, cyclopentenyl, cyclohexenyl, cycloheptenyl and cyclooctadienyl, or partially aromatic, such as, for example, tetrahydronaphthyl and indanyl.

Halogen and halo are fluorine, chlorine, bromine or iodine, preferably fluorine, chlorine or bromine.

Haloalkyl may contain identical or different halogen atoms and may be, for example, fluoromethyl, difluoromethyl, difluorochloromethyl, trifluoromethyl, chloromethyl, dichloromethyl, trichloromethyl, 2,2,2-trifluoroethyl, 2-fluoroethyl, 2-chloroethyl, 2,2,2-trichloroethyl or 3,3,3-trifluoropropyl.

Alkoxy is, for example, methoxy, ethoxy, propoxy, isopropoxy, n-butoxy, isobutoxy, sec-butoxy or tert-butoxy; preferably methoxy or ethoxy.

Haloalkoxy is, for example, difluoromethoxy, trifluoromethoxy, 2,2,2-trifluoroethoxy, 1,1,2,2-tetrafluoroethoxy, 2-fluoroethoxy, 2-chloroethoxy or 2,2-difluoroethoxy.

Cycloalkyl is cyclopropyl, cyclobutyl, cyclopentyl or cyclohexyl.

Alkanoyl is either straight-chain or branched. Examples are formyl, acetyl, propionyl, butyryl, pivaloyl and octanoyl.

Aryl is phenyl or naphthyl, preferably phenyl.

The term heteroaryl denotes 5- or 6-membered aromatic rings containing hetero atoms N, O and/or S, which may be benzo-fused. Examples are furan, pyrrole, pyridine, pyrimidine, pyrazine, thiazole, oxazole, isoxazole, isothiazole, triazine, quinoline, isoquinoline, pyridazine, pyrazole, imidazole, quinazoline, quinoxaline, benzimidazole, benzofuran, indole, isoindole, benzothiazole and benzoxazole.

Heterocyclyl denotes 5- to 7-membered, non-aromatic rings that contain from 1 to 3 identical or different hetero atoms N, O and S. Examples are $\Delta^2$-oxazoline, $\Delta^2$-thiazoline; 5,6-dihydro-4H-1,3-thiazine, 5,6-dihydro-4H-1,3-oxazine, pyrrolidine, indoline, piperidine, morpholine, 4-alkylpiperidine and azepine.

All of the above lists are given by way of example and are not limiting in any way.

The following groups are preferred:
(1) Compounds of formula I wherein:
W is a group a)

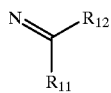

wherein
R$_{11}$ and R$_{12}$ are each independently of the other hydrogen, cyano, C$_1$–C$_{12}$alkyl, halo-C$_1$–C$_{12}$-alkyl, C$_2$–C$_{12}$alkenyl, C$_2$–C$_{12}$alkynyl, C$_3$–C$_6$cycloalkyl, cyclopropylmethyl, C$_1$–C$_4$alkoxy, C$_2$–C$_{12}$-alkoxyalkyl, C$_1$–C$_4$alkoxycarbonyl, aminocarbonyl, C$_1$–C$_4$alkylaminocarbonyl, bis(C$_1$–C$_4$alkyl)-aminocarbonyl, ureidocarbonyl, C$_1$–C$_4$alkylthio, C$_2$–C$_5$alkylthioalkyl; an unsubstituted or up to penta-substituted ring having a maximum of 15 ring carbon atoms that may be multi-membered and contains from 0 to 3 hetero atoms N, O and/or S, it being possible for the ring to be bonded by a bridge having a maximum of 4 chain atoms and that may be linear or branched and may contain CO, oxygen or sulfur; or R$_{11}$ and R$_{12}$ together with the common carbon atom are an unsubstituted or up to penta-substituted ring having a maximum of 15 ring carbon atoms that may be multi-membered and contains from 0 to 3 hetero atoms N, O and/or S;

the possible substituents of all of those groups mentioned for R$_{11}$ and R$_{12}$ individually or together being selected from C$_1$–C$_4$alkyl, C$_2$–C$_4$alkenyl, C$_2$–C$_4$alkynyl, C$_1$–C$_4$alkoxy, C$_1$–C$_4$alkyl-thio, C$_1$–C$_4$haloalkyl, C$_2$–C$_4$haloalkenyl, C$_2$–C$_4$haloalkynyl, C$_1$–C$_4$haloalkoxy, halogen, cyano, cyano-C$_1$–C$_2$alkyl, cyano-C$_1$–C$_2$alkoxy, oxo, thioxo, OH, NO$_2$, SCN, thiocyanomethyl, Si(CH$_3$)$_3$, NH$_2$, NH(C$_1$–C$_4$alkyl), N(C$_1$–C$_4$alkyl)$_2$, C$_1$–C$_4$alkoxy-C$_1$–C$_4$alkyl, C$_1$–C$_4$alkylcarbonyl, C$_1$–C$_4$haloalkylcarbonyl, C$_1$–C$_4$alkoxycarbonyl, C$_1$–C$_4$haloalkoxycarbonyl, aminocarbonyl, C$_1$–C$_4$alkylaminocarbonyl, bis(C$_1$–C$_4$alkylamino)carbonyl, arylaminocarbonyl, arylaminothiocarbonyl, C$_1$–C$_4$haloalkylcarbonyloxy, C$_1$–C$_4$alkylcarbonyloxy, C$_1$–C$_4$alkoxycarbonyloxy, aminocarbonyloxy, C$_1$–C$_4$alkylaminocarbonyloxy, bis(C$_1$–C$_4$alkylamino)carbonyloxy, arylaminocarbonyloxy, arylaminothiocarbonyloxy, C$_1$–C$_4$alkoximinomethyl, —CSNH$_2$, —SH, C$_1$–C$_4$-alkylthiomethyl, C$_2$–C$_4$alkenyloxy, C$_2$–C$_4$alkynyloxy, C$_2$–C$_4$haloalkenyloxy, C$_1$–C$_4$alkylsulfinylmethyl, C$_1$–C$_4$alkylsulfonylmethyl, phenylsulfinylmethyl, phenylsulfonylmethyl, trifluoromethylsulfonyl, C$_3$–C$_6$cycloalkyl, phenyl, benzyl, phenoxy, phenylthio, benzyloxy and benzylthio;

it being possible for the aromatic groups to carry a maximum of five further substituents selected from halogen, C$_1$–C$_4$alkyl, C$_1$–C$_4$alkoxy, C$_1$–C$_4$haloalkyl, C$_1$–C$_4$haloalkoxy, CN and NO$_2$, and it being possible for two adjacent substituents of the maximum of 5 substituents to form an aliphatic bridge having a maximum of 5 members, which bridge contains from 0 to 2 oxygen atoms and 0 or 1 carbonyl group and may be substituted a maximum of four times by halogen, C$_1$–C$_4$alkyl, C$_1$–C$_4$alkoxy and/or by a single phenyl group; or wherein R$_{12}$ is a group e)

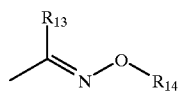

wherein:
R$_{13}$ is hydrogen, cyano, C$_1$–C$_6$alkyl, C$_3$–C$_6$cycloalkyl, C$_1$–C$_6$alkoxycarbonyl, heteroaryl, heterocyclyl, naphthyl, C$_1$–C$_6$alkoxy, aryloxy, heteroaryloxy, C$_1$–C$_6$alkylamino, bis(C$_1$–C$_6$-alkyl)amino, arylamino or heteroarylamino, it being possible for all of the radicals mentioned (with the exception of cyano) to be unsubstituted or substituted by alkyl, alkoxy, haloalkyl, haloalkoxy, alkylthio, alkylsulfenyl, alkylsulfinyl, halogen, nitro, cyano, aryl, aryloxy, heteroaryl or by heteroaryloxy, or a group f)

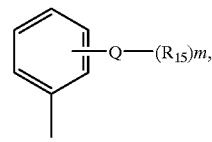

wherein
R$_{15}$ is C$_1$–C$_6$alkyl, halo-C$_1$–C$_6$alkyl, C$_1$–C$_6$alkoxy, halo-C$_1$–C$_6$alkoxy, halogen, C$_3$–C$_6$cycloalkyl unsubstituted or substituted by from 1 to 5 halogen atoms, C$_2$–C$_6$alkenyl, halo-C$_2$–C$_6$alkenyl, optionally substituted C$_3$–C$_6$alkynyl, cyano, cyano-C$_1$–C$_2$alkyl, cyano-C$_1$–C$_2$alkoxy, OH, NO$_2$, SCN, thiocyanomethyl, Si(CH$_3$)$_3$, NH$_2$, NH(C$_1$–C$_4$alkyl), N(C$_1$–C$_4$alkyl)$_2$, C$_1$–C$_4$alkoxymethyl, C$_1$–C$_4$haloalkylcarbonyl, C$_1$–C$_4$alkylcarbonyl, C$_1$–C$_4$alkoxycarbonyl, aminocarbonyl, C$_1$–C$_4$alkylaminocarbonyl, bis(C$_1$–C$_4$alkylamino)carbonyl, arylaminocarbonyl, arylaminothiocarbonyl, C$_1$–C$_4$alkoximinomethyl, —CSNH$_2$, —SH, C$_1$–C$_4$alkylthiomethyl, C$_2$–C$_4$alkenyloxy, C$_2$–C$_4$alkynyloxy, C$_2$–C$_4$haloalkenyloxy, C$_1$–C$_4$alkylsulfinylmethyl, C$_1$–C$_4$alkylsulfonylmethyl, phenylsulfinylmethyl, phenylsulfonylmethyl, trifluoromethylsulfonyl, C$_3$–C$_6$cycloalkyl, C$_1$–C$_4$haloalkylcarbonyloxy, C$_1$–C$_4$alkylcarbonyloxy, C$_1$–C$_4$alkoxycarbonyloxy, aminocarbonyloxy, C$_1$–C$_4$alkylaminocarbonyloxy, bis(C$_1$–C$_4$alkylamino)carbonyloxy, arylaminocarbonyloxy, arylaminothiocarbonyloxy, aryl, heteroaryl or heterocyclyl; the aromatic groups in R$_{15}$ each independently of the others being unsubstituted or mono- to penta-substituted by C$_1$–C$_6$alkyl, halo-C$_1$–C$_6$alkyl, halogen, C$_1$–C$_6$alkoxy or by halo-C$_1$–C$_6$alkoxy; tri(C$_1$–C$_4$alkyl)silyl or di(C$_1$–C$_4$alkyl)phenylsilyl;

wherein when n is greater than 1 the R$_{15}$ radicals may be identical or different;

Q is a direct bond, C$_1$–C$_8$alkylene, C$_2$–C$_6$alkenylene, C$_2$–C$_6$alkynylene, O, O(C$_1$–C$_6$alkylene), (C$_1$–C$_6$alkylene)O, S(=O)$_p$, S(=O)$_p$(C$_1$–C$_6$alkylene) or (C$_1$–C$_6$alkylene)S(=O)$_p$;

m is 0, 1, 2, 3, 4 or 5;
p is 0, 1 or 2; and
R$_{14}$ is hydrogen; C$_1$–C$_6$alkyl; C$_1$–C$_6$haloalkyl having from 1 to 15 halogen atoms; C$_1$–C$_4$-alkoxy- $C_1$–$C_2$alkyl; $C_2$–$C_4$alkenyl-$C_1$–$C_2$alkyl unsubstituted or substituted by from 1 to 3 halogen atoms; $C_2$–$C_4$alkynyl-$C_1$–$C_2$alkyl; $C_3$–$C_6$cycloalkyl unsubstituted or substituted by from 1 to 4 halogen atoms; $C_3$–$C_6$cycloalkyl-$C_1$–$C_4$alkyl unsubstituted or substituted by from 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl unsubstituted or substituted by halogen, $C_1$–$C_3$alkyl, $C_1$–$C_4$alkoxy, $C_1$–$C_4$haloalkyl, cyano, nitro and/or by $C_1$–$C_4$alkylenedioxy and wherein the phenyl group may be substituted by from 1 to 3 identical or different substituents; phenyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano; or pyridyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano.

(2) Compounds of formula I wherein:

$R_1$ is methyl;

$R_2$, $R_3$ and $R_5$ are each independently of the others $C_1$–$C_2$alkyl, preferably methyl; and $R_4$ is hydrogen.

(3) Compounds of formula I wherein:

X is N;

Y is O, S or S=O preferably O;

Z is $OR_2$, $SR_2$ or $N(R_3)H$; preferably $OR_2$ or $SR_2$; and $R_2$ and $R_3$ are $C_1$–$C_2$alkyl, preferably methyl.

(4) Compounds of formula I wherein:

X is CH;

Y is O, S or S=O, preferably O;

Z is $OR_2$; and $R_2$ is $C_1$–$C_2$alkyl, preferably methyl.

(5) Compounds of formula I wherein Y and Z together are a group

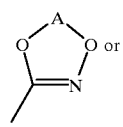 a)

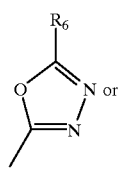 b)

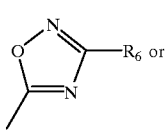 c)

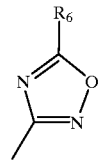 d)

wherein:

A is unsubstituted or methyl-substituted alkanediyl having from 1 to 3 carbon atoms, preferably dimethylene (ethane-1,2-diyl); and $R_6$ is hydrogen, $C_1$–$C_3$alkyl, cyclopropyl or $CF_3$;

(6) Compounds of formula I wherein:

$R_8$ and $R_9$ are hydrogen or methyl;

$R_{21}$ and $R_{22}$ are each independently of the other hydrogen, chlorine, bromine, $C_1$–$C_4$alkyl or $C_1$–$C_4$alkoxy;

$R_{23}$, $R_{24}$, $R_{25}$ and $R_{26}$ are hydrogen; and n is 0, 1 or 2.

(7) Compounds of formula I wherein:

$R_8$ and $R_9$ are hydrogen;

$R_{21}$ and $R_{22}$ are each independently of the other hydrogen or methyl; and n is 0.

(8) Compounds of formula I in which in group a)

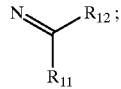

$R_{11}$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano; and $R_{12}$ is phenyl or pyridyl each unsubstituted or substituted.

(9) Compounds of formula I in which in group a)

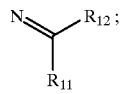

$R_{11}$ is $C_1$–$C_4$alkyl, cyclopropyl, or cyano; and $R_{12}$ is phenyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, $C_2$–$C_4$alkenyl, $C_2$–$C_4$alkynyl, nitro and cyano; or pyridyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano.

(10) Compounds of formula I in which in group a)

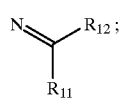

$R_{11}$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano; and $R_{12}$ is a group e)

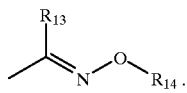

(11) Compounds of formula I in which in group e)

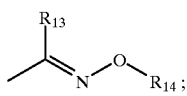

$R_{13}$ is hydrogen, $C_1$–$C_6$alkyl, $C_3$–$C_6$cycloalkyl, cyano or a group f)

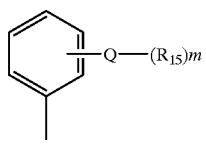

wherein $R_{15}$ is $C_1$–$C_6$alkyl, halo-$C_1$–$C_6$alkyl, cyclopropyl unsubstituted or substituted by from 1 to 5 chlorine atoms, $C_2$–$C_6$alkenyl unsubstituted or substituted by from 1 to 3 halogen atoms, or unsubstituted or substituted $C_3$–$C_6$alkynyl; also phenyl unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy; or pyridyl unsubstituted or mono- to tetra-substituted by $C_1$–$C_6$alkyl, halo-$C_1$–$C_6$alkyl, halogen, $C_1$–$C_6$alkoxy or by halo-$C_1$–$C_6$alkoxy;

Q is a direct bond, $C_1$–$C_4$alkylene, O, O($C_1$–$C_4$alkylene) or ($C_1$–$C_4$alkylene)O, m is 0, 1 or 2; and $R_{14}$ is hydrogen; $C_1$–$C_6$alkyl; $C_1$–$C_6$haloalkyl having from 1 to 15 halogen atoms; $C_1$–$C_4$-alkoxy-$C_1$–$C_2$alkyl; $C_2$–$C_4$alkenyl-$C_1$–$C_2$alkyl unsubstituted or substituted by from 1 to 3 halogen atoms; $C_2$–$C_4$alkynyl-$C_1$–$C_2$alkyl; $C_3$–$C_6$-cycloalkyl unsubstituted or substituted by from 1 to 4 halogen atoms; $C_3$–$C_6$cycloalkyl-$C_1$–$C_4$alkyl unsubstituted or substituted by from 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl unsubstituted or substituted by halogen, $C_1$–$C_3$alkyl, $C_1$–$C4$alkoxy, $C_1$–$C_4$haloalkyl, cyano, nitro and/or by $C_1$–$C_4$alkylenedioxy wherein the phenyl group may be substituted by from 1 to 3 identical or different substituents; phenyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano; or pyridyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano.

(12) Compounds of formula I in which in group a)

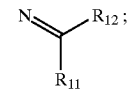

$R_{11}$ is methyl;
$R_{12}$ is a group e)

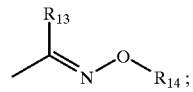

$R_{13}$ is a group f)

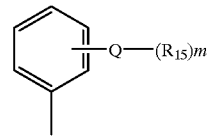

wherein $R_{15}$ is $C_1$–$C_6$alkyl, halo-$C_1$–$C_6$alkyl, $C_1$–$C_6$alkoxy, halo-$C_1$–$C_6$alkoxy, halogen, $C_3$–$C_6$-cycloalkyl unsubstituted or substituted by from 1 to 5 halogen atoms, $C_2$–$C_6$alkenyl, halo-$C_2$–$C_6$alkenyl, $C_3$–$C_6$alkynyl, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4alkyl)$, $N(C_1$–$C_4alkyl)_2$, $C_1$–$C_4$alkoxymethyl, $C_1$–$C_4$haloalkylcarbonyl, $C_1$–$C_4$alkylcarbonyl, $C_1$–$C_4$alkoxycarbonyl, aminocarbonyl, $C_1$–$C_4$alkylaminocarbonyl, bis($C_1$–$C_4$alkylamino)carbonyl, arylaminocarbonyl, arylaminothiocarbonyl, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$-alkylcarbonyloxy, $C_1$–$C_4$alkoxycarbonyloxy, aminocarbonyloxy, $C_1$–$C_4$alkylaminocarbonyloxy, bis($C_1$–$C_4$alkylamino)carbonyloxy, arylaminocarbonyloxy, arylaminothiocarbonyloxy, aryl, heteroaryl or heterocyclyl; wherein the aromatic groups in $R_{15}$ are each independently of the other unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy;

Q is a direct bond, $C_1$–$C_4$alkylene, $C_2$–$C_4$alkenylene, $C_2$–$C_4$alkynylene, O, O($C_1$–$C_2$alkylene) or ($C_1$–$C_2$alkylene)O;

m is 0 or 1; and
$R_{14}$ is methyl, ethyl or propargyl.

(13) Compounds of formula I in which in group e)

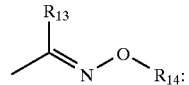

$R_{13}$ is heteroaryl or heterocyclyl, which are each independently of the other unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy.

(14) Compounds of formula I wherein in group e)

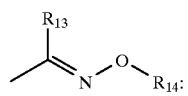

$R_{13}$ is pyridyl, pyrimidinyl, imidazolyl, thiazolyl or pyrrolyl each unsubstituted or mono- to tri-substituted by methyl, halo-$C_1$–$C_2$alkyl, $C_1$–$C_2$alkoxy, halo-$C_1$–$C_2$alkoxy or by halogen.

Compounds of formula I may be prepared as follows in accordance with Reaction Schemes 1 and 2.

In detail the reaction steps may be carried out as follows:

A), E), F) Under conditions that are known and can be used for Diels-Alder reactions, in the presence or absence of solvents, in the presence or absence of a catalyst, at from −40° to 250° C., preferably at from 20° to 200° C.

B), G) Reaction in a solvent under basic conditions.

C), K) Reaction with a chloroformic acid ester in the presence or absence of solvents, in the absence of water.

Scheme 1

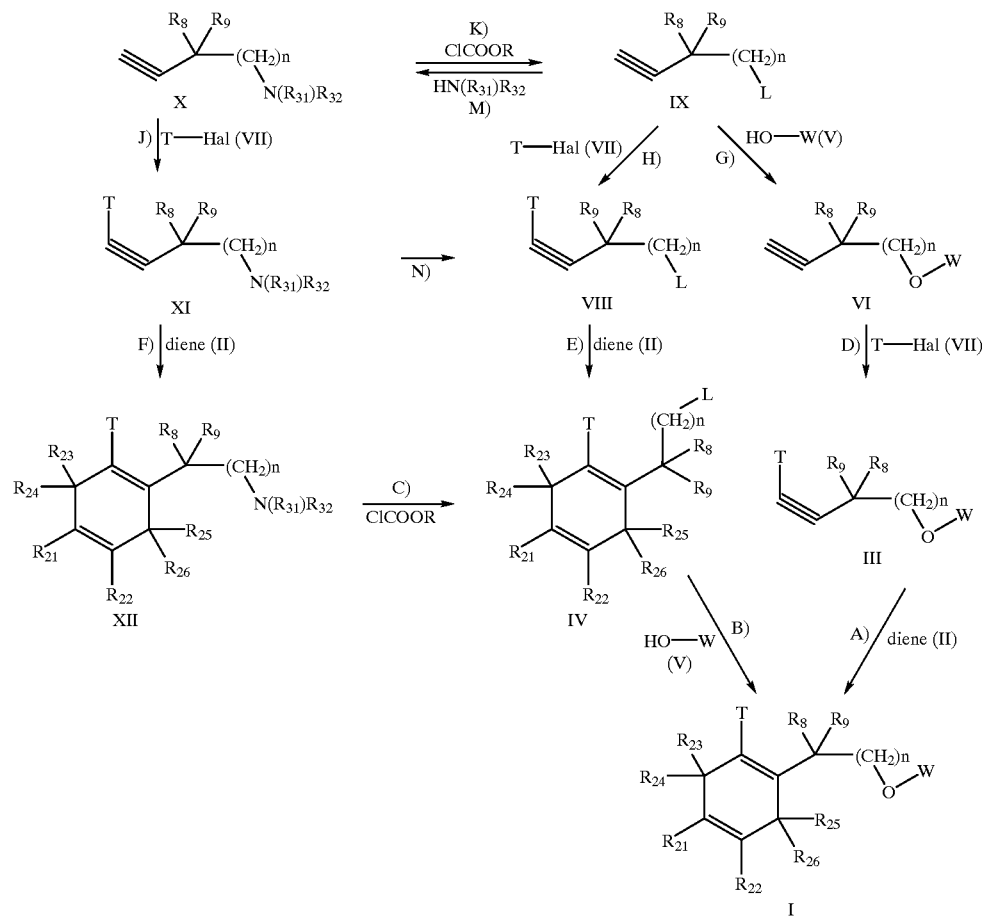

W: an aldimino or ketimino group

T: 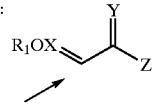

diene (II): 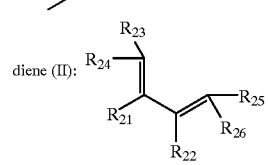

L: leaving group
Hal: halogen, especially chlorine or bromine

Scheme 2

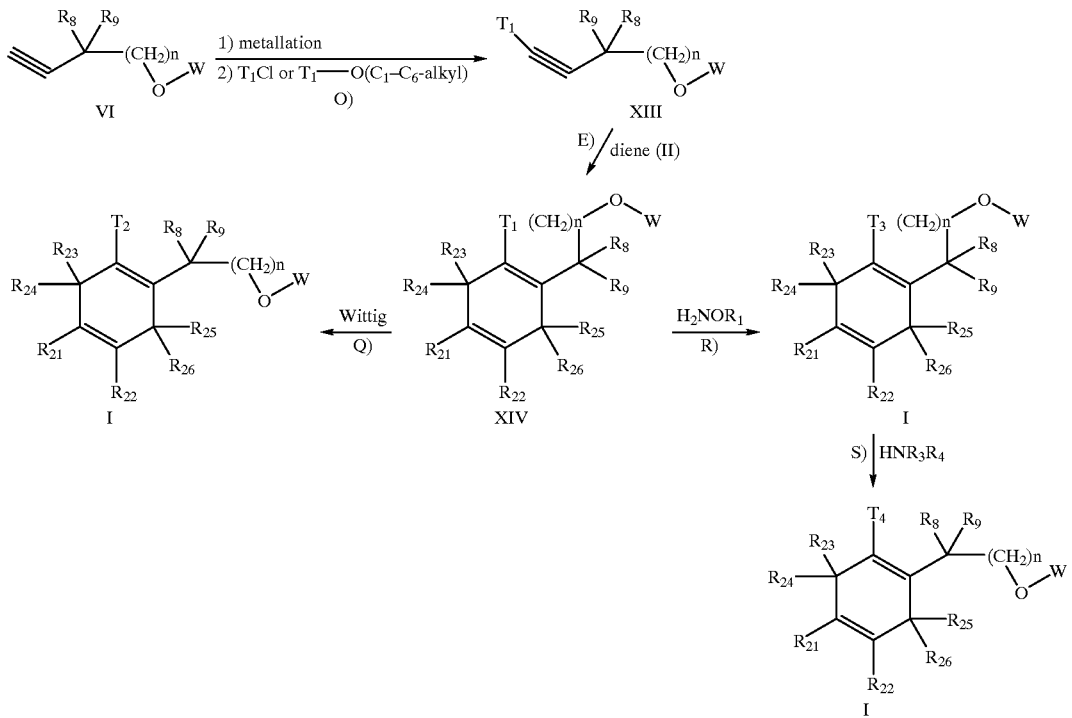

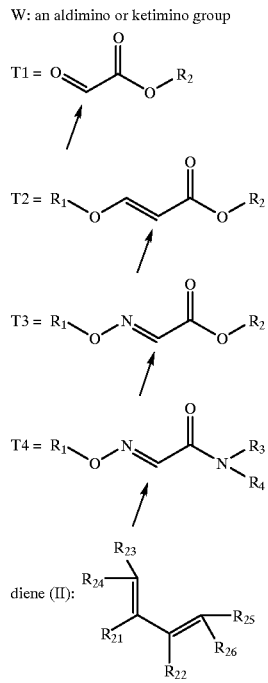

D), H), J) Under conditions that are known and can be used for Heck reactions in the presence of a palladium catalyst.

M) Replacement of the leaving group by an amino group under basic conditions.

N) Reaction with a chloroformic acid ester in the presence or absence of solvents, in the absence of water, to form a compound of formula VIII wherein L is chlorine, then, if desired, replacement of the chlorine atom by a different leaving group, such as bromine, tosylate or mesylate.

O) 1) Metallation with appropriate reagents, such as, for example, methylmagnesium chloride, sodium hydride, alkyllithium or potassium tert-butanolate and, if desired, transmetallation with copper iodide or similar salts and 2) subsequent acylation of the metal acetylide with an oxalic acid derivative T—Cl, especially with T1—Cl or $T_1$—O($C_1$-$C_6$alkyl) in a solvent.

Q) Wittig reaction with, for example, methoxymethyltriphenylphosphonium chloride and base in an inert solvent.

R) Oxime formation either (a) with a hydroxylamine derivative of formula $H_2NOR_1$ in a neutral or basic solvent, if desired with the addition of a base, or (b) with hydroxylamine $H_2NOH$ or a salt thereof and subsequent alkylation with an alkylation agent $R_1$-L in which L is a leaving group.

S) Conversion of an ester into an amide by treatment of the ester with an amine $HNR_3R_4$ in a suitable solvent.

Suitable bases are, for example, alkali metal or alkaline earth metal hydroxides, hydrides, amides, alkanolates, carbonates, dialkylamides or alkylsilylamides, alkylamines, alkylenediamines, unsubstituted or N-alkylated, saturated or unsaturated cycloalkylamines, basic heterocycles, ammonium hydroxides and also carbocyclic amines. There may be mentioned by way of example sodium hydroxide, hydride, amide, methanolate and carbonate, potassium tert-butanolate and carbonate, lithium diisopropylamide, potassium bis(trimethylsilyl)amide, calcium hydride, triethylamine, triethylenediamine, cyclohexylamine, bis(trimethylsilyl)amide, calcium hydride, triethylamine, triethylenediamine, cyclohexylamine, N-cyclohexyl-N,N-dimethylamine, N,N-diethylaniline, pyridine, 4-(N,N-dimethylamino)-pyridine, N-methylmorpholine, benzyltrimethylammonium hydroxide and also 1,8-diazabicyclo[5.4.0]undec-5-ene (DBU).

Leaving groups are, for example, chlorine, bromine, iodine, $C_1$-$C_8$alkylthio, such as methylthio, ethylthio or propylthio, $C_1$-$C_8$alkanoyloxy, such as acetoxy, (halo-)$C_1$-$C_8$alkanesulfonyloxy, such as methanesulfonyloxy, ethanesulfonyloxy or trifluoromethanesulfonyloxy, or unsubstituted or substituted phenylsulfonyloxy, such as benzenesulfonyloxy or p-toluenesulfonyloxy, imidazolyl or hydroxy, preferably chlorine, bromine, iodine, trifluoromethanesultonyloxy or p-toluenesulfonyloxy.

The reactants may be reacted with one another as they are, that is to say without the addition of a solvent or diluent, for example in the melt. Generally, however, the addition of an inert solvent or diluent or a mixture thereof is advantageous. Examples of such solvents or diluents include: aromatic, aliphatic and alicyclic hydrocarbons and halogenated hydrocarbons, such as benzene, toluene, xylene, chlorobenzene, bromobenzene, petroleum ether, hexane, cyclohexane, dichloromethane, trichloromethane, dichloroethane and trichloroethane; ethers, such as diethyl ether, tert-butyl methyl ether, tetrahydrofuran and dioxane; ketones, such as acetone and methyl ethyl ketone; alcohols, such as methanol, ethanol, propanol, butanol, ethylene glycol and glycerol; esters, such as ethyl acetate and butyl acetate; amides, such as N,N-dimethylformamide, N,N-dimethylacetamide, N-methylpyrrolidone and hexamethylphosphoric acid triamide; nitriles, such as acetonitrile; and sulfoxides, such as dimethyl sulfoxide. Bases used in excess, such as triethylamine, pyridine, N-methylmorpholine or N,N-diethylaniline, may also serve as solvents or diluents,.

The reaction may also be carried out with phase transfer catalysis in an organic solvent, for example methylene chloride or toluene, in the presence of an aqueous basic solution, for example sodium hydroxide solution, and of a phase transfer catalyst, for example tetrabutylammonium hydrogen sulfate.

Typical reaction conditions will be found in the Examples.

The invention relates also to novel starting materials and intermediates used in the preparation of compounds of formula 1, to the use thereof and to processes for the preparation thereof.

In that connection the following processes are especially important:

(1) A process for the preparation of a compound of formula I which comprises reacting a compound of formula II with a compound of formula III

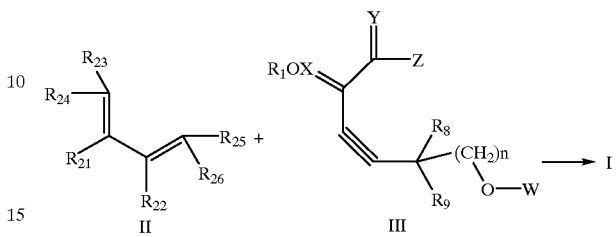

wherein n, X, Y, Z, $R_1$, $R_8$, $R_9$, W and $R_{21}$ to $R_{26}$ are as defined for formula I.

(2) A process for the preparation of a compound of formula I which comprises reacting a compound of formula IV with a compound of formula V

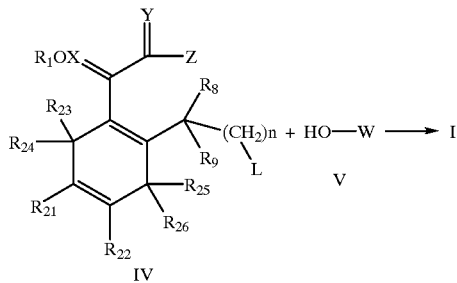

wherein n, X, Y, Z, $R_1$, $R_8$, $R_9$, $R_{21}$ to $R_{26}$ and W are as defined for formula I and L is a leaving group, in a solvent under basic conditions.

(3) A process for the preparation of a compound of formula XIV which comprises reacting a compound of formula II with a compound of formula XIII

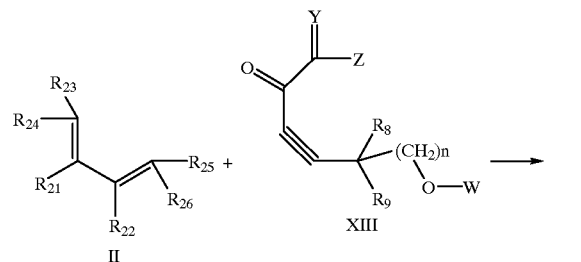

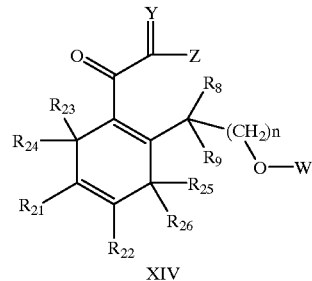

wherein n, Y, Z, $R_8$, $R_9$, W and $R_{21}$ to $R_{26}$ are as defined for formula I according to claim 1.

The following intermediates are of particular importance:

(1) Compounds of formula IV

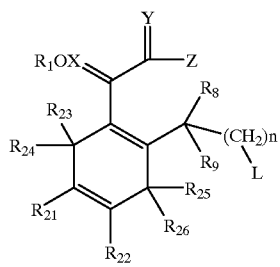

IV wherein n, X, Y, Z, $R_1$, $R_8$, $R_9$ and $R_{21}$ to $R_{26}$ are as defined for formula I and L is a leaving group.

(2) Compounds of formula XII

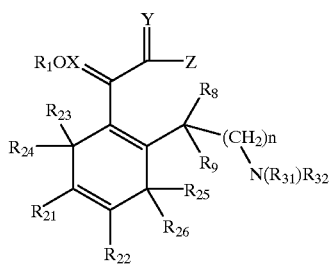

XII wherein n, X, Y, Z, $R_1$, $R_8$, $R_9$ and $R_{21}$ to $R26$ are as defined for formula I and wherein $R_{31}$ and $R_{32}$ are each independently of the other $C_1$–$C_6$alkyl, $C_1$–$C_6$alkenyl, $C_1$–$C_6$alkoxyalkyl, $C_3$–$C_6$cycloalkyl or unsubstituted or substituted benzyl, or $R_{31}$ and $R_{32}$ together with the nitrogen atom are an unsubstituted or substituted 6- or 7-membered ring that may contain a further hetero atom O, S or N in addition to the nitrogen atom, (3) Compounds of formula XIV

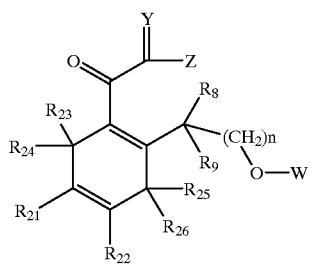

XIV wherein n, Y, Z, W, $R_8$, $R_9$ and $R_{21}$ to $R_{26}$ are as defined for formula I according to claim 1.

(4) Compounds of formula III

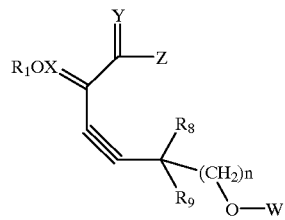

III wherein n, X, Y, Z, W, $R_1$, $R_8$ and $R_9$ are as defined for formula I according to claim 1.

(5) Compounds of formula XIII

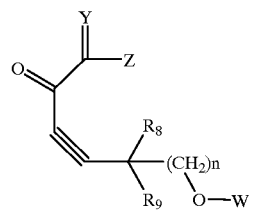

XIII wherein n, Y, Z, W, $R_1$, $R_8$ and $R_9$ are as defined for formula I according to claim 1.

(6) Compounds of formula XV

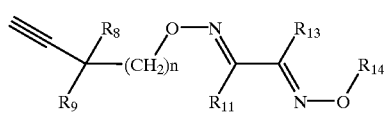

XV wherein n, $R_8$, $R_9$, $R_{11}$, $R_{13}$ and $R_{14}$ are as defined for formula I according to claim 1, with the exception of the following compound:

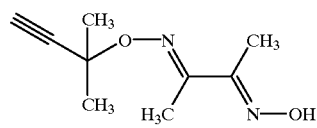

which is known from Tetrahedron Letters 1980, pages 1445–7.

The compounds of formula T-Hal (VII) wherein T is as defined hereinbefore and Hal is halogen may be prepared as described, for example, in WO/20569. The groups mentioned for X, Y and Z in formula I may also be converted one into another according to known methods, for example as described in WO 94/26700 and WO 95/04728, both in the final step and at any suitable intermediate step.

The compounds of formula I may be used preventatively and/or curatively in the agricultural sector and related fields as active ingredients in the control of plant pests. The compounds of formula I according to the invention are distinguished by excellent activity even at low rates of concentration, are well tolerated by plants and are environmentally friendly. They possess very advantageous, especially systemic, properties and can be used for the protection of a large number of crop plants. With the compounds of formula I it is possible to inhibit or destroy the pests that occur on plants or parts of plants (the fruit, blossom, leaves, stems, tubers or roots) of various crops of useful plants, while the parts of plants that grow later are also protected, for example, against phytopathogenic microorganisms.

The compounds I can also be used as dressings in the treatment of seed (fruit, tubers, grains) and plant cuttings to provide protection against fungus infections as well as against phytopathogenic fungi which occur in the soil.

The compounds I are effective, for example, against phytopathogenic fungi belonging to the following classes: Fungi imperfecti (e.g. Botrytis, Pyricularia, Helminthosporium, Fusarium, Septoria, Cercospora and Altemaria) and Basidiomycetes (e.g. Rhizoctonia, Hemileia, Puccinia). They are furthermore effective against the classes of the Ascomycetes (e.g. Venturia and Erysiphe, Podosphaera, Monilinia, Uncinula) and of the Oomycetes (e.g. Phytophthora, Pythium, Plasmopara).

Within the scope of the invention, target crops for plant protection use include e.g. the following species of plants: cereals (wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (marrows, cucumber, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); and plants such as tobacco, nuts, coffee, aubergines, sugar cane, tea, pepper, vines, hops, bananas and natural rubber plants, as well as ornamentals.

The compounds of formula I according to the invention, while being well tolerated by warm-blooded animals, fish and plants, are valuable active ingredients against insects and pests of the order Acarina as occur in useful plants and ornamentals in agriculture, horticulture and forestry. The compounds of formula I are suitable especially in the control of pests in cotton, vegetable, fruit and rice crops, such as spider mites, aphids, Lepidoptera caterpillars and rice cicadas. Mainly they can be used to control spider mites such as *Panonychus ulmi*, aphids such as *Aphis craccivora*, Lepidoptera caterpillars such as those of *Heliothis virescens*, and rice cicadas such as *Nilaparvata lugens* or *Nephotettix cincticeps*. The good pesticidal action of the compounds I according to the invention corresponds to a mortality rate of at least 50–60% of the mentioned pests.

Further areas of use of the compounds according to the invention are: protection of stored goods and materials, where the stored goods are protected against rotting and becoming mouldy and also against animal pests (e.g. grain weevils, mites, fly maggots etc.). In the hygiene sector, compounds of formula I are effective in the control of animal parasites, such as ticks, mites, botiflies etc., on domestic animals and productive livestock. The compounds I are effective against individual or all development stages of normally sensitive, but also resistant, species of pests. Their activity may manifest itself, for example, in the death of the pests, which occurs directly or happens only after some time, for example during shedding, or in a reduced oviposition and/or hatching rate.

The compounds I are usually used in the form of compositions and may be applied to the area or plant to be treated simultaneously with or in succession with other active ingredients. Those other active ingredients may be, for example, fertilisers, micronutrient donors or other preparations that influence plant growth. It is also possible to use selective herbicides and also insecticides, fungicides, bactericides, nematicides or molluscicides or mixtures of several of those preparations, where appropriate together with further carriers, surfactants or other application-promoting additives that are customary in formulation technology.

Suitable carriers and additives may be solid or liquid and are substances that are expedient in formulation technology, for example natural or regenerated mineral substances, solvents, dispersing agents, wetting agents, tackifiers, thickening agents, binders or fertilisers.

A preferred method of applying a compound of formula I or an agrochemical composition that comprises at least one of those compounds is foliar application. The frequency and rate of application depend on the risk of infestation by the pathogen in question. The compounds I may also penetrate the plants through the root system via the soil (systemic action) as a result of impregnation of the locus of the plant with a liquid preparation or by means of introduction of the compounds into the soil in solid form, for example in the form of granules (soil application). In the case of paddy rice crops, such granules may be applied in metered amounts to the flooded rice field. The compounds I may, however, for seed treatment, alternatively be applied to the seed grains (coating), either by means of impregnating the seeds or tubers with a liquid preparation of the active ingredient or coating them with a solid preparation.

The compounds of formula I may be used in unmodified form or preferably together with the adjuvants conventionally employed in formulation technology. For that purpose they are advantageously formulated in known manner, for example into emulsifiable concentrates, coatable pastes, directly sprayable or dilutable solutions, dilute emulsions, wettable powders, soluble powders, dusts or granules, e.g. by encapsulation in substances, for example polymeric substances. As with the nature of the compositions, the methods of application, such as spraying, atomising, dusting, scattering, coating or pouring, are chosen in accordance with the intended objectives and the prevailing circumstances.

Favourable rates of application are generally from 5 g to 2 kg of active ingredient (a.i.) per hectare (ha), preferably from 10 g to 1 kg a.i./ha, especially from 20 g to 600 g a.i./ha. When used as seed dressing, concentrations of from 10 mg to 1 g of active ingredient per kg of seed are advantageously employed.

The formulations, i.e. the compositions, preparations or mixtures comprising the compound (active ingredient) of formula I and, where appropriate, a solid or liquid adjuvant, are prepared in known manner, e.g. by intimately mixing and/or grinding the active ingredient with extenders, such as solvents, solid carriers and, where appropriate, surface-active compounds (surfactants).

Suitable solvents are: aromatic hydrocarbons, preferably the fractions containing 8 to 12 carbon atoms, such as xylene mixtures or substituted naphthalenes, phthalates, such as dibutyl or dioctyl phthalate, aliphatic hydrocarbons, such as cyclohexane, or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, and also vegetable oils or epoxidised vegetable oils, such as epoxidised coconut oil or soybean oil, and water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, such as dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and water-soluble synthetic surface-active compounds are suitable anionic surfactants.

Examples of non-ionic surfactants are nonylphenol polyethoxyethanols, castor oil polyglycol ethers, polypropylene/polyethylene oxide adducts, tributylphenoxypolyethylene ethanol, polyethylene glycol and octylphenoxypolyethoxyethanol. Fatty acids esters of polyoxyethylenesorbitan, e.g. polyoxyethylene sorbitan trioleate, are also suitable.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals.

Other surfactants customarily used in formulation technology are known to the person skilled in the art or can be found in the relevant specialised literature.

The agrochemical compositions usually contain 0.1 to 99% by weight, especially 0.1 to 95% by weight, of a compound of formula I, 99.9 to 1% by weight, especially 99.8 to 5% by weight, of a solid or liquid adjuvant, and 0 to 25% by weight, especially 0.1 to 25% by weight, of a surfactant.

Whereas commercial products are preferably formulated as concentrates, the end user will normally employ dilute formulations.

The compositions may also comprise further ingredients, such as stabilisers, anti-foams, viscosity regulators, binders or tackifiers, as well as fertilisers or other active ingredients for obtaining special effects.

PREPARATION EXAMPLES

Temperatures are Indicated in ° Celsius

P-1: Preparation of (3-trifluoromethylphenyl)ethanone O-prop-2-ynyloxime (Compd. 9.06)

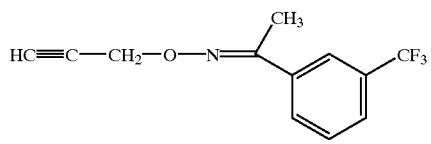

350 g of potassium carbonate (powder) are added to a solution of 256 g of 1-(3-trifluoromethylphenyl)ethanone oxime in 2 litres of acetonitrile. 100 ml of propargyl chloride are then added and the mixture is stirred for 14 hours at 70°. After filtering off with suction over Celite, the filtrate is concentrated by evaporation to yield 301 g of the title compound in the form of a light-brown oil.

P-2: Preparation of 2-methoxyimino-5-[1-(3-trifluoromethylphenyl)ethylideneaminoxy]pent-3-ynoic acid methyl ester (Compd. 7.06.)

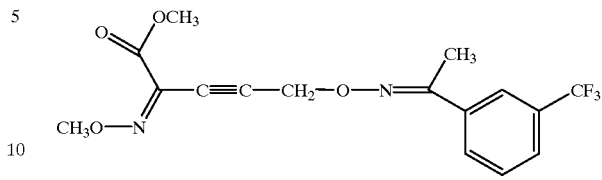

67.5 g of 1-(3-trifluoromethylphenyl)ethanone O-prop-2-ynyloxime and also 0.3 g of copper(I) iodide and 1 g of $Pd(TPP)_2Cl_2$ are added to a solution of 39.5 g of 2-methoxyiminooxalic acid monochloride monomethyl ester in 1000 ml of triethylamine and 80 ml of THF. The mixture is then stirred for 14 hours at 80° and subsequently filtered with suction and concentrated by evaporation. The oily residue is chromatographed on silica gel (ether/hexane 1:2) and the combined fractions are concentrated by evaporation and stirred with hexane. 38 g of the title compound are obtained in the form of light-yellow crystals having a melting point of 66–68°.

P-3: Preparation of {4,5-dimethyl-2-[1-(3-trifluoromethylphenyl)ethylideneaminoxymethyl]-cyclohexa-1,4-dienyl}methoxyiminoacetic acid methyl ester (Compd. 2.05.)

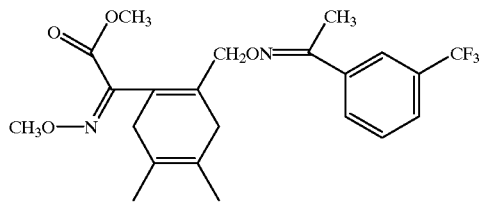

7.5 ml of 2,3-dimethylbuta-1,3-diene are added to a solution of 2.5 g of 2-methoxyimino-5-[1-(3-trifluoromethylphenyl)ethylideneaminoxy]pent-3-ynoic acid methyl ester in 5 ml of toluene. The reaction mixture is heated for 14 hours at 130° in an autoclave and is then concentrated by evaporation and chromatographed on silica gel. 2.6 g of the title compound are obtained in the form of a resin.

P-4: Preparation of 1-[4-(3-trifluoromethylphenoxy)phenyl] propane-1,2-dione 1-(O-methyloxime) 2-(O-prop-2-ynyloxime) (Compd. 9.21.)

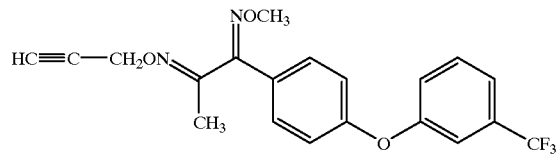

4.7 g of propargyl mesylate and 4.5 g of potassium carbonate are added to a solution of 6 g of 1-[4-(3-trifluoromethylphenoxy)phenyl]propane-1,2-dione 1-(O-methyloxime) 2-oxime in 100 ml of dimethylformamide. The mixture is stirred for 6 hours at 60° and then filtered over Celite and concentrated by evaporation under a high vacuum. 200 ml of water are added to the residue and extraction is carried out 3 times with 50 ml of ether each time. The extracts are then concentrated by evaporation and the residue is chromatographed on silica gel (ether/hexane 2:5). 4.9 g of the title compound are obtained in the form of a light-coloured oil.

P-5: Preparation of 1-[4-(3-trifluoromethylbenzyloxy) phenyl]propane-1,2-dione 1-(O-methyloxime) 2-(O-prop-2-ynyloxime) (Compd. 9.15.)

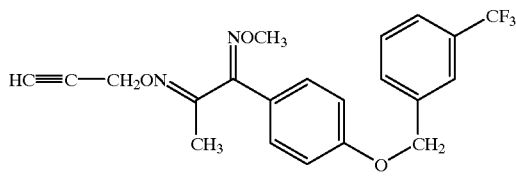

4.2 g of propargyl mesylate and 4.5 g of potassium carbonate are added to a solution of 5.6 g of 1-[4-(3-trifluoromethylbenzyloxy)phenyl]propane-1,2-dione 1-(O-methyloxime) 2-oxime in 100 ml of dimethylformamide. The mixture is stirred for 6 hours at 60° and then filtered over Celite and concentrated by evaporation under a high vacuum. 200 ml of water are added to the residue and extraction is carried out 3 times with 50 ml of ether each time. The extracts are then concentrated by evaporation and the residue is chromatographed on silica gel (ether/hexane 2:5). 4.9 g of the title compound are obtained in the form of a light-coloured oil.

P-6: Preparation of 5-(2,6-dimethylmorpholin-4-yl)-2-methoxyiminopent-3-ynoic acid methyl ester (cis and trans) (Compd. 8.14.)

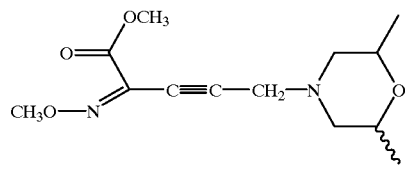

9 g of 2-methoxyimino-oxalic acid monochloride monomethyl ester and also 0.1 g of copper(I) iodide and 0.3 g of Pd(TPP)$_2$Cl$_2$ are added to a solution of 7.65 g of 2,6-dimethyl-4-prop-2-ynylmorpholine (cis/trans mixture) in 200 ml of triethylamine and 50 ml of THF. The mixture is then stirred for 14 hours at 80° and subsequently filtered with suction and concentrated by evaporation. The oily residue is chromatographed on silica gel (ether/hexane 1:2). 2.1 g of oil of the (trans) title compound and 4.2 g of oil of the (cis) title compound are obtained.

P-7: Preparation of [2-(2,6-dimethylmorpholin-4-ylmethyl)-4,5-dimethylcyclohexa-1,4-dienyl]-methoxyiminoacetic acid methyl ester (Compd.5.11.)

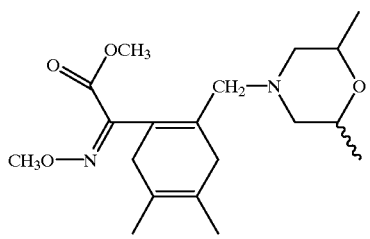

7.5 ml of 2,3-dimethylbuta-1,3-diene are added to a solution of 3.3 g of (cis)-5-(2,6-dimethylmorpholin-4-yl)-2-methoxyiminopent-3-ynoic acid methyl ester in 5 ml of toluene. The reaction mixture is heated for 14 hours at 130° in an autoclave, and is then concentrated by evaporation and chromatographed on silica gel. 2.6 g of the title compound are obtained in the form of a resin.

P-8: Preparation of 2-methoxyimino-5-morpholin-4-ylpent-3-ynoic acid methyl ester (Compd. 8.06.)

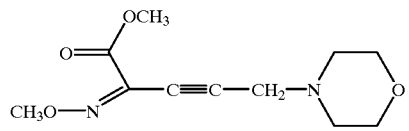

7.6 g of 2-methoxyimino-oxalic acid monochloride monomethyl ester and also 0.1 g of copper(I) iodide and 0.3 g of Pd(TPP)$_2$Cl$_2$ are added to a solution of 6.25 g of 4-prop-2-ynylmorpholine in 250 ml of triethylamine and 30 ml of THF. The mixture is then stirred for 14 hours at 80° and subsequently filtered with suction and concentrated by evaporation. The oily residue is chromatographed on silica gel (ethyl acetate/hexane 4:1). 6.65 g of oil of the title compound are obtained.

P-9: Preparation of (4,5-dimethyl-2-morpholin-4-ylmethylcyclohexa-1,4-dienyl)-methoxyiminoacetic acid methyl ester (Compd. 5.07)

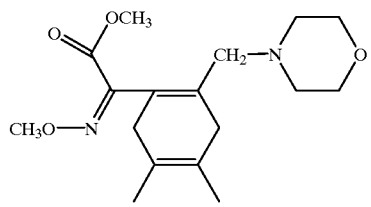

10 ml of 2,3-dimethylbuta-1,3-diene are added to a solution of 4.8 g of 2-methoxyimino-5-morpholin-4-ylpent-3-ynoic acid methyl ester in 10 ml of toluene. The reaction mixture is heated for 24 hours at 130° in an autoclave and is then concentrated by evaporation and chromatographed on silica gel (ethyl acetate/hexane 1:2). 3 g of the title compound are obtained in the form of a resin.

P-10: Preparation of (2-chloromethyl-4,5-dimethylcyclohexa-1,4-dienyl)methoxyiminoacetic acid methyl ester (Compd. 5.03.)

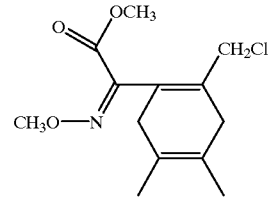

1.4 ml of chloroformic acid ethyl ester are added to a solution of 2.3 g of (4,5-dimethyl-2-morpholin-4-ylmethylcyclohexa-1,4-dienyl)methoxyiminoacetic acid methyl ester in 25 ml of THF. The mixture is then heated at 65° for 20 hours and, after concentration by evaporation, chromatographed on silica gel (ether/hexane 1:2). 1.5 g of the title compound are obtained in the form of a colourless oil.

P-11: Preparation of {4,5-dimethyl-2-[1-(3-trifluoromethylphenyl)ethylideneaminoxymethyl]-cyclohexa-1,4-dienyl}-methoxyiminoacetic acid methyl ester (Compd. 2.05.)

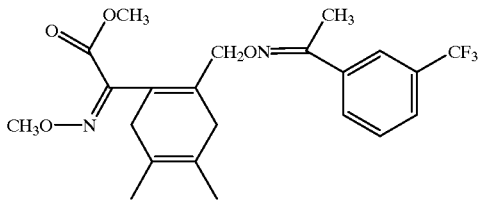

2.56 g of 1-(3-trifluoromethylphenyl)ethanone oxime and 3.5 g of potassium carbonate (powder) are added to a solution of 2.5 g of (2-chloromethyl-4,5-dimethylcyclohexa-1,4-dienyl)methoxyiminoacetic acid methyl ester in 5 ml of acetonitrile. The mixture is then stirred for 14 hours at 70° and subsequently filtered with suction and concentrated by evaporation. Chromatography on silica gel yields 3.5 g of the title compound in the form of a colourless resin.

P.12: Preparation of 2-{4,5-dimethyl-2-[1-(3-trifluoromethylphenyl)ethylideneaminoxymethyl] cyclohexa-1,4-dienyl}-2-methoxyimino-N-methylacetamide (Compd. 3.05.)

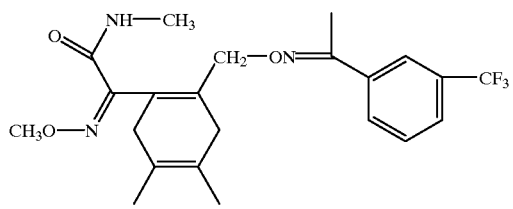

10 ml of methylamine solution (5N in methanol) are added to a solution of 4 g of {4,5-dimethyl-2-[1-(3-trifluoromethylphenyl)ethylideneaminoxymethyl] cyclohexa-1,4-dienyl}-methoxyiminoacetic acid methyl ester in 10 ml of methanol and the mixture is stirred for 6 hours at approximately 40° and then concentrated by evaporation and chromatographed on silica gel. 3.8 g of the title compound are obtained in the form of a resin.

P-13: Preparation of 5-chloro-2-methoxyiminopent-3-ynoic acid methyl ester (Compd. 8.04.)

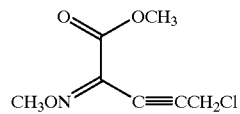

1.4 ml of chloroformic acid ethyl ester are added to a solution of 12.1 g of 2-methoxyimino-5-morpholin-4-ylpent-3-ynoic acid methyl ester in 25 ml of THF. The mixture is then heated for 20 hours at 65°. Concentration by evaporation followed by chromatography on silica gel (ether/hexane 1:2) yields 8.2 g of the title compound in the form of a colourless oil.

P-14: Preparation of 2-methoxyimino-5-[1-(3-trifluoromethytylphenyl)ethylideneaminoxy]-pent-3-ynoic acid methyl ester (Compd. 7.06.)

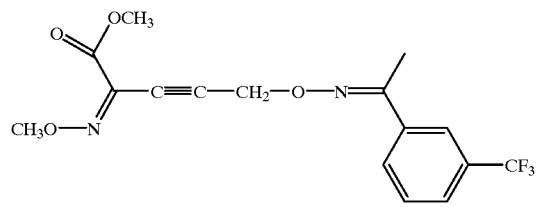

10.56 g of 1-(3-trifluoromethylphenyl)ethanone oxime and 14.5 g of potassium carbonate (powder) are added to a solution of 10.5 g of 5-chloro-2-methoxyiminopent-3-ynoic acid methyl ester in 5 ml of acetonitrile. The mixture is then stirred for 14 hours at 70° and subsequently filtered with suction and concentrated by evaporation. Chromatography on silica gel yields 13.5 g of the title compound in the form of a colourless resin.

P-15: Preparation of methoxyimino-(2-{2-methoxyimino-1-methyl-2-[4-(3-trifluoromethylbenzyloxy)phenyl] ethylideneaminoxymethyl}-4,5-dimethylcyclohexa-1,4-dienyl)acetic acid methyl ester (Compd. 3.18.)

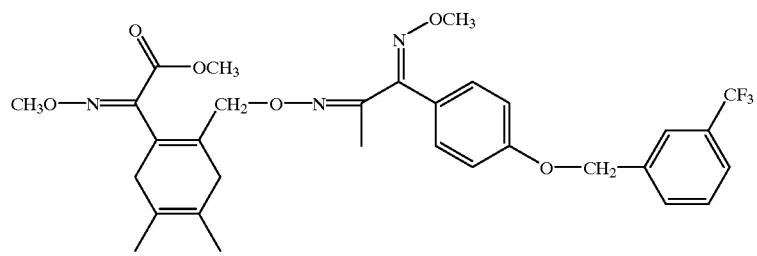

1.56 g of 1-[4-(3-trifluoromethylbenzyloxy)phenyl] lpropane-1,2-dione 1-(O-methyloxime) 2-oxime and 1.5 g of potassium carbonate (powder) are added to a solution of 1.5 g of (2-chloromethyl-4,5-dimethylcyclohexa-1,4-dienyl) methoxyiminoacetic acid methyl ester in 5 ml of acetonitrile. The mixture is then stirred for 14 hours at 70° and subsequently filtered with suction and concentrated by evaporation. Chromatography on silica gel yields 1.5 g of the title compound in the form of a colourless resin.

P-16: Preparation of 5-(1-methoxy-1-methylethoxy)-2-oxopent-3-ynoic acid tert-butyl ester (Compd. 10.26.)

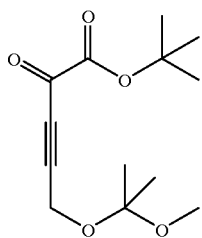

136 ml of a methylmagnesium chloride solution (approximately 3 molar in THF) are added dropwise at from 15° to 20° to a solution of 50 g of 3-(1-methoxy-1-methylethoxy)propyne in 200 ml of methylene chloride. The mixture is then stirred for 3 hours at room temperature. The solution so obtained is added dropwise over a period of one hour, at from –40° to –50° under nitrogen, to a solution of 131 g of oxalic acid tert-butyl ester ethyl ester in 100 ml of methylene chloride. The mixture is then hydrolysed with 10% ammonium chloride solution. The organic phase is separated off and dried over sodium sulphate. Concentration by evaporation yields 292 g of a solution that still contains methylene chloride and THF in addition to the title compound.

P-17: Preparation of 2-oxo-5-[1-(3-trifluoromethylphenyl)ethylideneaminoxy]pent-3-ynoic acid tert-butyl ester (Compd.11.23.)

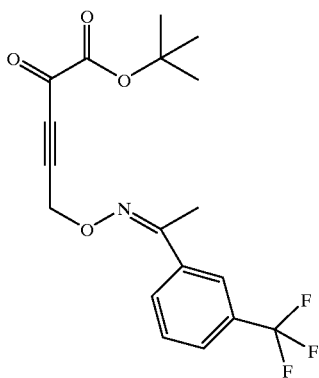

18 ml of a hexyllithium solution (2.5 molar in hexane) are added dropwise at –50° to a solution of (3-trifluoromethylphenyl)ethanone O-prop-2-ynyloxime (Compd. 9.06) in 95 ml of THF. The reaction mixture is then stirred for 90 minutes, the temperature rising to 0°. It is then cooled to –70° and a solution of 15.85 g of oxalic acid tert-butyl ester ethyl ester in 30 ml of THF is added dropwise. The mixture is stirred for 30 minutes, in the course of which the temperature is allowed to rise to –50°. The mixture is then poured into 1000 ml of ice-water, rendered slightly acidic with a small amount of hydrochloric acid and extracted three times with 200 ml of ethyl acetate each time. The organic phase is washed twice with brine and dried with sodium sulfate. Concentration by evaporation yields 21.9 g of a light-brown liquid which contains approximately 14 g of the title compound.

P-18: Preparation of {4-methyl-2-[1-(3-trifluoromethylphenyl)ethylideneaminoxymethyl]-cyclohexa-1,4-dienyl]oxoacetic acid tert-butyl ester (Compd. 12.171.)

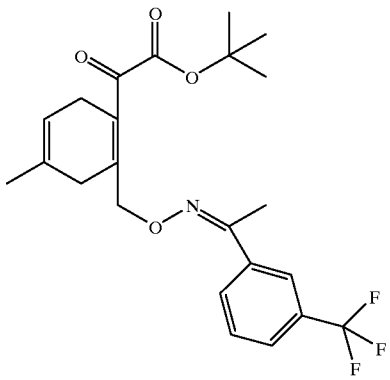

19 g of isoprene are added to 14.6 g of 2-oxo-5-[1-(3-trifluoromethylphenyl)ethylideneaminoxy]pent-3-ynoic acid tert-butyl ester and the reaction mixture is then left to stand for 5 days at room temperature. Concentration by evaporation yields 15.38 g of the title compound in the form of a colourless oil.

P-19: Preparation of Compound 14.102.

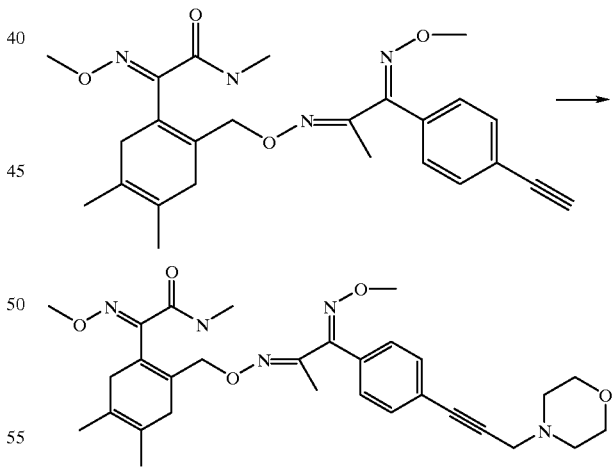

2.2 g of morpholine and 1.3 g of formaldehyde as well as 0.05 g of copper(I) chloride are added to a solution of 5.5 g of the starting material in 40 ml of 1-propanol. The mixture is heated for 3 hours at 70°, concentrated by evaporation and then chromatographed on silica gel (ethyl acetate). After stirring with hexane, 4.9 g of product having a melting point of 100–102° are obtained.

H-20: Preparation of Compound 14.103.

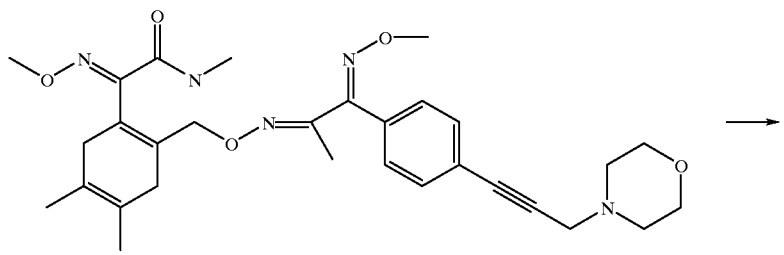

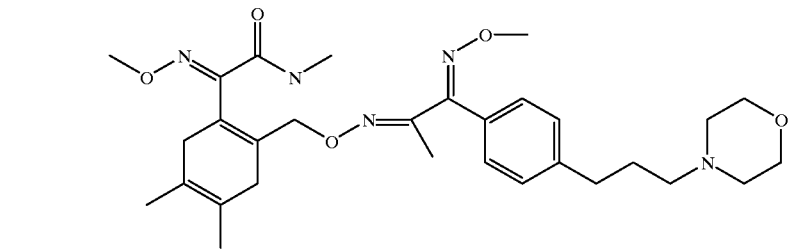

100 mg of Pd/C (5%) are added to a solution of 0.5 g of the starting material in 12 ml of tetrahydrofuran. The mixture is then hydrogenated until the theoretical amount of hydrogen has been consumed, and filtered with suction, concentrated by evaporation and chromatographed on silica gel (ethyl acetate). 0.45 g of product is obtained in the form of a resin.

P-21: Preparation of Compound 14.104.

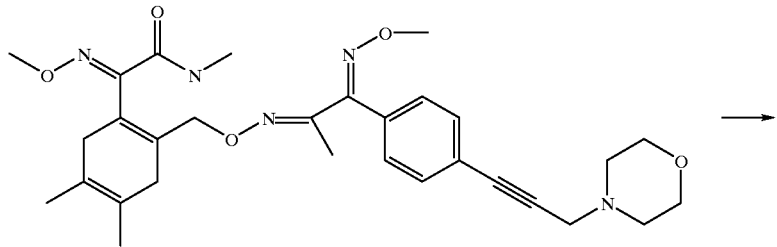

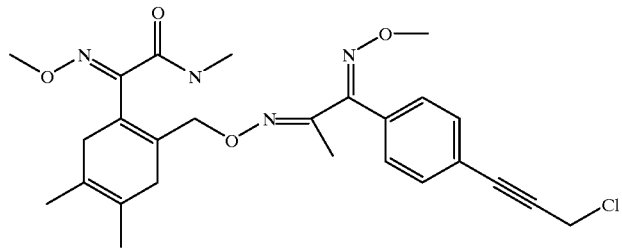

5 ml of chloroformic acid ethyl ester are added to a solution of 4.9 g of the starting material in 30 ml of tetrahydrofuran and the mixture is stirred for 14 hours at 60°. After concentration by evaporation, 150 ml of ether are added and the mixture is washed twice with sodium hydrogen carbonate solution. The organic phase is dried with magnesium sulfate, filtered with suction and concentrated by evaporation. After the concentration by evaporation, chromatography on silica gel (ethyl acetate/hexane 1:1) yields 2.1 g of product in the form of white crystals having a melting point of 126–129°.

P-22: Preparation of Compound 14.106.

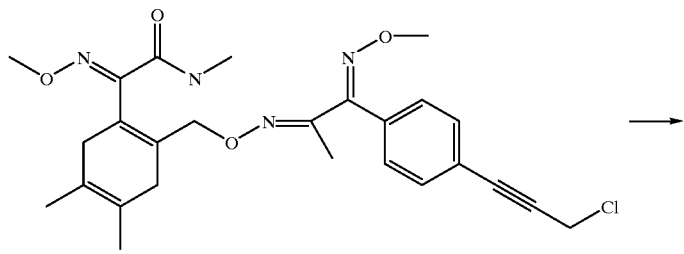

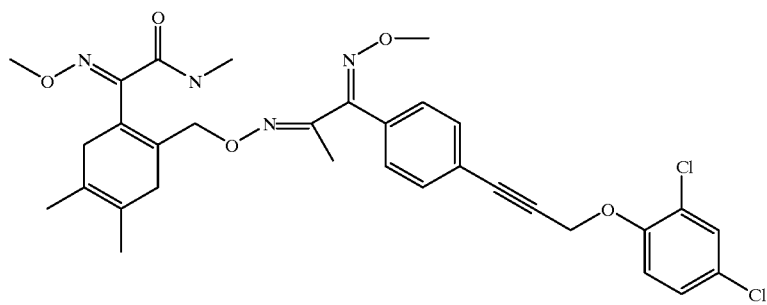

0.19 g of 2,4-dichlorophenol and 0.19 g of potassium carbonate are added to a solution of 0.46 g of the starting material in 2.5 ml of dimethyl sulfoxide and the mixture is stirred for 3 hours at 70°. After cooling, the reaction mixture is chromatographed on silica gel (ether/hexane 1:1) to yield 0.4 g of product in the form of colourless crystals having a melting point of 119–122°.

P-23: Preparation of Compound 3.190.

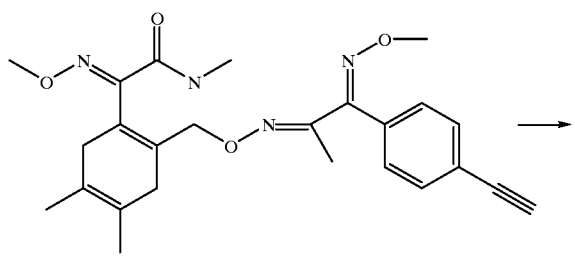

-continued

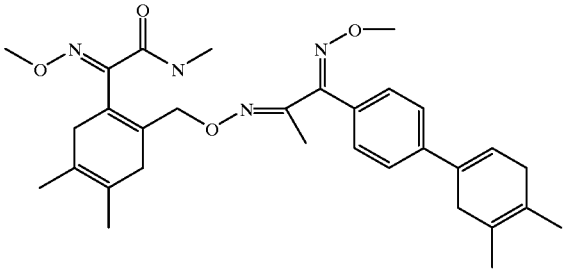

15 ml of 2,3-dimethylbutadiene are added to a solution of 5 g of the starting material in 5 ml of toluene. The mixture is then heated for 20 hours at 125° in a pressure tube. After cooling, the mixture is poured into 150 ml of methanol and then filtered over Celite. Concentration by evaporation followed by chromatography on silica gel (ether/hexane 1:1) yields 1.6 g of product.

P-24: Preparation of Compound 2.167.

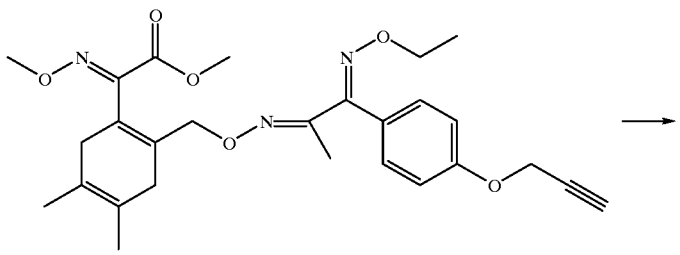

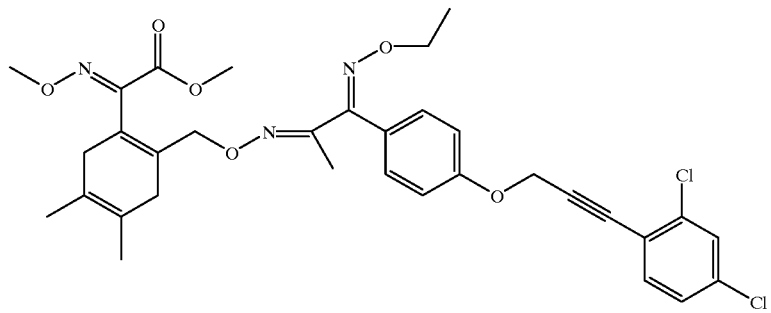

1.5 ml of iododichlorobenzene and 0.1 g of Pd(TPP)$_2$Cl$_2$ are added to a solution of 2.25 g of the starting material in 100 ml of triethylamine and 40 ml of tetrahydrofuran. The mixture is then stirred for 3 hours at 65°, filtered with suction, concentrated by evaporation and chromatographed on silica gel (ethyl acetate/hexane 1:2) to yield 2.2 g of product in the form of a colourless resin.

P-25: Preparation of Compound 2.168.

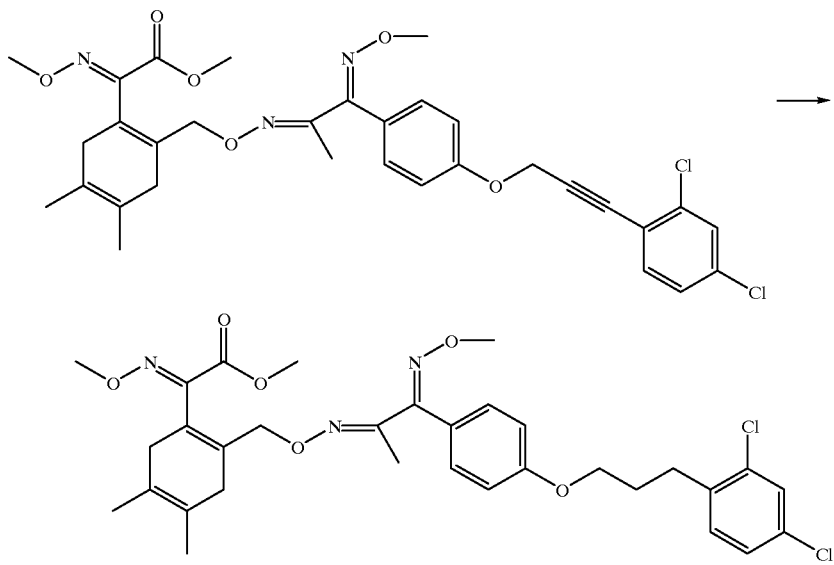

100 mg of Pd/C (5%) are added to a solution of 1.8 g of the starting material in 30 ml of tetrahydrofuran. The mixture is then hydrogenated until the theoretical amount of hydrogen has been consumed, filtered with suction, concentrated by evaporation and chromatographed on silica gel (ethyl acetate/hexane 1:2) to yield 1.5 g of product in the form of an oil.

P-26: Preparation of Compound 2.175.

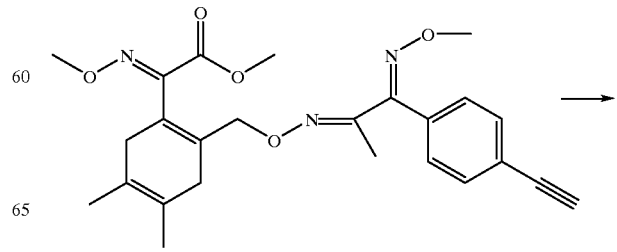

-continued

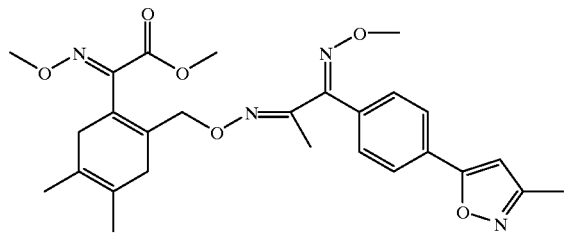

1.1 ml of phenyl isocyanate and 0.45 ml of nitroethane and also 5 g of drops of triethylamine are added to a solution of 2.1 g of the starting material in 40 ml of toluene. The mixture is then heated for 5 hours at 80°, filtered with suction, concentrated by evaporation and chromatographed on silica gel (ethyl acetate/hexane 1:2). After stirring with petroleum ether, 0.6 g of product is obtained in the form of a colourless resin.

P-27: Preparation of Compound 2.180.

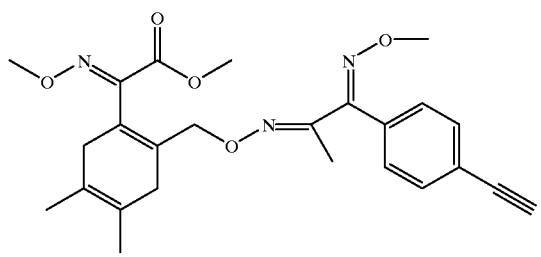

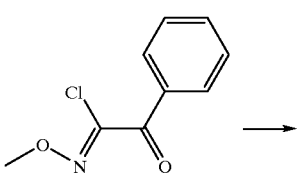

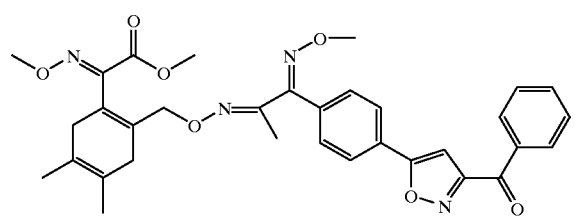

2 ml of triethylamine are added dropwise to a solution of 1.2 g of the starting material and 1.8 g of the chloroxime in 50 ml of toluene. The mixture is then heated for 4 hours at 65° and subsequently filtered with suction and concentrated by evaporation. Subsequent chromatography on silica gel (toluene/diisopropyl ether/hexane 1:1:2) yields 0.95 g of product in the form of crystals having a melting point of 121–123°.

P-28: Preparation of Compound 2.170.

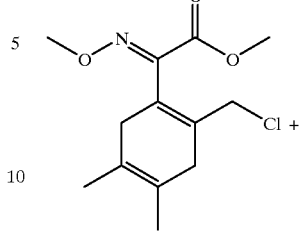

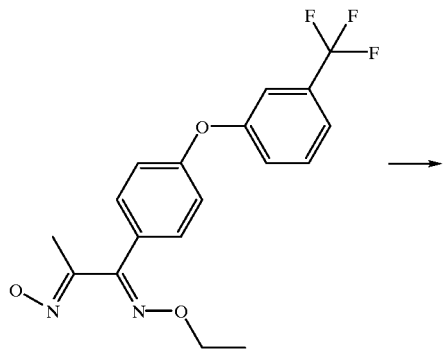

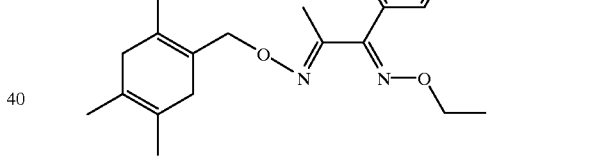

2 g of potassium carbonate are added to a solution of 1.5 g of (2-chloromethyl-4,5-dimethyl-cyclohexa-1,4-dienyl) methoxyiminoacetic acid methyl ester and 2 g of the bis-oxime in 40 ml of acetonitrile and the mixture is stirred for 6 hours at 80° and then filtered with suction and concentrated by evaporation. Subsequent chromatography on silica gel (diisopropyl ether/hexane 1:2) yields 2.4 g of product in the form of a resinous oil.

P-29: Preparation of Compound 2.164.

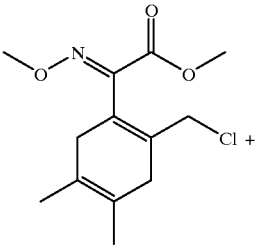

-continued

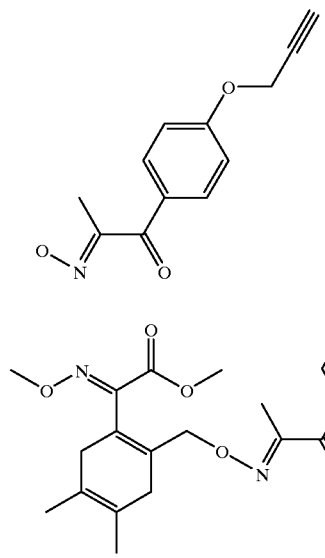

1.8 g of potassium carbonate are added to a solution of 1.35 g of (2-chloromethyl-4,5-dimethylcyclohexa-1,4-dienyl)methoxyiminoacetic acid methyl ester and 1.1 g of the bisoxime in 40 ml of acetonitrile and the mixture is stirred for 6 hours at 65°, filtered with suction and concentrated by evaporation. Subsequent chromatography on silica gel (ether/hexane 1:1) yields 1.5 g of the title compound in the form of a colourless resin.

P-30: Preparation of Compound 2.166.

P-31: Preparation of Compound 2.184.

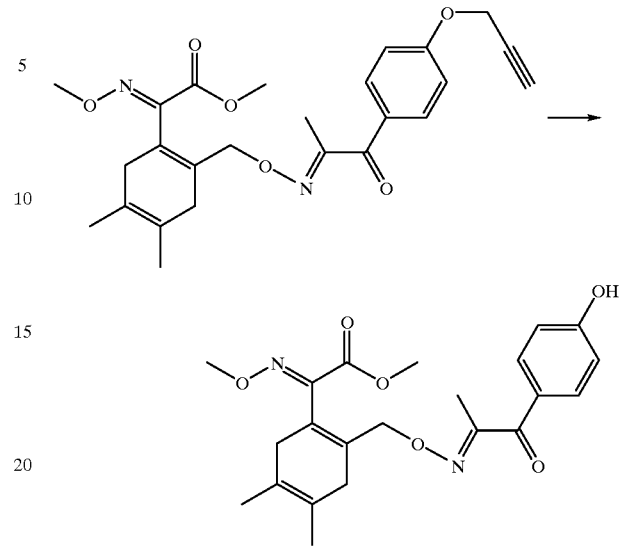

0.1 g of Pd(TPP)$_2$Cl$_2$ and 0.3 ml of triethylamine are added to a solution of 1 g of the starting material in 3 ml of methanol. The mixture is then stirred for 6 hours at 60°, poured into 40 ml of water and extracted twice with 20 ml of ether/THF 4:1 each time. Concentration by evaporation followed by chromatography on silica gel (ether/hexane 3:1) yields 0.5 g of product in the form of a resinous oil.

P-32:) Preparation of Compound 2.183.

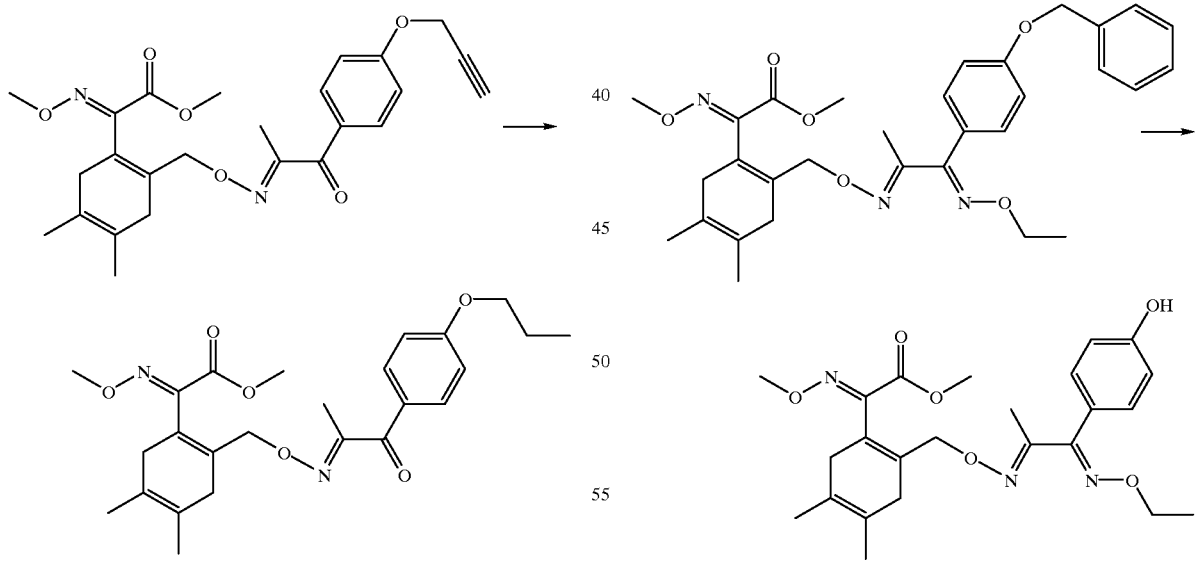

0.5 g of Raney nickel is added to a solution of 1 g of the starting material in 15 ml of tetrahydrofuran. The mixture is then hydrogenated until the theoretical amount of hydrogen has been consumed, filtered with suction and concentrated by evaporation. Subsequent chromatography on silica gel (ether/hexane 1:1) yields 0.7 g of product in the form of a colourless resin.

0.1 g of 10% Pd/C is added to a solution of 5 g of the starting material in 30 ml of tetrahydrofuran. The mixture is then hydrogenated until one equivalent of hydrogen has been consumed, and is subsequently filtered with suction, concentrated by evaporation and chromatographed on silica gel (ethyl acetate/hexane 1:2) to yield 3.5 g of product in the form of an oil.

P-33: Preparation of Compound 2.185.

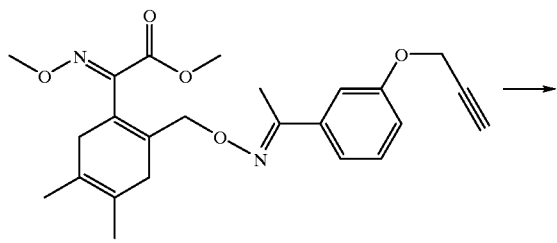

0.15 g of Pd(TPP)$_2$Cl$_2$ and also 0.6 ml of triethylamine are added to a solution of 3 g of the starting material in 3 ml of methanol. The mixture is then stirred for 6 hours at 60°, poured into 40 ml of water and extracted twice with 20 ml of ether/THF 4:1 each time. Concentration by evaporation followed by chromatography on silica gel (ether/hexane 3:1) yields 1.5 g of product in the form of a resinous oil.

P-34: Preparation of 2-methoxymethylene-5-[1-(3-trifluoromethylphenyl)ethylideneaminoxy]-pent-3-ynoic acid methyl ester (Compound 7.07.)

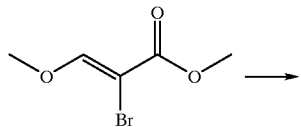

0.25 g of Pd(TPP)$_2$Cl$_2$ and also 0.1 g of copper(I) iodide are added, under an argon atmosphere, to a solution of 10.0 g of 1-(3-trifluoromethylphenyl)ethanone O-prop-2-ynyl-oxime in 150 ml of triethylamine and the mixture is heated to 70° C. 8.9 g of 2-bromo-3-methoxyacrylic acid methyl ester in 30 ml of tetrahydrofuran are then added and the mixture is stirred at 70° C. for 14 h and then filtered. The filtrate is concentrated by evaporation and chromatographed on silica gel (hexane/diethyl ether 2:1) to yield 4.6 g of the product having a melting point of 57–58° C.

P-35: Preparation of 2-{4,5-dimethyl-2-[1-(3-trifluoromethylphenyl)ethylideneaminoxy-methyl]cyclohexa-1,4-dienyl}-3-methoxacrylic acid methyl ester (Compound 1.05.)

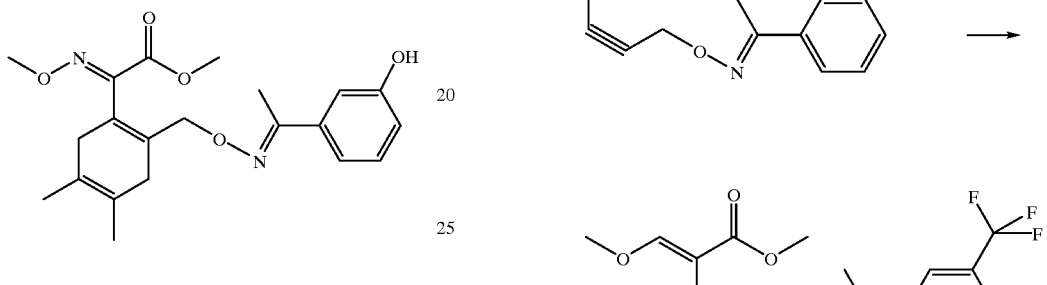

10 ml of 2,3-dimethylbutadiene are added to 2.00 g of 2-methoxymethylene-5-[1-(3-trifluoromethylphenyl)ethylideneaminoxy]pent-3-ynoic acid methyl ester in 5 ml of toluene and heated for 64 h at 140° C. in an autoclave. The reaction mixture is concentrated in vacuo and 25 ml of methanol are added. The resulting syrup is extracted with methanol. The methanol phase is filtered and concentrated. Chromatography on silica gel (hexane/toluene/diisopropyl ether 3:1:1) yields 145 mg of product in the form of a resin.

TABLE 1

Compounds of formula

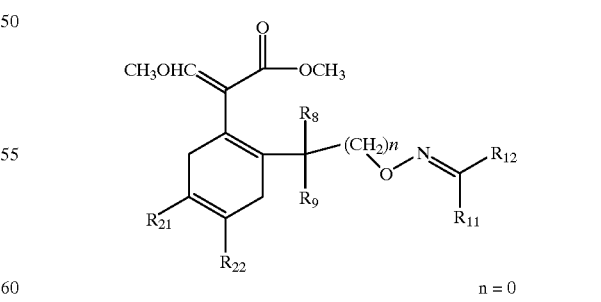

n = 0 wherein the substituents of compounds 1.01 to 1.189 have the meaning of the corresponding compounds of table 2.

Exmples:

| Ex. Nr. | R$_{21}$ | R$_{22}$ | [structure: R$_8$/R$_9$-C-O-N=C(R$_{11}$)(R$_{12}$)] | Phys. Data |
|---|---|---|---|---|
| 1.01. | CH$_3$ | CH$_3$ | 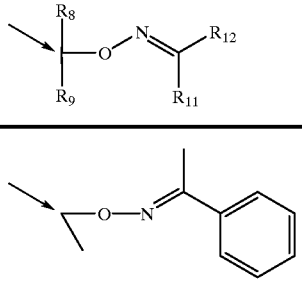 | |
| 1.02. | CH$_3$ | CH$_3$ | 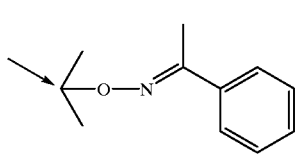 | |
| 1.05. | CH$_3$ | CH$_3$ | 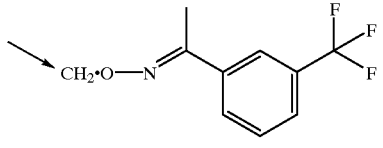 | resin |
| 1.12. | CH$_3$ | CH$_3$ | 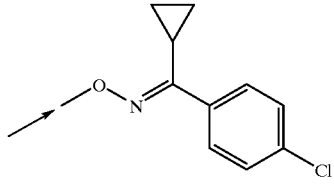 | |
| 1.20. | CH$_3$ | CH$_3$ | 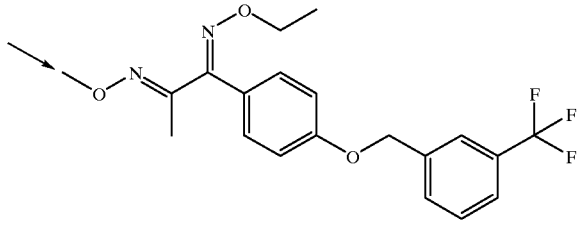 | |
| 1.21. | CH$_3$ | CH$_3$ | 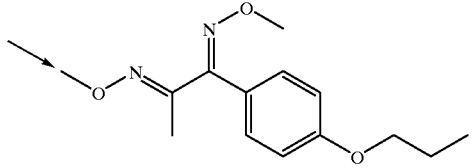 | |

-continued

| Ex. Nr. | R₂₁ | R₂₂ | (structure with R₈, R₉, R₁₁, R₁₂) | Phys. Data |
|---|---|---|---|---|
| 1.24. | CH₃ | CH₃ | | |
| 1.26. | CH₃ | CH₃ | | |
| 1.28. | CH₃ | CH₃ | | |
| 1.33. | CH₃ | CH₃ | | |
| 1.38. | CH₃ | CH₃ | | |
| 1.103. | CH₃ | CH₃ | | |

-continued

|  |  |  | ![structure](R8, R9 on C-O-N=C(R11)(R12)) |  |
|---|---|---|---|---|
| Ex. Nr. | R₂₁ | R₂₂ |  | Phys. Data |
| 1.105. | CH₃ | CH₃ | —CH(H)(H)—O—N=CH—C₆H₄—CH=N—O (para-substituted benzene with two CH=N-O groups) |  |
| 1.111. | CH₃ | CH₃ | —CH(H)(H)—O—N= (2,2,5,5-tetramethyltetrahydrofuran-3-ylidene) |  |
| 1.114. | CH₃ | CH₃ | —CH(H)(H)—O—N=C(phenyl)(2-amino-4-chlorophenyl) |  |
| 1.117. | CH₃ | CH₃ | —CH(H)(H)—O—N= (2-oxopiperidin-3-ylidene) |  |
| 1.118. | CH₃ | CH₃ | —CH(H)(H)—O—N=cyclohexylidene |  |
| 1.119. | CH₃ | CH₃ | —CH(H)(H)—O—N=CH—C(O)—(2,4-dimethoxyphenyl) |  |
| 1.120. | CH₃ | CH₃ | —CH(H)(H)—O—N=C(CH₃)—S—CH₂—CH=CH₂ |  |

-continued
| Ex. Nr. | R$_{21}$ | R$_{22}$ | 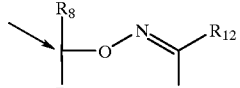 | Phys. Data |
|---|---|---|---|---|
| 1.121. | CH$_3$ | CH$_3$ | 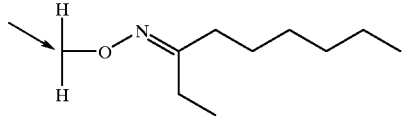 | |
| 1.122. | CH$_3$ | CH$_3$ | 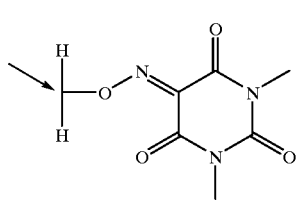 | |
| 1.123. | CH$_3$ | CH$_3$ | 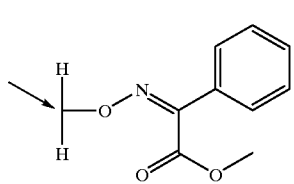 | |
| 1.134. | CH$_3$ | CH$_3$ | 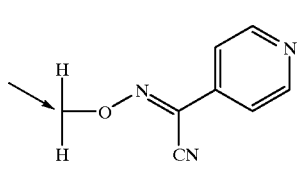 | |
| 1.135. | CH$_3$ | CH$_3$ | 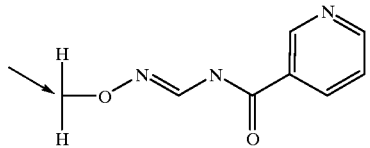 | |
| 1.136. | CH$_3$ | CH$_3$ | 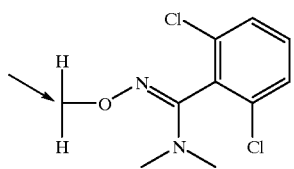 | |
| 1.137. | CH$_3$ | CH$_3$ | 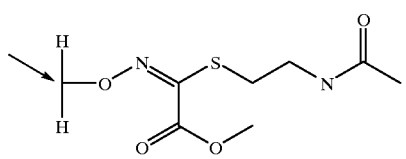 | |

-continued
| Ex. Nr. | R21 | R22 | ![R8,R9,O-N=CR11R12] | Phys. Data |
|---|---|---|---|---|
| 1.138. | CH3 | CH3 | 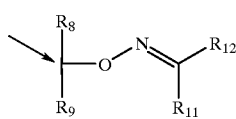 | |
| 1.140. | CH3 | CH3 | 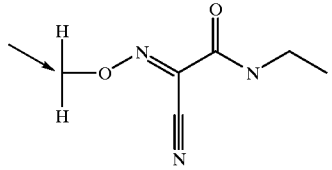 | |
| 1.148. | CH3 | CH3 | 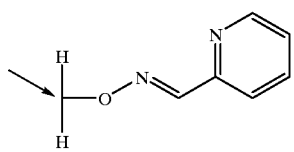 | |
| 1.149. | CH3 | CH3 | 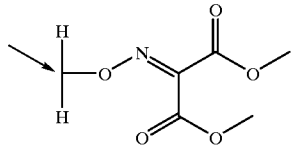 | |
| 1.150. | CH3 | CH3 | 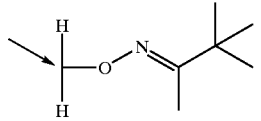 | |
| 1.153. | CH3 | CH3 | 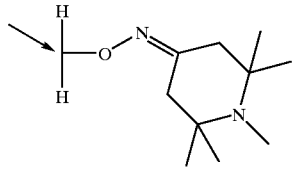 | |
| 1.154. | CH3 | CH3 | 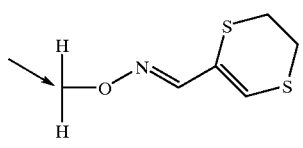 | |
| 1.160. | CH3 | CH3 | 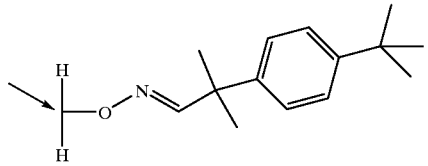 | |

-continued

| Ex. Nr. | R$_{21}$ | R$_{22}$ | ![structure](R$_8$, R$_9$, O-N=C(R$_{11}$)(R$_{12}$)) | Phys. Data |
|---|---|---|---|---|
| 1.161. | H | CH$_3$ | CH$_2$-O-N=C(CH$_3$)-[3-(CF$_3$)C$_6$H$_4$] | |
| 1.162. | H | H | CH$_2$-O-N=C(CH$_3$)-[3-(CF$_3$)C$_6$H$_4$] | |
| 1.163. | CH$_3$ | CH$_3$ | -O-N=C(CH$_3$)-C(=N-OCH$_3$)-[4-(CH$_2$CH$_2$-2,4-Cl$_2$C$_6$H$_3$)C$_6$H$_4$] | |
| 1.164. | CH$_3$ | CH$_3$ | -O-N=C(CH$_3$)-C(=O)-[4-(OCH$_2$C≡CH)C$_6$H$_4$] | |
| 1.165. | CH$_3$ | CH$_3$ | -O-N=C(CH$_3$)-C(=N-OC$_2$H$_5$)-[4-(OCH$_2$C≡CH)C$_6$H$_4$] | |
| 1.166. | CH$_3$ | CH$_3$ | -O-N=C(CH$_3$)-C(=O)-[4-(OC$_3$H$_7$)C$_6$H$_4$] | |

-continued
| Ex. Nr. | $R_{21}$ | $R_{22}$ | | Phys. Data |
|---|---|---|---|---|
Header structure: 
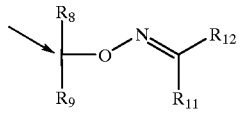
| 1.167. | $CH_3$ | $CH_3$ | 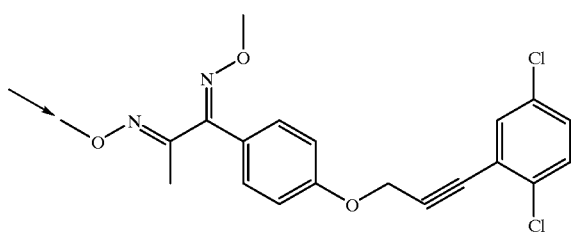 | |
| 1.168. | $CH_3$ | $CH_3$ | 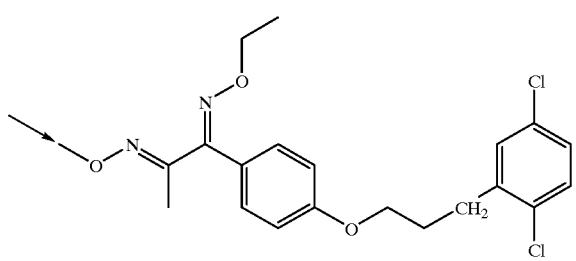 | |
| 1.169. | $CH_3$ | $CH_3$ | 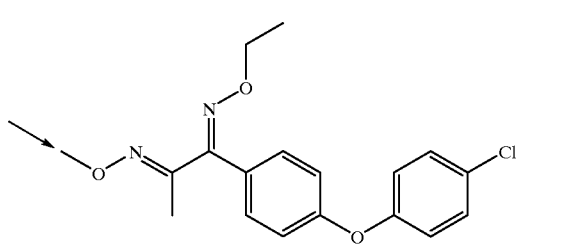 | |
| 1.170. | $CH_3$ | $CH_3$ | 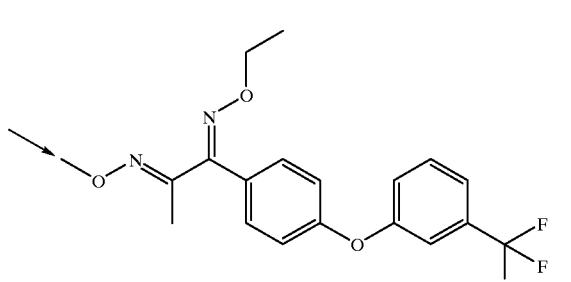 | |
| 1.171. | $CH_3$ | $CH_3$ | 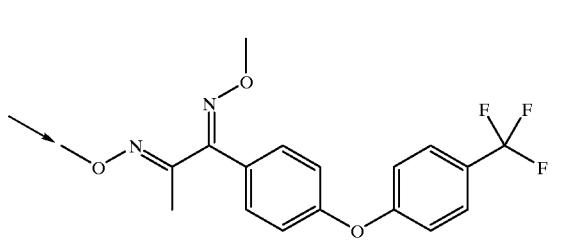 | |

-continued

| Ex. Nr. | $R_{21}$ | $R_{22}$ | structure | Phys. Data |
|---|---|---|---|---|
| 1.172. | $CH_3$ | $CH_3$ | | |
| 1.173. | $CH_3$ | $CH_3$ | | |
| 1.174. | $CH_3$ | $CH_3$ | | |
| 1.175. | $CH_3$ | $CH_3$ | | |
| 1.176. | $CH_3$ | $CH_3$ | | |
| 1.177. | $CH_3$ | $CH_3$ | | |

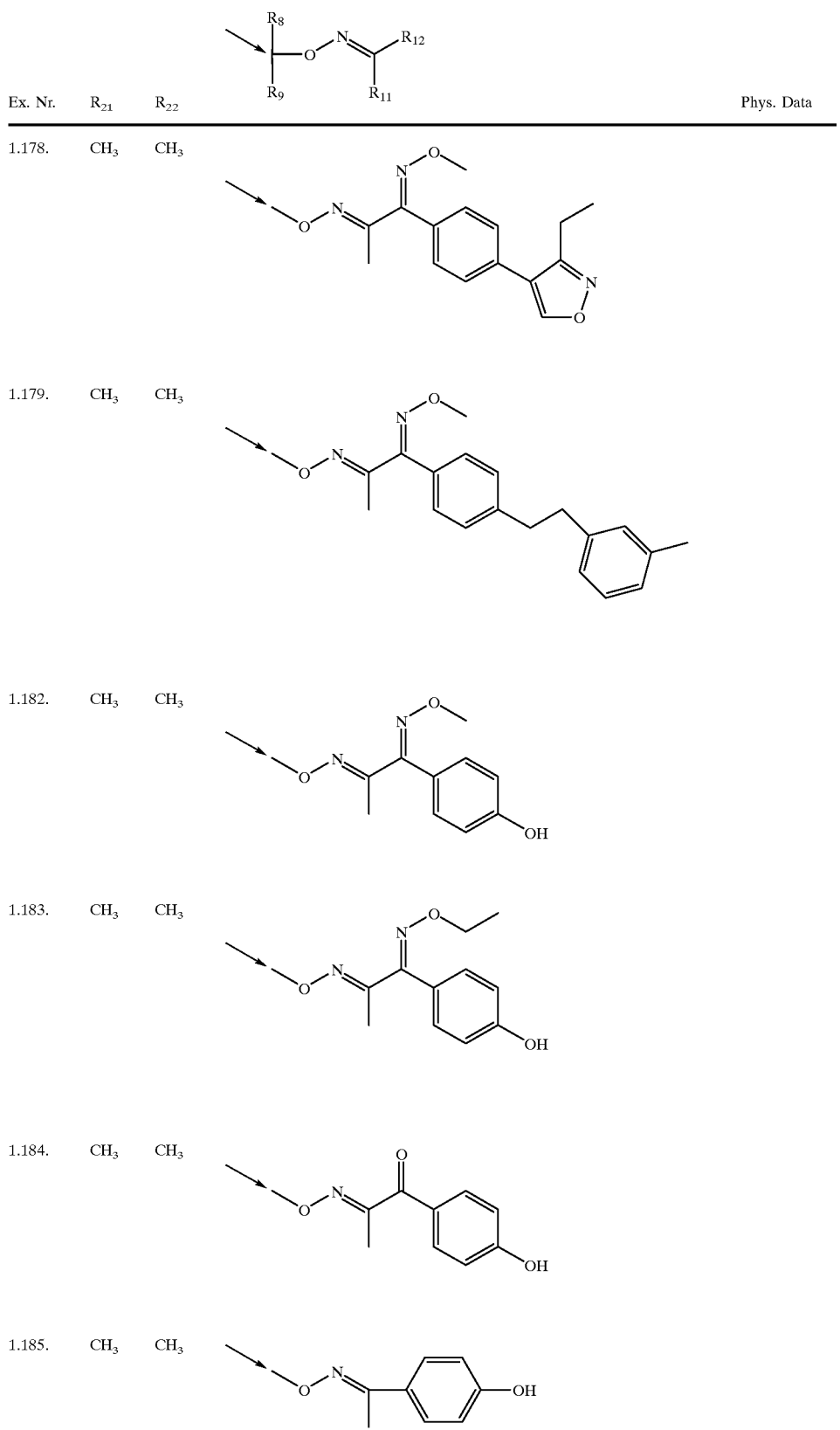

-continued

| Ex. Nr. | R21 | R22 | [structure: R8, R9, O-N=C(R11)(R12)] | Phys. Data |
|---|---|---|---|---|
| 1.187. | CH3 | CH3 | [structure with N-OEt oxime, phenyl-OH] | |
| 1.189. | CH3 | CH3 | [structure with O-N= and phenyl-OH] | |

TABLE 1a (as Table 1, but with n = 1)
Compounds of formula

[structure of compound with CH3OHC, OCH3, (CH2)n, R8, R9, O-N=C(R11)(R12), R21, R22]

n = 1

Examples

| Ex. Nr. | R21 | R22 | [structure: R8, R9, CH2-O-N=C(R11)(R12)] | Phys. Data |
|---|---|---|---|---|
| 1a.06. | CH3 | CH3 | [CH2-CH2-O-N=C(cyclopropyl)(benzodioxole)] | |
| 1a.12. | CH3 | CH3 | [O-N=C(cyclopropyl)(4-chlorophenyl)] | |

-continued
| Ex. Nr. | $R_{21}$ | $R_{22}$ | | Phys. Data |
|---|---|---|---|---|
| | | | ![structure header with $R_8$, $R_9$, CH$_2$-O-N=C($R_{11}$)($R_{12}$)] | |
| 1a.20. | CH$_3$ | CH$_3$ | [structure: propoxyimino with ethoxyimino, phenyl-O-CH$_2$-3-(trifluoromethyl)phenyl] | |
| 1a.40. | CH$_3$ | CH$_3$ | [structure: propoxyimino with ethoxyimino, 4-bromophenyl] | |
| 1a.98. | CH$_3$ | OCH$_3$ | [structure: propoxyimino with ketone, 4-allyloxyphenyl] | |
TABLE 1b
(as Table 1, but with n = 2)
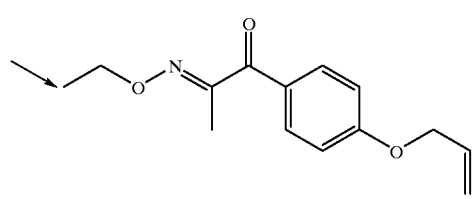
$n = 2$
Examples

| Ex. Nr. | R21 | R22 | | Phys. Data |
|---|---|---|---|---|
| 1b.06. | CH3 | CH3 | 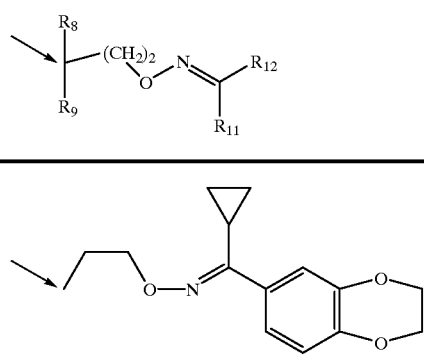 | |
| 1b.12. | CH3 | CH3 | 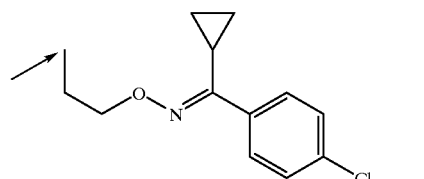 | |
| 1b.20. | CH3 | CH3 | 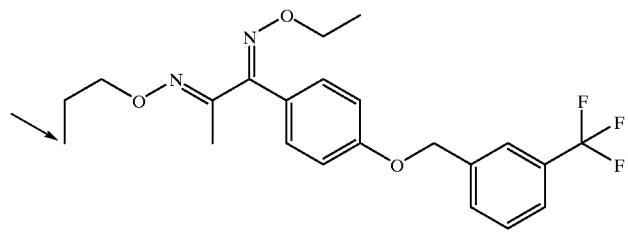 | |
| 1b.40. | CH3 | CH3 | 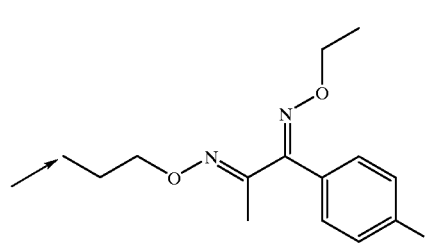 | |
| 1b.98. | CH3 | OCH3 | 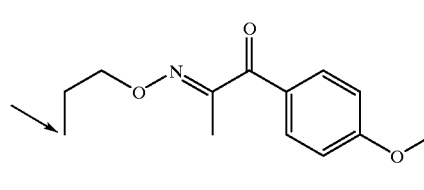 | |

TABLE 2
(n = 0)
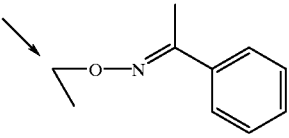
| Ex. Nr. | R₂₁ | R₂₂ | | Phys. Data |
|---|---|---|---|---|
| 2.01. | CH₃ | CH₃ | 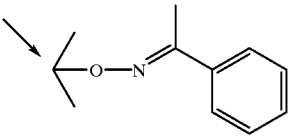 | |
| 2.02. | CH₃ | CH₃ | 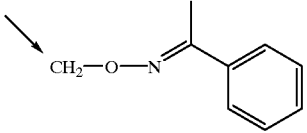 | |
| 2.03. | CH₃ | CH₃ | 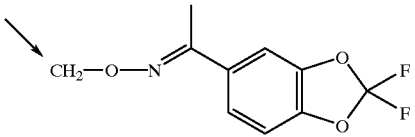 | |
| 2.04. | CH₃ | CH₃ | 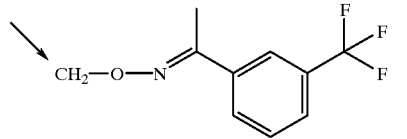 | |
| 2.05. | CH₃ | CH₃ | 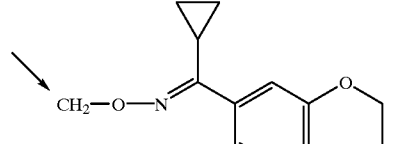 | resin |
| 2.06. | CH₃ | CH₃ | | |

TABLE 2-continued
| | | | |
|---|---|---|---|
| 2.07. | CH₃ | CH₃ | 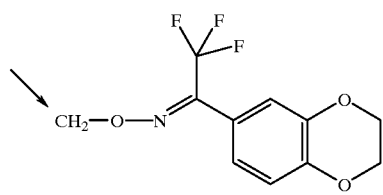 |
| 2.08. | CH₃ | CH₃ | 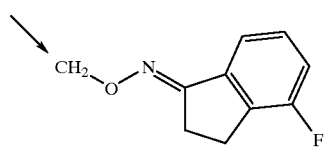 |
| 2.09. | CH₃ | CH₃ | 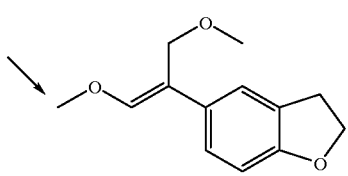 |
| 2.10. | CH₃ | CH₃ | 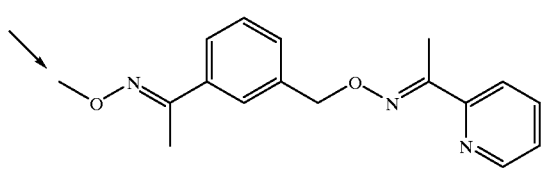 |
| 2.11. | CH₃ | CH₃ | 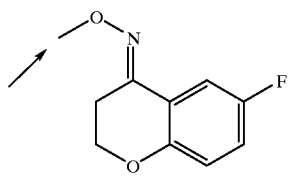 |
| 2.12. | CH₃ | CH₃ | 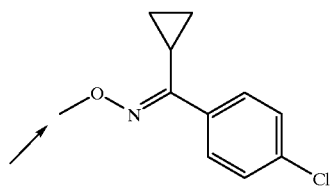 |
| 2.13. | CH₃ | CH₃ | 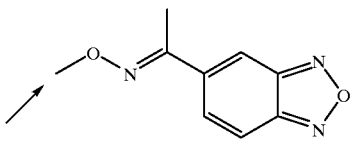 |
| 2.14. | CH₃ | CH₃ | 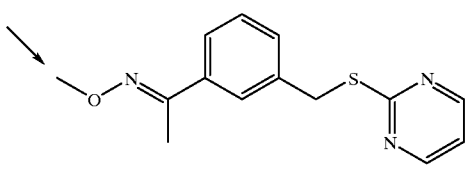 |

US 6,288,071 B1
TABLE 2-continued
| 2.15. | CH₃ | CH₃ | 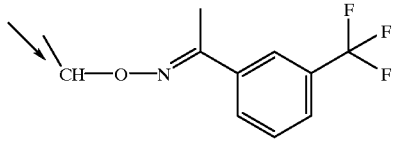 | oil |
| 2.16. | CH₃ | CH₃ | 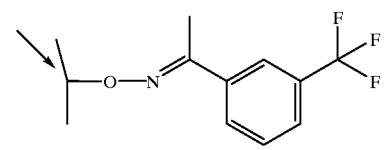 | oil |
| 2.17. | CH₃ | CH₃ | 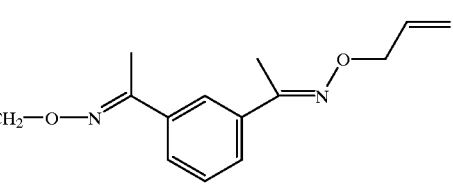 | |
| 2.18. | CH₃ | CH₃ | 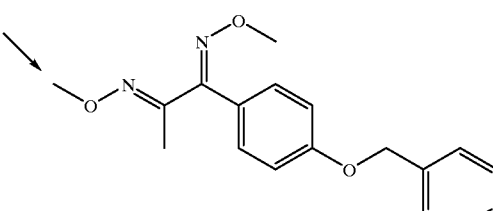 | resin |
| 2.19. | CH₃ | CH₃ | 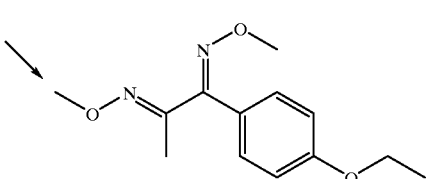 | |
| 2.20. | CH₃ | CH₃ | 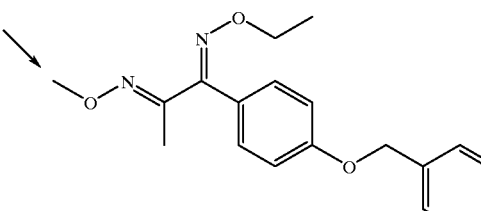 | |
| 2.21. | CH₃ | CH₃ | 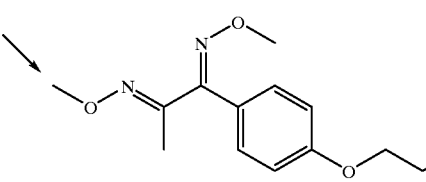 | |
| 2.22. | CH₃ | CH₃ | 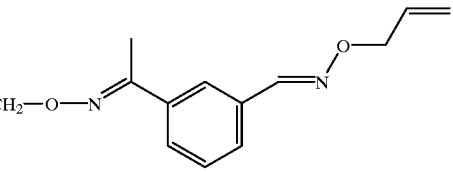 | |

TABLE 2-continued
| | | | | |
|---|---|---|---|---|
| 2.23. | CH₃ | CH₃ | 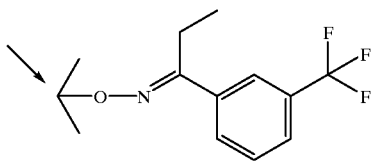 | |
| 2.24. | CH₃ | CH₃ | 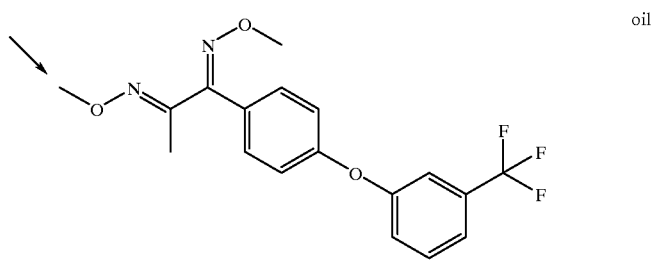 | oil |
| 2.25. | CH₃ | CH₃ | 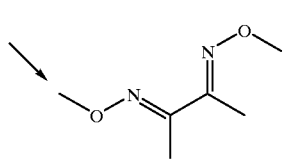 | |
| 2.26. | CH₃ | CH₃ | 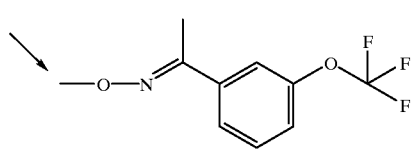 | |
| 2.27. | CH₃ | CH₃ | 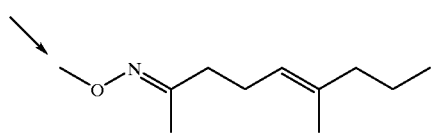 | |
| 2.28. | CH₃ | CH₃ | 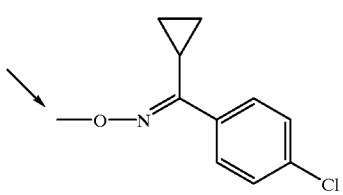 | |
| 2.29. | CH₃ | CH₃ | 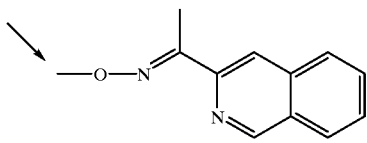 | |
| 2.30. | CH₃ | CH₃ | 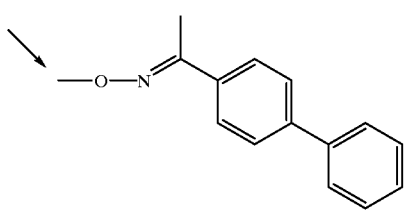 | |

TABLE 2-continued
| | | | |
|---|---|---|---|
| 2.31. | CH₃ | CH₃ | 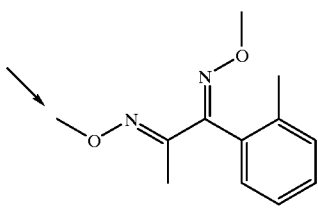 |
| 2.32. | CH₃ | CH₃ | 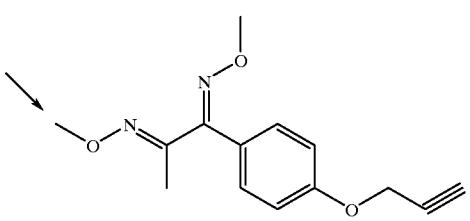 |
| 2.33. | CH₃ | CH₃ | 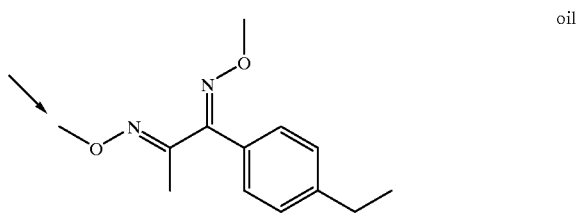 oil |
| 2.34. | CH₃ | CH₃ | 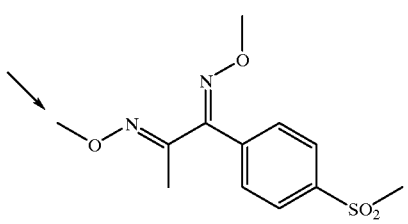 |
| 2.35. | CH₃ | CH₃ | 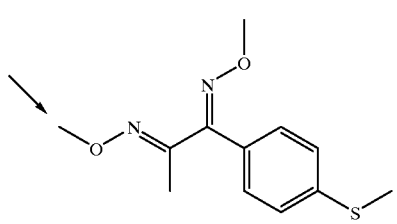 |
| 2.36. | CH₃ | CH₃ | 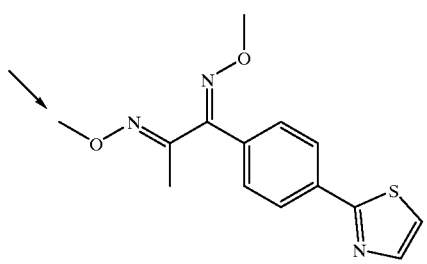 |

TABLE 2-continued
| | | | | |
|---|---|---|---|---|
| 2.37. | CH₃ | CH₃ | 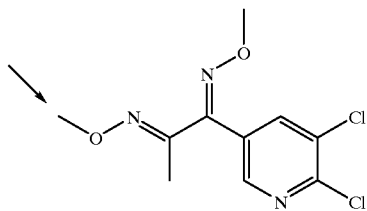 | |
| 2.38. | CH₃ | CH₃ | 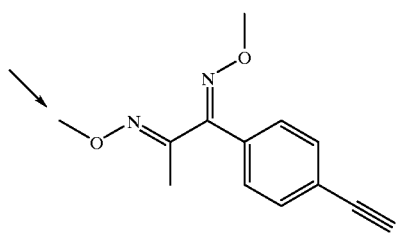 | resin |
| 2.39. | CH₃ | CH₃ | 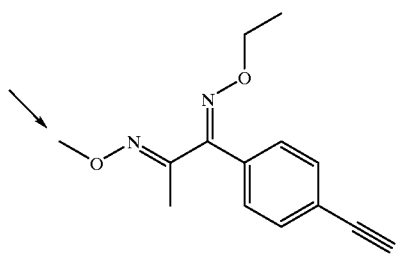 | |
| 2.40. | CH₃ | CH₃ | 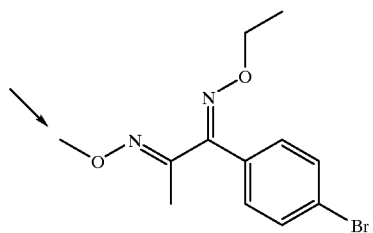 | |
| 2.41. | CH₃ | CH₃ | 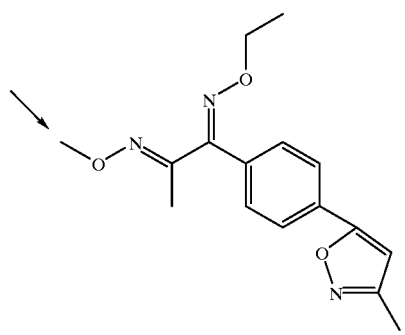 | |

TABLE 2-continued
| 2.42. | CH₃ | CH₃ | 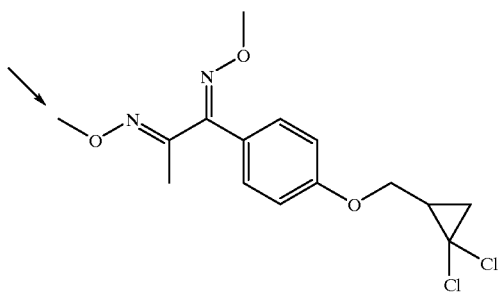 |
| 2.43. | CH₃ | CH₃ | 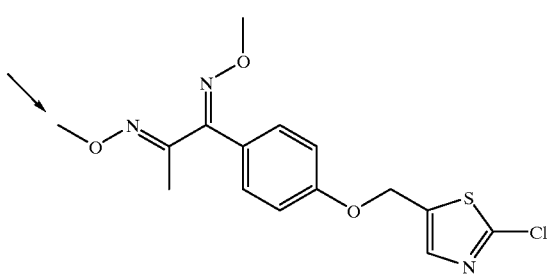 |
| 2.44. | CH₃ | CH₃ | 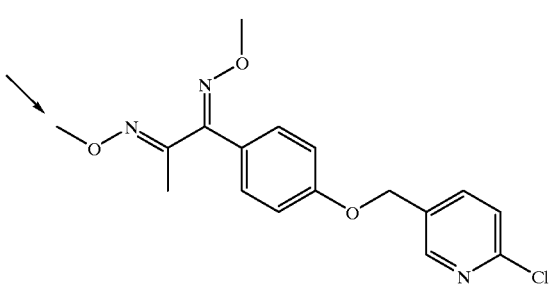 |
| 2.45. | CH₃ | CH₃ | 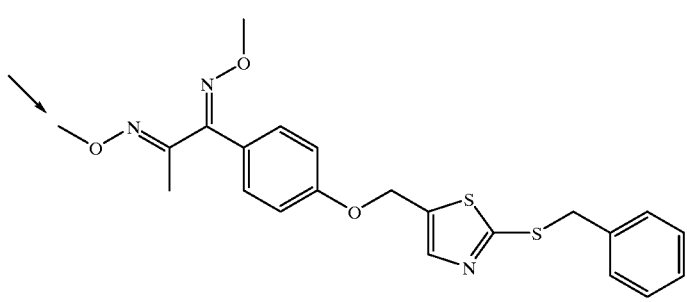 |
| 2.46. | CH₃ | CH₃ | 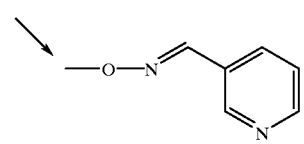 |
| 2.47. | CH₃ | CH₃ | 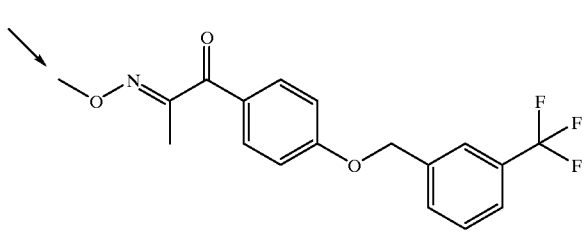 |

TABLE 2-continued
| | | | |
|---|---|---|---|
| 2.48. | CH₃ | CH₃ | 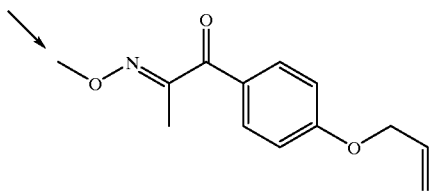 |
| 2.49. | CH₃ | CH₃ | 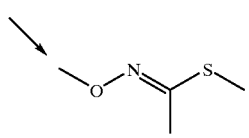 |
| 2.50. | CH₃ | CH₃ | 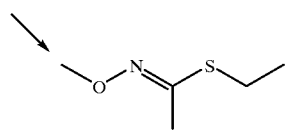 |
| 2.51. | CH₃ | H | 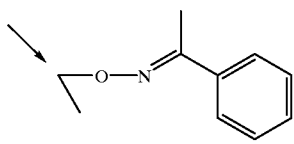 |
| 2.52. | CH₃ | H | 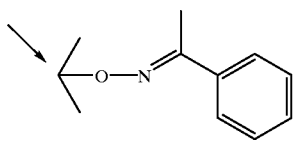 |
| 2.53. | CH₃ | H | 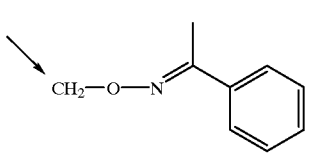 |
| 2.54. | CH₃ | H | 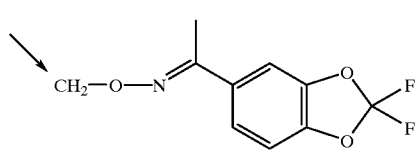 |
| 2.55. | CH₃ | H | 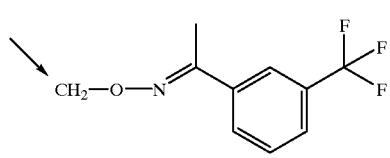 |
| 2.56. | H | CH₃ | 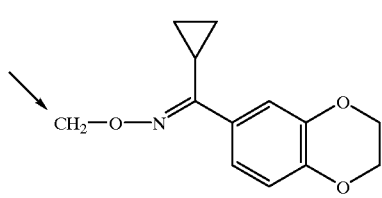 |

TABLE 2-continued
| | | | |
|---|---|---|---|
| 2.57. | H | CH₃ | 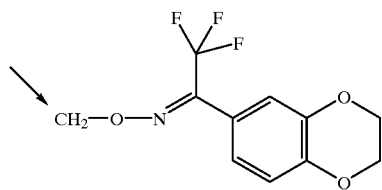 |
| 2.58. | H | CH₃ | 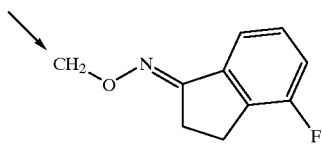 |
| 2.59. | H | CH₃ | 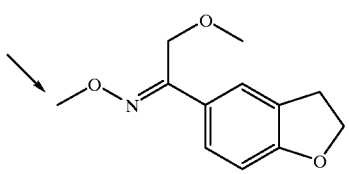 |
| 2.60. | H | CH₃ | 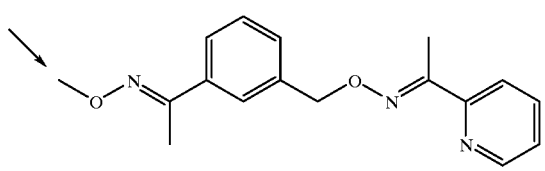 |
| 2.61. | H | H | 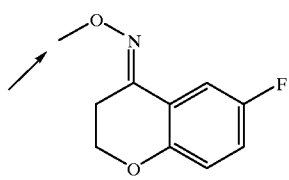 |
| 2.62. | H | H | 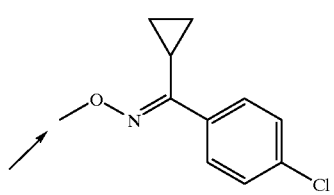 |
| 2.63. | H | H | 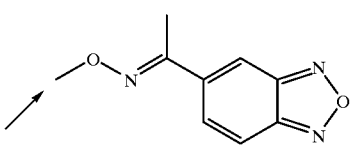 |
| 2.64. | H | H | 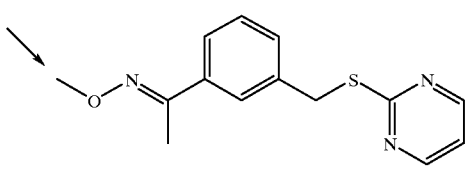 |

TABLE 2-continued
| | | | |
|---|---|---|---|
| 2.65. | H | H | |
| 2.66. | H | H | |
| 2.67. | H | H | |
| 2.68. | H | H | |
| 2.69. | H | H | |
| 2.70. | H | H | |
| 2.71. | Cl | H | |
| 2.72. | Cl | H | |
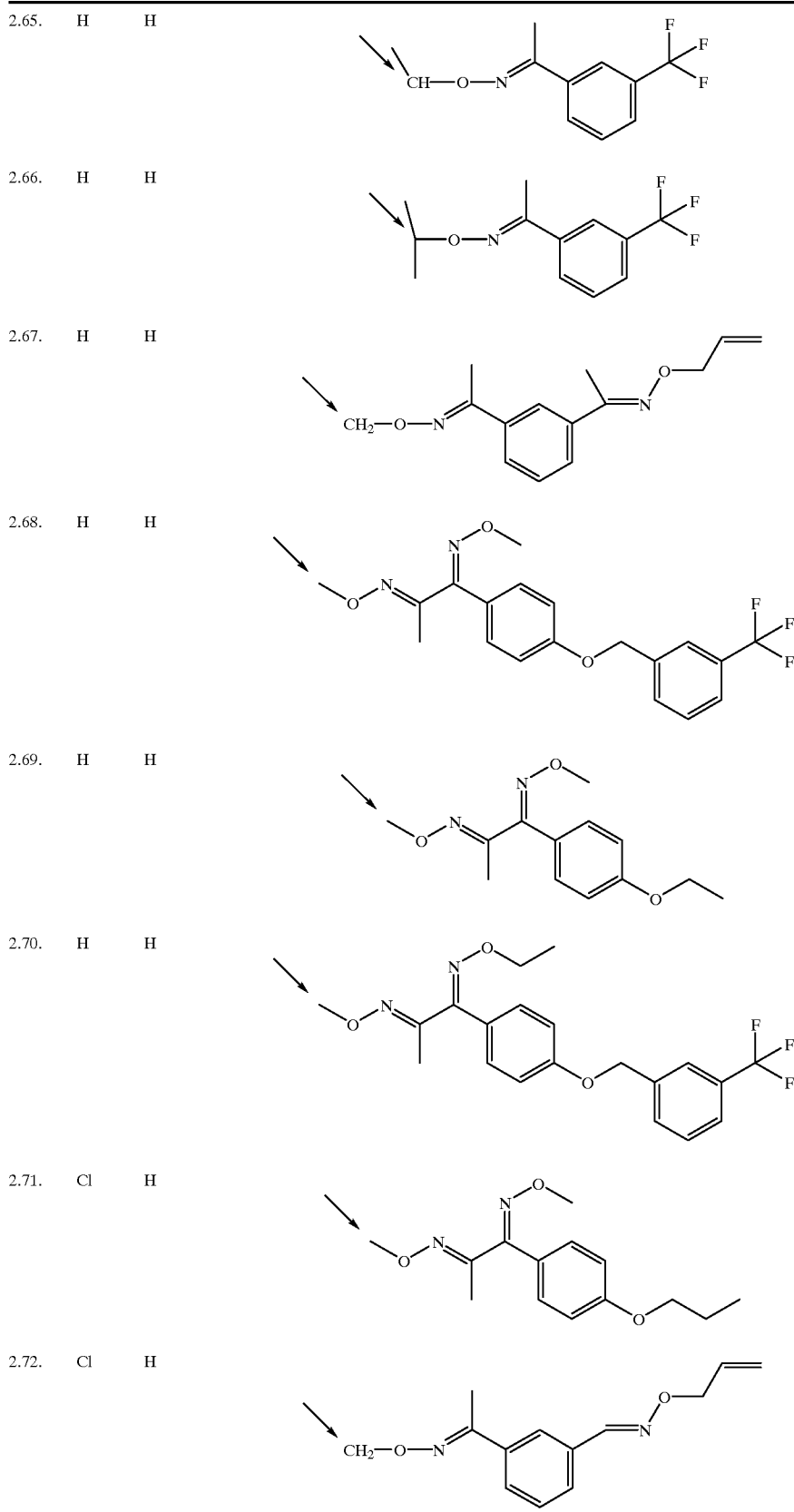

TABLE 2-continued
| 2.73. | Cl | H | 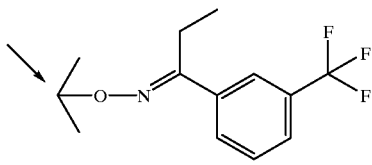 |
| 2.74. | Cl | H | 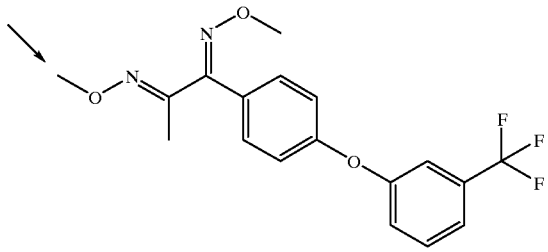 |
| 2.75. | Cl | H | 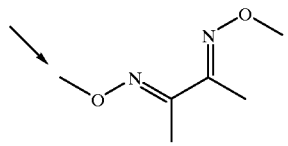 |
| 2.76. | Cl | H | 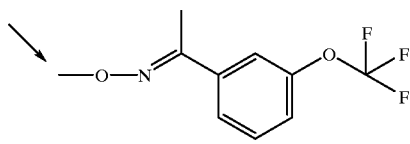 |
| 2.77. | Cl | H | 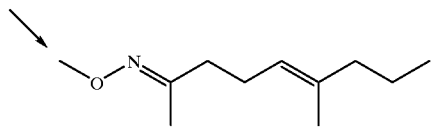 |
| 2.78. | Cl | H | 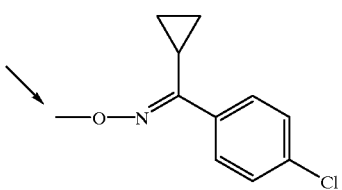 |
| 2.79. | Cl | H | 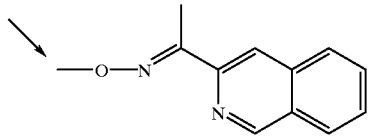 |
| 2.80. | Cl | H | 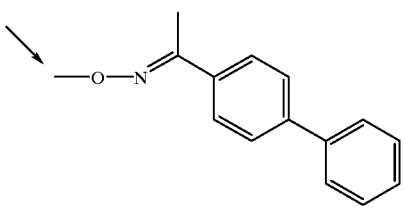 |

TABLE 2-continued
| 2.81. | H | Cl | 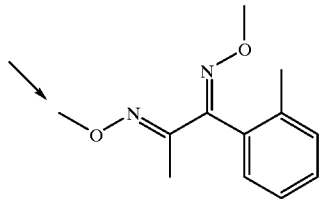 |
| 2.82. | H | Cl | 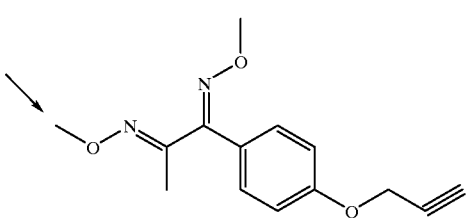 |
| 2.83. | H | Cl | 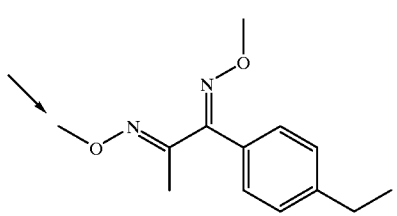 |
| 2.84. | H | Cl | 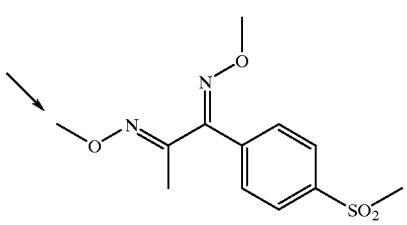 |
| 2.85. | H | Cl | 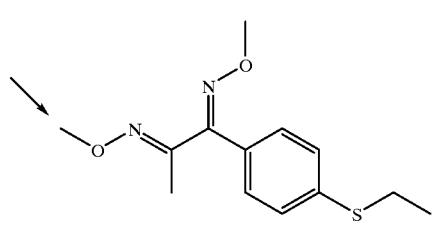 |
| 2.86. | H | Cl | 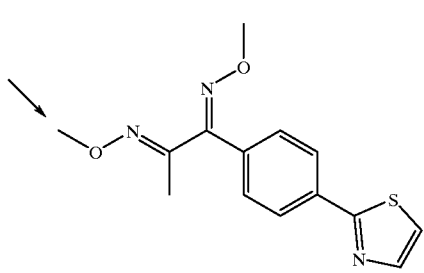 |

TABLE 2-continued
| 2.87. | H | Cl | 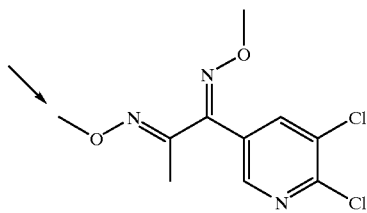 |
| 2.88. | H | Cl | 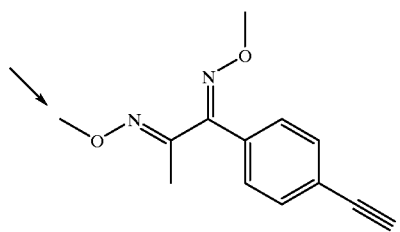 |
| 2.89. | H | Cl | 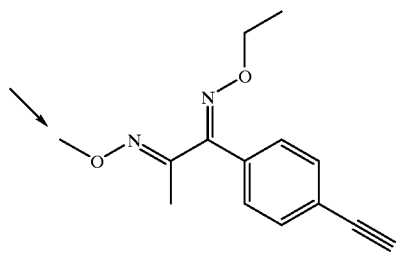 |
| 2.90. | H | Cl | 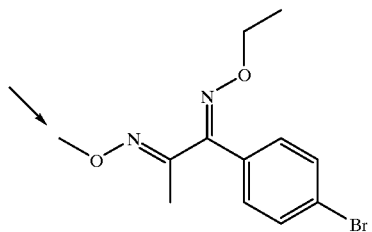 |
| 2.91. | OCH₃ | H | 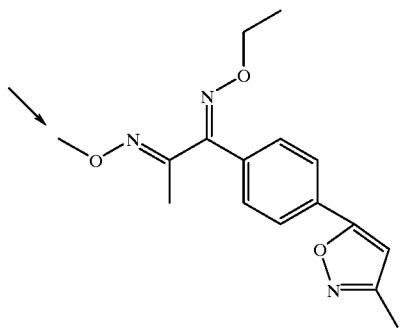 |

TABLE 2-continued
| 2.92. | OCH₃ | H | 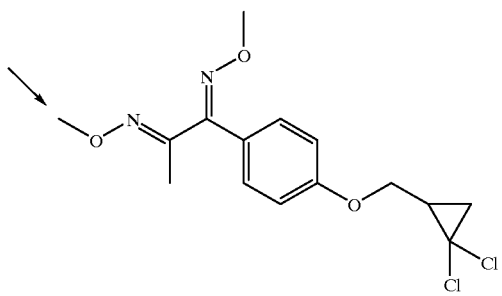 |
| 2.93. | OCH₃ | H | 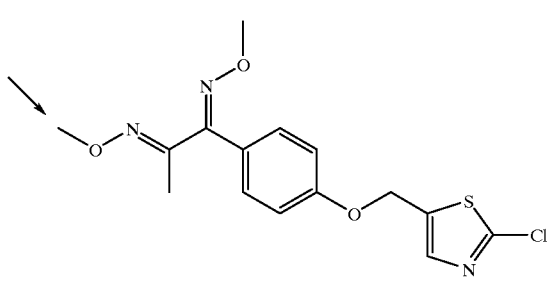 |
| 2.94. | OCH₃ | H | 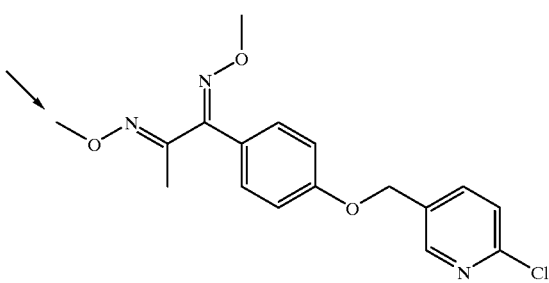 |
| 2.95. | OCH₃ | H | 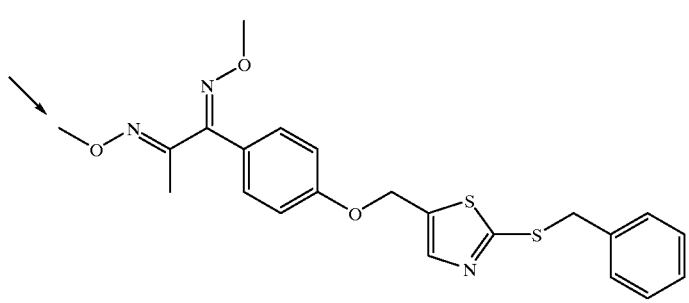 |
| 2.96. | H | OCH₃ | 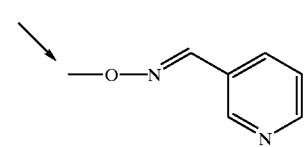 |
| 2.97. | H | OCH₃ | 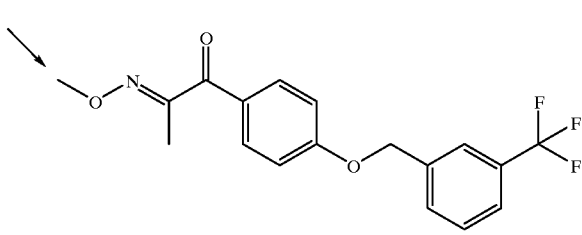 |

TABLE 2-continued
| | | | | |
|---|---|---|---|---|
| 2.98. | CH$_3$ | OCH$_3$ | 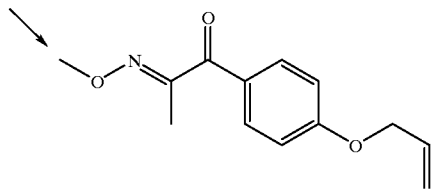 | |
| 2.99. | CH$_3$ | OCH$_3$ | 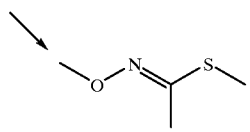 | |
| 2.100. | OCH$_3$ | CH$_3$ | 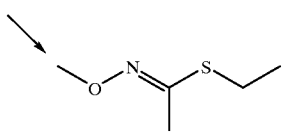 | |
| 2.101. | OCH$_3$ | H | 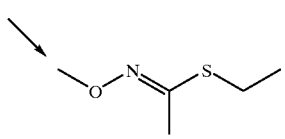 | |
| 2.102. | CH$_3$ | CH$_3$ | 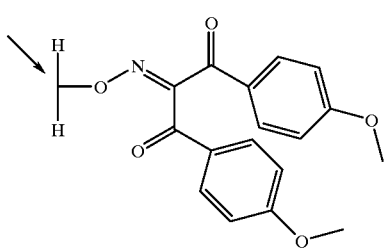 | |
| 2.103. | CH$_3$ | CH$_3$ | 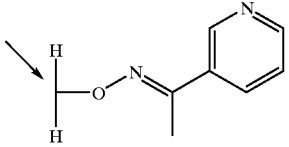 | |
| 2.104. | CH$_3$ | CH$_3$ | 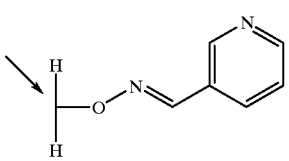 | resin |
| 2.105. | CH$_3$ | CH$_3$ | 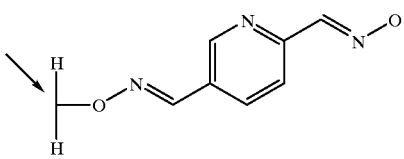 | |
| 2.106. | CH$_3$ | CH$_3$ | 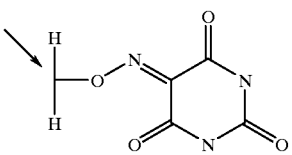 | |

TABLE 2-continued
| | | | |
|---|---|---|---|
| 2.107. | CH₃ | CH₃ | 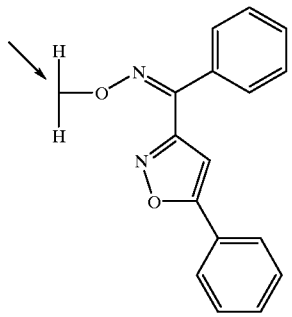 |
| 2.108. | CH₃ | CH₃ | 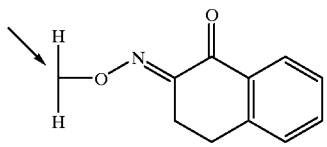 |
| 2.109. | CH₃ | CH₃ | 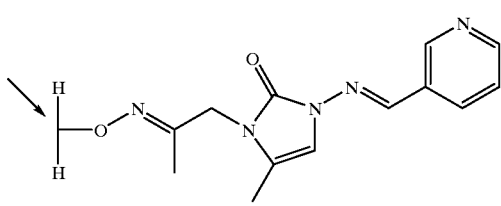 |
| 2.110. | CH₃ | CH₃ | 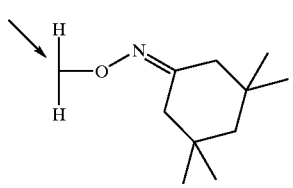 |
| 2.111. | CH₃ | CH₃ | 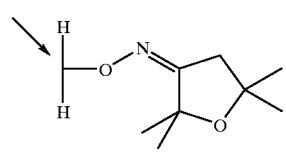 |
| 2.112. | CH₃ | CH₃ | 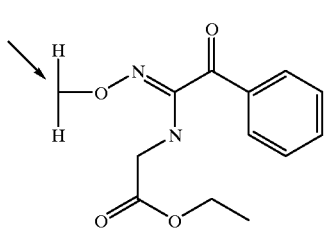 |
| 2.113. | CH₃ | CH₃ | 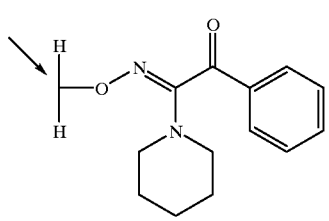 |

TABLE 2-continued
| 2.114. | CH₃ | CH₃ | 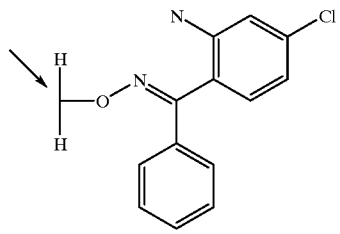 | resin |
| 2.115. | CH₃ | CH₃ | 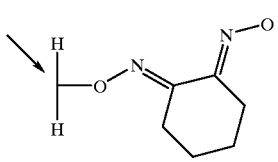 | |
| 2.116. | CH₃ | CH₃ | 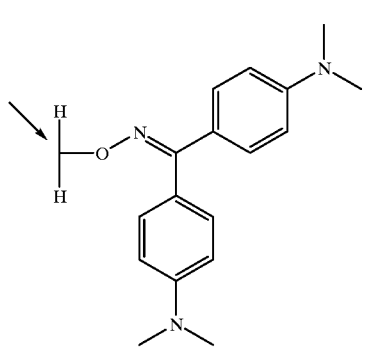 | |
| 2.117. | CH₃ | CH₃ | 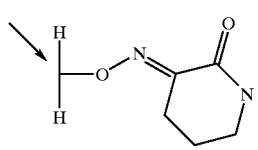 | resin |
| 2.118. | CH₃ | CH₃ | 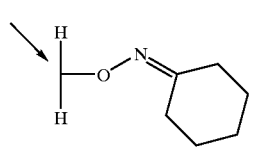 | |
| 2.119. | CH₃ | CH₃ | 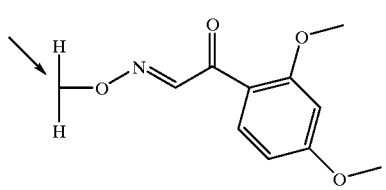 | resin |
| 2.120. | CH₃ | CH₃ | 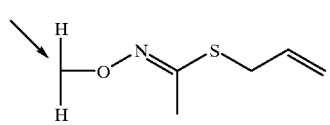 | |
| 2.121. | CH₃ | CH₃ | 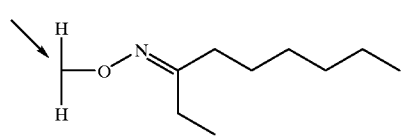 | |

TABLE 2-continued
| | | | | |
|---|---|---|---|---|
| 2.122. | CH₃ | CH₃ | 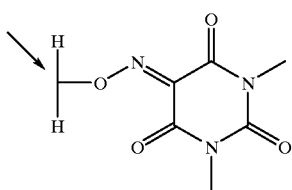 | |
| 2.123. | CH₃ | CH₃ | 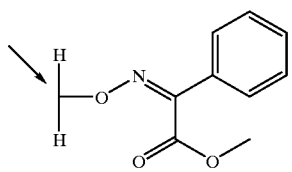 | Resin |
| 2.124. | CH₃ | CH₃ | 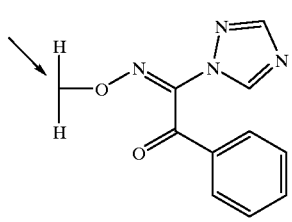 | |
| 2.125. | CH₃ | CH₃ | 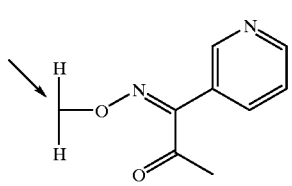 | |
| 2.126. | CH₃ | CH₃ | 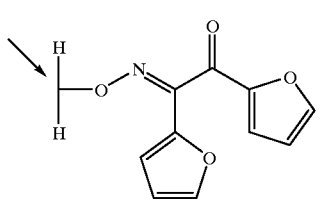 | |
| 2.127. | CH₃ | CH₃ | 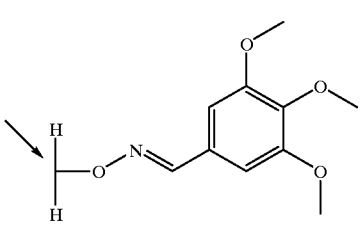 | |
| 2.128. | CH₃ | CH₃ | 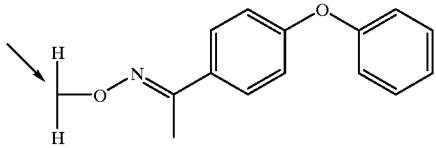 | |
| 2.129. | CH₃ | CH₃ | 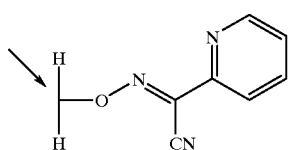 | |

TABLE 2-continued
| | | | | |
|---|---|---|---|---|
| 2.130. | CH₃ | CH₃ | 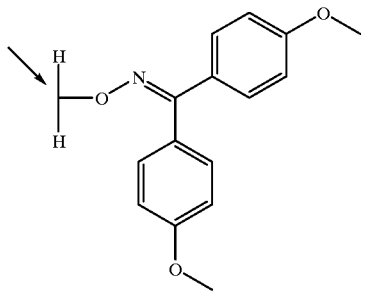 | |
| 2.131. | CH₃ | CH₃ | 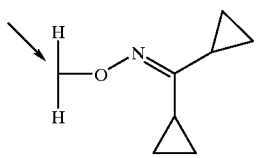 | |
| 2.132. | CH₃ | CH₃ | 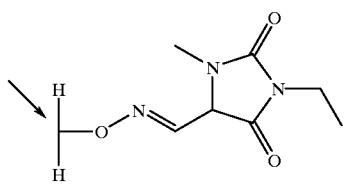 | |
| 2.133. | CH₃ | CH₃ | 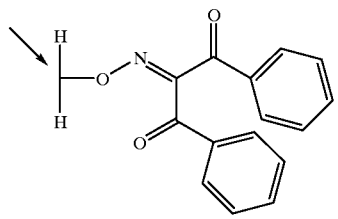 | |
| 2.134. | CH₃ | CH₃ | 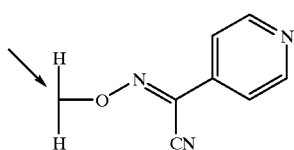 | |
| 2.135. | CH₃ | CH₃ | 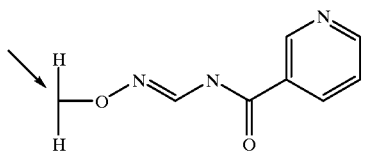 | |
| 2.136. | CH₃ | CH₃ | 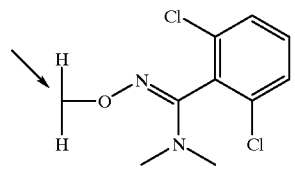 | |
| 2.137. | CH₃ | CH₃ | 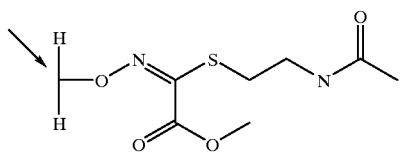 | oil |

TABLE 2-continued
| 2.138. | CH₃ | CH₃ | 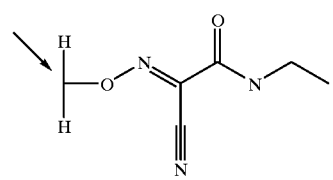 | 150–151° |
| 2.139. | CH₃ | CH₃ | 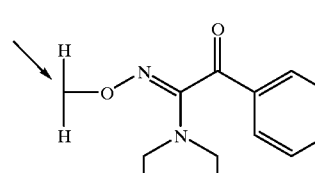 | |
| 2.140. | CH₃ | CH₃ | 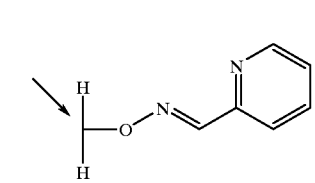 | oil |
| 2.141. | CH₃ | CH₃ | 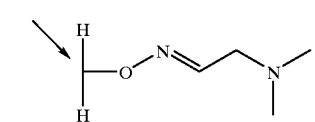 | |
| 2.142. | CH₃ | CH₃ | 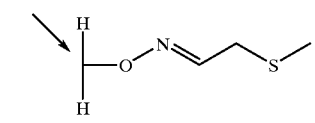 | |
| 2.143a. | CH₃ | CH₃ | 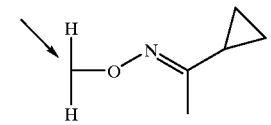 | |
| 2.143b. | CH₃ | CH₃ | 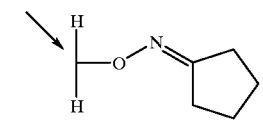 | |
| 2.144. | CH₃ | CH₃ | 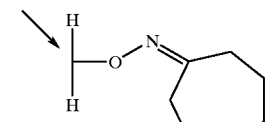 | |
| 2.145. | CH₃ | CH₃ | 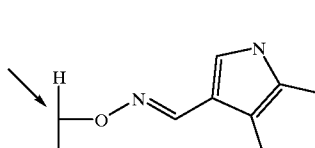 | |

TABLE 2-continued
| 2.146. | CH$_3$ | CH$_3$ | 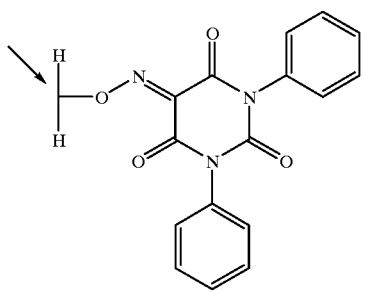 | |
| 2.147. | CH$_3$ | CH$_3$ | 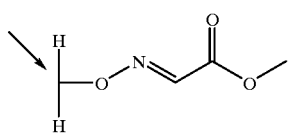 | |
| 2.148. | CH$_3$ | CH$_3$ | 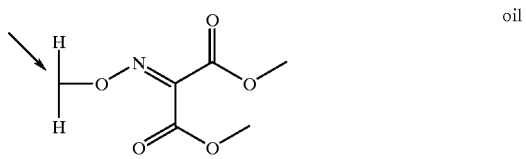 | oil |
| 2.149. | CH$_3$ | CH$_3$ | 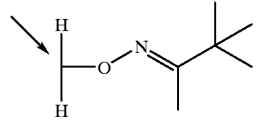 | |
| 2.150. | CH$_3$ | CH$_3$ | 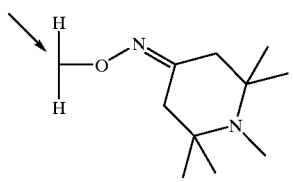 | |
| 2.151. | CH$_3$ | CH$_3$ | 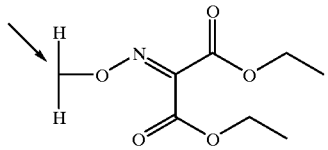 | |
| 2.152. | CH$_3$ | CH$_3$ | 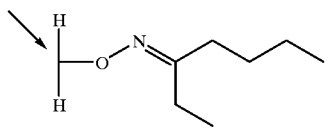 | |
| 2.153. | CH$_3$ | CH$_3$ | 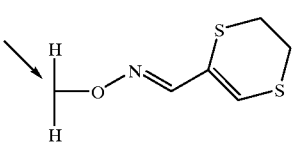 | |

TABLE 2-continued
| 2.154. | CH₃ | CH₃ | 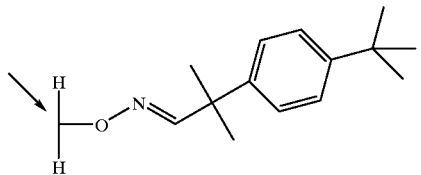 | |
| 2.155. | CH₃ | CH₃ | 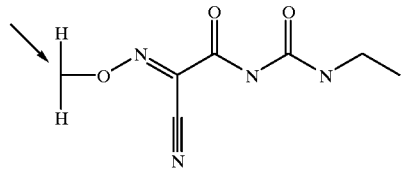 | |
| 2.156. | CH₃ | CH₃ | 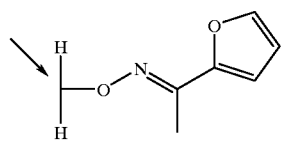 | |
| 2.157. | CH₃ | CH₃ | 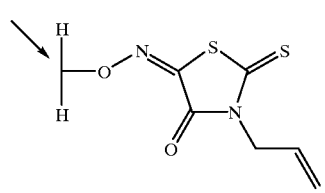 | |
| 2.158. | CH₃ | CH₃ | 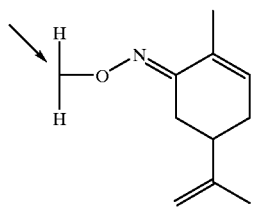 | |
| 2.159. | CH₃ | CH₃ | 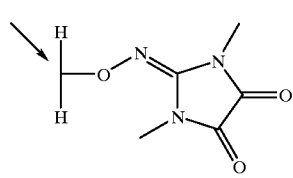 | |
| 2.160. | CH₃ | CH₃ | 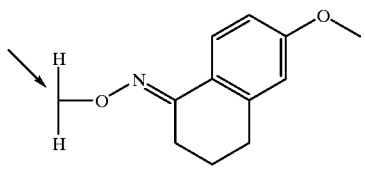 | |
| 2.161. | H | CH₃ | 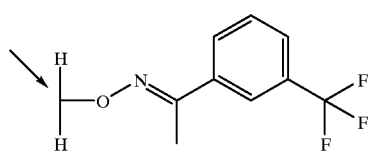 | oil |

TABLE 2-continued
| | | | |
|---|---|---|---|
| 2.162. | H | H | 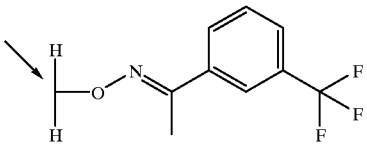 | oil |
| 2.163. | CH₃ | CH₃ | 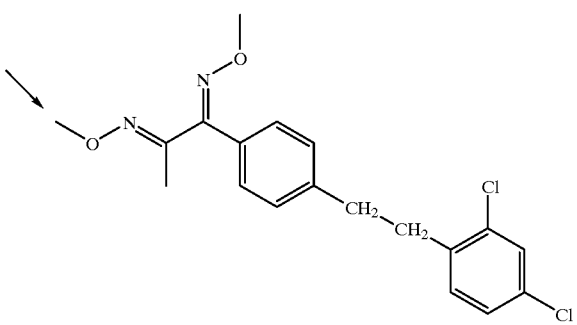 | oil |
| 2.164. | CH₃ | CH₃ | 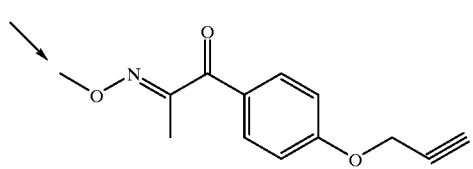 | oil |
| 2.165. | CH₃ | CH₃ | 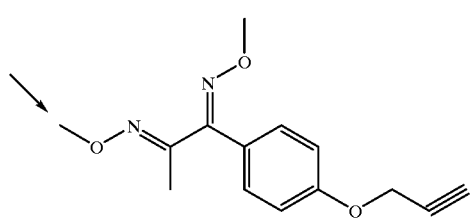 | oil |
| 2.166. | CH₃ | CH₃ | 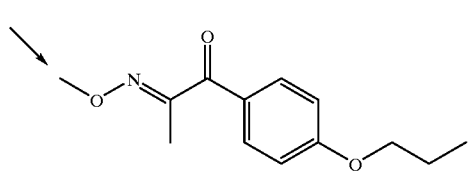 | oil |
| 2.167. | CH₃ | CH₃ | 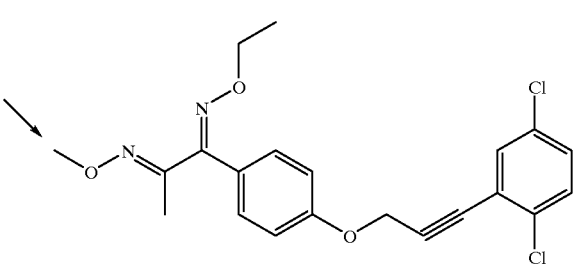 | oil |
| 2.168. | CH₃ | CH₃ | 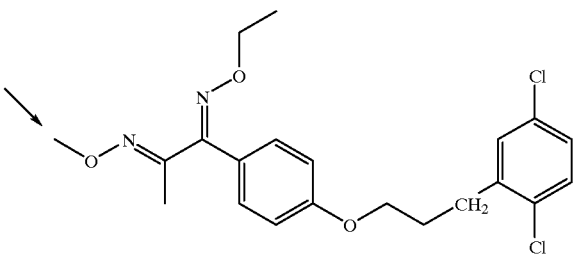 | oil |

TABLE 2-continued
| Ex. Nr. | R21 | R22 | | Phys. Data |
|---|---|---|---|---|
| 2.169. | CH3 | CH3 | 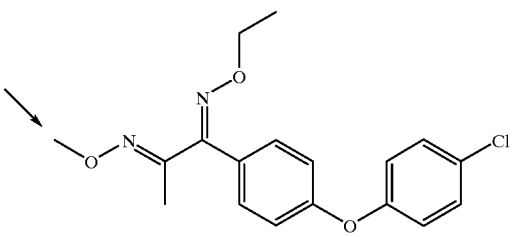 | oil |
| 2.170. | CH3 | CH3 | 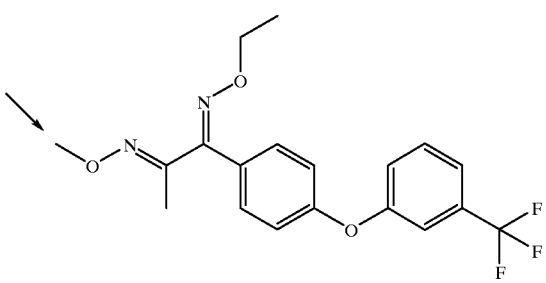 | oil |
| 2.171. | CH3 | CH3 | 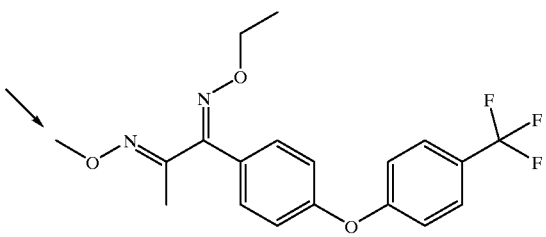 | oil |
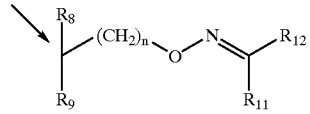
| Ex. Nr. | R21 | R22 | | Phys. Data |
|---|---|---|---|---|
| 2.172. | CH3 | CH3 | 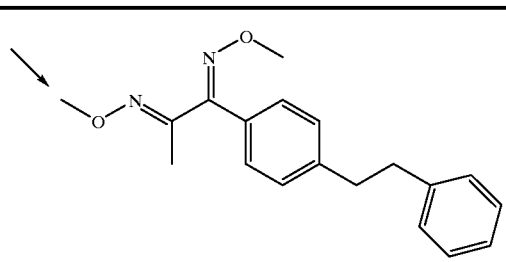 | 78–79° |
| 2.173. | CH3 | CH3 | 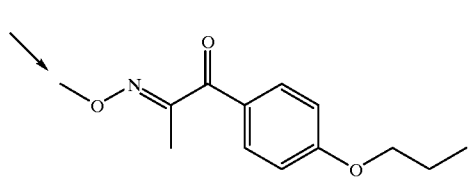 | 82–84° |
| 2.174. | CH3 | CH3 | 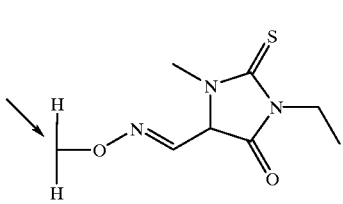 | oil |

TABLE 2-continued

| 2.175. | CH₃ | CH₃ | | oil |
| 2.176. | CH₃ | CH₃ | | 79–81° |
| 2.177. | CH₃ | CH₃ | | 110–113° |
| 2.178. | CH₃ | CH₃ | | resin |
| 2.179. | CH₃ | CH₃ | | 82–84° |
| 2.180. | CH₃ | CH₃ | | 121–123° |

TABLE 2-continued
| | | | | |
|---|---|---|---|---|
| 2.181. | CH₃ | CH₃ | 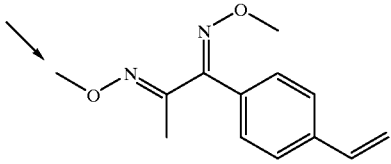 | 95–97° |
| 2.182. | CH₃ | CH₃ | 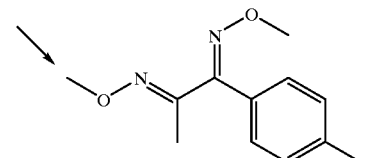 | resin |
| 2.183. | CH₃ | CH₃ | 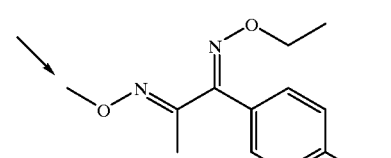 | resin |
| 2.184. | CH₃ | CH₃ | 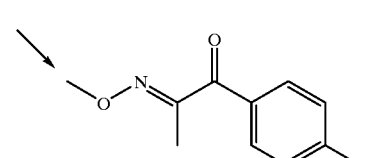 | resin |
| 2.185. | CH₃ | CH₃ | 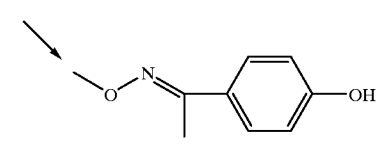 | resin |
| 2.186. | CH₃ | CH₃ | 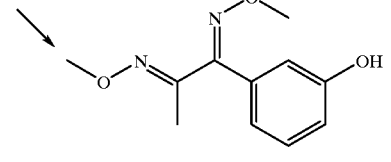 | resin |
| 2.187. | CH₃ | CH₃ | 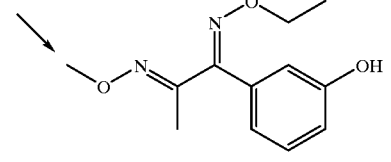 | resin |
| 2.188. | CH₃ | CH₃ | 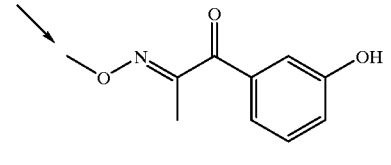 | resin |
| 2.189. | CH₃ | CH₃ | 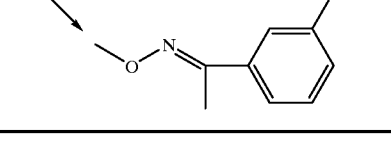 | resin |

TABLE 2a
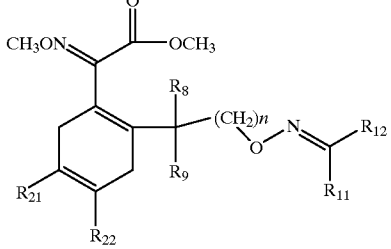
(as Table 2, but with n = 1)
n = 1
Examples
| Ex. Nr. | $R_{21}$ | $R_{22}$ | (structure) | Phys. Data |
|---|---|---|---|---|
| 2a.06. | $CH_3$ | $CH_3$ | 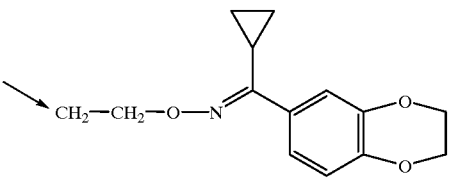 | |
| 2a.12. | $CH_3$ | $CH_3$ | 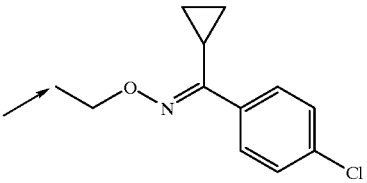 | |
| 2a.20. | $CH_3$ | $CH_3$ | 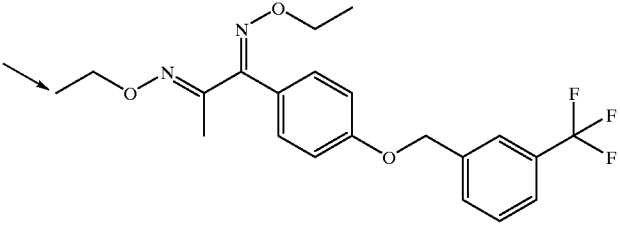 | |
| 2a.40. | $CH_3$ | $CH_3$ | 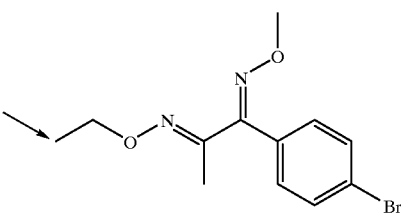 | |

-continued
| Ex. Nr. | $R_{21}$ | $R_{22}$ | 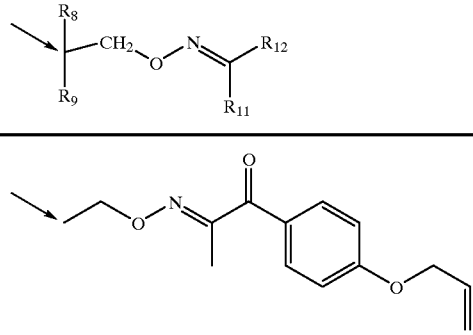 | Phys. Data |
|---|---|---|---|---|
| 2a.98. | $CH_3$ | $OCH_3$ | | |
TABLE 2b
(as Table 2, but with n = 2)
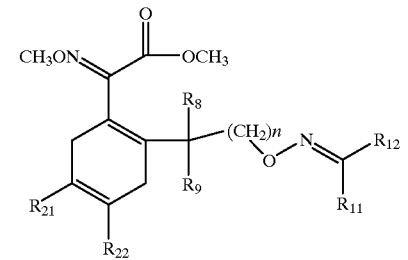
n = 2
Examles:
| Ex. Nr. | $R_{21}$ | $R_{22}$ | | Phys. Data |
|---|---|---|---|---|
| 2b.06. | $CH_3$ | $CH_3$ | | |
| 2b.12. | $CH_3$ | $CH_3$ | | |

-continued
| Ex. Nr. | $R_{21}$ | $R_{22}$ | | Phys. Data |
|---|---|---|---|---|
| 2b.20. | $CH_3$ | $CH_3$ | | |
| 2b.40. | $CH_3$ | $CH_3$ | | |
| 2b.98. | $CH_3$ | $OCH_3$ | | |
| 2b.169. | $CH_3$ | $CH_3$ | | oil |
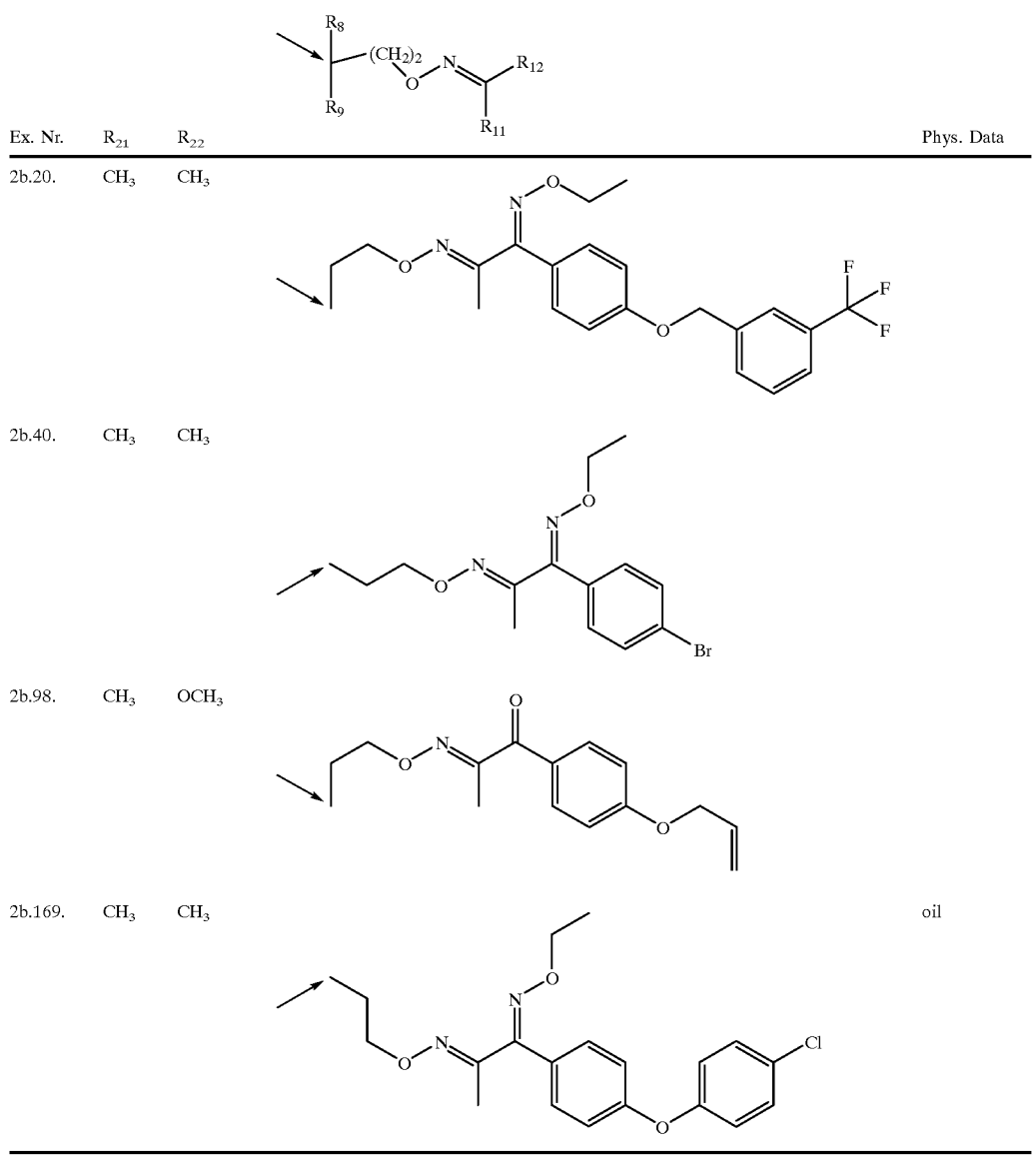
TABLE 3
(n = 0)
Compounds of formula
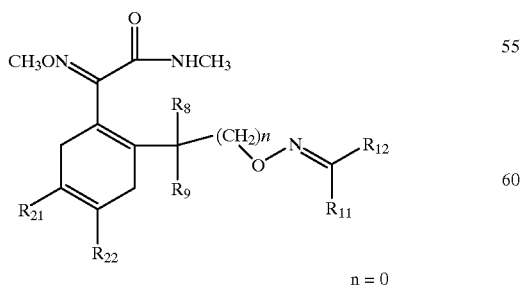
n = 0
wherein the substituents of compounds 3.1 to 3.189 have the meaning of the corresponding compounds of Table 2.

Examples

| Ex. Nr. | R$_{21}$ | R$_{22}$ | [structure with R$_8$, R$_9$, O-N=C(R$_{11}$)(R$_{12}$)] | Phys. Data |
|---|---|---|---|---|
| 3.4. | CH$_3$ | CH$_3$ | CH$_2$-O-N=C(CH$_3$)-(2,2-difluoro-benzo[1,3]dioxol-5-yl) | |
| 3.5. | CH$_3$ | CH$_3$ | CH$_2$-O-N=C(CH$_3$)-(3-trifluoromethylphenyl) | 111–114° |
| 3.8. | CH$_3$ | CH$_3$ | CH$_2$-O-N=(4-fluoro-indan-1-ylidene) | |
| 3.12. | CH$_3$ | CH$_3$ | O-N=C(cyclopropyl)(4-chlorophenyl) | |
| 3.15. | CH$_3$ | CH$_3$ | CH-O-N=C(CH$_3$)-(3-trifluoromethylphenyl) | |
| 3.16. | CH$_3$ | CH$_3$ | O-N=C(CH$_3$)-(3-trifluoromethylphenyl) | |
| 3.17. | CH$_3$ | CH$_3$ | CH$_2$-O-N=C(CH$_3$)-(3-(C(CH$_3$)=N-O-allyl)phenyl) | |
| 3.18. | CH$_3$ | CH$_3$ | O-N=C(CH$_3$)-C(=N-OCH$_3$)-(4-((3-trifluoromethylbenzyl)oxy)phenyl) | resin |

-continued

| Ex. Nr. | R₂₁ | R₂₂ | | Phys. Data |
|---|---|---|---|---|
| 3.20. | CH₃ | CH₃ | | |
| 3.23. | CH₃ | CH₃ | | |
| 3.30. | CH₃ | CH₃ | | |
| 3.31. | CH₃ | CH₃ | | |
| 3.37. | CH₃ | CH₃ | | |
| 3.38. | CH₃ | CH₃ | | 146–168° |

-continued
| Ex. Nr. | $R_{21}$ | $R_{22}$ | | Phys. Data |
|---|---|---|---|---|
| 3.39. | $CH_3$ | $CH_3$ | | |
| 3.40. | $CH_3$ | $CH_3$ | | |
| 3.42. | $CH_3$ | $CH_3$ | | |
| 3.46. | $CH_3$ | $CH_3$ | | |
| 3.47. | $CH_3$ | $CH_3$ | | |
| 3.48. | $CH_3$ | $CH_3$ | | |
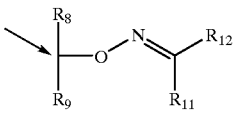

-continued
| Ex. Nr. | R$_{21}$ | R$_{22}$ | | Phys. Data |
|---|---|---|---|---|
| 3.57. | H | CH$_3$ | | |
| 3.58. | H | CH$_3$ | | |
| 3.62. | H | H | | |
| 3.65. | H | H | | |
| 3.66. | H | H | | |
| 3.70. | H | H | | |
| 3.73. | Cl | H | | |
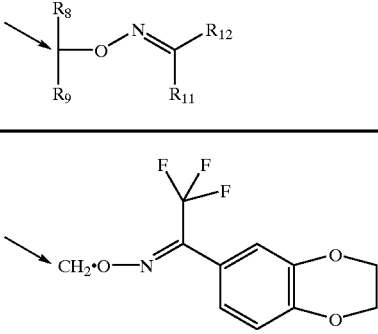

-continued
| Ex. Nr. | R21 | R22 | | Phys. Data |
|---|---|---|---|---|
| 3.74. | Cl | H | 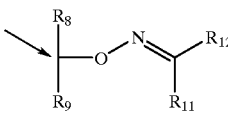 | |
| 3.92. | OCH3 | H | 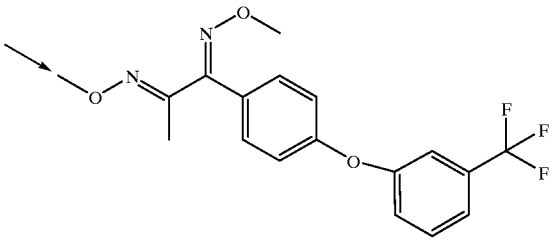 | |
| 3.93. | OCH3 | H | 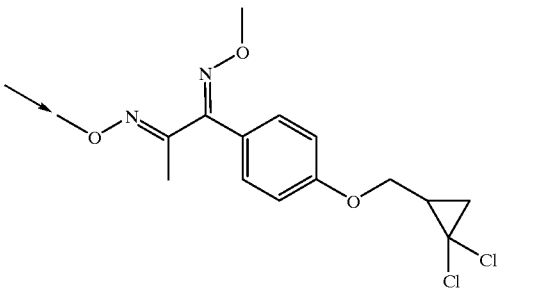 | |
| 3.94. | OCH3 | H | 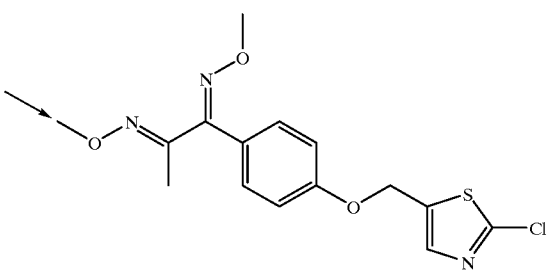 | |
| 3.95. | OCH3 | H | 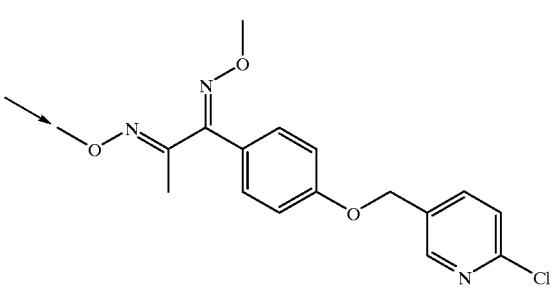 | |

-continued
| Ex. Nr. | R$_{21}$ | R$_{22}$ | | Phys. Data |
|---|---|---|---|---|
| 3.96. | H | OCH$_3$ | 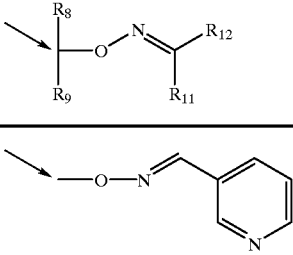 | |
| 3.97. | H | OCH$_3$ | 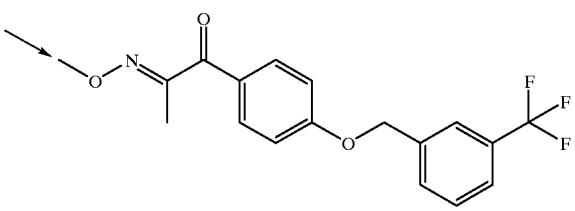 | |
| 3.98. | CH$_3$ | OCH$_3$ | 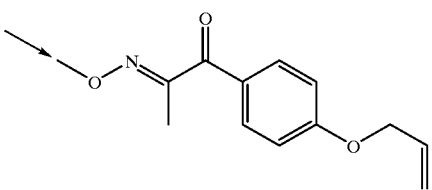 | |
| 3.99. | CH$_3$ | OCH$_3$ | 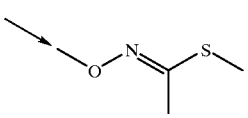 | |
| 3.100. | OCH$_3$ | CH$_3$ | 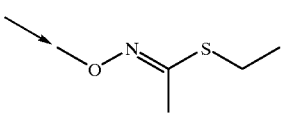 | |
| 3.101. | H | H | 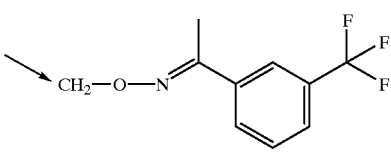 | oil |
| 3.111. | CH$_3$ | CH$_3$ | 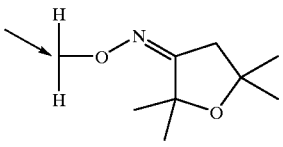 | |
| 3.112. | CH$_3$ | CH$_3$ | 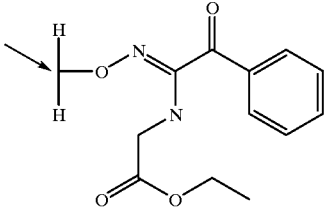 | |

-continued

|  | | | ![structure](R8, R9, O-N=C(R11)(R12)) | |
|---|---|---|---|---|
| Ex. Nr. | R₂₁ | R₂₂ | | Phys. Data |
| 3.125. | CH₃ | CH₃ | CH(H)(H)-O-N=C(3-pyridyl)(C(=O)CH₃) | |
| 3.131. | CH₃ | CH₃ | CH(H)(H)-O-N=C(cyclopropyl)(cyclopropyl) | |
| 3.132. | CH₃ | CH₃ | CH(H)(H)-O-N=C(CH₃)(1-methyl-3-ethyl-hydantoin-5-yl) | |
| 3.133. | CH₃ | CH₃ | CH(H)(H)-O-N=C(C(=O)Ph)(C(=O)Ph) | |
| 3.134. | CH₃ | CH₃ | CH(H)(H)-O-N=C(4-pyridyl)(CN) | |
| 3.136. | CH₃ | CH₃ | CH(H)(H)-O-N=C(2,6-dichlorophenyl)(N(CH₃)₂) | |
| 3.137. | CH₃ | CH₃ | CH(H)(H)-O-N=C(C(=O)OCH₃)(SCH₂CH₂NHC(=O)CH₃) | |
| 3.149. | CH₃ | CH₃ | CH(H)(H)-O-N=C(CH₃)(C(CH₃)₃) | |

-continued
| Ex. Nr. | R$_{21}$ | R$_{22}$ | | Phys. Data |
|---|---|---|---|---|
| 3.150. | CH$_3$ | CH$_3$ | 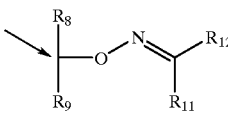 | |
| 3.161. | H | CH$_3$ | 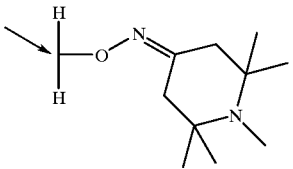 | resin |
| 3.163. | H | H | 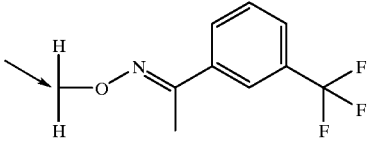 | |
| 3.179. | CH$_3$ | CH$_3$ | 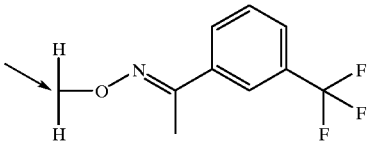 | resin |
| 3.180. | CH$_3$ | CH$_3$ | 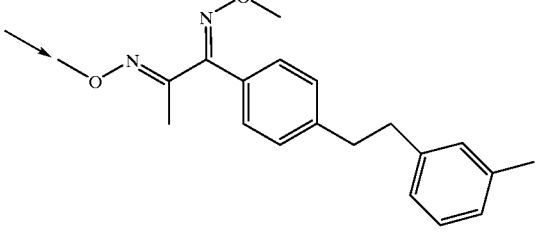 | |
| 3.181. | CH$_3$ | CH$_3$ | 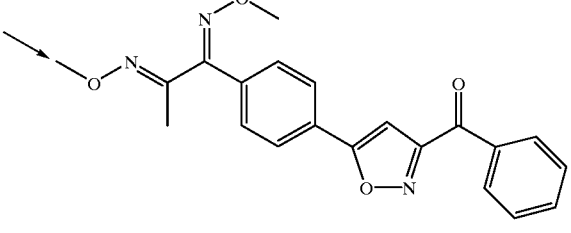 | 130–131° |
| 3.182. | CH$_3$ | CH$_3$ | 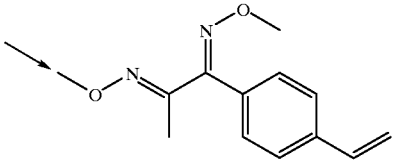 | |

-continued

| Ex. Nr. | $R_{21}$ | $R_{22}$ | ![structure with $R_8$, $R_9$, O-N=C($R_{11}$)($R_{12}$)] | Phys. Data |
|---|---|---|---|---|
| 3.183. | $CH_3$ | $CH_3$ | ethoxyimino-(4-hydroxyphenyl)methyl oxime structure | |
| 3.184. | $CH_3$ | $CH_3$ | keto-(4-hydroxyphenyl) oxime structure | |
| 3.185. | $CH_3$ | $CH_3$ | (4-hydroxyphenyl)ethylidene oxime structure | |
| 3.187. | $CH_3$ | $CH_3$ | ethoxyimino-(3-hydroxyphenyl)methyl oxime structure | |
| 3.189. | $CH_3$ | $CH_3$ | (3-hydroxyphenyl)ethylidene oxime structure | |

TABLE 3a (as Table 3, but with n = 1)

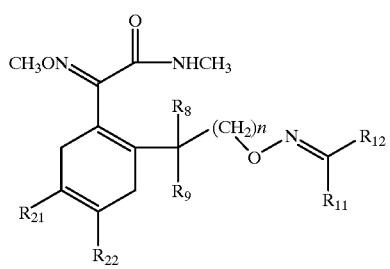

n = 1

Examples
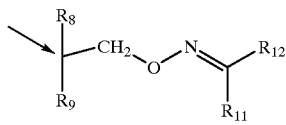
| Ex. Nr. | $R_{21}$ | $R_{22}$ | | Phys. Data |
|---|---|---|---|---|
| 3a.06. | $CH_3$ | $CH_3$ | 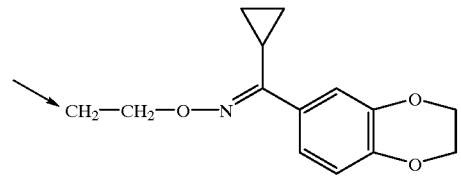 | |
| 3a.12. | $CH_3$ | $CH_3$ | 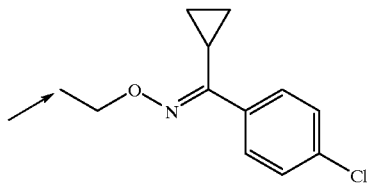 | |
| 3a.20. | $CH_3$ | $CH_3$ | 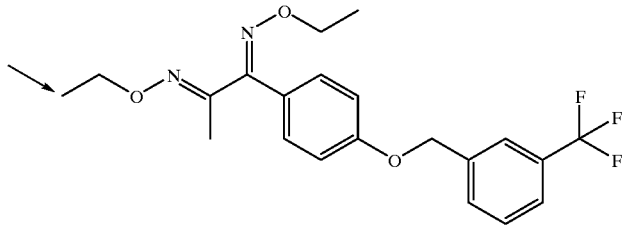 | |
| 3a.40. | $CH_3$ | $CH_3$ | 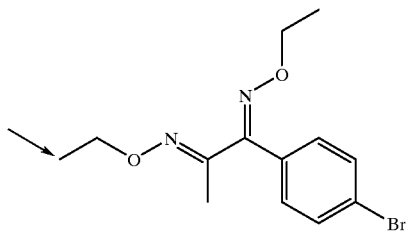 | |
| 3a.98. | $CH_3$ | $OCH_3$ | 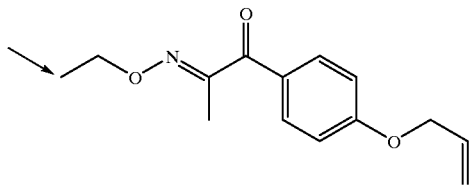 | |

TABLE 3b
(as Table 3, but with n = 2)
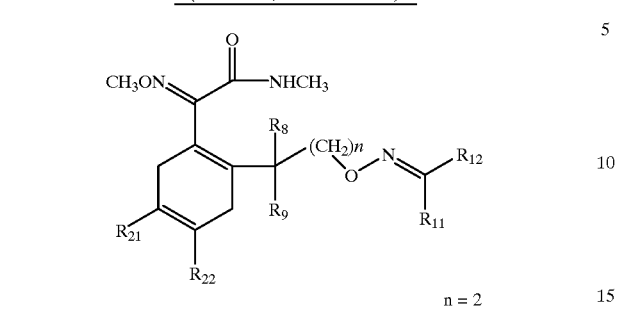
n = 2
Examples
| Ex. Nr. | $R_{21}$ | $R_{22}$ | | Phys. Data |
|---|---|---|---|---|
| 3b.06. | $CH_3$ | $CH_3$ | 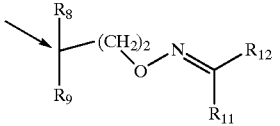 | |
| 3b.12. | $CH_3$ | $CH_3$ | 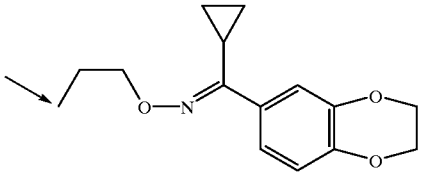 | |
| 3b.20. | $CH_3$ | $CH_3$ | 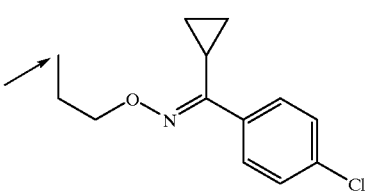 | |
| 3b.40. | $CH_3$ | $CH_3$ | 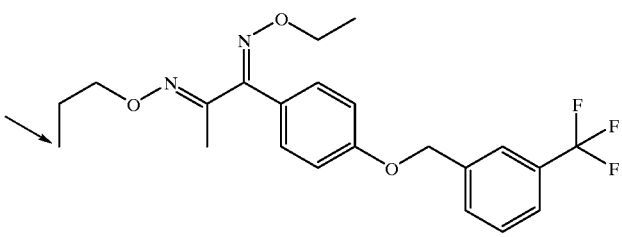 | |

-continued

| Ex. Nr. | R₂₁ | R₂₂ | | Phys. Data |
|---|---|---|---|---|
| 3b.98. | CH₃ | OCH₃ | | |

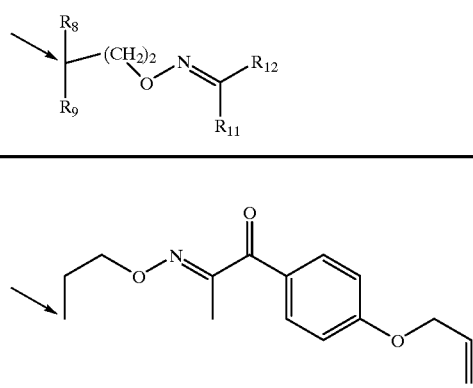

TABLE 4

(n = 0; intermediates)

| Ex. Nr. | R₂₁ | R₂₂ | | Phys. Data |
|---|---|---|---|---|
| 4.01. | CH₃ | CH₃ | —C(CH₃)₂—Cl | |
| 4.02. | CH₃ | CH₃ | —CH(CH₃)—Cl | |
| 4.03. | CH₃ | CH₃ | —CH₂·Cl | |
| 4.04. | CH₃ | CH₃ | —CH₂—N(piperidine) | |
| 4.05. | CH₃ | CH₃ | —CH(CH₃)—N(piperidine) | |
| 4.06. | CH₃ | CH₃ | —C(CH₃)₂—N(piperidine) | |

TABLE 4-continued (n = 0; intermediates)

| Ex. Nr. | R₂₁ | R₂₂ | | Phys. Data |
|---|---|---|---|---|
| 4.07. | CH₃ | CH₃ | —CH₂—N(morpholine) | |
| 4.08. | CH₃ | CH₃ | —CH(CH₃)—N(morpholine) | |
| 4.09. | CH₃ | CH₃ | —C(CH₃)₂—N(morpholine) | |
| 4.10. | CH₃ | CH₃ | —CH₂—N(2,6-dimethylmorpholine) | |

TABLE 4-continued
(n = 0; intermediates)
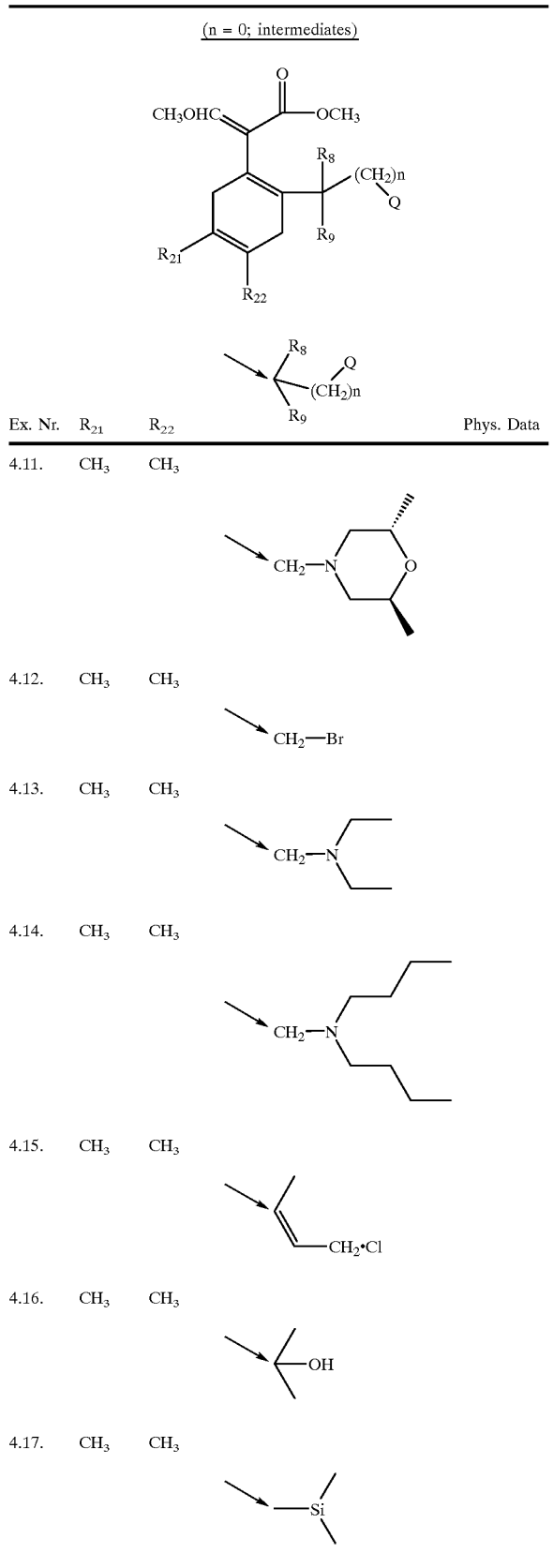
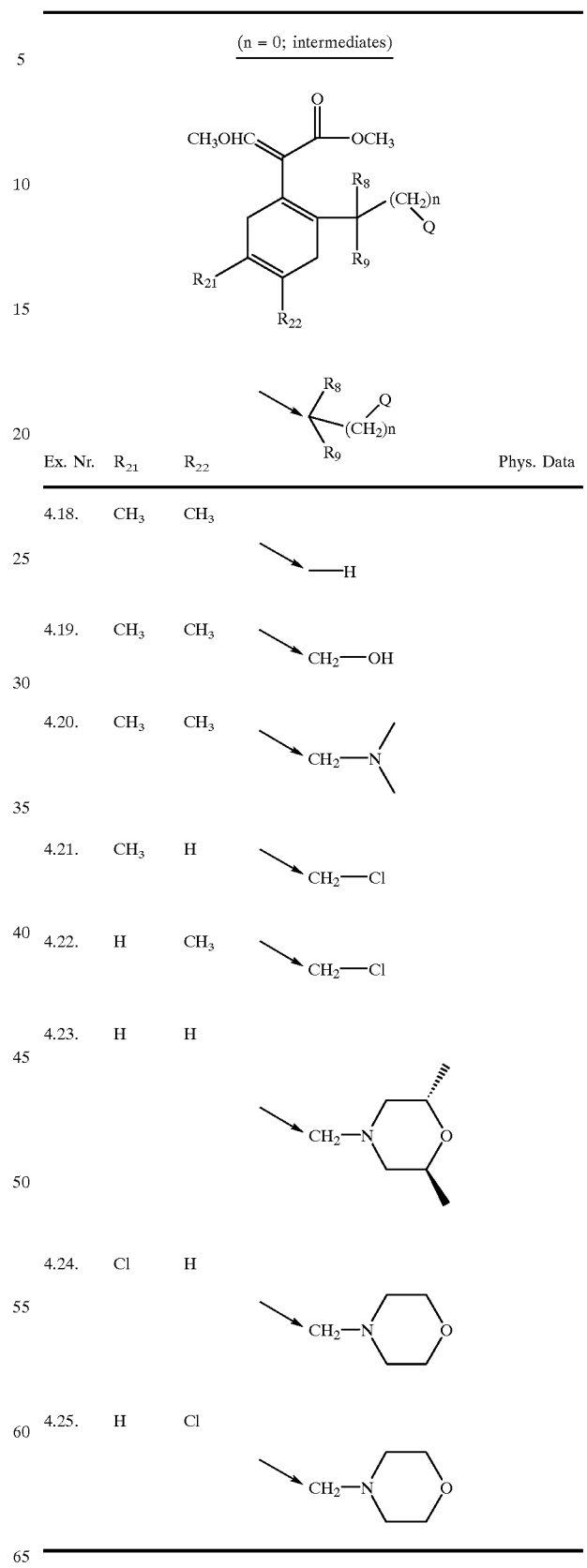

TABLE 5

(n = 0; intermediates)

| Ex. Nr. | R₂₁ | R₂₂ | $\begin{array}{c}R_8\\|\\-C-(CH_2)_n-Q\\|\\R_9\end{array}$ | Phys. Data |
|---|---|---|---|---|
| 5.01. | CH₃ | CH₃ | -C(CH₃)₂-Cl | |
| 5.02. | CH₃ | CH₃ | -CH(CH₃)-Cl | |
| 5.03. | CH₃ | CH₃ | -CH₂·Cl | 77–79° |
| 5.04. | CH₃ | CH₃ | -CH₂-piperidine | |
| 5.05. | CH₃ | CH₃ | -CH(CH₃)-piperidine | |
| 5.06. | CH₃ | CH₃ | -C(CH₃)₂-piperidine | |
| 5.07. | CH₃ | CH₃ | -CH₂-morpholine | 64–66° |
| 5.08. | CH₃ | CH₃ | -CH(CH₃)-morpholine | |
| 5.09. | CH₃ | CH₃ | -C(CH₃)₂-morpholine | |
| 5.10. | CH₃ | CH₃ | -CH₂-(2,6-dimethylmorpholine) | resin |

TABLE 5-continued (n = 0; intermediates)

| Ex. Nr. | R₂₁ | R₂₂ | $\begin{array}{c}R_8\\|\\-C-(CH_2)_n-Q\\|\\R_9\end{array}$ | Phys. Data |
|---|---|---|---|---|
| 5.11. | CH₃ | CH₃ | -CH₂-(2,6-dimethylmorpholine) | resin |
| 5.12. | CH₃ | CH₃ | -CH₂-Br | |
| 5.13. | CH₃ | CH₃ | -CH₂-N(Et)₂ | |
| 5.14. | CH₃ | CH₃ | -CH₂-N(Bu)₂ | |
| 5.15. | CH₃ | CH₃ | -C(CH₃)=CH-CH₂·Cl | |
| 5.16. | CH₃ | CH₃ | -C(CH₃)₂-OH | |
| 5.17. | CH₃ | CH₃ | -Si(CH₃)₃ | |
| 5.18. | CH₃ | CH₃ | -H | |
| 5.19. | CH₃ | CH₃ | -CH₂-OH | |
| 5.20. | CH₃ | CH₃ | -CH₂-N(CH₃)₂ | |

TABLE 5-continued (n = 0; intermediates)

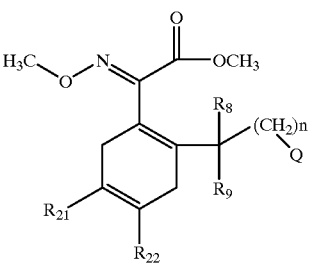

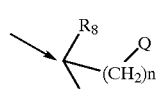

| Ex. Nr. | $R_{21}$ | $R_{22}$ | | Phys. Data |
|---|---|---|---|---|
| 5.21. | $CH_3$ | H | $CH_2$—Cl | |
| 5.22. | H | $CH_3$ | $CH_2$—Cl | |
| 5.23. | H | H | $CH_2$—N(morpholine with 2,6-diMe) | |
| 5.24. | Cl | H | $CH_2$—N(morpholine) | |
| 5.25. | H | Cl | $CH_2$—N(morpholine) | |

TABLE 6

(n = 0; intermediates)

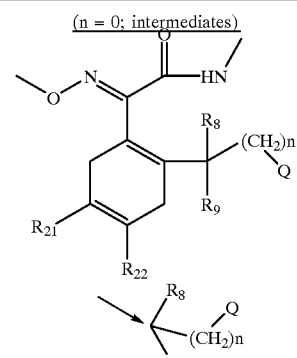

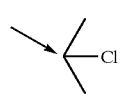

| Ex. Nr. | $R_{21}$ | $R_{22}$ | | Phys. Data |
|---|---|---|---|---|
| 6.01. | $CH_3$ | $CH_3$ | —Cl | |
| 6.02. | $CH_3$ | $CH_3$ | —Cl | |

TABLE 6-continued (n = 0; intermediates)

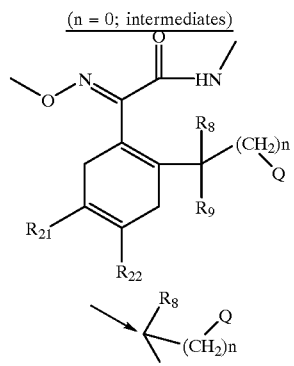

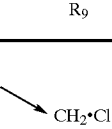

| Ex. Nr. | $R_{21}$ | $R_{22}$ | | Phys. Data |
|---|---|---|---|---|
| 6.03. | $CH_3$ | $CH_3$ | $CH_2 \cdot Cl$ | oil |
| 6.04. | $CH_3$ | $CH_3$ | $CH_2$—N(piperidine) | |
| 6.05. | $CH_3$ | $CH_3$ | CH—N(piperidine) | |
| 6.06. | $CH_3$ | $CH_3$ | C—N(piperidine) | |
| 6.07. | $CH_3$ | $CH_3$ | $CH_2$—N(morpholine) | resin |
| 6.08. | $CH_3$ | $CH_3$ | CH—N(morpholine) | |
| 6.09. | $CH_3$ | $CH_3$ | C—N(morpholine) | |
| 6.10. | $CH_3$ | $CH_3$ | $CH_2$—N(2,6-dimethylmorpholine) | resin |
| 6.11. | $CH_3$ | $CH_3$ | $CH_2$—N(2,6-dimethylmorpholine) | resin |

TABLE 6-continued (n = 0; intermediates)

| Ex. Nr. | R21 | R22 | -C(R8)(R9)(CH2)nQ group | Phys. Data |
|---|---|---|---|---|
| 6.12. | CH3 | CH3 | CH2—Br | |
| 6.13. | CH3 | CH3 | CH2—N(Et)2 | |
| 6.14. | CH3 | CH3 | CH2—N(Bu)2 | |
| 6.15. | CH3 | CH3 | CH=CH—CH2·Cl | |
| 6.16. | CH3 | CH3 | —C(CH3)2—OH | |
| 6.17. | CH3 | CH3 | Si(CH3)3 | |
| 6.18. | CH3 | CH3 | —H | |
| 6.19. | CH3 | CH3 | CH2—OH | |

TABLE 6-continued (n = 0; intermediates)

| Ex. Nr. | R21 | R22 | -C(R8)(R9)(CH2)nQ group | Phys. Data |
|---|---|---|---|---|
| 6.20. | CH3 | CH3 | CH2—N(CH3)2 | |
| 6.21. | CH3 | H | CH2—Cl | |
| 6.22. | H | CH3 | CH2—Cl | |
| 6.23. | H | H | CH2—N(2,6-dimethylmorpholinyl) | |
| 6.24. | Cl | H | CH2—N(morpholinyl) | |
| 6.25. | H | Cl | CH2—N(morpholinyl) | |

TABLE 7
(n = 0; intermediates)
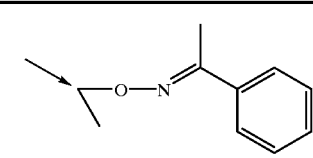
| Ex. Nr | $R_1$ | X | Y | Z | | Phys. Data |
|---|---|---|---|---|---|---|
| 7.1. | $CH_3$ | CH | O | $OCH_3$ | 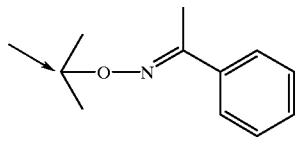 | |
| 7.2. | $CH_3$ | CH | O | $OCH_3$ | 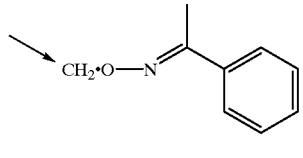 | |
| 7.3. | $CH_3$ | CH | O | $OCH_3$ | 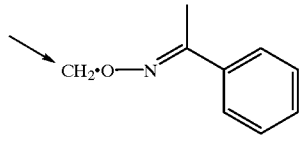 | |
| 7.4. | $CH_3$ | N | O | $OCH_3$ | 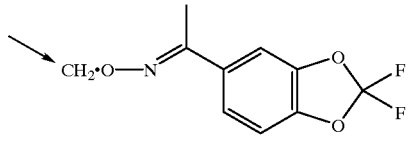 | |
| 7.5. | $CH_3$ | N | O | $OCH_3$ | 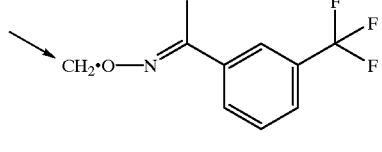 | |
| 7.6. | $CH_3$ | N | O | $OCH_3$ | 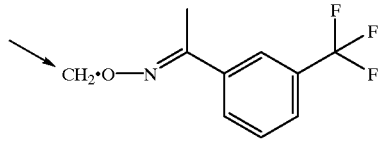 | 66–68° |
| 7.7. | $CH_3$ | CH | O | $OCH_3$ | 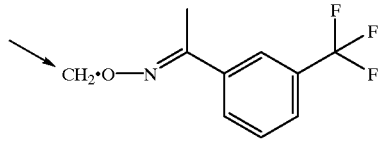 | 57–58° |

TABLE 7-continued
(n = 0; intermediates)
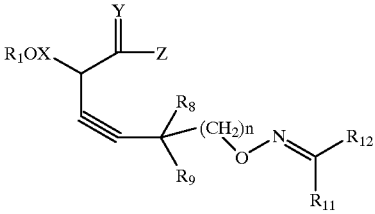
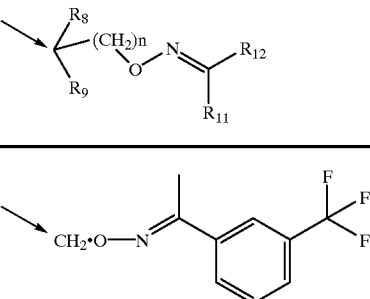
| Ex. Nr | R$_1$ | X | Y | Z | | Phys. Data |
|---|---|---|---|---|---|---|
| 7.8. | CH$_3$ | N | O | NHCH$_3$ | 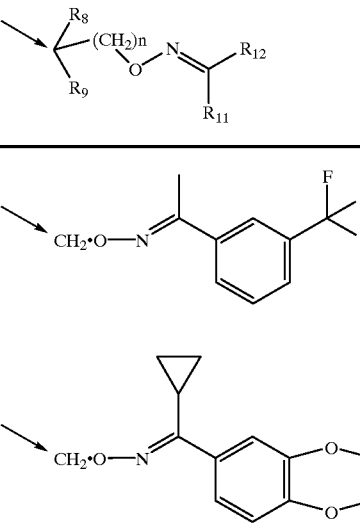 | |
| 7.9. | CH$_3$ | N | S | NHCH$_3$ | 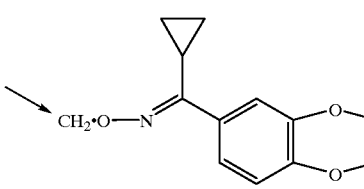 | |
| 7.10. | CH$_3$ | N | S | NHCH$_3$ | 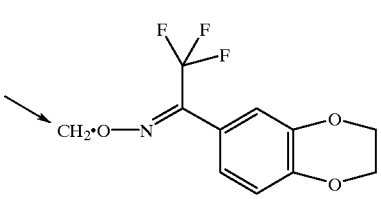 | |
| 7.11. | CH$_3$ | N | S | SCH$_3$ | 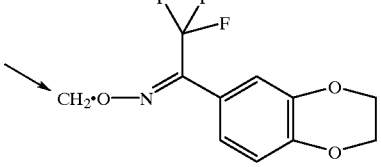 | |
| 7.12. | CH$_3$ | N | SO | SCH$_3$ | 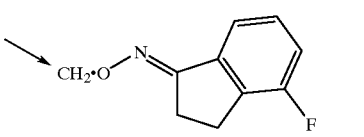 | |
| 7.13. | CH$_3$ | N | SO | SCH$_3$ | 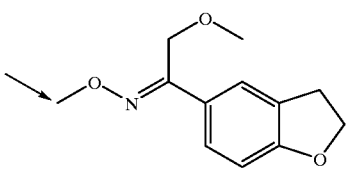 | |

TABLE 7-continued
(n = 0; intermediates)
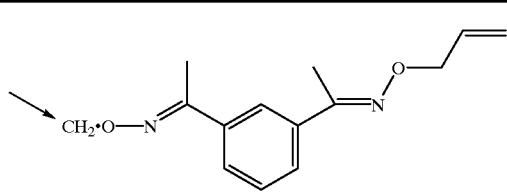
| Ex. Nr | $R_1$ | X | Y | Z | | Phys. Data |
|---|---|---|---|---|---|---|
| 7.14. | $CH_3$ | CH | O | $SCH_3$ | 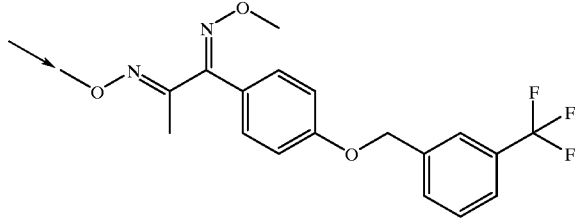 | |
| 7.15. | $CH_3$ | CH | O | $SCH_3$ | 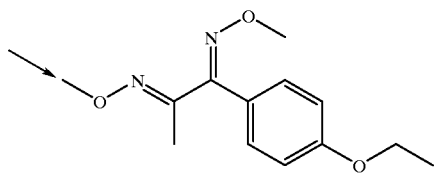 | |
| 7.16. | $CH_3$ | N | O | $OCH_3$ | 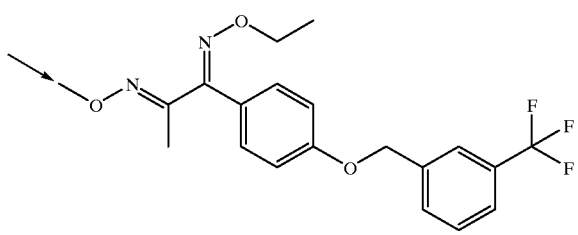 | |
| 7.17. | $CH_3$ | N | O | $NHCH_3$ | 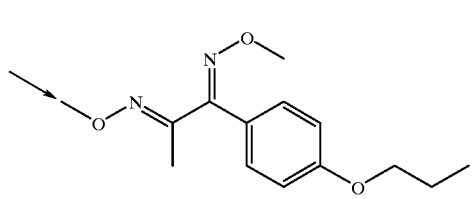 | |
| 7.18. | $CH_3$ | N | O | $NHCH_3$ | | |

TABLE 7-continued
(n = 0; intermediates)
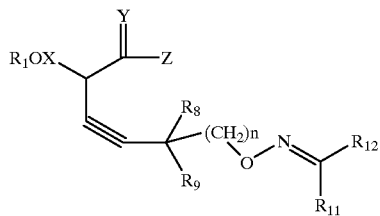
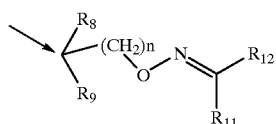
| Ex. Nr | R₁ | X | Y | Z | | Phys. Data |
|---|---|---|---|---|---|---|
| 7.19. | CH₃ | N | S | NHCH₃ | 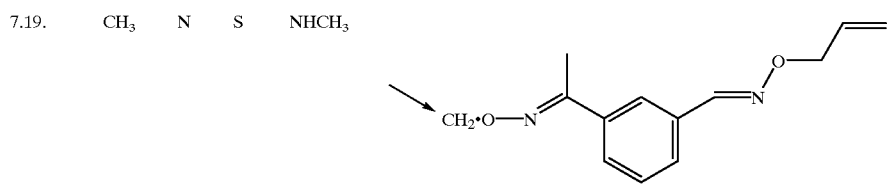 | |
| 7.20. | CH₃ | N | O | NHCH₃ | 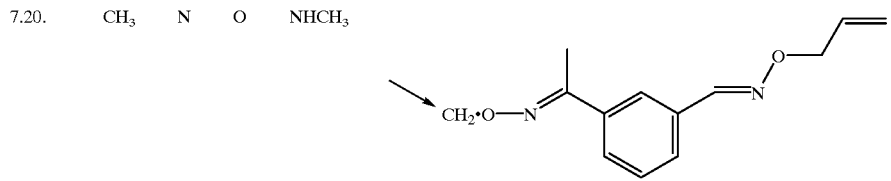 | |
| 7.21. | CH₃ | N | S | SCH₃ | 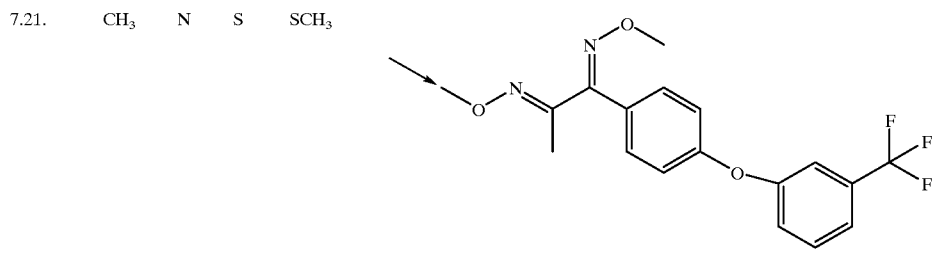 | |
| 7.22. | CH₃ | N | S | SCH₃ | 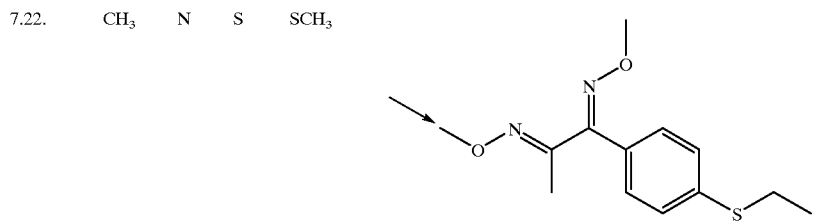 | |
| 7.23. | CH₃ | N | O | OCH₃ | 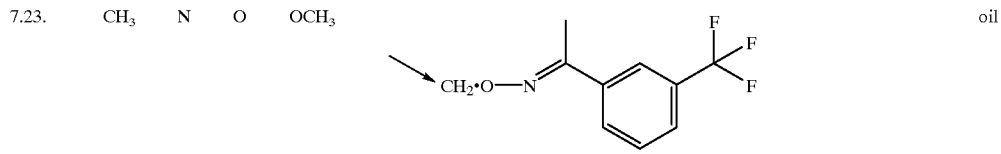 | oil |

TABLE 7-continued
(n = 0; intermediates)
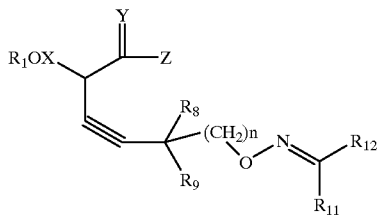
| Ex. Nr | $R_1$ | X | Y | Z | | Phys. Data |
|---|---|---|---|---|---|---|
| 7.24. | $CH_3$ | N | O | $OCH_3$ | 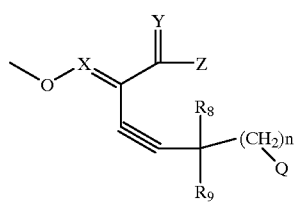 | oil |
TABLE 8
(n = 0; intermediates)
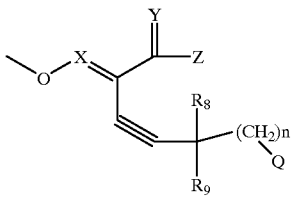
| Ex.-Nr. | $R_1$ | X | Y | Z | | Phys. Data |
|---|---|---|---|---|---|---|
| 8.01. | Me | CH | O | OMe | ![](Cl tBu) | |
| 8.02. | Me | CH | O | OMe | ![](Cl iPr) | |
| 8.03. | Me | CH | O | OMe | | |
| 8.04. | Me | N | O | OMe | | oil |
| 8.05. | Me | N | O | OMe | | |
| 8.06. | Me | N | O | OMe | | oil |
| 8.07. | Me | CH | O | OMe | | 70–72° |
| 8.08. | Me | N | O | NHMe | | |
| 8.09. | Me | N | O | OMe | | oil |

TABLE 8-continued (n = 0; intermediates)

| Ex.-Nr. | $R_1$ | X | Y | Z | $R_8,R_9,(CH_2)_n Q$ group | Phys. Data |
|---|---|---|---|---|---|---|
| 8.10. | Me | N | S | NHMe | CH$_2$–N(morpholine, 2,6-dimethyl) | |
| 8.11. | Me | N | S | SMe | CH$_2$–N(morpholine, 2,6-dimethyl) | |
| 8.12. | Me | N | SO | SMe | CH$_2$–N(morpholine, 2,6-dimethyl) | |
| 8.13. | Me | N | SO | SMe | CH$_2$–N(morpholine, 2,6-dimethyl, cis) | |
| 8.14. | Me | N | O | OMe | CH$_2$–N(morpholine, 2,6-dimethyl, cis) | oil |
| 8.15. | Me | CH | O | SMe | CH$_2$–N(morpholine, 2,6-dimethyl, cis) | |
| 8.16. | Me | N | O | OMe | CH$_2$–Br | |
| 8.17. | Me | N | O | NHMe | CH$_2$–Br | |
| 8.18. | Me | CH | O | OMe | CH$_2$–Br | |
| 8.19. | Me | N | S | NHMe | CH$_2$–N(Et)$_2$ | |
| 8.20. | Me | N | O | NHMe | CH$_2$–N(Et)$_2$ | |
| 8.21. | Me | N | S | SMe | CH$_2$–N(Et)$_2$ | |
| 8.22. | Me | N | S | SMe | CH$_2$–OH | |
| 8.23. | Me | N | O | OMe | CH$_2$–N(morpholine, 2,6-dimethyl) | oil |
| 8.24. | Me | CH | O | OMe | C(Me)$_2$–OH | resin |

TABLE 9
(n = 0; intermediates)
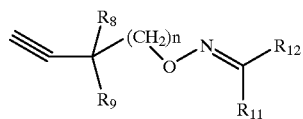
| Ex. Nr | | Phys. Data |
|---|---|---|
| 9.01. | | |
| 9.02. | | |
| 9.03. | | |
| 9.04. | | |
| 9.05. | | |
| 9.06. | | oil |
| 9.07. | | |

TABLE 9-continued
(n = 0; intermediates)
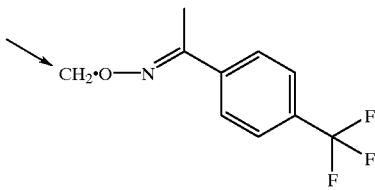
| Ex. Nr | | Phys. Data |
|---|---|---|
| 9.08. | 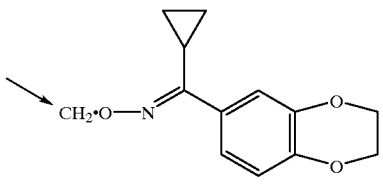 | |
| 9.09. | 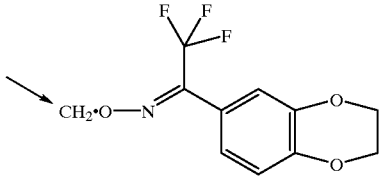 | |
| 9.10. | 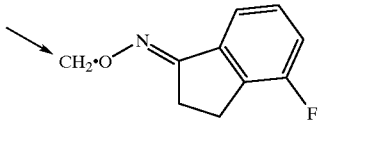 | |
| 9.11. | 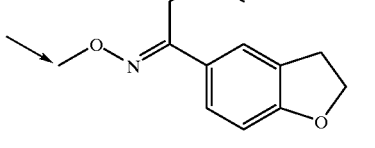 | |
| 9.12. | 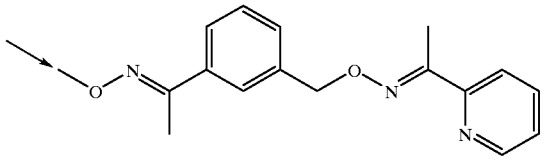 | |
| 9.13. | | |

TABLE 9-continued
(n = 0; intermediates)
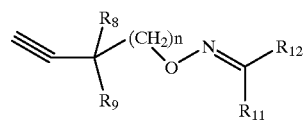
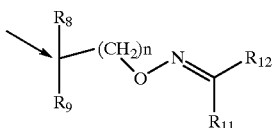
| Ex. Nr | | Phys. Data |
|---|---|---|
| 9.14. | 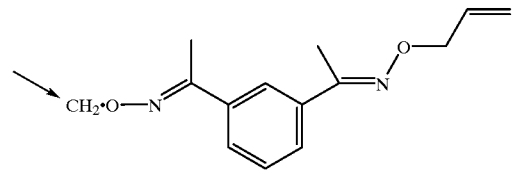 | |
| 9.15. | 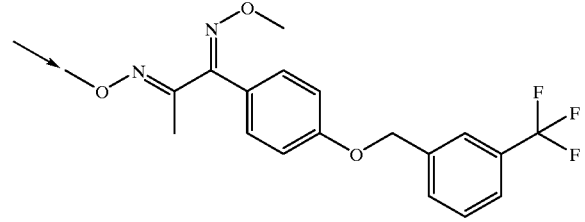 | oil |
| 9.16. | 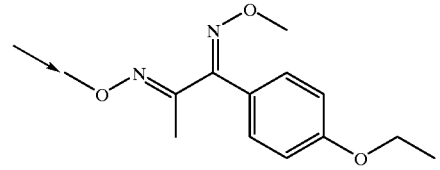 | |
| 9.17. | 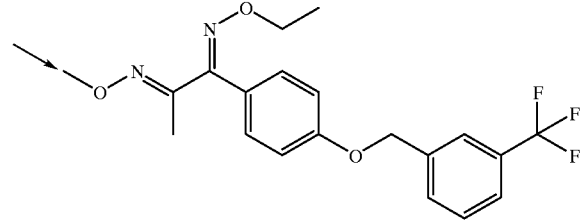 | |
| 9.18. | 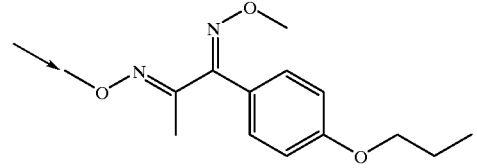 | |
| 9.19. | 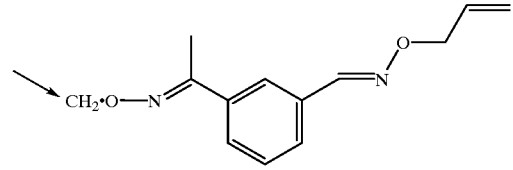 | |

TABLE 9-continued
(n = 0; intermediates)
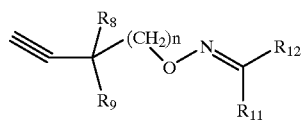
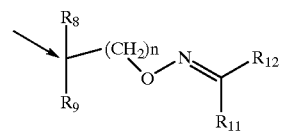
| Ex. Nr | | Phys. Data |
|---|---|---|
| 9.20. | 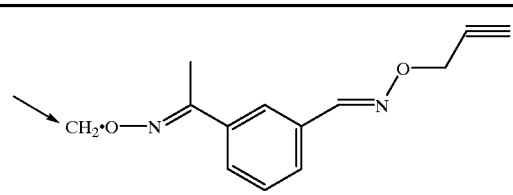 | |
| 9.21. | 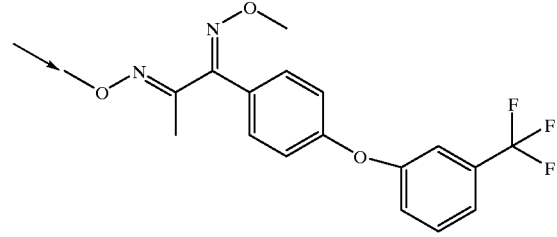 | oil |
| 9.22. | 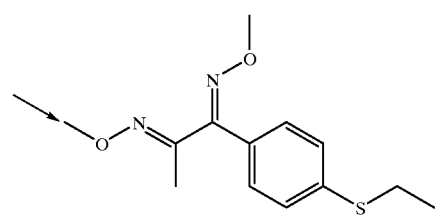 | |
| 9.23. | 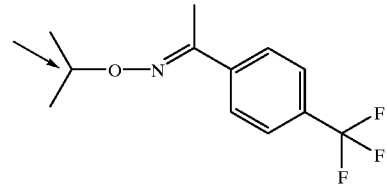 | oil |
| 9.24. | 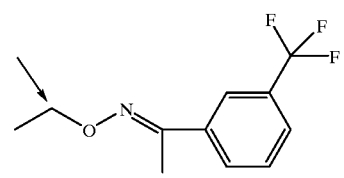 | oil |
| 9.25. | 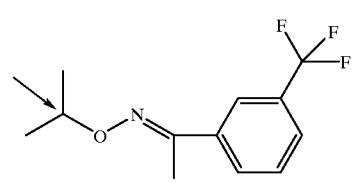 | resin |

TABLE 10

(n = 0; intermediates)

| Ex.-Nr. | Y | Z | R₈/R₉/Q group | Phys. Data |
|---------|---|---|---------------|------------|
| 10.01. | O | OMe | C(Me)₂—Cl | |
| 10.02. | O | OMe | CH(Me)—Cl | |
| 10.03. | O | OMe | CH₂—Cl (gem-dimethyl) | |
| 10.04. | O | OMe | CH₂—Cl | |
| 10.05. | O | OMe | CH₂—piperidine | |
| 10.06. | O | OMe | CH₂—morpholine | |
| 10.07. | O | OMe | CH₂—morpholine | |
| 10.08. | O | NHMe | CH₂—morpholine | |
| 10.09. | O | OMe | CH₂—2,6-dimethylmorpholine | |
| 10.10. | S | NHMe | CH₂—2,6-dimethylmorpholine | |

TABLE 10-continued (n = 0; intermediates)

| Ex.-Nr. | Y | Z | R₈/R₉/Q group | Phys. Data |
|---------|---|---|---------------|------------|
| 10.11. | S | SMe | CH₂—2,6-dimethylmorpholine | |
| 10.12. | SO | SMe | CH₂—2,6-dimethylmorpholine | |
| 10.13. | SO | SMe | CH₂—2,6-dimethylmorpholine (stereo) | |
| 10.14. | O | OMe | CH₂—2,6-dimethylmorpholine (stereo) | |
| 10.15. | O | SMe | CH₂—2,6-dimethylmorpholine (stereo) | |
| 10.16. | O | OMe | CH₂—Br | |

TABLE 10-continued
(n = 0; intermediates)
| Ex.-Nr. | Y | Z | | Phys. Data |
|---|---|---|---|---|
| 10.17. | O | NHMe | CH₂—Br | |
| 10.18. | O | OMe | CH₂—Br | |
| 10.19. | S | NHMe | CH₂—NEt₂ | |
| 10.20. | O | NHMe | CH₂—NEt₂ | |
| 10.21. | S | SMe | CH₂—NEt₂ | |
| 10.22. | S | SMe | CH₂—OH | |
TABLE 10-continued
(n = 0; intermediates)
| Ex.-Nr. | Y | Z | | Phys. Data |
|---|---|---|---|---|
| 10.23. | O | OMe | CH₂–N(2,6-dimethylmorpholine) | |
| 10.24. | O | OBu(t) | CH₂–N(2,6-dimethylmorpholine) | |
| 10.25. | O | OBu(t) | CH₂–N(morpholine) | |
| 10.26. | O | OBu(t) | CH₂–O–C(CH₃)₂–OMe | oil |
TABLE 11
(n = 0; intermediates)
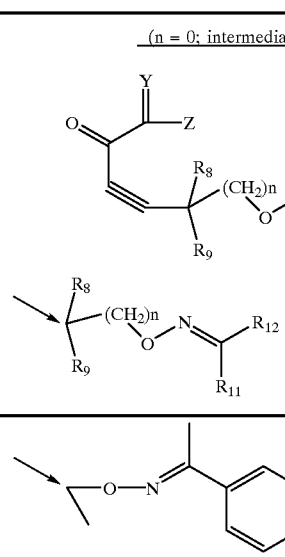
| Ex. Nr | Y | Z | | Phys. Data |
|---|---|---|---|---|
| 11.01. | O | OCH₃ | —O—N=C(Ph)(CH₃) | |

TABLE 11-continued (n = 0; intermediates)

| Ex. Nr | Y | Z | | Phys. Data |
|---|---|---|---|---|
| 11.02. | O | OCH₃ | | |
| 11.03. | O | OCH₃ | | |
| 11.04. | O | OCH₃ | | |
| 11.05. | O | OCH₃ | | |
| 11.06. | O | OCH₃ | | |
| 11.07. | O | OCH₃ | | |
| 11.08. | O | NHCH₃ | | |

TABLE 11-continued
(n = 0; intermediates)
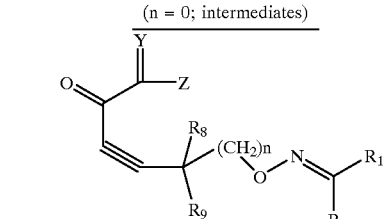
| Ex. Nr | Y | Z | | Phys. Data |
|---|---|---|---|---|
| 11.09. | S | NHCH$_3$ | 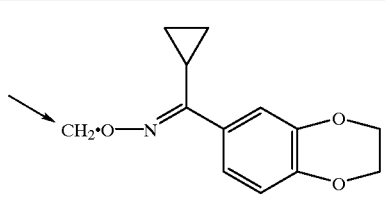 | |
| 11.10. | S | NHCH$_3$ | 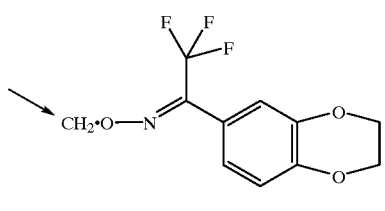 | |
| 11.11. | S | SCH$_3$ | 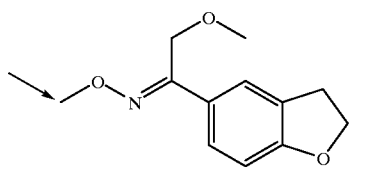 | |
| 11.12. | SO | SCH$_3$ | 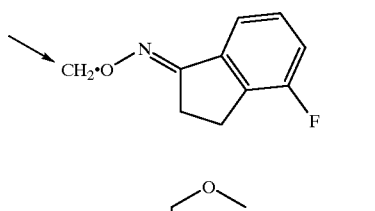 | |
| 11.13. | SO | SCH$_3$ | 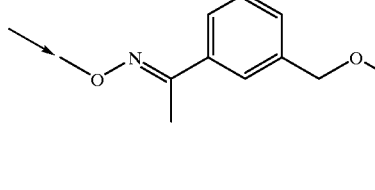 | |
| 11.14. | O | SCH$_3$ | 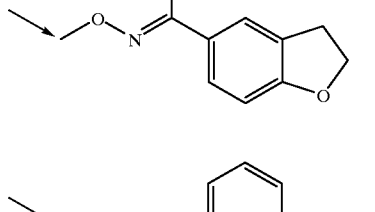 | |

TABLE 11-continued

| Ex. Nr | Y | Z | | Phys. Data |
|---|---|---|---|---|
| 11.15. | O | SCH$_3$ | | |
| 11.16. | O | OCH$_3$ | | |
| 11.17. | O | NHCH$_3$ | | |
| 11.18. | O | NHCH$_3$ | | |
| 11.19. | S | NHCH$_3$ | | |
| 11.20. | O | NHCH$_3$ | | |

TABLE 11-continued
(n = 0; intermediates)
| Ex. Nr | Y | Z | | Phys. Data |
|---|---|---|---|---|
| 11.21. | S | SCH₃ | 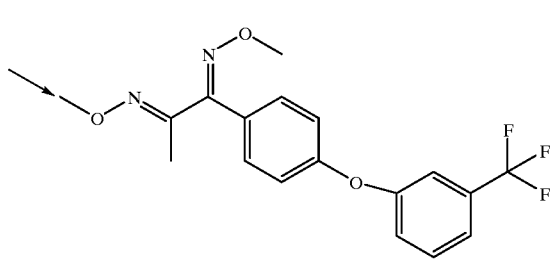 | |
| 11.22. | S | SCH₃ | 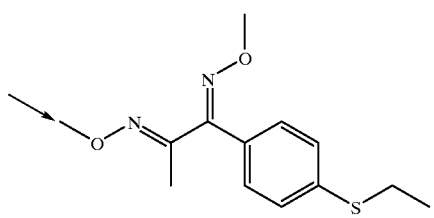 | |
| 11.23. | O | OBu(t) | 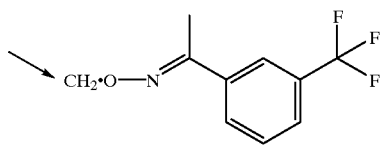 | oil |

TABLE 12

(n = 0; intermediates)

| Ex. Nr. | Z | $R_{21}$ | $R_{22}$ | | Phys. Data |
|---|---|---|---|---|---|
| 12.01. | $OCH_3$ | $CH_3$ | $CH_3$ | ethoxyimino-1-phenylethyl | |
| 12.02. | $OCH_3$ | $CH_3$ | $CH_3$ | isopropoxyimino-1-phenylethyl | |
| 12.03. | $OCH_3$ | $CH_3$ | $CH_3$ | methoxyimino-1-phenylethyl | |
| 12.04. | $OCH_3$ | $CH_3$ | $CH_3$ | methoxyimino-1-(2,2-difluoro-benzo[1,3]dioxol-5-yl)ethyl | |
| 12.05. | $OCH_3$ | $CH_3$ | $CH_3$ | methoxyimino-1-(3-trifluoromethylphenyl)ethyl | |
| 12.06. | $OCH_3$ | $CH_3$ | $CH_3$ | methoxyimino-cyclopropyl-(2,3-dihydro-benzo[1,4]dioxin-6-yl)methyl | |

TABLE 12-continued
(n = 0; intermediates)
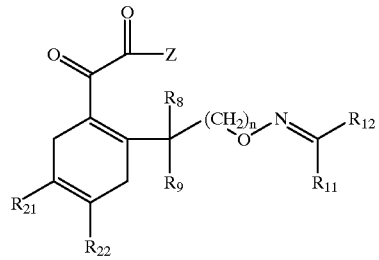
| Ex. Nr. | Z | R₂₁ | R₂₂ | | Phys. Data |
|---|---|---|---|---|---|
| 12.07. | OCH₃ | CH₃ | CH₃ | 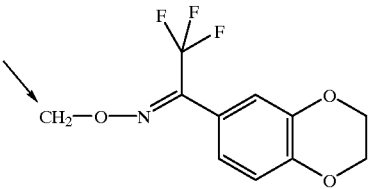 | |
| 12.08. | OCH₃ | CH₃ | CH₃ | 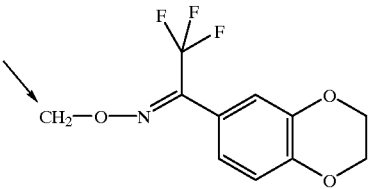 | |
| 12.09. | OCH₃ | CH₃ | CH₃ | 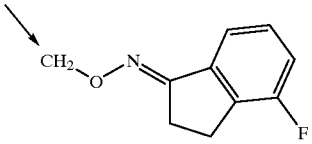 | |
| 12.10. | OCH₃ | CH₃ | CH₃ | 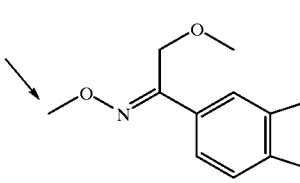 | |
| 12.11. | OCH₃ | CH₃ | CH₃ | 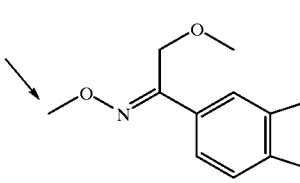 | |
| 12.12. | OCH₃ | CH₃ | CH₃ | 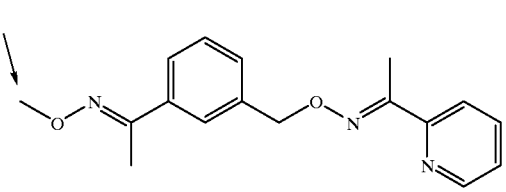 | |

TABLE 12-continued
(n = 0; intermediates)
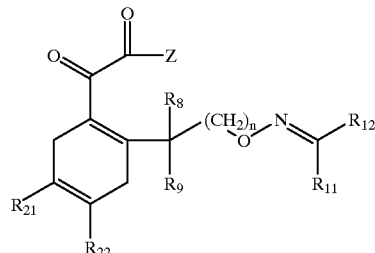
| Ex. Nr. | Z | $R_{21}$ | $R_{22}$ | | Phys. Data |
|---|---|---|---|---|---|
| 12.13. | $OCH_3$ | $CH_3$ | $CH_3$ | 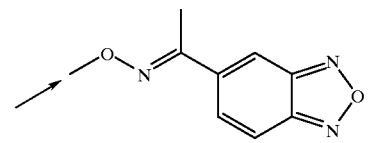 | |
| 12.14. | $OCH_3$ | $CH_3$ | $CH_3$ | | |
| 12.15. | $OCH_3$ | $CH_3$ | $CH_3$ | 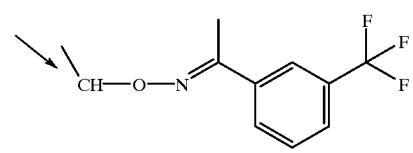 | |
| 12.16. | $OCH_3$ | $CH_3$ | $CH_3$ | 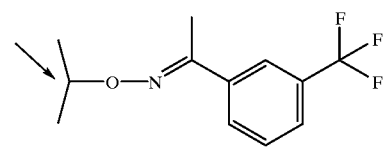 | |
| 12.17. | $OCH_3$ | $CH_3$ | $CH_3$ | 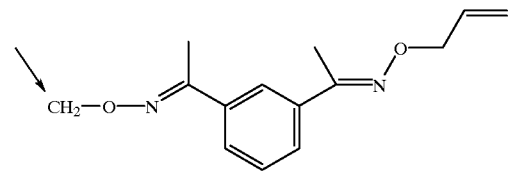 | |
| 12.18. | $OCH_3$ | $CH_3$ | $CH_3$ | 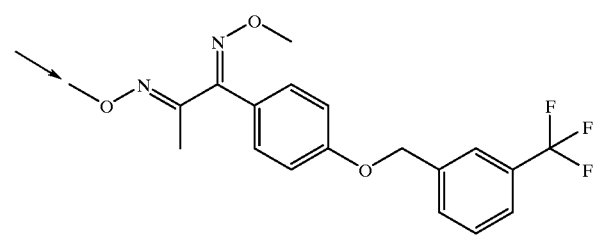 | |

TABLE 12-continued (n = 0; intermediates)

| Ex. Nr. | Z | R₂₁ | R₂₂ | | Phys. Data |
|---------|---|-----|-----|---|------------|
| 12.19.  | OCH₃ | CH₃ | CH₃ | | |
| 12.20.  | OCH₃ | CH₃ | CH₃ | | |
| 12.21.  | OCH₃ | CH₃ | CH₃ | | |
| 12.22.  | OCH₃ | CH₃ | CH₃ | | |
| 12.23.  | OCH₃ | CH₃ | CH₃ | | |

TABLE 12-continued (n = 0; intermediates)

| Ex. Nr. | Z | $R_{21}$ | $R_{22}$ | | Phys. Data |
|---|---|---|---|---|---|
| 12.24. | OCH$_3$ | CH$_3$ | CH$_3$ | | |
| 12.25. | OCH$_3$ | CH$_3$ | CH$_3$ | | |
| 12.26. | OCH$_3$ | CH$_3$ | CH$_3$ | | |
| 12.27. | OCH$_3$ | CH$_3$ | CH$_3$ | | |
| 12.28. | OCH$_3$ | CH$_3$ | CH$_3$ | | |
| 12.29. | OCH$_3$ | CH$_3$ | CH$_3$ | | |

TABLE 12-continued
(n = 0; intermediates)
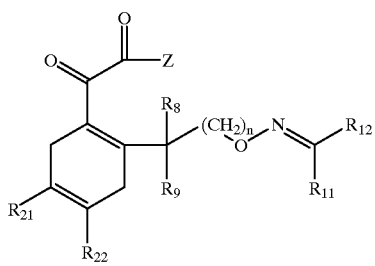
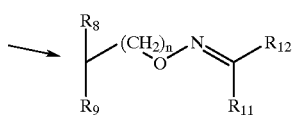
| Ex. Nr. | Z | $R_{21}$ | $R_{22}$ | | Phys. Data |
|---|---|---|---|---|---|
| 12.30. | $OCH_3$ | $CH_3$ | $CH_3$ | | |
| 12.31. | $OCH_3$ | $CH_3$ | $CH_3$ | | |
| 12.32. | $OCH_3$ | $CH_3$ | $CH_3$ | | |
| 12.33. | $OCH_3$ | $CH_3$ | $CH_3$ | | |
| 12.34. | $OCH_3$ | $CH_3$ | $CH_3$ | | |

TABLE 12-continued
(n = 0; intermediates)
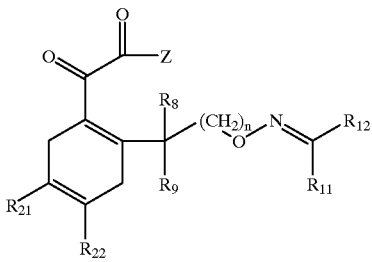
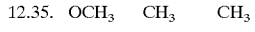
| Ex. Nr. | Z | $R_{21}$ | $R_{22}$ | | Phys. Data |
|---|---|---|---|---|---|
| 12.35. | $OCH_3$ | $CH_3$ | $CH_3$ | 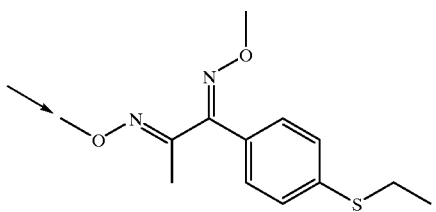 | |
| 12.36. | $OCH_3$ | $CH_3$ | $CH_3$ | 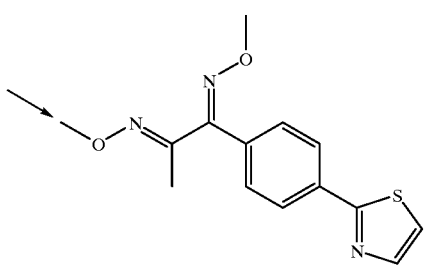 | |
| 12.37. | $OCH_3$ | $CH_3$ | $CH_3$ | 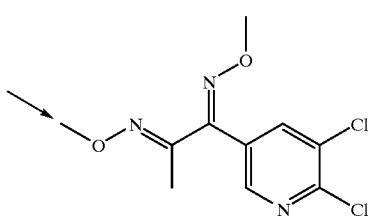 | |
| 12.38. | $OCH_3$ | $CH_3$ | $CH_3$ | 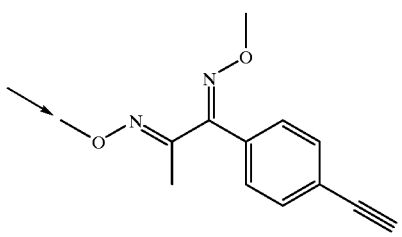 | |

TABLE 12-continued
(n = 0; intermediates)
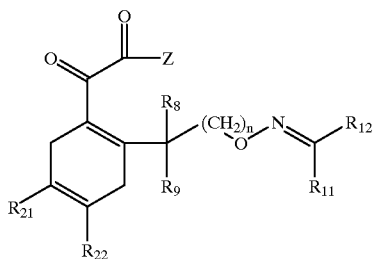
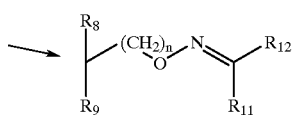
| Ex. Nr. | Z | R₂₁ | R₂₂ | | Phys. Data |
|---|---|---|---|---|---|
| 12.39. | OCH₃ | CH₃ | CH₃ | | |
| 12.40. | OCH₃ | CH₃ | CH₃ | | |
| 12.41. | OCH₃ | CH₃ | CH₃ | | |
| 12.42. | OCH₃ | CH₃ | CH₃ | | |

TABLE 12-continued
(n = 0; intermediates)
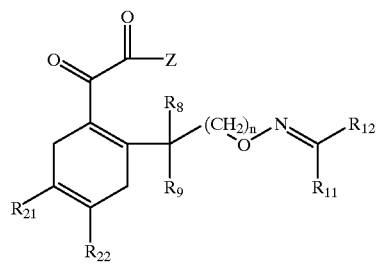
| Ex. Nr. | Z | $R_{21}$ | $R_{22}$ | | Phys. Data |
|---|---|---|---|---|---|
| 12.43. | OCH$_3$ | CH$_3$ | CH$_3$ | 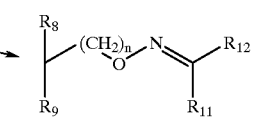 | |
| 12.44. | OCH$_3$ | CH$_3$ | CH$_3$ | 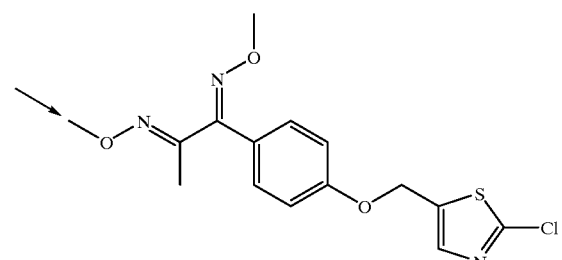 | |
| 12.45. | OCH$_3$ | CH$_3$ | CH$_3$ | 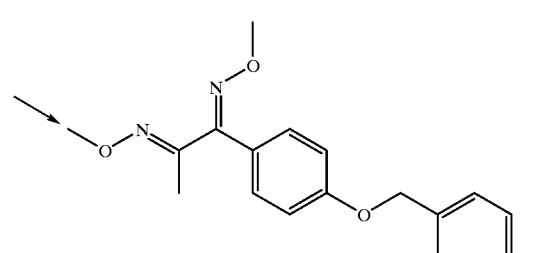 | |
| 12.46. | OCH$_3$ | CH$_3$ | CH$_3$ | 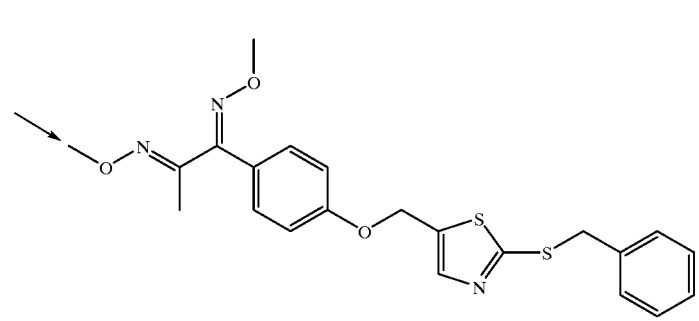 | |

TABLE 12-continued (n = 0; intermediates)

| Ex. Nr. | Z | R₂₁ | R₂₂ | (structure) | Phys. Data |
|---|---|---|---|---|---|
| 12.47 | OCH₃ | CH₃ | CH₃ | | |
| 12.48. | OCH₃ | CH₃ | CH₃ | | |
| 12.49. | OCH₃ | CH₃ | CH₃ | | |
| 12.50. | OCH₃ | CH₃ | CH₃ | | |
| 12.51. | OCH₃ | CH₃ | H | | |
| 12.52. | OCH₃ | CH₃ | H | | |

TABLE 12-continued
(n = 0; intermediates)
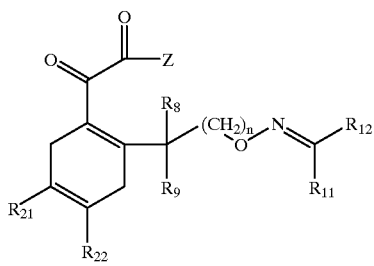
| Ex. Nr. | Z | R21 | R22 | | Phys. Data |
|---|---|---|---|---|---|
| 12.53. | OCH3 | CH3 | H | (CH2—O—N=C(CH3)—phenyl) | |
| 12.54. | OCH3 | CH3 | H | (CH2—O—N=C(CH3)—2,2-difluoro-1,3-benzodioxol-5-yl) | |
| 12.55. | OCH3 | CH3 | H | (CH2—O—N=C(CH3)—3-(trifluoromethyl)phenyl) | |
| 12.56. | OCH3 | H | CH3 | (CH2—O—N=C(cyclopropyl)—2,3-dihydro-1,4-benzodioxin-6-yl) | |
| 12.57. | OCH3 | H | CH3 | (CH2—O—N=C(CF3)—2,3-dihydro-1,4-benzodioxin-6-yl) | |
| 12.58. | OCH3 | H | CH3 | (CH2—O—N=(4-fluoro-indan-1-ylidene)) | |

TABLE 12-continued (n = 0; intermediates)

| Ex. Nr. | Z | $R_{21}$ | $R_{22}$ | | Phys. Data |
|---|---|---|---|---|---|
| 12.59. | $OCH_3$ | H | $CH_3$ | 2,3-dihydrobenzofuran-5-yl methoxyimino-methoxymethyl derivative | |
| 12.60. | $OCH_3$ | H | $CH_3$ | 3-(pyridin-2-yl-methoxyimino-methyl)phenyl methoxyimino derivative | |
| 12.61. | $OCH_3$ | H | H | 6-fluoro-chroman-4-ylidene methoxyimino | |
| 12.62. | $OCH_3$ | H | H | cyclopropyl(4-chlorophenyl)methylene methoxyimino | |
| 12.63. | $OCH_3$ | H | H | benzo[1,2,5]oxadiazol-5-yl methoxyimino ethyl derivative | |
| 12.64. | $OCH_3$ | H | H | 3-(pyrimidin-2-yl-thiomethyl)phenyl methoxyimino ethyl derivative | |

TABLE 12-continued
(n = 0; intermediates)
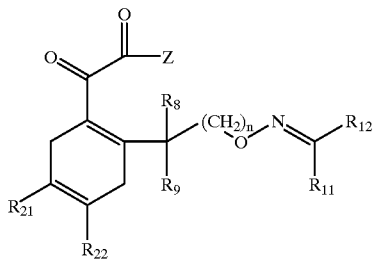
| Ex. Nr. | Z | $R_{21}$ | $R_{22}$ | | Phys. Data |
|---|---|---|---|---|---|
| 12.65. | $OCH_3$ | H | H | | |
| 12.66. | $OCH_3$ | H | H | | |
| 12.67. | H | H | H | | |
| 12.68. | $OCH_3$ | H | H | | |
| 12.69. | $OCH_3$ | H | H | | |

TABLE 12-continued (n = 0; intermediates)

| Ex. Nr. | Z | $R_{21}$ | $R_{22}$ | | Phys. Data |
|---|---|---|---|---|---|
| 12.70. | $OCH_3$ | H | H | | |
| 12.71. | $OCH_3$ | Cl | H | | |
| 12.72. | $OCH_3$ | Cl | H | | |
| 12.73. | $OCH_3$ | Cl | H | | |
| 12.74. | $OCH_3$ | Cl | H | | |

TABLE 12-continued (n = 0; intermediates)

| Ex. Nr. | Z | $R_{21}$ | $R_{22}$ | structure | Phys. Data |
|---|---|---|---|---|---|
| 12.75. | $OCH_3$ | Cl | H | | |
| 12.76. | $OCH_3$ | Cl | H | | |
| 12.77. | $OCH_3$ | Cl | H | | |
| 12.78. | $OCH_3$ | Cl | H | | |
| 12.79. | $OCH_3$ | Cl | H | | |
| 12.80. | $OCH_3$ | Cl | H | | |

TABLE 12-continued (n = 0; intermediates)

| Ex. Nr. | Z | R21 | R22 | | Phys. Data |
|---|---|---|---|---|---|
| 12.81. | OCH3 | H | Cl | (2-methylphenyl derivative) | |
| 12.82. | OCH3 | H | Cl | (4-(prop-2-ynyloxy)phenyl derivative) | |
| 12.83. | OCH3 | H | Cl | (4-ethylphenyl derivative) | |
| 12.84. | OCH3 | H | Cl | (4-methylsulfonylphenyl derivative) | |
| 12.85. | OCH3 | H | Cl | (4-ethylthiophenyl derivative) | |

TABLE 12-continued
(n = 0; intermediates)
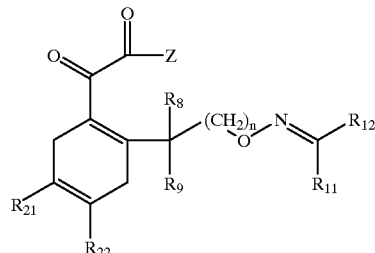
| Ex. Nr. | Z | R$_{21}$ | R$_{22}$ | | Phys. Data |
|---|---|---|---|---|---|
| 12.86. | OCH$_3$ | H | Cl | 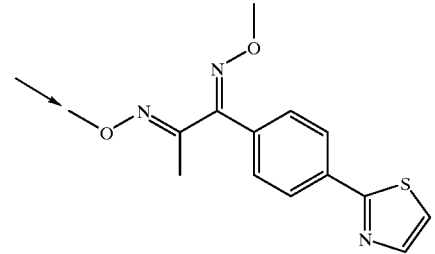 | |
| 12.87. | OCH$_3$ | H | Cl | 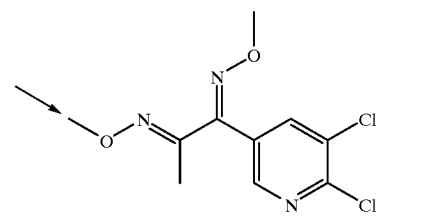 | |
| 12.88. | OCH$_3$ | H | Cl | 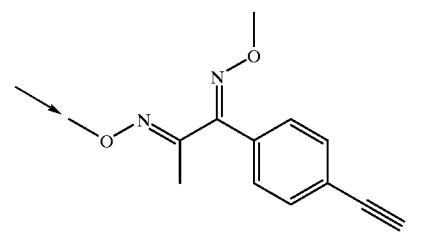 | |
| 12.89. | OCH$_3$ | H | Cl | 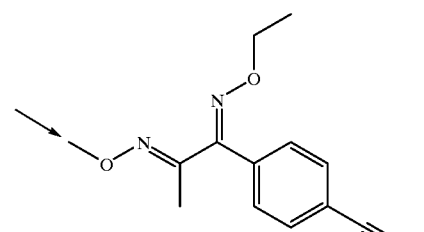 | |

TABLE 12-continued (n = 0; intermediates)

| Ex. Nr. | Z | R₂₁ | R₂₂ | | Phys. Data |
|---|---|---|---|---|---|
| 12.90. | OCH₃ | H | Cl | | |
| 12.91. | OCH₃ | OCH₃ | H | | |
| 12.92. | OCH₃ | OCH₃ | H | | |

TABLE 12-continued
(n = 0; intermediates)
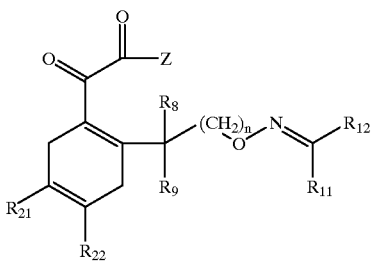
| Ex. Nr. | Z | $R_{21}$ | $R_{22}$ | | Phys. Data |
|---|---|---|---|---|---|
| 12.93. | $OCH_3$ | $OCH_3$ | H | 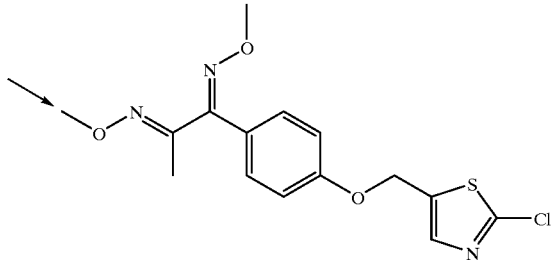 | |
| 12.94. | $OCH_3$ | $OCH_3$ | H | 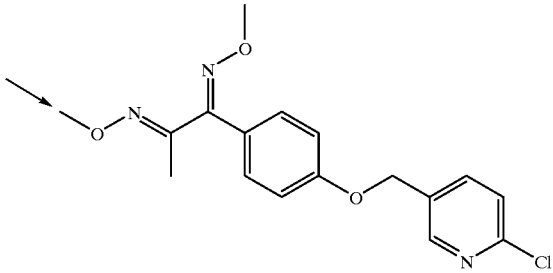 | |
| 12.95. | $OCH_3$ | $OCH_3$ | H | 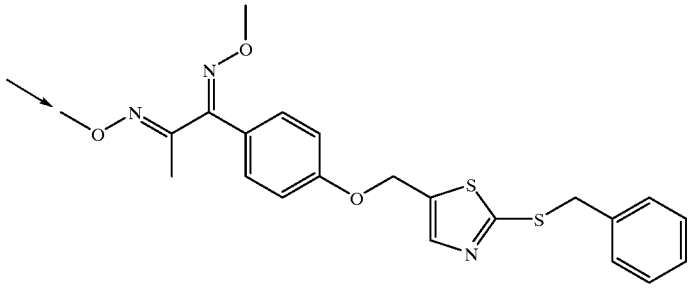 | |
| 12.96. | $OCH_3$ | H | $OCH_3$ | 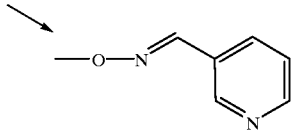 | |

TABLE 12-continued (n = 0; intermediates)

| Ex. Nr. | Z | $R_{21}$ | $R_{22}$ | | Phys. Data |
|---|---|---|---|---|---|
| 12.97. | $OCH_3$ | H | $OCH_3$ | | |
| 12.98. | $OCH_3$ | $CH_3$ | $OCH_3$ | | |
| 12.99. | $OCH_3$ | $CH_3$ | $OCH_3$ | | |
| 12.100. | $OCH_3$ | $OCH_3$ | $CH_3$ | | |
| 12.101. | $OCH_3$ | $OCH_3$ | H | | |
| 12.102. | $OCH_3$ | $CH_3$ | $CH_3$ | | |

TABLE 12-continued
(n = 0; intermediates)
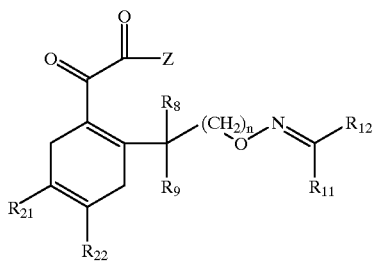
| Ex. Nr. | Z | R21 | R22 | | Phys. Data |
|---|---|---|---|---|---|
| 12.103. | OCH3 | CH3 | CH3 | 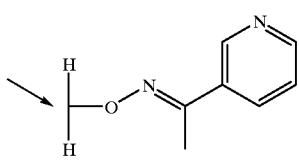 | |
| 12.104. | OCH3 | CH3 | CH3 | 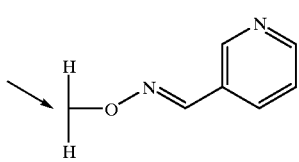 | |
| 12.105. | OCH3 | CH3 | CH3 | 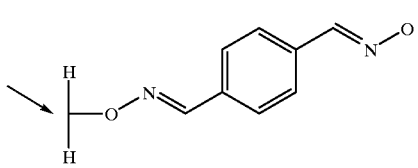 | |
| 12.106. | OCH3 | CH3 | CH3 | 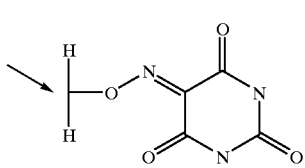 | |
| 12.107. | OCH3 | CH3 | CH3 | 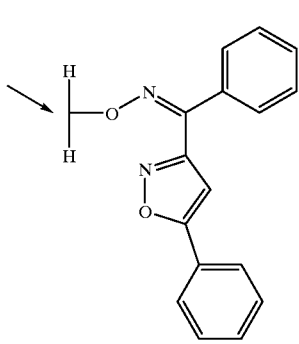 | |

TABLE 12-continued (n = 0; intermediates)

| Ex. Nr. | Z | $R_{21}$ | $R_{22}$ | | Phys. Data |
|---|---|---|---|---|---|
| 12.108. | $OCH_3$ | $CH_3$ | $CH_3$ | | |
| 12.109. | $OCH_3$ | $CH_3$ | $CH_3$ | | |
| 12.110. | $OCH_3$ | $CH_3$ | $CH_3$ | | |
| 12.111. | $OCH_3$ | $CH_3$ | $CH_3$ | | |
| 12.112. | $OCH_3$ | $CH_3$ | $CH_3$ | | |

TABLE 12-continued
(n = 0; intermediates)
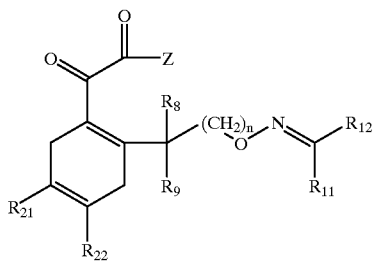
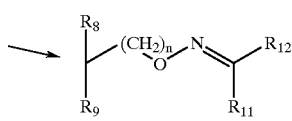
| Ex. Nr. | Z | R$_{21}$ | R$_{22}$ | | Phys. Data |
|---|---|---|---|---|---|
| 12.113. | OCH$_3$ | CH$_3$ | CH$_3$ | 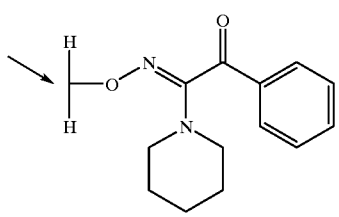 | |
| 12.114. | OCH$_3$ | CH$_3$ | CH$_3$ | 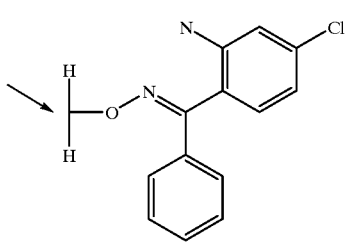 | |
| 12.115. | OCH$_3$ | CH$_3$ | CH$_3$ | 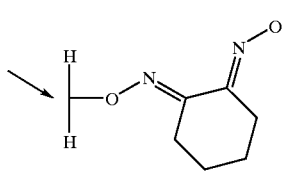 | |
| 12.116. | OCH$_3$ | CH$_3$ | CH$_3$ | 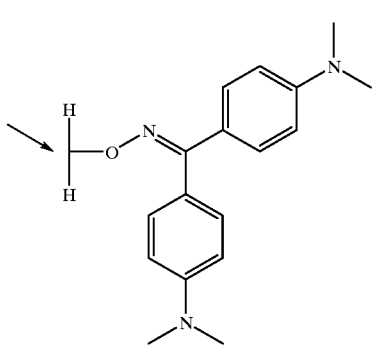 | |

TABLE 12-continued
(n = 0; intermediates)
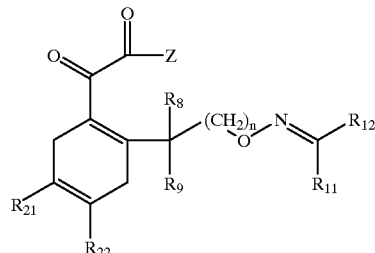
| Ex. Nr. | Z | R21 | R22 | | Phys. Data |
|---|---|---|---|---|---|
| 12.117. | OCH3 | CH3 | CH3 | 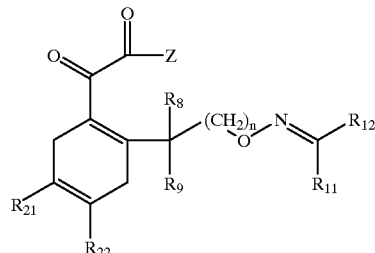 | |
| 12.118. | OCH3 | CH3 | CH3 | 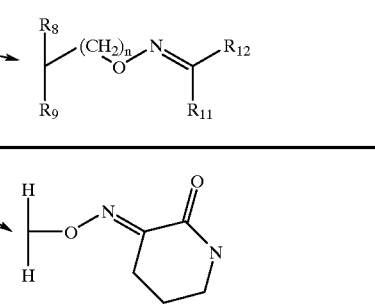 | |
| 12.119. | OCH3 | CH3 | CH3 | 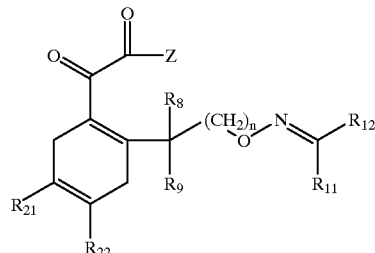 | |
| 12.120. | OCH3 | CH3 | CH3 | 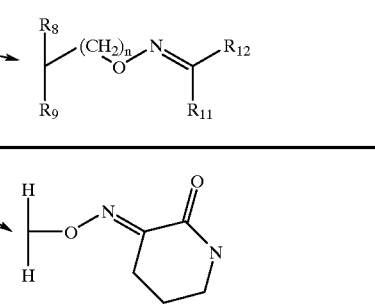 | |
| 12.121. | OCH3 | CH3 | CH3 | 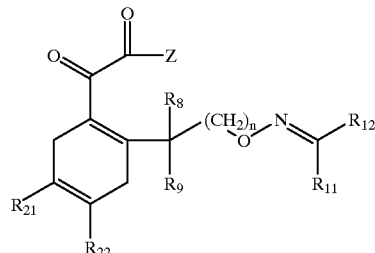 | |
| 12.122. | OCH3 | CH3 | CH3 | 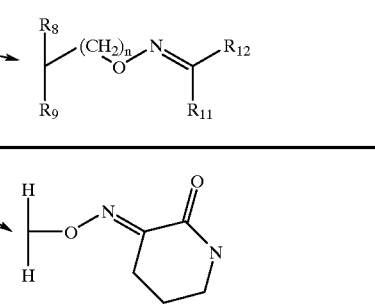 | |

TABLE 12-continued
(n = 0; intermediates)
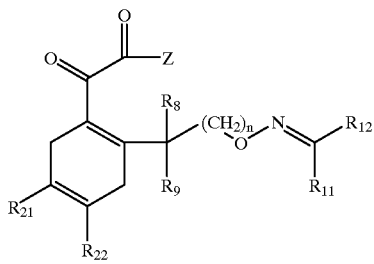
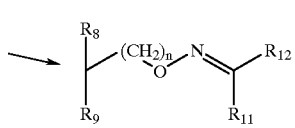
| Ex. Nr. | Z | $R_{21}$ | $R_{22}$ | | Phys. Data |
|---|---|---|---|---|---|
| 12.123. | $OCH_3$ | $CH_3$ | $CH_3$ | 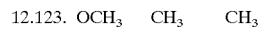 | |
| | | | | 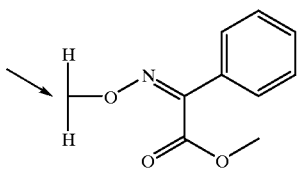 | |
| 12.124. | $OCH_3$ | $CH_3$ | $CH_3$ | 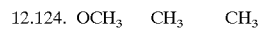 | |
| | | | | 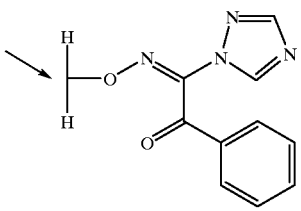 | |
| 12.125. | $OCH_3$ | $CH_3$ | $CH_3$ |  | |
| | | | | 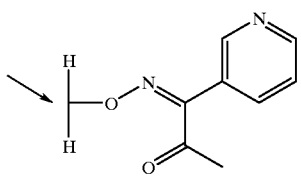 | |
| 12.126. | $OCH_3$ | $CH_3$ | $CH_3$ | 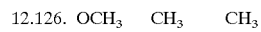 | |
| | | | | 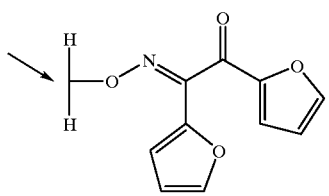 | |
| 12.127. | $OCH_3$ | $CH_3$ | $CH_3$ | 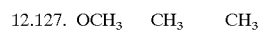 | |
| | | | | 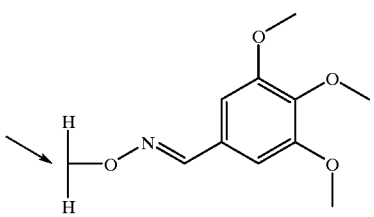 | |

TABLE 12-continued (n = 0; intermediates)

| Ex. Nr. | Z | R$_{21}$ | R$_{22}$ | | Phys. Data |
|---|---|---|---|---|---|
| 12.128. | OCH$_3$ | CH$_3$ | CH$_3$ | –CH$_2$–O–N=C(CH$_3$)–(4-phenoxyphenyl) | |
| 12.129. | OCH$_3$ | CH$_3$ | CH$_3$ | –CH$_2$–O–N=C(CN)–(2-pyridyl) | |
| 12.130. | OCH$_3$ | CH$_3$ | CH$_3$ | –CH$_2$–O–N=C(4-methoxyphenyl)$_2$ | |
| 12.131. | OCH$_3$ | CH$_3$ | CH$_3$ | –CH$_2$–O–N=C(cyclopropyl)$_2$ | |
| 12.132. | OCH$_3$ | CH$_3$ | CH$_3$ | –CH$_2$–O–N=CH–(1-methyl-3-ethyl-2,5-dioxoimidazolidin-4-yl) | |

TABLE 12-continued
(n = 0; intermediates)
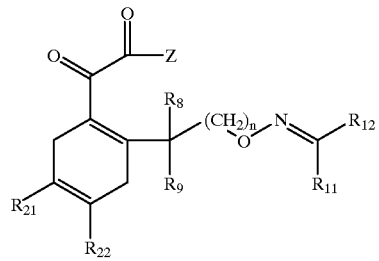
| Ex. Nr. | Z | $R_{21}$ | $R_{22}$ | | Phys. Data |
|---|---|---|---|---|---|
| 12.133. | OCH$_3$ | CH$_3$ | CH$_3$ | 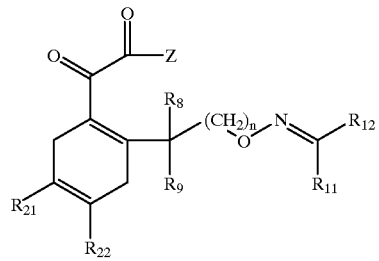 | |
| 12.134. | OCH$_3$ | CH$_3$ | CH$_3$ | 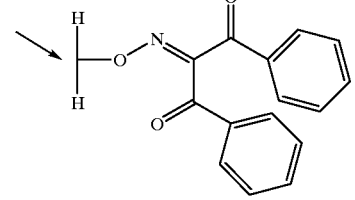 | |
| 12.135. | OCH$_3$ | CH$_3$ | CH$_3$ | 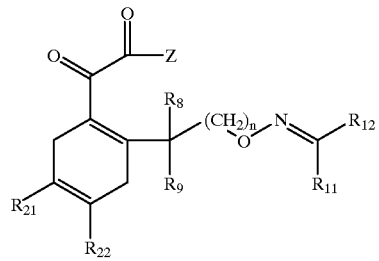 | |
| 12.136. | OCH$_3$ | CH$_3$ | CH$_3$ | 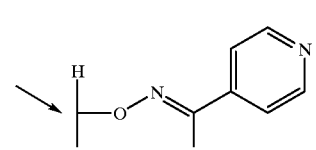 | |
| 12.137. | OCH$_3$ | CH$_3$ | CH$_3$ | 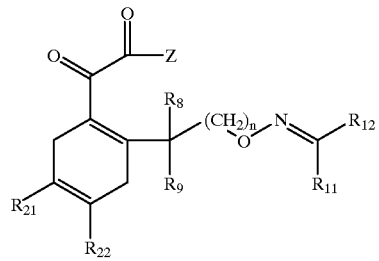 | |
| 12.138. | OCH$_3$ | CH$_3$ | CH$_3$ | 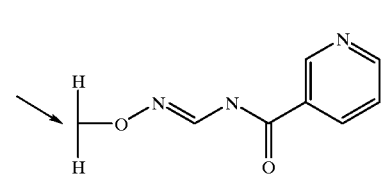 | |

TABLE 12-continued (n = 0; intermediates)

| Ex. Nr. | Z | R₂₁ | R₂₂ | (structure) | Phys. Data |
|---|---|---|---|---|---|
| 12.139. | OCH₃ | CH₃ | CH₃ | –CH₂–O–N=C(NEt₂)–C(O)–C₆H₅ | |
| 12.140. | OCH₃ | CH₃ | CH₃ | –CH₂–O–N=CH–(2-pyridyl) | |
| 12.141. | OCH₃ | CH₃ | CH₃ | –CH₂–O–N=CH–CH₂–N(CH₃)₂ | |
| 12.142. | OCH₃ | CH₃ | CH₃ | –CH₂–O–N=CH–CH₂–S–CH₃ | |
| 12.143. | OCH₃ | CH₃ | CH₃ | –CH₂–O–N=C(CH₃)–cyclopropyl | |
| 12.143. | OCH₃ | CH₃ | CH₃ | –CH₂–O–N=cyclopentylidene | |
| 12.144. | OCH₃ | CH₃ | CH₃ | –CH₂–O–N=cycloheptylidene | |

TABLE 12-continued (n = 0; intermediates)

| Ex. Nr. | Z | $R_{21}$ | $R_{22}$ | | Phys. Data |
|---|---|---|---|---|---|
| 12.145. | $OCH_3$ | $CH_3$ | $CH_3$ | (indol-3-yl-methylene aminooxymethyl) | |
| 12.146. | $OCH_3$ | $CH_3$ | $CH_3$ | (1,3-diphenyl-2,4,6-trioxo-pyrimidin-5-ylidene aminooxymethyl) | |
| 12.147. | $OCH_3$ | $CH_3$ | $CH_3$ | (methoxycarbonyl-methylene aminooxymethyl) | |
| 12.148. | $OCH_3$ | $CH_3$ | $CH_3$ | (bis-methoxycarbonyl-methylene aminooxymethyl) | |
| 12.149. | $OCH_3$ | $CH_3$ | $CH_3$ | (3,3-dimethyl-butan-2-ylidene aminooxymethyl) | |
| 12.150. | $OCH_3$ | $CH_3$ | $CH_3$ | (1,2,2,6,6-pentamethyl-piperidin-4-ylidene aminooxymethyl) | |

TABLE 12-continued (n = 0; intermediates)

| Ex. Nr. | Z | R₂₁ | R₂₂ | | Phys. Data |
|---|---|---|---|---|---|
| 12.151. | OCH₃ | CH₃ | CH₃ | diethyl 2-(aminooxymethylene)malonate-derived oxime ether | |
| 12.152. | OCH₃ | CH₃ | CH₃ | hexan-3-one O-methyl oxime | |
| 12.153. | OCH₃ | CH₃ | CH₃ | 1,4-dithiine-2-carbaldehyde O-methyl oxime | |
| 12.154. | OCH₃ | CH₃ | CH₃ | 2-(4-tert-butylphenyl)-2-methylpropanal O-methyl oxime | |
| 12.155. | OCH₃ | CH₃ | CH₃ | N-ethyl-N'-(2-cyano-2-methoxyiminoacetyl)urea | |
| 12.156. | OCH₃ | CH₃ | CH₃ | 1-(2-furyl)ethanone O-methyl oxime | |

TABLE 12-continued
(n = 0; intermediates)
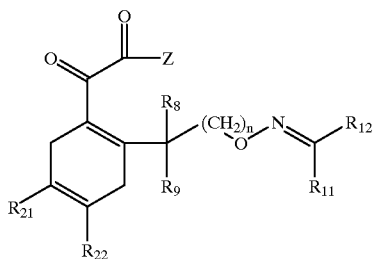
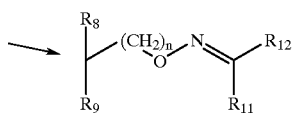
| Ex. Nr. | Z | $R_{21}$ | $R_{22}$ | | Phys. Data |
|---|---|---|---|---|---|
| 12.157. | $OCH_3$ | $CH_3$ | $CH_3$ | | |
| 12.158. | $OCH_3$ | $CH_3$ | $CH_3$ | | |
| 12.159. | $OCH_3$ | $CH_3$ | $CH_3$ | | |
| 12.160. | $OCH_3$ | $CH_3$ | $CH_3$ | | |
| 12.161. | H | H | $CH_3$ | | |
| 12.162. | H | H | H | | |

TABLE 12-continued
(n = 0; intermediates)
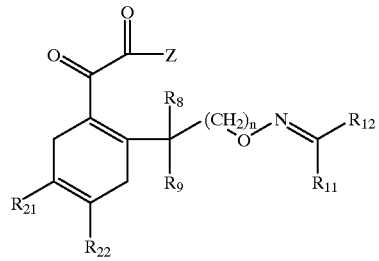
| Ex. Nr. | Z | $R_{21}$ | $R_{22}$ | | Phys. Data |
|---|---|---|---|---|---|
| 12.163. | $OCH_3$ | $CH_3$ | $CH_3$ | 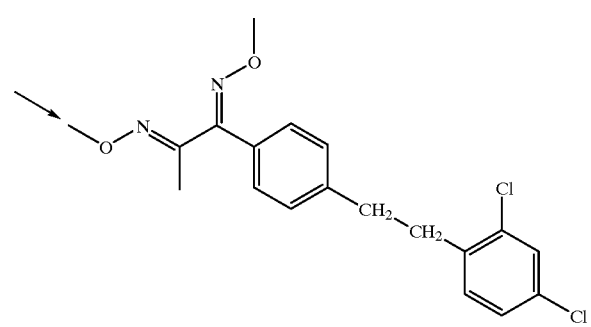 | |
| 12.164. | $OCH_3$ | $CH_3$ | $CH_3$ | 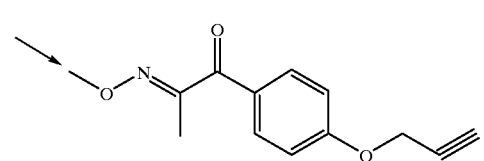 | |
| 12.165. | $OCH_3$ | $CH_3$ | $CH_3$ | 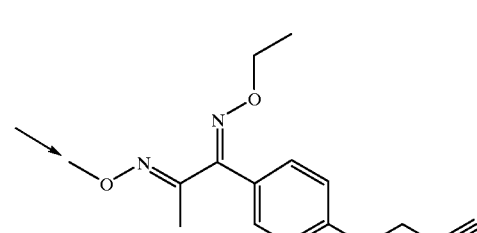 | |
| 12.166. | $OCH_3$ | $CH_3$ | $CH_3$ | 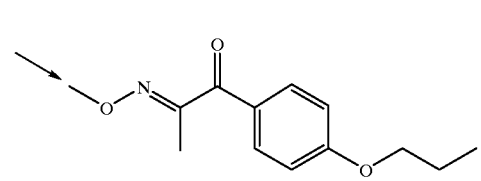 | |

TABLE 12-continued (n = 0; intermediates)

| Ex. Nr. | Z | R$_{21}$ | R$_{22}$ | | Phys. Data |
|---|---|---|---|---|---|
| 12.167. | OCH$_3$ | CH$_3$ | CH$_3$ | | |
| 12.168. | OCH$_3$ | CH$_3$ | CH$_3$ | | |
| 12.169. | OCH$_3$ | CH$_3$ | CH$_3$ | | |
| 12.170. | OCH$_3$ | CH$_3$ | CH$_3$ | | |

TABLE 12-continued (n = 0; intermediates)

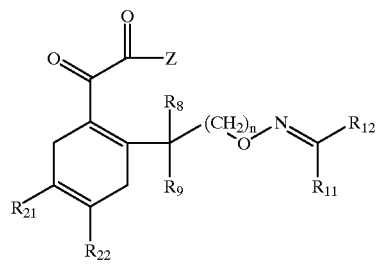

| Ex. Nr. | Z | $R_{21}$ | $R_{22}$ | | Phys. Data |
|---|---|---|---|---|---|
| 12.171. | OBu(t) | $CH_3$ | $CH_3$ | | oil |

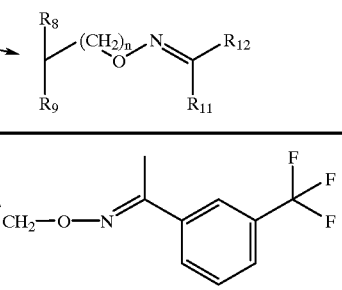

TABLE 13

(n = 0, $R_8$ = H, $R_9$ = H; intermediates)

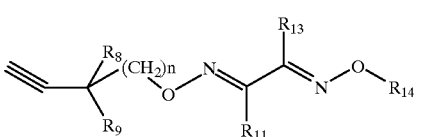

| Ex. Nr. | $R_{11}$ | $R_{14}$ | $R_{13}$ | Phys. Data |
|---|---|---|---|---|
| 13.01. | Me | Me | $4-C_6H_4-C\equiv C-C_6H_3Cl_2(2',4')$ | |
| 13.02. | Me | Me | $4-C_6H_4-C\equiv C-C_6H_5$ | |
| 13.03. | Me | Me | $4-C_6H_4-C\equiv C-C_6H_4(OCH_3)(4')$ | |
| 13.04. | Me | Me | $4-C_6H_4-C\equiv C-C_6H_3(CF_3)(3',5')$ | |
| 13.05. | Me | Me | $4-C_6H_4-C\equiv C-C_6H_4(CF_3)(3')$ | |
| 13.06. | Me | Me | $4-C_6H_4-C\equiv C-CO-C_6H_4(CF_3)(3')$ | |
| 13.07. | Me | Me | $4-C_6H_4-C\equiv C-CO-C_6H_5$ | |
| 13.08. | Me | Me | $4-C_6H_4-C\equiv C-CO-C_6H_4(Cl)(3')$ | |
| 13.09. | Me | Me | $4-C_6H_4-C\equiv C-C\equiv C-C_3H_7(i)$ | |
| 13.10. | Me | Me | $4-C_6H_4-C\equiv C-C\equiv C-C(CH_3)_2-OH$ | |
| 13.11. | Me | Me | $4-C_6H_4-(C\equiv C)_2-C(CH_3)_2-OCOCH_3$ | |
| 13.12. | Me | Me | $4-C_6H_4-C\equiv C-C(CH_3)_2-OH$ | |
| 13.13. | Me | Me | $4-C_6H_4-C\equiv C-Pyrazinyl(2')$ | |
| 13.14. | Me | Me | $4-C_6H_4-C\equiv C-Pyridyl(3')$ | |
| 13.15. | Me | Me | $4-C_6H_4-C\equiv C-CO-Pyridyl(3')$ | |
| 13.16. | Me | Me | $4-C_6H_4-C\equiv C-Pyridyl(2')$ | |
| 13.17. | Me | Me | $4-C_6H_4-C\equiv C-Pyridyl(4')$ | |
| 13.18. | Me | Me | $4-C_6H_4-C\equiv C-C_6H_4(CF_3)(4')$ | |
| 13.19. | Me | Me | $4-C_6H_4-C\equiv C-C_6H_4(Cl)(4')$ | |
| 13.20. | Me | Me | $4-C_6H_4-C\equiv C-CH_2-OH$ | |
| 13.21. | Me | Me | $4-C_6H_4-C\equiv C-Pyrimidinyl(2')$ | |
| 13.22. | Me | Me | $4-C_6H_4-C\equiv C-Pyrimidinyl(4')$ | |
| 13.23. | Me | Me | $4-C_6H_4-C\equiv C-Pyrimidinyl(5')$ | |
| 13.24. | Me | Me | $4-C_6H_4-C\equiv C-I$ | |
| 13.25. | Me | Me | $4-C_6H_4-C\equiv C-CH_3$ | |
| 13.26. | Me | Me | $4-C_6H_4-C\equiv C-Br$ | |
| 13.27. | Me | Me | $4-C_6H_4-C\equiv C-C_6H_4(Br)(4')$ | |
| 13.28. | Me | Me | $4-C_6H_4-C\equiv C-C_6H_3(OCH_3)_3(3',4',5')$ | |

TABLE 13-continued (n = 0, $R_8$ = H, $R_9$ = H; intermediates)

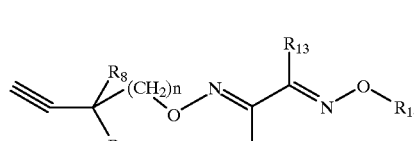

| Ex. Nr. | $R_{11}$ | $R_{14}$ | $R_{13}$ | Phys. Data |
|---|---|---|---|---|
| 13.29. | Me | Me | $4-C_6H_4-C\equiv C-C_6H_3(CH_3)_2(3',5')$ | |
| 13.30. | Me | Me | $4-C_6H_4-C\equiv C-Thiazolyl(2')$ | |
| 13.31. | Me | Me | $4-C_6H_4-C\equiv C-Oxazolyl(2')$ | |
| 13.32. | Me | Me | $4-C_6H_4-C\equiv C-Thienyl(2')$ | |
| 13.33. | Me | Me | $4-C_6H_4-C\equiv C-Thienyl(3')$ | |
| 13.34. | Me | Me | $4-C_6H_4-C\equiv C-Et$ | |
| 13.35. | Me | Me | $3-C_6H_4-C\equiv C-H$ | |
| 13.36. | Me | Me | $2-C_6H_4-C\equiv C-H$ | |
| 13.37. | Me | Me | $3-C_6H_4-C\equiv C-CH_3$ | |
| 13.38. | Me | Me | $2-C_6H_4-C\equiv C-Br$ | |
| 13.39. | Me | Me | $2-C_6H_4-C\equiv C-C(CH_3)_2-OH$ | |
| 13.40. | Me | Me | $3-C_6H_4-C\equiv C-C(CH_3)_2-OH$ | |
| 13.41. | Me | Me | $4-C_6H_4-C\equiv C-CF_3$ | |
| 13.42. | Me | Me | $4-C_6H_4-C\equiv C-COOEt$ | |
| 13.43. | Me | Me | $4-C_6H_4-C\equiv C-COOMe$ | |
| 13.44. | Me | Me | $2-C_6H_4-C\equiv C-C(CH_3)_2-OH$ | |
| 13.45. | Me | Me | $4-C_6H_4-C\equiv C-C(CH_3)_2-O-CH_3$ | |
| 13.46. | Me | Me | $3-C_6H_4-C\equiv C-C(CH_3)_2-O-CH_3$ | |
| 13.47. | Me | Me | $4-C_6H_4-C\equiv C-CH_2-OMe$ | |
| 13.48. | Me | Me | $4-C_6H_4-C\equiv C-C_4H_9(n)$ | |

TABLE 14

(Structure: dimethylcyclohexadiene with CH₃ON= methoxyimino acetyl-Z group and CH₂-O-N=C(CH₃)-C(R13)=N-OCH₃ side chain)

| Ex. Nr. | Z | R13 | Phys. Data |
|---|---|---|---|
| 14.01. | OMe | 4-C₆H₄—C≡C—C₆H₃Cl₂(2',4') | resin |
| 14.02. | OMe | 4-C₆H₄—C≡C—C₆H₅ | 142–144° |
| 14.03. | OMe | 4-C₆H₄—C≡C—C₆H₄(OCH₃)(4') | |
| 14.04. | OMe | 4-C₆H₄—C≡C—C₆H₃(CF₃)(3',5') | |
| 14.05. | OMe | 4-C₆H₄—C≡C—C₆H₄(CF₃)(3') | |
| 14.06. | OMe | 4-C₆H₄—C≡C—CO—C₆H₄(CF₃)(3') | |
| 14.07. | OMe | 4-C₆H₄—C≡C—CO—C₆H₅ | |
| 14.08. | OMe | 4-C₆H₄—C≡C—CO—C₆H₄(Cl)(3') | |
| 14.09. | OMe | 4-C₆H₄—C≡C—C≡C—C₃H₇(i) | |
| 14.10. | OMe | 4-C₆H₄—C≡C—C≡C—C(CH₃)₂—OH | |
| 14.11. | OMe | 4-C₆H₄—(C≡C)₂—C(CH₃)₂—OCOCH₃ | |
| 14.12. | OMe | 4-C₆H₄—C≡C—C(CH₃)₂—OH | |
| 14.13. | OMe | 4-C₆H₄—C≡C-Pyrazinyl(2') | |
| 14.14. | OMe | 4-C₆H₄—C≡C-Pyridyl(3') | |
| 14.15. | OMe | 4-C₆H₄—C≡C—CO-Pyridyl(3') | |
| 14.16. | OMe | 4-C₆H₄—C≡C-Pyridyl(2') | 142–144° |
| 14.17. | OMe | 4-C₆H₄—C≡C-Pyridyl(4') | |
| 14.18. | OMe | 4-C₆H₄—C≡C—C₆H₄(CF₃)(4') | |
| 14.19. | OMe | 4-C₆H₄—C≡C—C₆H₄(Cl)(4') | |
| 14.20. | OMe | 4-C₆H₄—C≡C—CH₂—OH | |
| 14.21. | OMe | 4-C₆H₄—C≡C-Pyrimidinyl(2') | |
| 14.22. | OMe | 4-C₆H₄—C≡C-Pyrimidinyl(4') | |
| 14.23. | OMe | 4-C₆H₄—C≡C-Pyrimidinyl(5') | |
| 14.24. | OMe | 4-C₆H₄—C≡C—I | |
| 14.25. | OMe | 4-C₆H₄—C≡C—CH₃ | |
| 14.26. | OMe | 4-C₆H₄—C≡C—Br | |
| 14.27. | OMe | 4-C₆H₄—C≡C—C₆H₄(Br)(4') | |
| 14.28. | OMe | 4-C₆H₄—C≡C—C₆H₃(OCH₃)₃(3',4',5') | |
| 14.29. | OMe | 4-C₆H₄—C≡C—C₆H₃(CH₃)₂(3',5') | |
| 14.30. | OMe | 4-C₆H₄—C≡C-Thiazol(2') | |
| 14.31. | OMe | 4-C₆H₄—C≡C-Oxazolyl(2') | |
| 14.32. | OMe | 4-C₆H₄—C≡C-Thienyl(2') | |
| 14.33. | OMe | 4-C₆H₄—C≡C-Thienyl(3') | |
| 14.34. | OMe | 4-C₆H₄—C≡C—Et | |
| 14.35. | OMe | 3-C₆H₄—C≡C—H | |
| 14.36. | OMe | 2-C₆H₄—C≡C—H | |
| 14.37. | OMe | 3-C₆H₄—C≡C—CH₃ | |
| 14.38. | OMe | 2-C₆H₄—C≡C—Br | |
| 14.39. | OMe | 2-C₆H₄—C≡C—C(CH₃)₂—OH | |
| 14.40. | OMe | 3-C₆H₄—C≡C—C(CH₃)₂—OH | |
| 14.41. | OMe | 4-C₆H₄—C≡C—CF₃ | |
| 14.42. | OMe | 4-C₆H₄—C≡C—COOEt | |
| 14.43. | OMe | 4-C₆H₄—C≡C—COOMe | |
| 14.44. | OMe | 2-C₆H₄—C≡C—C(CH₃)₂—OH | |
| 14.45. | OMe | 4-C₆H₄—C≡C—C(CH₃)₂—O—CH₃ | |
| 14.46. | OMe | 3-C₆H₄—C≡C—C(CH₃)₂—O—CH₃ | |
| 14.47. | OMe | 4-C₆H₄—C≡C—CH₂—OMe | |
| 14.48. | OMe | 4-C₆H₄—C≡C—C₄H₉(n) | |
| 14.49. | OMe | 4-C₆H₄—C≡C—C₃H₇(n) | |
| 14.50. | OMe | 4-C₆H₄—C≡C—C₈H₁₇(n) | |
| 14.51. | NHMe | 4-C₆H₄—C≡C—C₆H₃Cl₂(2',4') | |
| 14.52. | NHMe | 4-C₆H₄—C≡C—C₆H₅ | |
| 14.53. | NHMe | 4-C₆H₄—C≡C—C₆H₄(OCH₃)(4') | |
| 14.54. | NHMe | 4-C₆H₄—C≡C—C₆H₃(CF₃)(3',5') | |
| 14.55. | NHMe | 4-C₆H₄—C≡C—C₆H₄(CF₃)(3') | |
| 14.56. | NHMe | 4-C₆H₄—C≡C—CO—C₆H₄(CF₃)(3') | |
| 14.57. | NHMe | 4-C₆H₄—C≡C—CO—C₆H₅ | |
| 14.58. | NHMe | 4-C₆H₄—C≡C—CO—C₆H₄(Cl)(3') | |
| 14.59. | NHMe | 4-C₆H₄—C≡C—C≡C—C₃H₇(i) | |
| 14.60. | NHMe | 4-C₆H₄—C≡C—C≡C—C(CH₃)₂—OH | |
| 14.61. | NHMe | 4-C₆H₄—(C≡C)₂—C(CH₃)₂—OCOCH₃ | |
| 14.62. | NHMe | 4-C₆H₄—C≡C—C(CH₃)₂—OH | |
| 14.63. | NHMe | 4-C₆H₄—C≡C-Pyrazinyl(2') | |
| 14.64. | NHMe | 4-C₆H₄—C≡C-Pyridyl(3') | |
| 14.65. | NHMe | 4-C₆H₄—C≡C—CO-Pyridyl(3') | |
| 14.66. | NHMe | 4-C₆H₄—C≡C-Pyridyl(2') | |
| 14.67. | NHMe | 4-C₆H₄—C≡C-Pyridyl(4') | |
| 14.68. | NHMe | 4-C₆H₄—C≡C—C₆H₄(CF₃)(4') | |
| 14.69. | NHMe | 4-C₆H₄—C≡C—C₆H₄(Cl)(4') | |
| 14.70. | NHMe | 4-C₆H₄—C≡C—CH₂—OH | |
| 14.71. | NHMe | 4-C₆H₄—C≡C-Pyrimidinyl(2') | |
| 14.72. | NHMe | 4-C₆H₄—C≡C-Pyrimidinyl(4') | |
| 14.73. | NHMe | 4-C₆H₄—C≡C-Pyrimidinyl(5') | |
| 14.74. | NHMe | 4-C₆H₄—C≡C—I | |
| 14.75. | NHMe | 4-C₆H₄—C≡C—CH₃ | |
| 14.76. | NHMe | 4-C₆H₄—C≡C—Br | |
| 14.77. | NHMe | 4-C₆H₄—C≡C—C₆H₄(Br)(4') | |
| 14.78. | NHMe | 4-C₆H₄—C≡C—C₆H₃(OCH₃)₃(3',4',5') | |
| 14.79. | NHMe | 4-C₆H₄—C≡C—C₆H₃(CH₃)₂(3',5') | |
| 14.80. | NHMe | 4-C₆H₄—C≡C-Thiazolyl(2') | |
| 14.81. | NHMe | 4-C₆H₄—C≡C-Oxazolyl(2') | |
| 14.82. | NHMe | 4-C₆H₄—C≡C-Thienyl(2') | |
| 14.83. | NHMe | 4-C₆H₄—C≡C-Thienyl(3') | |
| 14.84. | NHMe | 4-C₆H₄—C≡C—Et | |
| 14.85. | NHMe | 3-C₆H₄—C≡C—H | |
| 14.86. | NHMe | 2-C₆H₄—C≡C—H | |
| 14.87. | NHMe | 3-C₆H₄—C≡C—CH₃ | |
| 14.88. | NHMe | 2-C₆H₄—C≡C—Br | |
| 14.89. | NHMe | 2-C₆H₄—C≡C—C(CH₃)₂—OH | |
| 14.90. | NHMe | 3-C₆H₄—C≡C—C(CH₃)₂—OH | |
| 14.91. | NHMe | 4-C₆H₄—C≡C—CF₃ | |
| 14.92. | NHMe | 4-C₆H₄—C≡C—COOEt | |
| 14.93. | NHMe | 4-C₆H₄—C≡C—COOMe | |
| 14.94. | NHMe | 2-C₆H₄—C≡C—C(CH₃)₂—OH | |
| 14.95. | NHMe | 4-C₆H₄—C≡C—C(CH₃)₂—O—CH₃ | |
| 14.96. | NHMe | 3-C₆H₄—C≡C—C(CH₃)₂—O—CH₃ | |
| 14.97. | NHMe | 4-C₆H₄—C≡C—CH₂—OMe | |
| 14.98. | NHMe | 4-C₆H₄—C≡C—C₄H₉(n) | |
| 14.99. | NHMe | 4-C₆H₄—C≡C—C₃H₇(n) | |
| 14.100. | NHMe | 4-C₆H₄—C≡C—C₈H₁₇(n) | |
| 14.101. | NHMe | 4-C6H4—C≡C—C6H4(CH3)(3') | 133–135° |
| 14.102. | NHMe | 4-C6H4—C≡C—CH2-morpholinyl(1) | 100–102° |
| 14.103. | NHMe | 4-C6H4—CH2—CH2—CH2—morpholinyl(1) | resin |
| 14.104. | NHMe | 4-C6H4—C≡C—CH2Cl | 126–129° |
| 14.105. | OMe | 4-C6H4—C≡C—C6H4(CH3)(3') | 127–130° |
| 14.106. | NHMe | 4-C6H4—C≡C—CH2—O—C6H3(Cl2)(2',4') | 119–122° |
| 14.107. | NHMe | 4-C6H4—C≡C—CH2—O—C6H3(CH3)(2') | 96–98° |
| 14.108. | NHMe | 4-C6H4—C≡C—CH2—O—C6H3(CH3)(3') | 78–80° |

TABLE 15

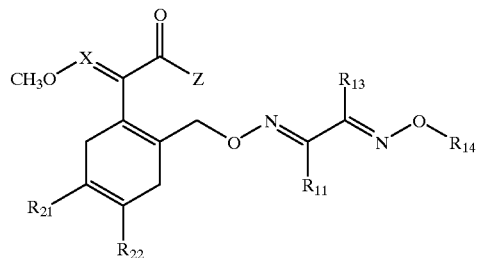

| Ex. Nr. | X | R11 | R14 | R21 | R22 | Z | R13 | Phys. Data |
|---|---|---|---|---|---|---|---|---|
| 15.001 | N | Me | Me | Me | Me | OMe | 4-$C_6H_4$—CH=CH—$C_6H_3Cl_2$(2',4') | |
| 15.002 | N | Me | Me | Me | Me | OMe | 4-$C_6H_4$—CH=CH—$C_6H_5$ | |
| 15.003 | N | Me | Me | Me | Me | OMe | 4-$C_6H_4$—CH=CH—$C_6H_4$($OCH_3$)(4') | |
| 15.004 | N | Me | Me | Me | Me | OMe | 4-$C_6H_4$—CH=CH—$C_6H_3$($CF_3$)(3',5') | |
| 15.005 | N | Me | Me | Me | Me | OMe | 4-$C_6H_4$—CH=CH—$C_6H_4$($CF_3$)(3') | |
| 15.006 | N | Me | Me | Me | Me | OMe | 4-$C_6H_4$—CH=CH—CO—$C_6H_4$($CF_3$)(3') | |
| 15.007 | N | Me | Me | Me | Me | OMe | 4-$C_6H_4$—CH=CH—CO—$C_6H_5$ | |
| 15.008 | N | Me | Me | Me | Me | OMe | 4-$C_6H_4$—CH=CH—CO—$C_6H_4$(Cl)(3') | |
| 15.009 | N | Me | Me | Me | Me | OMe | 4-$C_6H_4$—CH=CH—C($CH_3$)$_2$—OH | |
| 15.010 | N | Me | Me | Me | Me | OMe | 4-$C_6H_4$—CH=CH-Pyrazinyl(2') | |
| 15.011 | N | Me | Me | Me | Me | OMe | 4-$C_6H_4$—CH=CH-Pyridyl(3') | |
| 15.012 | N | Me | Me | Me | Me | OMe | 4-$C_6H_4$—CH=CH—CO-Pyridyl(3') | |
| 15.013 | N | Me | Me | Me | Me | OMe | 4-$C_6H_4$—CH=CH-Pyridyl(2') | |
| 15.014 | N | Me | Me | Me | Me | OMe | 4-$C_6H_4$—CH=CH-Pyridyl(4') | |
| 15.015 | N | Me | Me | Me | Me | OMe | 4-$C_6H_4$—CH=CH—$C_6H_4$($CF_3$)(4') | |
| 15.016 | N | Me | Me | Me | Me | OMe | 4-$C_6H_4$—CH=CH—$C_6H_4$(Cl)(4') | |
| 15.017 | N | Me | Me | Me | Me | OMe | 4-$C_6H_4$—CH=CH—$CH_2$—OH | |
| 15.018 | N | Me | Me | Me | Me | OMe | 4-$C_6H_4$—CH=CH-Pyrimidinyl(2') | |
| 15.019 | N | Me | Me | Me | Me | OMe | 4-$C_6H_4$—CH=CH-Pyrimidinyl(4') | |
| 15.020 | N | Me | Me | Me | Me | OMe | 4-$C_6H_4$—CH=CH-Pyrimidinyl(5') | |
| 15.021 | N | Me | Me | Me | Me | OMe | 4-$C_6H_4$—CH=CH—I | |
| 15.022 | N | Me | Me | Me | Me | OMe | 4-$C_6H_4$—CH=CH—$CH_3$ | |
| 15.023 | N | Me | Me | Me | Me | OMe | 4-$C_6H_4$—CH=CH—Br | |
| 15.024 | N | Me | Me | Me | Me | OMe | 4-$C_6H_4$—CH=CH—$C_6H_4$(Br)(4') | |
| 15.025 | N | Me | Me | Me | Me | OMe | 4-$C_6H_4$—CH=CH—$C_6H_2$($OCH_3$)$_3$(3',4',5') | |
| 15.026 | N | Me | Me | Me | Me | OMe | 4-$C_6H_4$—CH=CH—$C_6H_3$($CH_3$)$_2$(3',5') | |
| 15.027 | N | Me | Me | Me | Me | OMe | 4-$C_6H_4$—CH=CH-Thiazolyl(2') | |
| 15.028 | N | Me | Me | Me | Me | OMe | 4-$C_6H_4$—CH=CH-Oxazolyl(2') | |
| 15.029 | N | Me | Me | Me | Me | OMe | 4-$C_6H_4$—CH=CH-Thienyl(2') | |
| 15.030 | N | Me | Me | Me | Me | OMe | 4-$C_6H_4$—CH=CH-Thienyl(3') | |
| 15.031 | N | Me | Me | Me | Me | OMe | 4-$C_6H_4$—CH=CH—Et | |
| 15.032 | N | Me | Me | Me | Me | OMe | 3-$C_6H_4$—CH=CH2 | |
| 15.033 | N | Me | Me | Me | Me | OMe | 2-$C_6H_4$—CH=CH2 | |
| 15.034 | N | Me | Me | Me | Me | OMe | 3-$C_6H_4$—CH=CH—$CH_3$ | |
| 15.035 | N | Me | Me | Me | Me | OMe | 2-$C_6H_4$—CH=CH—Br | |
| 15.036 | N | Me | Me | Me | Me | OMe | 2-$C_6H_4$—CH=CH—C($CH_3$)$_2$—OH | |
| 15.037 | N | Me | Me | Me | Me | OMe | 3-$C_6H_4$—CH=CH—($CH_3$)$_2$—OH | |
| 15.038 | N | Me | Me | Me | Me | OMe | 4-$C_6H_4$—CH=CH—$CF_3$ | |
| 15.039 | N | Me | Me | Me | Me | OMe | 4-$C_6H_4$—CH=CH—COOEt | |
| 15.040 | N | Me | Me | Me | Me | OMe | 4-$C_6H_4$—CH=CH—COOMe | |
| 15.041 | N | Me | Me | Me | Me | OMe | 2-$C_6H_4$—CH=CH—C($CH_3$)$_2$—OH | |
| 15.042 | N | Me | Me | Me | Me | OMe | 4-$C_6H_4$—CH=CH—C($CH_3$)$_2$—O—$CH_3$ | |
| 15.043 | N | Me | Me | Me | Me | OMe | 3-$C_6H_4$—CH=CH—C($CH_3$)$_2$—O—$CH_3$ | |
| 15.044 | N | Me | Me | Me | Me | OMe | 4-$C_6H_4$—CH=CH—$CH_2$—OMe | |
| 15.045 | N | Me | Me | Me | Me | OMe | 4-$C_6H_4$—CH=CH—$C_4H_9$(n) | |
| 15.046 | N | Me | Me | Me | Me | OMe | 4-$C_6H_4$—CH=CH—$C_3H_7$(n) | |
| 15.047 | N | Me | Me | Me | Me | OMe | 4-$C_6H_4$—CH=CH—$C_8H_{17}$(n) | |
| 15.048 | N | Me | Me | Me | Me | NHMe | 4-$C_6H_4$—CH=CH—$C_6H_3Cl_2$(2',4') | |
| 15.049 | N | Me | Me | Me | Me | NHMe | 4-$C_6H_4$—CH=CH—$C_6H_5$ | |
| 15.050 | N | Me | Me | Me | Me | NHMe | 4-$C_6H_4$—CH=CH—$C_6H_4$($OCH_3$)(4') | |
| 15.051 | N | Me | Me | Me | Me | NHMe | 4-$C_6H_4$—CH=CH—$C_6H_3$($CF_3$)(3',5') | |
| 15.052 | N | Me | Me | Me | Me | NHMe | 4-$C_6H_4$—CH=CH—$C_6H_4$($CF_3$)(3') | |
| 15.053 | N | Me | Me | Me | Me | NHMe | 4-$C_6H_4$—CH=CH—CO—$C_6H_4$($CF_3$)(3') | |
| 15.054 | N | Me | Me | Me | Me | NHMe | 4-$C_6H_4$—CH=CH—CO—$C_6H_5$ | |
| 15.055 | N | Me | Me | Me | Me | NHMe | 4-$C_6H_4$—CH=CH—CO—$C_6H_4$(Cl)(3') | |
| 15.056 | N | Me | Me | Me | Me | NHMe | 4-$C_6H_4$—CH=CH—C($CH_3$)$_2$—OH | |
| 15.057 | N | Me | Me | Me | Me | NHMe | 4-$C_6H_4$—CH=CH-Pyrazinyl(2') | |
| 15.058 | N | Me | Me | Me | Me | NHMe | 4-$C_6H_4$—CH=CH-Pyridyl(3') | |
| 15.059 | N | Me | Me | Me | Me | NHMe | 4-$C_6H_4$—CH=CH—CO-Pyridyl(3') | |
| 15.060 | N | Me | Me | Me | Me | NHMe | 4-$C_6H_4$—CH=CH-Pyridyl(2') | |
| 15.061 | N | Me | Me | Me | Me | NHMe | 4-$C_6H_4$—CH=CH-Pyridyl(4') | |
| 15.062 | N | Me | Me | Me | Me | NHMe | 4-$C_6H_4$—CH=CH—$C_6H_4$($CF_3$)(4') | |

TABLE 15-continued

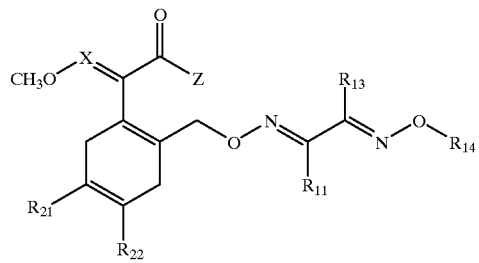

| Ex. Nr. | X | R11 | R14 | R21 | R22 | Z | R13 | Phys. Data |
|---|---|---|---|---|---|---|---|---|
| 15.063 | N | Me | Me | Me | Me | NHMe | 4-C$_6$H$_4$—CH=CH—C$_6$H$_4$(Cl)(4') | |
| 15.064 | N | Me | Me | Me | Me | NHMe | 4-C$_6$H$_4$—CH=CH—CH$_2$—OH | |
| 15.065 | N | Me | Me | Me | Me | NHMe | 4-C$_6$H$_4$—CH=CH-Pyrimidinyl(2') | |
| 15.066 | N | Me | Me | Me | Me | NHMe | 4-C$_6$H$_4$—CH=CH-Pyrimidinyl(4') | |
| 15.067 | N | Me | Me | Me | Me | NHMe | 4-C$_6$H$_4$—CH=CH-Pyrimidinyl(5') | |
| 15.068 | N | Me | Me | Me | Me | NHMe | 4-C$_6$H$_4$—CH=CH—I | |
| 15.069 | N | Me | Me | Me | Me | NHMe | 4-C$_6$H$_4$—CH=CH—CH$_3$ | |
| 15.070 | N | Me | Me | Me | Me | NHMe | 4-C$_6$H$_4$—CH=CH—Br | |
| 15.071 | N | Me | Me | Me | Me | NHMe | 4-C$_6$H$_4$—CH=CH—C$_6$H$_4$(Br)(4') | |
| 15.072 | N | Me | Me | Me | Me | NHMe | 4-C$_6$H$_4$—CH=CH—C$_6$H$_2$(OCH$_3$)$_3$(3',4',5') | |
| 15.073 | N | Me | Me | Me | Me | NHMe | 4-C$_6$H$_4$—CH=CH—C$_6$H$_3$(CH$_3$)$_2$(3',5') | |
| 15.074 | N | Me | Me | Me | Me | NHMe | 4-C$_6$H$_4$—CH=CH-Thiazolyl(2') | |
| 15.075 | N | Me | Me | Me | Me | NHMe | 4-C$_6$H$_4$—CH=CH-Oxazolyl(2') | |
| 15.076 | N | Me | Me | Me | Me | NHMe | 4-C$_6$H$_4$—CH=CH-Thienyl(2') | |
| 15.077 | N | Me | Me | Me | Me | NHMe | 4-C$_6$H$_4$—CH=CH-Thienyl(3') | |
| 15.078 | N | Me | Me | Me | Me | NHMe | 4-C$_6$H$_4$—CH=CH—Et | |
| 15.079 | N | Me | Me | Me | Me | NHMe | 3-C$_6$H$_4$—CH=CH$_2$ | |
| 15.080 | N | Me | Me | Me | Me | NHMe | 2-C$_6$H$_4$—CH=CH$_2$ | |
| 15.081 | N | Me | Me | Me | Me | NHMe | 3-C$_6$H$_4$—CH=CH—CH$_3$ | |
| 15.082 | N | Me | Me | Me | Me | NHMe | 2-C$_6$H$_4$—CH=CH—Br | |
| 15.083 | N | Me | Me | Me | Me | NHMe | 2-C$_6$H$_4$—CH=CH—C(CH$_3$)$_2$—OH | |
| 15.084 | N | Me | Me | Me | Me | NHMe | 3-C$_6$H$_4$—CH=CH—C(CH$_3$)$_2$—OH | |
| 15.085 | N | Me | Me | Me | Me | NHMe | 4-C$_6$H$_4$—CH=CH—CF$_3$ | |
| 15.086 | N | Me | Me | Me | Me | NHMe | 4-C$_6$H$_4$—CH=CH—COOEt | |
| 15.087 | N | Me | Me | Me | Me | NHMe | 4-C$_6$H$_4$—CH=CH—COOMe | |
| 15.088 | N | Me | Me | Me | Me | NHMe | 2-C$_6$H$_4$—CH=CH—C(CH$_3$)$_2$—OH | |
| 15.089 | N | Me | Me | Me | Me | NHMe | 4-C$_6$H$_4$—CH=CH—C(CH$_3$)$_2$—O—CH$_3$ | |
| 15.090 | N | Me | Me | Me | Me | NHMe | 3-C$_6$H$_4$—CH=CH—C(CH$_3$)$_2$—O—CH$_3$ | |
| 15.091 | N | Me | Me | Me | Me | NHMe | 4-C$_6$H$_4$—CH=CH—CH$_2$—OMe | |
| 15.092 | N | Me | Me | Me | Me | NHMe | 4-C$_6$H$_4$—CH=CH—C$_4$H$_9$(n) | |
| 15.093 | N | Me | Me | Me | Me | NHMe | 4-C$_6$H$_4$—CH=CH—C$_3$H$_7$(n) | |
| 15.094 | N | Me | Me | Me | Me | NHMe | 4-C$_6$H$_4$—CH=CH—C$_8$H$_{11}$(n) | |

TABLE 16

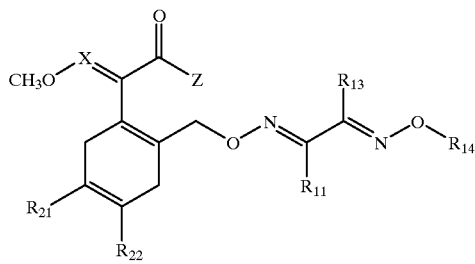

| Ex. Nr. | X | R11 | R14 | R21 | R22 | Z | R13 | Phys. Data |
|---|---|---|---|---|---|---|---|---|
| 16.001 | N | Me | Me | Me | Me | OMe | 4-C$_{64}$—CH2—CH2—C$_6$H$_3$Cl$_2$(2',4') | |
| 16.002 | N | Me | Me | Me | Me | OMe | 4-C$_{64}$—CH2—CH2—C$_6$H$_5$ | |
| 16.003 | N | Me | Me | Me | Me | OMe | 4-C$_{64}$—CH2—CH2—C$_6$H$_4$(OCH$_3$)(4') | |
| 16.004 | N | Me | Me | Me | Me | OMe | 4-C$_{64}$—CH2—CH2—C$_6$H$_3$(CF$_3$)(3',5') | |
| 16.005 | N | Me | Me | Me | Me | OMe | 4-C$_{64}$—CH2—CH2—C$_6$H$_4$(CF$_3$)(3') | |
| 16.006 | N | Me | Me | Me | Me | OMe | 4-C$_{64}$—CH2—CH2—CO—C$_6$H$_4$(CF$_3$)(3') | |
| 16.007 | N | Me | Me | Me | Me | OMe | 4-C$_{64}$—CH2—CH2—CO—C$_6$H$_5$ | |

TABLE 16-continued

| Ex. Nr. | X | R11 | R14 | R21 | R22 | Z | R13 | Phys. Data |
|---|---|---|---|---|---|---|---|---|
| 16.008 | N | Me | Me | Me | Me | OMe | 4-$C_{64}$—CH2—CH2—CO—$C_6H_4$(Cl)(3') | |
| 16.009 | N | Me | Me | Me | Me | OMe | 4-$C_{64}$—CH2—CH2—C(CH$_3$)$_2$—OH | |
| 16.010 | N | Me | Me | Me | Me | OMe | 4-$C_{64}$—CH2—CH2—Pyrazinyl(2') | |
| 16.011 | N | Me | Me | Me | Me | OMe | 4-$C_{64}$—CH2—CH2—Pyridyl(3') | |
| 16.012 | N | Me | Me | Me | Me | OMe | 4-$C_{64}$—CH2—CH2—CO-Pyridyl(3') | |
| 16.013 | N | Me | Me | Me | Me | OMe | 4-$C_{64}$—CH2—CH2—Pyridyl(2') | |
| 16.014 | N | Me | Me | Me | Me | OMe | 4-$C_{64}$—CH2—CH2—Pyridyl(4') | |
| 16.015 | N | Me | Me | Me | Me | OMe | 4-$C_{64}$—CH2—CH2—$C_6H_4$(CF$_3$)(4') | |
| 16.016 | N | Me | Me | Me | Me | OMe | 4-$C_{64}$—CH2—CH2—$C_6H_4$(Cl)(4') | |
| 16.017 | N | Me | Me | Me | Me | OMe | 4-$C_{64}$—CH2—CH2—CH$_2$—OH | |
| 16.018 | N | Me | Me | Me | Me | OMe | 4-$C_{64}$—CH2—CH2—Pyrimidinyl(2') | |
| 16.019 | N | Me | Me | Me | Me | OMe | 4-$C_{64}$—CH2—CH2—Pyrimidinyl(4') | |
| 16.020 | N | Me | Me | Me | Me | OMe | 4-$C_{64}$—CH2—CH2—Pyrimidinyl(5') | |
| 16.021 | N | Me | Me | Me | Me | OMe | 4-$C_{64}$—CH2—CH2—I | |
| 16.022 | N | Me | Me | Me | Me | OMe | 4-$C_{64}$—CH2—CH2—CH$_3$ | |
| 16.023 | N | Me | Me | Me | Me | OMe | 4-$C_{64}$—CH2—CH2—Br | |
| 16.024 | N | Me | Me | Me | Me | OMe | 4-$C_{64}$—CH2—CH2—$C_6H_4$(Br)(4') | |
| 16.025 | N | Me | Me | Me | Me | OMe | 4-$C_{64}$—CH2—CH2—$C_6H_2$(OCH$_3$)$_3$(3',4',5') | |
| 16.026 | N | Me | Me | Me | Me | OMe | 4-$C_{64}$—CH2—CH2—$C_6H2_3$(CH$_3$)$_2$(3',5') | |
| 16.027 | N | Me | Me | Me | Me | OMe | 4-$C_{64}$—CH2—CH2-Thiazolyl(2') | |
| 16.028 | N | Me | Me | Me | Me | OMe | 4-$C_{64}$—CH2—CH2-Oxazolyl(2') | |
| 16.029 | N | Me | Me | Me | Me | OMe | 4-$C_{64}$—CH2—CH2-Thienyl(2') | |
| 16.030 | N | Me | Me | Me | Me | OMe | 4-$C_{64}$—CH2—CH2-Thienyl(3') | |
| 16.031 | N | Me | Me | Me | Me | OMe | 4-$C_{64}$—CH2—CH2—Et | |
| 16.032 | N | Me | Me | Me | Me | OMe | 3-$C_{64}$—CH2—CH3 | |
| 16.033 | N | Me | Me | Me | Me | OMe | 2-$C_{64}$—CH2—CH3 | |
| 16.034 | N | Me | Me | Me | Me | OMe | 3-$C_{64}$—CH2—CH2—CH$_3$ | |
| 16.035 | N | Me | Me | Me | Me | OMe | 2-$C_{64}$—CH2—CH2—Br | |
| 16.036 | N | Me | Me | Me | Me | OMe | 2-$C_{64}$—CH2—CH2—C(CH$_3$)$_2$—OH | |
| 16.037 | N | Me | Me | Me | Me | OMe | 3-$C_{64}$—CH2—CH2—C(CH$_3$)$_2$—OH | |
| 16.038 | N | Me | Me | Me | Me | OMe | 4-$C_{64}$—CH2—CH2—CF$_3$ | |
| 16.039 | N | Me | Me | Me | Me | OMe | 4-$C_{64}$—CH2—CH2—COOEt | |
| 16.040 | N | Me | Me | Me | Me | OMe | 4-$C_{64}$—CH2—CH2—COOMe | |
| 16.041 | N | Me | Me | Me | Me | OMe | 2-$C_{64}$—CH2—CH2—C(CH$_3$)$_2$—OH | |
| 16.042 | N | Me | Me | Me | Me | OMe | 4-$C_{64}$—CH2—CH2—C(CH$_3$)$_2$—O—CH$_3$ | |
| 16.043 | N | Me | Me | Me | Me | OMe | 3-$C_{64}$—CH2—CH2—C(CH$_3$)$_2$—O—CH$_3$ | |
| 16.044 | N | Me | Me | Me | Me | OMe | 4-$C_{64}$—CH2—CH2—OMe | |
| 16.045 | N | Me | Me | Me | Me | OMe | 4-$C_{64}$—CH2—CH2—$C_4H_9$(n) | |
| 16.046 | N | Me | Me | Me | Me | OMe | 4-$C_{64}$—CH2—CH2—$C_3H_7$(n) | |
| 16.047 | N | Me | Me | Me | Me | OMe | 4-$C_{64}$—CH2—CH2—$C_8H_{17}$(n) | |
| 16.048 | N | Me | Me | Me | Me | NHMe | 4-$C_{64}$—CH2—CH2—$C_6H_3Cl_2$(2',4') | |
| 16.049 | N | Me | Me | Me | Me | NHMe | 4-$C_{64}$—CH2—CH2—$C_6H_5$ | |
| 16.050 | N | Me | Me | Me | Me | NHMe | 4-$C_{64}$—CH2—CH2—$C_6H_4$(OCH$_3$)(4') | |
| 16.051 | N | Me | Me | Me | Me | NHMe | 4-$C_{64}$—CH2—CH2—$C_6H_3$(CF$_3$)(3',5') | |
| 16.052 | N | Me | Me | Me | Me | NHMe | 4-$C_{64}$—CH2—CH2—$C_6H_4$(CF$_3$)(3') | |
| 16.053 | N | Me | Me | Me | Me | NHMe | 4-$C_{64}$—CH2—CH2—CO—$C_6H_4$(CF$_3$)(3') | |
| 16.054 | N | Me | Me | Me | Me | NHMe | 4-$C_{64}$—CH2—CH2—CO-$C_6H_5$ | |
| 16.055 | N | Me | Me | Me | Me | NHMe | 4-$C_{64}$—CH2—CH2—CO-$C_6H_4$(Cl)(3') | |
| 16.056 | N | Me | Me | Me | Me | NHMe | 4-$C_{64}$—CH2—CH2—C(CH$_3$)$_2$—OH | |
| 16.057 | N | Me | Me | Me | Me | NHMe | 4-$C_{64}$—CH2—CH2—Pyrazinyl(2') | |
| 16.058 | N | Me | Me | Me | Me | NHMe | 4-$C_{64}$—CH2—CH2—Pyridyl(3') | |
| 16.059 | N | Me | Me | Me | Me | NHMe | 4-$C_{64}$—CH2—CH2—CO-Pyridyl(3') | |
| 16.060 | N | Me | Me | Me | Me | NHMe | 4-$C_{64}$—CH2—CH2—Pyridyl(2') | |
| 16.061 | N | Me | Me | Me | Me | NHMe | 4-$C_{64}$—CH2—CH2—Pyridyl(4') | |
| 16.062 | N | Me | Me | Me | Me | NHMe | 4-$C_{64}$—CH2—CH2—$C_6H_4$(CF$_3$)(4') | |
| 16.063 | N | Me | Me | Me | Me | NHMe | 4-$C_{64}$—CH2—CH2—$C_6H_4$(Cl)(4') | |
| 16.064 | N | Me | Me | Me | Me | NHMe | 4-$C_{64}$—CH2—CH2—CH2—OH | |
| 16.065 | N | Me | Me | Me | Me | NHMe | 4-$C_{64}$—CH2—CH2—Pyrimidinyl(2') | |
| 16.066 | N | Me | Me | Me | Me | NHMe | 4-$C_{64}$—CH2—CH2—Pyrimidinyl(4') | |
| 16.067 | N | Me | Me | Me | Me | NHMe | 4-$C_{64}$—CH2—CH2—Pyrimidinyl(5') | |
| 16.068 | N | Me | Me | Me | Me | NHMe | 4-$C_{64}$—CH2—CH2—I | |

TABLE 16-continued

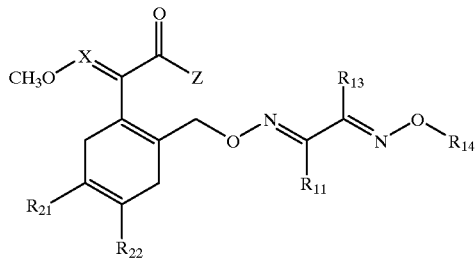

| Ex. Nr. | X | R11 | R14 | R21 | R22 | Z | R13 | Phys. Data |
|---|---|---|---|---|---|---|---|---|
| 16.069 | N | Me | Me | Me | Me | NHMe | 4-C$_{64}$—CH2—CH2—CH$_3$ | |
| 16.070 | N | Me | Me | Me | Me | NHMe | 4-C$_{64}$—CH2—CH2—Br | |
| 16.071 | N | Me | Me | Me | Me | NHMe | 4-C$_{64}$—CH2—CH2—C$_6$H$_4$(Br)(4') | |
| 16.072 | N | Me | Me | Me | Me | NHMe | 4-C$_{64}$—CH2—CH2—C$_6$H$_2$(OCH$_3$)$_3$(3',4',5') | |
| 16.073 | N | Me | Me | Me | Me | NHMe | 4-C$_{64}$—CH2—CH2—C$_6$H$_3$(CH$_3$)$_2$(3',5') | |
| 16.074 | N | Me | Me | Me | Me | NHMe | 4-C$_{64}$—CH2—CH2-Thiazolyl(2') | |
| 16.075 | N | Me | Me | Me | Me | NHMe | 4-C$_{64}$—CH2—CH2-Oxazolyl(2') | |
| 16.076 | N | Me | Me | Me | Me | NHMe | 4-C$_{64}$—CH2—CH2-Thienyl(2') | |
| 16.077 | N | Me | Me | Me | Me | NHMe | 4-C$_{64}$—CH2—CH2-Thienyl(3') | |
| 16.078 | N | Me | Me | Me | Me | NHMe | 4-C$_{64}$—CH2—CH2—Et | |
| 16.079 | N | Me | Me | Me | Me | NHMe | 3-C$_{64}$—CH2—CH3 | |
| 16.080 | N | Me | Me | Me | Me | NHMe | 2-C$_{64}$—CH2—CH3 | |
| 16.081 | N | Me | Me | Me | Me | NHMe | 3-C$_{64}$—CH2—CH2—CH$_3$ | |
| 16.082 | N | Me | Me | Me | Me | NHMe | 2-C$_{64}$—CH2—CH2—Br | |
| 16.083 | N | Me | Me | Me | Me | NHMe | 2-C$_{64}$—CH2—CH2—C(CH$_3$)$_2$—OH | |
| 16.084 | N | Me | Me | Me | Me | NHMe | 3-C$_{64}$—CH2—CH2—C(CH$_3$)$_2$—OH | |
| 16.085 | N | Me | Me | Me | Me | NHMe | 4-C$_{64}$—CH2—CH2—CF$_3$ | |
| 16.086 | N | Me | Me | Me | Me | NHMe | 4-C$_{64}$—CH2—CH2—COOEt | |
| 16.087 | N | Me | Me | Me | Me | NHMe | 4-C$_{64}$—CH2—CH2—COOMe | |
| 16.088 | N | Me | Me | Me | Me | NHMe | 2-C$_{64}$—CH2—CH2—C(CH$_3$)$_2$—OH | |
| 16.089 | N | Me | Me | Me | Me | NHMe | 4-C$_{64}$—CH2—CH2—C(CH$_3$)$_2$—O—CH$_3$ | |
| 16.090 | N | Me | Me | Me | Me | NHMe | 3-C$_{64}$—CH2—CH2—C(CH$_3$)$_2$—O—CH$_3$ | |
| 16.091 | N | Me | Me | Me | Me | NHMe | 4-C$_{64}$—CH2—CH2—CH$_2$—OMe | |
| 16.092 | N | Me | Me | Me | Me | NHMe | 4-C$_{64}$—CH2—CH2—C$_4$H$_9$(n) | |
| 16.093 | N | Me | Me | Me | Me | NHMe | 4-C$_{64}$—CH2—CH2—C$_3$H$_7$(n) | |
| 16.094 | N | Me | Me | Me | Me | NHMe | 4-C$_{64}$—CH2—CH2—C$_8$H$_{17}$(n) | |

TABLE 17

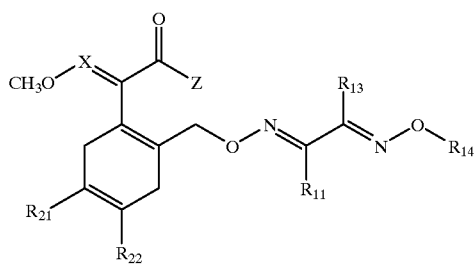

| Ex. Nr. | X | R11 | R14 | R21 | R22 | Z | R13 | Phys. Data |
|---|---|---|---|---|---|---|---|---|
| 17.001 | N | Me | Me | Me | Me | OMe | 4-C$_6$H$_4$—O—CH2—C$_6$H$_3$Cl$_2$(2',4') | |
| 17.002 | N | Me | Me | Me | Me | OMe | 4-C$_6$H$_4$—O—CH2—C$_6$H$_5$ | |
| 17.003 | N | Me | Me | Me | Me | OMe | 4-C$_6$H$_4$—O—CH2—C$_6$H$_4$(OCH$_3$)(4') | |
| 17.004 | N | Me | Me | Me | Me | OMe | 4-C$_6$H$_4$—O—CH2—C$_6$H$_3$(CF$_3$)$_2$(3',5') | |
| 17.005 | N | Me | Me | Me | Me | OMe | 4-C$_6$H$_4$—O—CH2—C$_6$H$_4$(CF$_3$)(3') | |
| 17.006 | N | Me | Me | Me | Me | OMe | 4-C$_6$H$_4$—O—CH2—CO—C$_6$H$_4$(CF$_3$)(3') | |
| 17.007 | N | Me | Me | Me | Me | OMe | 4-C$_6$H$_4$—O—CH2—CO—C$_6$H$_5$ | |
| 17.008 | N | Me | Me | Me | Me | OMe | 4-C$_6$H$_4$—O—CH2—CO—C$_6$H$_4$(Cl)(3') | |
| 17.009 | N | Me | Me | Me | Me | OMe | 4-C$_6$H$_4$—O—CH2—C(CH$_3$)$_2$—OH | |
| 17.010 | N | Me | Me | Me | Me | OMe | 4-C$_6$H$_4$—O—CH2-Pyrazinyl(2') | |
| 17.011 | N | Me | Me | Me | Me | OMe | 4-C$_6$H$_4$—O—CH2-Pyridyl(3') | |
| 17.012 | N | Me | Me | Me | Me | OMe | 4-C$_6$H$_4$—O—CH2—CO-Pyridyl(3') | |
| 17.013 | N | Me | Me | Me | Me | OMe | 4-C$_6$H$_4$—O—CH2-Pyridyl(2') | |

TABLE 17-continued

| Ex. Nr. | X | R11 | R14 | R21 | R22 | Z | R13 | Phys. Data |
|---|---|---|---|---|---|---|---|---|
| 17.014 | N | Me | Me | Me | Me | OMe | 4-$C_6H_4$—O—CH2—Pyridyl(4') | |
| 17.015 | N | Me | Me | Me | Me | OMe | 4-$C_6H_4$—O—CH2—$C_6H_4(CF_3)$(4') | |
| 17.016 | N | Me | Me | Me | Me | OMe | 4-$C_6H_4$—O—CH2—$C_6H_4(Cl)$(4') | |
| 17.017 | N | Me | Me | Me | Me | OMe | 4-$C_6H_4$—O—CH2—$CH_2$—OH | |
| 17.018 | N | Me | Me | Me | Me | OMe | 4-$C_6H_4$—O—CH2—Pyrimidinyl(2') | |
| 17.019 | N | Me | Me | Me | Me | OMe | 4-$C_6H_4$—O—CH2—Pyrimidinyl(4') | |
| 17.020 | N | Me | Me | Me | Me | OMe | 4-$C_6H_4$—O—CH2—Pyrimidinyl(5') | |
| 17.021 | N | Me | Me | Me | Me | OMe | 4-$C_6H_4$—O—CH2—I | |
| 17.022 | N | Me | Me | Me | Me | OMe | 4-$C_6H_4$—O—CH2—$CH_3$ | |
| 17.023 | N | Me | Me | Me | Me | OMe | 4-$C_6H_4$—O—CH2—Br | |
| 17.024 | N | Me | Me | Me | Me | OMe | 4-$C_6H_4$—O—CH2—$C_6H_4(Br)$(4') | |
| 17.025 | N | Me | Me | Me | Me | OMe | 4-$C_6H_4$—O—CH2—$C_6H_2(OCH_3)_3$(3',4',5') | |
| 17.026 | N | Me | Me | Me | Me | OMe | 4-$C_6H_4$—O—CH2—$C_6H_3(CH_3)_2$(3',5') | |
| 17.027 | N | Me | Me | Me | Me | OMe | 4-$C_6H_4$—O—CH2-Thiazolyl(2') | |
| 17.028 | N | Me | Me | Me | Me | OMe | 4-$C_6H_4$—O—CH2-Oxazolyl(2') | |
| 17.029 | N | Me | Me | Me | Me | OMe | 4-$C_6H_4$—O—CH2-Thienyl(2') | |
| 17.030 | N | Me | Me | Me | Me | OMe | 4-$C_6H_4$—O—CH2-Thienyl(3') | |
| 17.031 | N | Me | Me | Me | Me | OMe | 4-$C_6H_4$—O—CH2—Et | |
| 17.032 | N | Me | Me | Me | Me | OMe | 3-$C_6H_4$—O—CH3 | |
| 17.033 | N | Me | Me | Me | Me | OMe | 2-$C_6H_4$—O—CH3 | |
| 17.034 | N | Me | Me | Me | Me | OMe | 3-$C_6H_4$—O—CH2—CH3 | |
| 17.035 | N | Me | Me | Me | Me | OMe | 2-$C_6H_4$—O—CH2—Br | |
| 17.036 | N | Me | Me | Me | Me | OMe | 2-$C_6H_4$—O—CH2—$C(CH_3)_2$—OH | |
| 17.037 | N | Me | Me | Me | Me | OMe | 3-$C_6H_4$—O—CH2—$(CH_3)_2$—OH | |
| 17.038 | N | Me | Me | Me | Me | OMe | 4-$C_6H_4$—O—CH2—$CF_3$ | |
| 17.039 | N | Me | Me | Me | Me | OMe | 4-$C_6H_4$—O—CH2—COOEt | |
| 17.040 | N | Me | Me | Me | Me | OMe | 4-$C_6H_4$—O—CH2—COOMe | |
| 17.041 | N | Me | Me | Me | Me | OMe | 2-$C_6H_4$—O—CH2—$C(CH_3)_2$—OH | |
| 17.042 | N | Me | Me | Me | Me | OMe | 4-$C_6H_4$—O—CH2—$C(CH_3)_2$—O—$CH_3$ | |
| 17.043 | N | Me | Me | Me | Me | OMe | 3-$C_6H_4$—O—CH2—$C(CH_3)_2$—O—$CH_3$ | |
| 17.044 | N | Me | Me | Me | Me | OMe | 4-$C_6H_4$—O—CH2—$CH_2$—OMe | |
| 17.045 | N | Me | Me | Me | Me | OMe | 4-$C_6H_4$—O—CH2—$C_4H_9$(n) | |
| 17.046 | N | Me | Me | Me | Me | OMe | 4-$C_6H_4$—O—CH2—$C_3H_7$(n) | |
| 17.047 | N | Me | Me | Me | Me | OMe | 4-$C_6H_4$—O—CH2—$C_8H_{17}$(n) | |
| 17.048 | N | Me | Me | Me | Me | NHMe | 4-$C_6H_4$—O—CH2—$C_6H_3Cl_2$(2',4') | |
| 17.049 | N | Me | Me | Me | Me | NHMe | 4-$C_6H_4$—O—CH2—$C_6H_5$ | |
| 17.050 | N | Me | Me | Me | Me | NHMe | 4-$C_6H_4$—O—CH2—$C_6H_4(OCH_3)$(4') | |
| 17.051 | N | Me | Me | Me | Me | NHMe | 4-$C_6H_4$—O—CH2—$C_6H_3(CF_3)$(3',5') | |
| 17.052 | N | Me | Me | Me | Me | NHMe | 4-$C_6H_4$—O—CH2—$C_6H_4(CF_3)$(3') | |
| 17.053 | N | Me | Me | Me | Me | NHMe | 4-$C_6H_4$—O—CH2—CO—$C_6H_4(CF_3)$(3') | |
| 17.054 | N | Me | Me | Me | Me | NHMe | 4-$C_6H_4$—O—CH2—CO—$C_6H_5$ | |
| 17.055 | N | Me | Me | Me | Me | NHMe | 4-$C_6H_4$—O—CH2—CO—$C_6H_4(Cl)$(3') | |
| 17.056 | N | Me | Me | Me | Me | NHMe | 4-$C_6H_4$—O—CH2—$C(CH_3)_2$—OH | |
| 17.057 | N | Me | Me | Me | Me | NHMe | 4-$C_6H_4$—O—CH2—Pyrazinyl(2') | |
| 17.058 | N | Me | Me | Me | Me | NHMe | 4-$C_6H_4$—O—CH2—Pyridyl(3') | |
| 17.059 | N | Me | Me | Me | Me | NHMe | 4-$C_6H_4$—O—CH2—CO-Pyridyl(3') | |
| 17.060 | N | Me | Me | Me | Me | NHMe | 4-$C_6H_4$—O—CH2—Pyridyl(2') | |
| 17.061 | N | Me | Me | Me | Me | NHMe | 4-$C_6H_4$—O—CH2—Pyridyl(4') | |
| 17.062 | N | Me | Me | Me | Me | NHMe | 4-$C_6H_4$—O—CH2—$C_6H_4(CF_3)$(4') | |
| 17.063 | N | Me | Me | Me | Me | NHMe | 4-$C_6H_4$—O—CH2—$C_6H_4(Cl)$(4') | |
| 17.064 | N | Me | Me | Me | Me | NHMe | 4-$C_6H_4$—O—CH2—$CH_2$—OH | |
| 17.065 | N | Me | Me | Me | Me | NHMe | 4-$C_6H_4$—O—CH2—Pyrimidinyl(2') | |
| 17.066 | N | Me | Me | Me | Me | NHMe | 4-$C_6H_4$—O—CH2—Pyrimidinyl(4') | |
| 17.067 | N | Me | Me | Me | Me | NHMe | 4-$C_6H_4$—O—CH2—Pyrimidinyl(5') | |
| 17.068 | N | Me | Me | Me | Me | NHMe | 4-$C_6H_4$—O—CH2—I | |
| 17.069 | N | Me | Me | Me | Me | NHMe | 4-$C_6H_4$—O—CH2—$CH_3$ | |
| 17.070 | N | Me | Me | Me | Me | NHMe | 4-$C_6H_4$—O—CH2—Br | |
| 17.071 | N | Me | Me | Me | Me | NHMe | 4-$C_6H_4$—O—CH2—$C_6H_4(Br)$(4') | |
| 17.072 | N | Me | Me | Me | Me | NHMe | 4-$C_6H_4$—O—CH2—$C_6H_2(OCH_3)_3$(3',4',5') | |
| 17.073 | N | Me | Me | Me | Me | NHMe | 4-$C_6H_4$—O—CH2—$C_6H_3(CH_3)_2$(3',5') | |
| 17.074 | N | Me | Me | Me | Me | NHMe | 4-$C_6H_4$—O—CH2-Thiazolyl(2') | |

TABLE 17-continued

| Ex. Nr. | X | R11 | R14 | R21 | R22 | Z | R13 | Phys. Data |
|---|---|---|---|---|---|---|---|---|
| 17.075 | N | Me | Me | Me | Me | NHMe | 4-C$_6$H$_4$—O—CH2-Oxazolyl(2') | |
| 17.076 | N | Me | Me | Me | Me | NHMe | 4-C$_6$H$_4$—O—CH2-Thienyl(2') | |
| 17.077 | N | Me | Me | Me | Me | NHMe | 4-C$_6$H$_4$—O—CH2-Thienyl(3') | |
| 17.078 | N | Me | Me | Me | Me | NHMe | 4-C$_6$H$_4$—O—CH2—Et | |
| 17.079 | N | Me | Me | Me | Me | NHMe | 3-C$_6$H$_4$—O—CH3 | |
| 17.080 | N | Me | Me | Me | Me | NHMe | 2-C$_6$H$_4$—O—CH3 | |
| 17.081 | N | Me | Me | Me | Me | NHMe | 3-C$_6$H$_4$—O—CH2—CH3 | |
| 17.082 | N | Me | Me | Me | Me | NHMe | 2-C$_6$H$_4$—O—CH2—Br | |
| 17.083 | N | Me | Me | Me | Me | NHMe | 2-C$_6$H$_4$—O—CH2—C(CH$_3$)$_2$—OH | |
| 17.084 | N | Me | Me | Me | Me | NHMe | 3-C$_6$H$_4$—O—CH2—C(CH$_3$)$_2$—OH | |
| 17.085 | N | Me | Me | Me | Me | NHMe | 4-C$_6$H$_4$—O—CH2—CF$_3$ | |
| 17.086 | N | Me | Me | Me | Me | NHMe | 4-C$_6$H$_4$—O—CH2—COOEt | |
| 17.087 | N | Me | Me | Me | Me | NHMe | 4-C$_6$H$_4$—O—CH2—COOMe | |
| 17.088 | N | Me | Me | Me | Me | NHMe | 2-C$_6$H$_4$—O—CH2—C(CH$_3$)$_2$—OH | |
| 17.089 | N | Me | Me | Me | Me | NHMe | 4-C$_6$H$_4$—O—CH2—C(CH$_3$)$_2$—O—CH3 | |
| 17.090 | N | Me | Me | Me | Me | NHMe | 3-C$_6$H$_4$—O—CH2—C(CH$_3$)$_2$—O—CH3 | |
| 17.091 | N | Me | Me | Me | Me | NHMe | 4-C$_6$H$_4$—O—CH2—CH$_2$—OMe | |
| 17.092 | N | Me | Me | Me | Me | NHMe | 4-C$_6$H$_4$—O—CH2—C$_4$H$_9$(n) | |
| 17.093 | N | Me | Me | Me | Me | NHMe | 4-C$_6$H$_4$—O—CH2—C$_3$H$_7$(n) | |
| 17.094 | N | Me | Me | Me | Me | NHMe | 4-C$_6$H$_4$—O—CH2—C$_8$H$_{17}$(n) | |

TABLE 18

| Ex. Nr. | X | R11 | R14 | R21 | R22 | Z | R13 | Phys. Data |
|---|---|---|---|---|---|---|---|---|
| 18.001 | N | Me | Me | Me | Me | OMe | 4-C$_6$H$_4$—O—C$_6$H$_3$Cl$_2$(2',4') | |
| 18.002 | N | Me | Me | Me | Me | OMe | 4-C$_6$H$_4$—O—C$_6$H$_5$ | |
| 18.003 | N | Me | Me | Me | Me | OMe | 4-C$_6$H$_4$—O—C$_6$H$_4$(OCH$_3$)(4') | |
| 18.004 | N | Me | Me | Me | Me | OMe | 4-C$_6$H$_4$—O—C$_6$H$_3$(CF$_3$)(3',5') | |
| 18.005 | N | Me | Me | Me | Me | OMe | 4-C$_6$H$_4$—O—C$_6$H$_4$(CF$_3$)(3') | |
| 18.006 | N | Me | Me | Me | Me | OMe | 4-C$_6$H$_4$—O—CO—C$_6$H$_4$(CF$_3$)(3') | |
| 18.007 | N | Me | Me | Me | Me | OMe | 4-C$_6$H$_4$—O—CO—C$_6$H$_5$ | |
| 18.008 | N | Me | Me | Me | Me | OMe | 4-C$_6$H$_4$—O—CO—C$_6$H$_4$(Cl)(3') | |
| 18.009 | N | Me | Me | Me | Me | OMe | 4-C$_6$H$_4$—O—C$_6$H$_3$(CN)(3')(NO$_2$)(4') | |
| 18.010 | N | Me | Me | Me | Me | OMe | 4-C$_6$H$_4$—O-Pyrazinyl(2') | |
| 18.011 | N | Me | Me | Me | Me | OMe | 4-C$_6$H$_4$—O-Pyridyl(3') | |
| 18.012 | N | Me | Me | Me | Me | OMe | 4-C$_6$H$_4$—O—CO-Pyridyl(3') | |
| 18.013 | N | Me | Me | Me | Me | OMe | 4-C$_6$H$_4$—O-Pyridyl(2') | |
| 18.014 | N | Me | Me | Me | Me | OMe | 4-C$_6$H$_4$—O-Pyridyl(4') | |
| 18.015 | N | Me | Me | Me | Me | OMe | 4-C$_6$H$_4$—O—C$_6$H$_4$(CF$_3$)(4') | |
| 18.016 | N | Me | Me | Me | Me | OMe | 4-C$_6$H$_4$—O—C$_6$H$_4$(Cl)(4') | |
| 18.017 | N | Me | Me | Me | Me | OMe | 4-C$_6$H$_4$—O—C$_6$H$_4$(NO$_2$)(4') | |
| 18.018 | N | Me | Me | Me | Me | OMe | 4-C$_6$H$_4$—O-Pyrimidinyl(2') | |
| 18.019 | N | Me | Me | Me | Me | OMe | 4-C$_6$H$_4$—O-Pyrimidinyl(4') | |
| 18.020 | N | Me | Me | Me | Me | OMe | 4-C$_6$H$_4$—O-Pyrimidinyl(5') | |

TABLE 18-continued

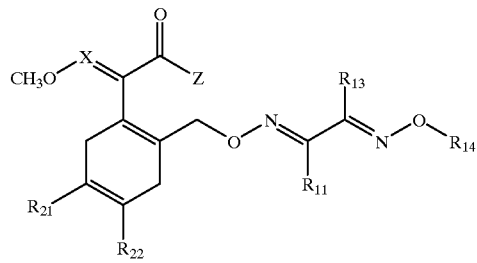

| Ex. Nr. | X | R11 | R14 | R21 | R22 | Z | R13 | Phys. Data |
|---|---|---|---|---|---|---|---|---|
| 18.021 | N | Me | Me | Me | Me | OMe | 4-$C_6H_4$—O—CO—NH—$C_6H_4$—(OMe)(4') | |
| 18.022 | N | Me | Me | Me | Me | OMe | 4-$C_6H_4$—O—$CH_3$ | |
| 18.023 | N | Me | Me | Me | Me | OMe | 4-$C_6H_4$—O—CO—NH—$C_6H_4$—($CF_3$)(3') | |
| 18.024 | N | Me | Me | Me | Me | OMe | 4-$C_6H_4$—O—$C_6H_4$(Br)(4') | |
| 18.025 | N | Me | Me | Me | Me | OMe | 4-$C_6H_4$—O—$C_6H_2$($OCH_3$)$_3$(3',4',5') | |
| 18.026 | N | Me | Me | Me | Me | OMe | 4-$C_6H_4$—O—$C_6H_3$($CH_3$)$_2$(3',5') | |
| 18.027 | N | Me | Me | Me | Me | OMe | 4-$C_6H_4$—O-Thiazolyl(2') | |
| 18.028 | N | Me | Me | Me | Me | OMe | 4-$C_6H_4$—O-Oxazolyl(2') | |
| 18.029 | N | Me | Me | Me | Me | OMe | 4-$C_6H_4$—O-Thienyl(2') | |
| 18.030 | N | Me | Me | Me | Me | OMe | 4-$C_6H_4$—O-Thienyl(3') | |
| 18.031 | N | Me | Me | Me | Me | OMe | 4-$C_6H_4$—O—Et | |
| 18.032 | N | Me | Me | Me | Me | OMe | 3-$C_6H_4$—O—H | |
| 18.033 | N | Me | Me | Me | Me | OMe | 2-$C_6H_4$—O—H | |
| 18.034 | N | Me | Me | Me | Me | OMe | 3-$C_6H_4$—O—$CH_3$ | |
| 18.035 | N | Me | Me | Me | Me | OMe | 4-$C_6H_4$—O—CO-NH-$C_6H_4$—(Cl)(4') | |
| 18.036 | N | Me | Me | Me | Me | OMe | 4-$C_6H_4$—O—CO-NH-$C_6H_3$-($Cl_2$)(2',4') | |
| 18.037 | N | Me | Me | Me | Me | OMe | 4-$C_6H_4$—O—CO-NH-$C_6H_4$—($NO_2$)(4') | |
| 18.038 | N | Me | Me | Me | Me | OMe | 4-$C_6H_4$—O—$CF_3$ | |
| 18.039 | N | Me | Me | Me | Me | OMe | 4-$C_6H_4$—O—COOEt | |
| 18.040 | N | Me | Me | Me | Me | OMe | 4-$C_6H_4$—O—COOMe | |
| 18.041 | N | Me | Me | Me | Me | OMe | 4-$C_6H_4$—O—CO—NH—$C_6H_4$—(Br)(4') | |
| 18.042 | N | Me | Me | Me | Me | OMe | 4-$C_6H_4$—O—CO—NH—$C_6H_4$—(I)(4') | |
| 18.043 | N | Me | Me | Me | Me | OMe | 4-$C_6H_4$—O—CO—NH—$C_6H_4$—($CH_3$)(2') | |
| 18.044 | N | Me | Me | Me | Me | OMe | 4-$C_6H_4$—O—$CH_2$—OMe | |
| 18.045 | N | Me | Me | Me | Me | OMe | 4-$C_6H_4$—O—$C_4H_9$(n) | |
| 18.046 | N | Me | Me | Me | Me | OMe | 4-$C_6H_4$—O—$C_3H_7$(n) | |
| 18.047 | N | Me | Me | Me | Me | OMe | 4-$C_6H_4$—O—$C_8H_{17}$(n) | |
| 18.048 | N | Me | Me | Me | Me | NHMe | 4-$C_6H_4$—O—$C_6H_3Cl_2$(2',4') | |
| 18.049 | N | Me | Me | Me | Me | NHMe | 4-$C_6H_4$—O—$C_6H_5$ | |
| 18.050 | N | Me | Me | Me | Me | NHMe | 4-$C_6H_4$—O—$C_6H_4$($OCH_3$)(4') | |
| 18.051 | N | Me | Me | Me | Me | NHMe | 4-$C_6H_4$—O—$C_6H_3$($CF_3$)(3',5') | |
| 18.052 | N | Me | Me | Me | Me | NHMe | 4-$C_6H_4$—O—$C_6H_4$($CF_3$)(3') | |
| 18.053 | N | Me | Me | Me | Me | NHMe | 4-$C_6H_4$—O—CO—$C_6H_4$($CF_3$)(3') | |
| 18.054 | N | Me | Me | Me | Me | NHMe | 4-$C_6H_4$—O—CO—$C_6H_5$ | |
| 18.055 | N | Me | Me | Me | Me | NHMe | 4-$C_6H_4$—O—CO—$C_6H_4$(Cl)(3') | |
| 18.056 | N | Me | Me | Me | Me | OMe | 4-$C_6H_4$—O—CO—NH—$C_6H_3$—($CH_3$)$_2$(2',6') | |
| 18.057 | N | Me | Me | Me | Me | NHMe | 4-$C_6H_4$—O-Pyrazinyl(2') | |
| 18.058 | N | Me | Me | Me | Me | NHMe | 4-$C_6H_4$—O-Pyridyl(3') | |
| 18.059 | N | Me | Me | Me | Me | NHMe | 4-$C_6H_4$—O—CO-Pyridyl(3') | |
| 18.060 | N | Me | Me | Me | Me | NHMe | 4-$C_6H_4$—O-Pyridyl(2') | |
| 18.061 | N | Me | Me | Me | Me | NHMe | 4-$C_6H_4$—O-Pyridyl(4') | |
| 18.062 | N | Me | Me | Me | Me | NHMe | 4-$C_6H_4$—O—$C_6H_4$($CF_3$)(4') | |
| 18.063 | N | Me | Me | Me | Me | NHMe | 4-$C_6H_4$—O—$C_6H_4$(Cl)(4') | |
| 18.064 | N | Me | Me | Me | Me | OMe | 4-$C_6H_4$—O—CO—NH—$C_6H_3$—(Me)(2')(Et)(6') | |
| 18.065 | N | Me | Me | Me | Me | NHMe | 4-$C_6H_4$O-Pyrimidinyl(2') | |
| 18.066 | N | Me | Me | Me | Me | NHMe | 4-$C_6H_4$—O-Pyrimidinyl(4') | |
| 18.067 | N | Me | Me | Me | Me | NHMe | 4-$C_6H_4$—O-Pyrimidinyl(5') | |
| 18.068 | N | Me | Me | Me | Me | OMe | 4-$C_6H_4$—O—CO—NH—$C_6H_3$—(Me)$_2$(2',4') | |
| 18.069 | N | Me | Me | Me | Me | NHMe | 4-$C_6H_4$—O—$CH_3$ | |
| 18.070 | N | Me | Me | Me | Me | OMe | 4-$C_6H_4$—O—CO—NH—$C_6H_4$—(Cl)(3') | |
| 18.071 | N | Me | Me | Me | Me | NHMe | 4-$C_6H_4$—O—$C_6H_4$(Br)(4') | |
| 18.072 | N | Me | Me | Me | Me | NHMe | 4-$C_6H_4$—O—$C_6H_2$($OCH_3$)$_3$(3',4',5') | |
| 18.073 | N | Me | Me | Me | Me | NHMe | 4-$C_6H_4$—O—$C_6H_3$($CH_3$)$_2$(3',5') | |
| 18.074 | N | Me | Me | Me | Me | NHMe | 4-$C_6H_4$—O-Thiazolyl(2') | |
| 18.075 | N | Me | Me | Me | Me | NHMe | 4-$C_6H_4$—O-Oxazolyl(2') | |
| 18.076 | N | Me | Me | Me | Me | NHMe | 4-$C_6H_4$—O-Thienyl(2') | |
| 18.077 | N | Me | Me | Me | Me | NHMe | 4-$C_6H_4$—O-Thienyl(3') | |
| 18.078 | N | Me | Me | Me | Me | NHMe | 4-$C_6H_4$—O—Et | |
| 18.079 | N | Me | Me | Me | Me | NHMe | 3-$C_6H_4$—O—CH3 | |
| 18.080 | N | Me | Me | Me | Me | NHMe | 2-$C_6H_4$—O—CH3 | |
| 18.081 | N | Me | Me | Me | Me | NHMe | 3-$C_6H_4$—O—$CH_3$ | |

TABLE 18-continued

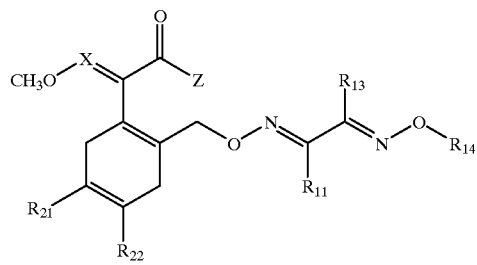

| Ex. Nr. | X | R11 | R14 | R21 | R22 | Z | R13 | Phys. Data |
|---|---|---|---|---|---|---|---|---|
| 18.082 | N | Me | Me | Me | Me | OMe | 4-C$_6$H$_4$—O—CO—NH—C$_6$H$_4$—(Cl)(2') | |
| 18.083 | N | Me | Me | Me | Me | OMe | 4-C$_6$H$_4$—O—CO—NH—C$_6$H$_3$—(Cl)2(3',5') | |
| 18.084 | N | Me | Me | Me | Me | OMe | 4-C$_6$H$_4$—O—CO—NH—C$_6$H$_3$(CF$_3$)$_2$(3',5') | |
| 18.085 | N | Me | Me | Me | Me | NHMe | 4-C$_6$H$_4$—O—CF$_3$ | |
| 18.086 | N | Me | Me | Me | Me | NHMe | 4-C$_6$H$_4$—O—COOEt | |
| 18.087 | N | Me | Me | Me | Me | NHMe | 4-C$_6$H$_4$—O—COOMe | |
| 18.088 | N | Me | Me | Me | Me | OMe | 4-C$_6$H$_4$—O—CO—NH—C$_6$H$_4$—(CF$_3$)(4') | |
| 18.089 | N | Me | Me | Me | Me | OMe | 4-C$_6$H$_4$—O—CO—NH—C$_6$H$_4$—(OCH$_3$)(4') | |
| 18.056 | N | Me | Me | Me | Me | OMe | 4-C$_6$H$_4$—O—CO—NH—C$_6$H$_4$—(OCF$_3$)(4') | |
| 18.091 | N | Me | Me | Me | Me | NHMe | 4-C$_6$H$_4$—O—CH$_2$—OMe | |
| 18.092 | N | Me | Me | Me | Me | NHMe | 4-C$_6$H$_4$—O—C$_4$H$_9$(n) | |
| 18.093 | N | Me | Me | Me | Me | NHMe | 4-C$_6$H$_4$—O—C$_3$H$_7$(n) | |
| 18.094 | N | Me | Me | Me | Me | NHMe | 4-C$_6$H$_4$—O—C$_8$H$_{17}$(n) | |

TABLE 19

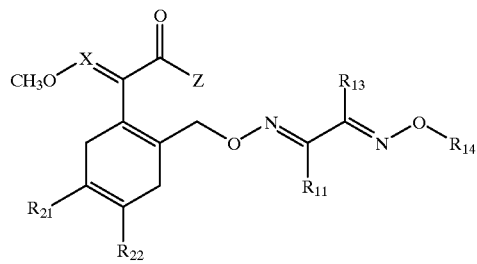

| Ex. Nr. | X | R11 | R14 | R21 | R22 | Z | R13 | Phys. Data |
|---|---|---|---|---|---|---|---|---|
| 19.001 | N | Me | Et | Me | Me | OMe | 4-C$_6$H$_4$—O—C$_6$H$_3$Cl$_2$(2',4') | |
| 19.002 | N | Me | Et | Me | Me | OMe | 4-C$_6$H$_4$—O—C$_6$H$_5$ | |
| 19.003 | N | Me | Et | Me | Me | OMe | 4-C$_6$H$_4$—O—C$_6$H$_4$(OCH$_3$)(4') | |
| 19.004 | N | Me | Et | Me | Me | OMe | 4-C$_6$H$_4$—O—C$_6$H$_3$(CF$_3$)(3',5') | |
| 19.005 | N | Me | Et | Me | Me | OMe | 4-C$_6$H$_4$—O—C$_6$H$_4$(CF$_3$)(3') | |
| 19.006 | N | Me | Et | Me | Me | OMe | 4-C$_6$H$_4$—O—CO—C$_6$H$_4$(CF$_3$)(3') | |
| 19.007 | N | Me | Et | Me | Me | OMe | 4-C$_6$H$_4$—O—CO—C$_6$H$_5$ | |
| 19.008 | N | Me | Et | Me | Me | OMe | 4-C$_6$H$_4$—O—CO—C$_6$H$_4$(Cl)(3') | |
| 19.009 | N | Me | Et | Me | Me | OMe | 4-C$_6$H$_4$—O—C$_6$H$_3$(CN)(3')(NO$_2$)(4') | |
| 19.010 | N | Me | Et | Me | Me | OMe | 4-C$_6$H$_4$—O-Pyrazinyl(2') | |
| 19.011 | N | Me | Et | Me | Me | OMe | 4-C$_6$H$_4$—O-Pyridyl(3') | |
| 19.012 | N | Me | Et | Me | Me | OMe | 4-C$_6$H$_4$—O—CO-Pyridyl(3') | |
| 19.013 | N | Me | Et | Me | Me | OMe | 4-C$_6$H$_4$—O-Pyridyl(2') | |
| 19.014 | N | Me | Et | Me | Me | OMe | 4-C$_6$H$_4$—O-Pyridyl(4') | |
| 19.015 | N | Me | Et | Me | Me | OMe | 4-C$_6$H$_4$—O—C$_6$H$_4$(CF$_3$)(4') | |
| 19.016 | N | Me | Et | Me | Me | OMe | 4-C$_6$H$_4$—O—C$_6$H$_4$(Cl)(4') | |
| 19.017 | N | Me | Et | Me | Me | OMe | 4-C$_6$H$_4$—O—C$_6$H$_4$(NO$_2$)(4') | |
| 19.018 | N | Me | Et | Me | Me | OMe | 4-C$_6$H$_4$—O-Pyrimidinyl(2') | |
| 19.019 | N | Me | Et | Me | Me | OMe | 4-C$_6$H$_4$—O-Pyrimidinyl(4') | |
| 19.020 | N | Me | Et | Me | Me | OMe | 4-C$_6$H$_4$—O-Pyrimidinyl(5') | |
| 19.021 | N | Me | Et | Me | Me | OMe | 4-C$_6$H$_4$—O—CO—NH—C$_6$H$_4$—(OMe)(4') | |
| 19.022 | N | Me | Et | Me | Me | OMe | 4-C$_6$H$_4$—O—CH$_3$ | |
| 19.023 | N | Me | Et | Me | Me | OMe | 4-C$_6$H$_4$—O—CO—NH—C$_6$H$_4$—(CF$_3$)(3') | |
| 19.024 | N | Me | Et | Me | Me | OMe | 4-C$_6$H$_4$—O—C$_6$H$_4$(Br)(4') | |
| 19.025 | N | Me | Et | Me | Me | OMe | 4-C$_6$H$_4$—O—C$_6$H$_2$(OCH$_3$)$_3$(3',4',5') | |
| 19.026 | N | Me | Et | Me | Me | OMe | 4-C$_6$H$_4$—O—C$_6$H$_3$(CH$_3$)$_2$(3',5') | |
| 19.027 | N | Me | Et | Me | Me | OMe | 4-C$_6$H$_4$—O-Thiazolyl(2') | |

TABLE 19-continued

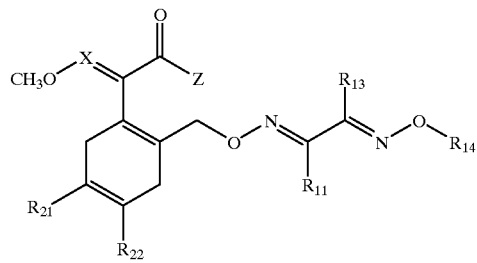

| Ex. Nr. | X | R11 | R14 | R21 | R22 | Z | R13 | Phys. Data |
|---|---|---|---|---|---|---|---|---|
| 19.028 | N | Me | Et | Me | Me | OMe | 4-C$_6$H$_4$—O-Oxazolyl(2') | |
| 19.029 | N | Me | Et | Me | Me | OMe | 4-C$_6$H$_4$—O-Thienyl(2') | |
| 19.030 | N | Me | Et | Me | Me | OMe | 4-C$_6$H$_4$—O-Thienyl(3') | |
| 19.031 | N | Me | Et | Me | Me | OMe | 4-C$_6$H$_4$—O—Et | |
| 19.032 | N | Me | Et | Me | Me | OMe | 3-C$_6$H$_4$—O—H | |
| 19.033 | N | Me | Et | Me | Me | OMe | 2-C$_6$H$_4$—O—H | |
| 19.034 | N | Me | Et | Me | Me | OMe | 3-C$_6$H$_4$—O—CH$_3$ | |
| 19.035 | N | Me | Et | Me | Me | OMe | 4-C$_6$H$_4$—O—CO—NH—C$_6$H$_4$—(Cl)(4') | |
| 19.036 | N | Me | Et | Me | Me | OMe | 4-C$_6$H$_4$—O—CO—NH—C$_6$H$_3$—(Cl$_2$)(2',4') | |
| 19.037 | N | Me | Et | Me | Me | OMe | 4-C$_6$H$_4$—O—CO—NH—C$_6$H$_4$—(NO$_2$)(4') | |
| 19.038 | N | Me | Et | Me | Me | OMe | 4-C$_6$H$_4$—O—CF$_3$ | |
| 19.039 | N | Me | Et | Me | Me | OMe | 4-C$_6$H$_4$—O—COOEt | |
| 19.040 | N | Me | Et | Me | Me | OMe | 4-C$_6$H$_4$—O—COOMe | |
| 19.041 | N | Me | Et | Me | Me | OMe | 4-C$_6$H$_4$—O—CO—NH—C$_6$H$_4$—(Br)(4') | |
| 19.042 | N | Me | Et | Me | Me | OMe | 4-C$_6$H$_4$—O—CO—NH—C$_6$H$_4$—(I)(4') | |
| 19.043 | N | Me | Et | Me | Me | OMe | 4-C$_6$H$_4$—O—CO—NH—C$_6$H$_4$—(CH$_3$)(2') | |
| 19.044 | N | Me | Et | Me | Me | OMe | 4-C$_6$H$_4$—O—CH$_2$—OMe | |
| 19.045 | N | Me | Et | Me | Me | OMe | 4-C$_6$H$_4$—O—C$_4$H$_9$(n) | |
| 19.046 | N | Me | Et | Me | Me | OMe | 4-C$_6$H$_4$—O—C$_3$H$_7$(n) | |
| 19.047 | N | Me | Et | Me | Me | OMe | 4-C$_6$H$_4$—O—C$_8$H$_{17(n)}$ | |
| 19.048 | N | Me | Et | Me | Me | NHMe | 4-C$_6$H$_4$—O—C$_6$H$_3$Cl$_2$(2',4') | |
| 19.049 | N | Me | Et | Me | Me | NHMe | 4-C$_6$H$_4$—O—C$_6$H$_5$ | |
| 19.050 | N | Me | Et | Me | Me | NHMe | 4-C$_6$H$_4$—O—C$_6$H$_4$(OCH$_3$)(4') | |
| 19.051 | N | Me | Et | Me | Me | NHMe | 4-C$_6$H$_4$—O—C$_6$H$_3$(CF$_3$)(3',5') | |
| 19.052 | N | Me | Et | Me | Me | NHMe | 4-C$_6$H$_4$—O—C$_6$H$_4$(CF$_3$)(3') | |
| 19.053 | N | Me | Et | Me | Me | NHMe | 4-C$_6$H$_4$—O—CO—C$_6$H$_4$(CF$_3$)(3') | |
| 19.054 | N | Me | Et | Me | Me | NHMe | 4-C$_6$H$_4$—O—CO—C$_6$H$_5$ | |
| 19.055 | N | Me | Et | Me | Me | NHMe | 4-C$_6$H$_4$—O—CO—C$_6$H$_4$(Cl)(3') | |
| 19.056 | N | Me | Et | Me | Me | OMe | 4-C$_6$H$_4$—O—CO—NH—C$_6$H$_3$—(CH$_3$)$_2$(2',6') | |
| 19.057 | N | Me | Et | Me | Me | NHMe | 4-C$_6$H$_4$—O-Pyrazinyl(2') | |
| 19.058 | N | Me | Et | Me | Me | NHMe | 4-C$_6$H$_4$—O-Pyridyl(3') | |
| 19.059 | N | Me | Et | Me | Me | NHMe | 4-C$_6$H$_4$—O—CO-Pyridyl(3') | |
| 19.060 | N | Me | Et | Me | Me | NHMe | 4-C$_6$H$_4$—O-Pyridyl(2') | |
| 19.061 | N | Me | Et | Me | Me | NHMe | 4-C$_6$H$_4$—O-Pyridyl(4') | |
| 19.062 | N | Me | Et | Me | Me | NHMe | 4-C$_6$H$_4$—O—C$_6$H$_4$(CF$_3$)(4') | |
| 19.063 | N | Me | Et | Me | Me | NHMe | 4-C$_6$H$_4$—O—C$_6$H$_4$(Cl)(4') | |
| 19.064 | N | Me | Et | Me | Me | OMe | 4-C$_6$H$_4$—O—CO—NH—C$_6$H$_3$—(Me)(2')(Et)(6') | |
| 19.065 | N | Me | Et | Me | Me | NHMe | 4-C$_6$H$_4$—O-Pyrimidinyl(2') | |
| 19.066 | N | Me | Et | Me | Me | NHMe | 4-C$_6$H$_4$—O-Pyrimidinyl(4') | |
| 19.067 | N | Me | Et | Me | Me | NHMe | 4-C$_6$H$_4$—O-Pyrimidinyl(5') | |
| 19.068 | N | Me | Et | Me | Me | OMe | 4-C$_6$H$_4$—O—CO—NH—C$_6$H$_3$—(Me)$_2$(2',4') | |
| 19.069 | N | Me | Et | Me | Me | NHMe | 4-C$_6$H$_4$—O—CH$_3$ | |
| 19.070 | N | Me | Et | Me | Me | OMe | 4-C$_6$H$_4$—O—CO—NH—C$_6$H$_4$—(Cl)(3') | |
| 19.071 | N | Me | Et | Me | Me | NHMe | 4-C$_6$H$_4$—O—C$_6$H$_4$(Br)(4') | |
| 19.072 | N | Me | Et | Me | Me | NHMe | 4-C$_6$H$_4$—O—C$_6$H$_2$(OCH$_3$)$_3$(3',4',5') | |
| 19.073 | N | Me | Et | Me | Me | NHMe | 4-C$_6$H$_4$—O—C$_6$H$_3$(CH$_3$)$_2$(3',5') | |
| 19.074 | N | Me | Et | Me | Me | NHMe | 4-C$_6$H$_4$—O-Thiazolyl(2') | |
| 19.075 | N | Me | Et | Me | Me | NHMe | 4-C$_6$H$_4$—O-Oxazolyl(2') | |
| 19.076 | N | Me | Et | Me | Me | NHMe | 4-C$_6$H$_4$—O-Thienyl(2') | |
| 19.077 | N | Me | Et | Me | Me | NHMe | 4-C$_6$H$_4$—O-Thienyl(3') | |
| 19.078 | N | Me | Et | Me | Me | NHMe | 4-C$_6$H$_4$—O—Et | |
| 19.079 | N | Me | Et | Me | Me | NHMe | 3-C$_6$H$_4$—O—CH3 | |
| 19.080 | N | Me | Et | Me | Me | NHMe | 2-C$_6$H$_4$—O—CH3 | |
| 19.081 | N | Me | Et | Me | Me | NHMe | 3-C$_6$H$_4$—O—CH3 | |
| 19.082 | N | Me | Et | Me | Me | OMe | 4-C$_6$H$_4$—O—CO—NH—C$_6$H$_4$—(Cl)(2') | |
| 19.083 | N | Me | Et | Me | Me | OMe | 4-C$_6$H$_4$—O—CO—NH—C$_6$H$_3$—(Cl)2(3',5') | |
| 19.084 | N | Me | Et | Me | Me | OMe | 4-C$_6$H$_4$—O—CO—NH—C$_6$H$_3$—(CF$_3$)$_2$(3',5') | |
| 19.085 | N | Me | Et | Me | Me | NHMe | 4-C$_6$H$_4$—O—CF$_3$ | |
| 19.086 | N | Me | Et | Me | Me | NHMe | 4-C$_6$H$_4$—O—COOEt | |
| 19.087 | N | Me | Et | Me | Me | NHMe | 4-C$_6$H$_4$—O—COOMe | |
| 19.088 | N | Me | Et | Me | Me | OMe | 4-C$_6$H$_4$—O—CO—NH—C$_6$H$_4$—(CF$_3$)(4') | |

TABLE 19-continued

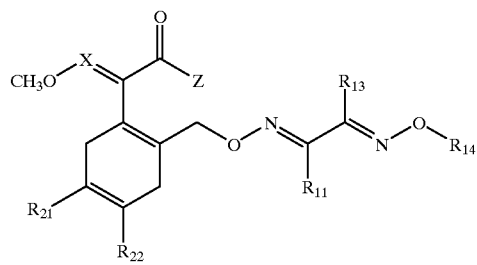

| Ex. Nr. | X | R11 | R14 | R21 | R22 | Z | R13 | Phys. Data |
|---|---|---|---|---|---|---|---|---|
| 19.089 | N | Me | Et | Me | Me | OMe | 4-C$_6$H$_4$—O—CO—NH—C$_6$H$_4$—(OCH$_3$)(4') | |
| 19.056 | N | Me | Et | Me | Me | OMe | 4-C$_6$H$_4$—O—CO—NH—C$_6$H$_4$—(OCF$_3$)(4') | |
| 19.091 | N | Me | Et | Me | Me | NHMe | 4-C$_6$H$_4$—O—CH$_2$—OMe | |
| 19.092 | N | Me | Et | Me | Me | NHMe | 4-C$_6$H$_4$—O—C$_4$H$_9$(n) | |
| 19.093 | N | Me | Et | Me | Me | NHMe | 4-C$_6$H$_4$—O—C$_3$H$_7$(n) | |
| 19.094 | N | Me | Et | Me | Me | NHMe | 4-C$_6$H$_4$—O—C$_8$H$_{17}$(n) | |

TABLE 20

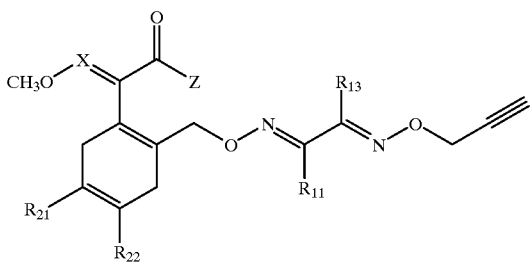

| Ex. Nr. | X | R11 | R21 | R22 | Z | R13 | Phys. Data |
|---|---|---|---|---|---|---|---|
| 20.001 | N | Me | Me | Me | OMe | 4-C$_6$H$_4$—O—C$_6$H$_3$Cl$_2$(2',4') | |
| 20.002 | N | Me | Me | Me | OMe | 4-C$_6$H$_4$—O—C$_6$H$_5$ | |
| 20.003 | N | Me | Me | Me | OMe | 4-C$_6$H$_4$—O—C$_6$H$_4$(OCH$_3$)(4') | |
| 20.004 | N | Me | Me | Me | OMe | 4-C$_6$H$_4$—O—C$_6$H$_3$(CF$_3$)(3',5') | |
| 20.005 | N | Me | Me | Me | OMe | 4-C$_6$H$_4$—O—C$_6$H$_4$(CF$_3$)(3') | |
| 20.006 | N | Me | Me | Me | OMe | 4-C$_6$H$_4$—O—CO—C$_6$H$_4$(CF$_3$)(3') | |
| 20.007 | N | Me | Me | Me | OMe | 4-C$_6$H$_4$—O—CO—C$_6$H$_5$ | |
| 20.008 | N | Me | Me | Me | OMe | 4-C$_6$H$_4$—O—CO—C$_6$H$_4$(Cl)(3') | |
| 20.009 | N | Me | Me | Me | OMe | 4-C$_6$H$_4$—O—C$_6$H$_3$(CN)(3')(NO$_2$)(4') | |
| 20.010 | N | Me | Me | Me | OMe | 4-C$_6$H$_4$—O-Pyrazinyl(2') | |
| 20.011 | N | Me | Me | Me | OMe | 4-C$_6$H$_4$—O-Pyridyl(3') | |
| 20.012 | N | Me | Me | Me | OMe | 4-C$_6$H$_4$—O—CO-Pyridyl(3') | |
| 20.013 | N | Me | Me | Me | OMe | 4-C$_6$H$_4$—O-Pyridyl(2') | |
| 20.014 | N | Me | Me | Me | OMe | 4-C$_6$H$_4$—O-Pyridyl(4') | |
| 20.015 | N | Me | Me | Me | OMe | 4-C$_6$H$_4$—O—C$_6$H$_4$(CF$_3$)(4') | |
| 20.016 | N | Me | Me | Me | OMe | 4-C$_6$H$_4$—O—C$_6$H$_4$(Cl)(4') | |
| 20.017 | N | Me | Me | Me | OMe | 4-C$_6$H$_4$—O—C$_6$H$_4$(NO$_2$)(4') | |
| 20.018 | N | Me | Me | Me | OMe | 4-C$_6$H$_4$—O-Pyrimidinyl(2') | |
| 20.019 | N | Me | Me | Me | OMe | 4-C$_6$H$_4$-O-Pyrimidinyl(4') | |
| 20.020 | N | Me | Me | Me | OMe | 4-C$_6$H$_4$—O-Pyrimidinyl(5') | |
| 20.021 | N | Me | Me | Me | OMe | 4-C$_6$H$_4$—O—CO—NH—C$_6$H$_4$—(OMe)(4') | |
| 20.022 | N | Me | Me | Me | OMe | 4-C$_6$H$_4$—O—CH$_3$ | |
| 20.023 | N | Me | Me | Me | OMe | 4-C$_6$H$_4$—O—CO—NH—C$_6$H$_4$—(CF$_3$)(3') | |
| 20.024 | N | Me | Me | Me | OMe | 4-C$_6$H$_4$—O—C$_6$H$_4$(Br)(4') | |
| 20.025 | N | Me | Me | Me | OMe | 4-C$_6$H$_4$—O—C$_6$H$_2$(OCH$_3$)$_3$(3',4',5') | |
| 20.026 | N | Me | Me | Me | OMe | 4-C$_6$H$_4$-O—C$_6$H$_3$(CH$_3$)$_2$(3',5') | |
| 20.027 | N | Me | Me | Me | OMe | 4-C$_6$H$_4$—O-Thiazolyl(2') | |
| 20.028 | N | Me | Me | Me | OMe | 4-C$_6$H$_4$—O-Oxazolyl(2') | |
| 20.029 | N | Me | Me | Me | OMe | 4-C$_6$H$_4$—O-Thienyl(2') | |
| 20.030 | N | Me | Me | Me | OMe | 4-C$_6$H$_4$—O-Thienyl(3') | |
| 20.031 | N | Me | Me | Me | OMe | 4-C$_6$H$_4$—O—Et | |
| 20.032 | N | Me | Me | Me | OMe | 3-C$_6$H$_4$—O—H | |
| 20.033 | N | Me | Me | Me | OMe | 2-C$_6$H$_4$—O—H | |
| 20.034 | N | Me | Me | Me | OMe | 3-C$_6$H$_4$—O—CH$_3$ | |

TABLE 20-continued

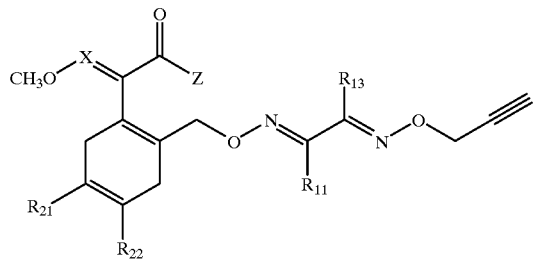

| Ex. Nr. | X | R11 | R21 | R22 | Z | R13 | Phys. Data |
|---|---|---|---|---|---|---|---|
| 20.035 | N | Me | Me | Me | OMe | 4-C$_6$H$_4$—O—CO—NH—C$_6$H$_4$—(Cl)(4') | |
| 20.036 | N | Me | Me | Me | OMe | 4-C$_6$H$_4$—O—CO—NH—C$_6$H$_3$—(Cl$_2$)(2',4') | |
| 20.037 | N | Me | Me | Me | OMe | 4-C$_6$H$_4$—O—CO—NH—C$_6$H$_4$—(NO$_2$)(4') | |
| 20.038 | N | Me | Me | Me | OMe | 4-C$_6$H$_4$—O—CF$_3$ | |
| 20.039 | N | Me | Me | Me | OMe | 4-C$_6$H$_4$—O—COOEt | |
| 20.040 | N | Me | Me | Me | OMe | 4-C$_6$H$_4$—O—COOMe | |
| 20.041 | N | Me | Me | Me | OMe | 4-C$_6$H$_4$—O—CO—NH—C$_6$H$_4$—(Br)(4') | |
| 20.042 | N | Me | Me | Me | OMe | 4-C$_6$H$_4$—O—CO—NH—C$_6$H$_4$—(I)(4') | |
| 20.043 | N | Me | Me | Me | OMe | 4-C$_6$H$_4$—O—CO—NH—C$_6$H$_4$—(CH$_3$)(2') | |
| 20.044 | N | Me | Me | Me | OMe | 4-C$_6$H$_4$—O—CH$_2$—OMe | |
| 20.045 | N | Me | Me | Me | OMe | 4-C$_6$H$_4$—O—C$_4$H$_9$(n) | |
| 20.046 | N | Me | Me | Me | OMe | 4-C$_6$H$_4$—O—C$_3$H$_7$(n) | |
| 20.047 | N | Me | Me | Me | OMe | 4-C$_6$H$_4$—O—C$_8$H$_{17}$(n) | |
| 20.048 | N | Me | Me | Me | NHMe | 4-C$_6$H$_4$—O—C$_6$H$_3$Cl$_2$(2',4') | |
| 20.049 | N | Me | Me | Me | NHMe | 4-C$_6$H$_4$—O—C$_6$H$_5$ | |
| 20.050 | N | Me | Me | Me | NHMe | 4-C$_6$H$_4$—O—C$_6$H$_4$(OCH$_3$)(4') | |
| 20.051 | N | Me | Me | Me | NHMe | 4-C$_6$H$_4$—O—C$_6$H$_3$(CF$_3$)(3',5') | |
| 20.052 | N | Me | Me | Me | NHMe | 4-C$_6$H$_4$—O—C$_6$H$_4$(CF$_3$)(3') | |
| 20.053 | N | Me | Me | Me | NHMe | 4-C$_6$H$_4$—O—CO—C$_6$H$_4$(CF$_3$)(3') | |
| 20.054 | N | Me | Me | Me | NHMe | 4-C$_6$H$_4$—O—CO—C$_6$H$_5$ | |
| 20.055 | N | Me | Me | Me | NHMe | 4-C$_6$H$_4$—O—CO—C$_6$H$_4$(Cl)(3') | |
| 20.056 | N | Me | Me | Me | OMe | 4-C$_6$H$_4$—O—CO—NH—C$_6$H$_3$—(CH$_3$)$_2$(2',6') | |
| 20.057 | N | Me | Me | Me | NHMe | 4-C$_6$H$_4$-O-Pyrazinyl(2') | |
| 20.058 | N | Me | Me | Me | NHMe | 4-C$_6$H$_4$-O-Pyridyl(3') | |
| 20.059 | N | Me | Me | Me | NHMe | 4-C$_6$H$_4$-O-CO-Pyridyl(3') | |
| 20.060 | N | Me | Me | Me | NHMe | 4-C$_6$H$_4$-O-Pyridyl(2') | |
| 20.061 | N | Me | Me | Me | NHMe | 4-C$_6$H$_4$-O-Pyridyl(4') | |
| 20.062 | N | Me | Me | Me | NHMe | 4-C$_6$H$_4$—O—C$_6$H$_4$(CF$_3$)(4') | |
| 20.063 | N | Me | Me | Me | NHMe | 4-C$_6$H$_4$—O—C$_6$H$_4$(Cl)(4') | |
| 20.064 | N | Me | Me | Me | OMe | 4-C$_6$H$_4$—O—CO—NH—C$_6$H$_3$—(Me)(2')(Et)(6') | |
| 20.065 | N | Me | Me | Me | NHMe | 4-C$_6$H$_4$-O-Pyrimidinyl(2') | |
| 20.066 | N | Me | Me | Me | NHMe | 4-C$_6$H$_4$-O-Pyrimidinyl(4') | |
| 20.067 | N | Me | Me | Me | NHMe | 4-C$_6$H$_4$-O-Pyrimidinyl(5') | |
| 20.068 | N | Me | Me | Me | OMe | 4-C$_6$H$_4$—O—CO—NH—C$_6$H$_3$—(Me)$_2$(2',4') | |
| 20.069 | N | Me | Me | Me | NHMe | 4-C$_6$H$_4$—O—CH$_3$ | |
| 20.070 | N | Me | Me | Me | OMe | 4-C$_6$H$_4$—O—CO—NH—C$_6$H$_4$—(Cl)(3') | |
| 20.071 | N | Me | Me | Me | NHMe | 4-C$_6$H$_4$—O—C$_6$H$_4$(Br)(4') | |
| 20.072 | N | Me | Me | Me | NHMe | 4-C$_6$H$_4$—O—C$_6$H$_2$(OCH$_3$)$_3$(3',4',5') | |
| 20.073 | N | Me | Me | Me | NHMe | 4-C$_6$H$_4$—O—C$_6$H$_3$(CH$_3$)$_2$(3',5') | |
| 20.074 | N | Me | Me | Me | NHMe | 4-C$_6$H$_4$-O-Thiazolyl(2') | |
| 20.075 | N | Me | Me | Me | NHMe | 4-C$_6$H$_4$-O-Oxazolyl(2') | |
| 20.076 | N | Me | Me | Me | NHMe | 4-C$_6$H$_4$-O-Thienyl(2') | |
| 20.077 | N | Me | Me | Me | NHMe | 4-C$_6$H$_4$-O-Thienyl(3') | |
| 20.078 | N | Me | Me | Me | NHMe | 4-C$_6$H$_4$—O—Et | |
| 20.079 | N | Me | Me | Me | NHMe | 3-C$_6$H$_4$—O—CH3 | |
| 20.080 | N | Me | Me | Me | NHMe | 2-C$_6$H$_4$—O—CH3 | |
| 20.081 | N | Me | Me | Me | NHMe | 3-C$_6$H$_4$—O—CH$_3$ | |
| 20.082 | N | Me | Me | Me | OMe | 4-C$_6$H$_4$—O—CO—NH—C$_6$H$_4$—(Cl)(2') | |
| 20.083 | N | Me | Me | Me | OMe | 4-C$_6$H$_4$—O—CO—NH—C$_6$H$_3$—(Cl)$_2$(3',5') | |
| 20.084 | N | Me | Me | Me | OMe | 4-C$_6$H$_4$—O—CO—NH—C$_6$H$_3$—(CF$_3$)$_2$(3',5') | |
| 20.085 | N | Me | Me | Me | NHMe | 4-C$_6$H$_4$—O—CF$_3$ | |
| 20.086 | N | Me | Me | Me | NHMe | 4-C$_6$H$_4$—O—COOEt | |
| 20.087 | N | Me | Me | Me | NHMe | 4-C$_6$H$_4$—O—COOMe | |
| 20.088 | N | Me | Me | Me | OMe | 4-C$_6$H$_4$—O—CO—NH—C$_6$H$_4$—(CF$_3$)(4') | |
| 20.089 | N | Me | Me | Me | OMe | 4-C$_6$H$_4$—O—CO—NH—C$_6$H$_4$—(OCH$_3$)(4') | |
| 20.056 | N | Me | Me | Me | OMe | 4-C$_6$H$_4$—O—CO—NH—C$_6$H$_4$—(OCF$_3$)(4') | |
| 20.091 | N | Me | Me | Me | NHMe | 4-C$_6$H$_4$—O—CH$_2$—OMe | |
| 20.092 | N | Me | Me | Me | NHMe | 4-C$_6$H$_4$—O—C$_4$H$_9$(n) | |
| 20.093 | N | Me | Me | Me | NHMe | 4-C$_6$H$_4$—O—C$_3$H$_7$(n) | |
| 20.094 | N | Me | Me | Me | NHMe | 4-C$_6$H$_4$—O—C$_8$H$_7$(n) | |

2. Formulation Examples for active ingredients from the Tables (throughout, percentages are by weight

| 2.1 Wettable powders | a) | b) | c) |
|---|---|---|---|
| active ingredient from the Tables | 25% | 50% | 75% |
| sodium lignosulfonate | 5% | 5% | — |
| sodium lauryl sulfate | 3% | — | 5% |
| sodium diisobutylnaphthalene sulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is mixed with the adjuvants and the mixture is homogeneously ground in a suitable mill, affording wettable powders which can be diluted with water to give suspensions of any desired concentration.

| 2.2 Emulsifiable concentrate | |
|---|---|
| active ingredient from the Tables | 10% |
| octylphenol polyethylene glycol ether (4–5 mol of ethylene oxide) | 3% |
| calcium dodecylbenzenesulfonate | 3% |
| castor oil polyglycol ether (35 mol of ethylene oxide) | 4% |
| cyclohexanone | 30% |
| xylene mixture | 50% |

Emulsions of any required dilution can be obtained from this concentrate by dilution with water.

| 2.3 Dusts | a) | b) |
|---|---|---|
| active ingredient from the Tables | 5% | 8% |
| talcum | 95% | — |
| kaolin | — | 92% |

Ready-for-use dusts are obtained by mixing the active ingredient with the carriers and grinding the mixture in a suitable mill.

| 2.4 Extruder granules | |
|---|---|
| active ingredient from the Tables | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5 Coated granules | |
|---|---|
| active ingredient from the Tables | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 2.6 Suspension concentrate | |
|---|---|
| active ingredient from the Tables | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired dilution can be obtained by dilution with water.

BIOLOGICAL EXAMPLES

A. Microbicidal Action

Example E-1

Action against *Puccinia graminis* on Wheat a) Residual-protective action 6 days after sowing, wheat plants are sprayed to drip point with an aqueous spray mixture (0.02% active ingredient) prepared from a wettable powder formulation of the test compound and infected 24 hours later with a uredospore suspension of the fungus. After an incubation period of 48 hours (conditions: 95 to 100% relative humidity at 20°), the plants are placed in a greenhouse at 22°. The fungus infestation is evaluated 12 days after infection.

b) Systemic Action 5 days after sowing, wheat plants are watered with an aqueous spray mixture (0.006% active ingredient, based on the volume of the soil) prepared from a wettable powder formulation of the test compound. Care is taken that the spray mixture does not come into contact with the parts of the plants above the soil. The plants are infected 48 hours later with a uredospore suspension of the fungus. After an incubation period of 48 hours (conditions: 95 to 100% relative humidity at 20°), the plants are placed in a greenhouse at 22°. The fungus infestation is evaluated 12 days after infection.

Compounds from the Tables exhibit a good activity.

Example E-2

Action Against *Phytophthora infestans* on Tomatoes a) Residual-protective Action After a cultivation period of three weeks, tomato plants are sprayed to drip point with an aqueous spray mixture (0.02% active ingredient) prepared from a wettable powder formulation of the test compound and infected 24 hours later with a sporangia suspension of the fungus. The fungus infestation is evaluated 5 days after infection, during which period 90 to 100% relative humidity and a temperature of 200 are maintained.

b) Systemic Action

After a cultivation period of three weeks, tomato plants are watered with an aqueous spray mixture (0.006% active ingredient, based on the volume of the soil) prepared from a wettable powder formulation of the test compound. Care is taken that the spray mixture does not come into contact with the parts of the plants above the soil. The plants are infected 48 hours later with a sporangia suspension of the fungus. The fungus infestation is evaluated 5 days after infection, during which period 90 to 100% relative humidity and a temperature of 20° are maintained.

Compounds from the Tables exhibit a good activity.

Example E-3

Residual-protective Action Against *Cercospora arachidicola* on Groundnuts

Groundnut plants 10 to 15 cm in height are sprayed to drip point with an aqueous spray mixture (0.02% active ingredient) prepared from a wettable powder formulation of the test compound, and infected 48 hours later with a conidia suspension of the fungus. The plants are incubated for 72 hours at 21° and high humidity and then placed in a greenhouse until the typical leaf specks appear. The action of the active ingredient is evaluated 12 days after infection and is based on the number and size of the leaf specks.

Compounds from the Tables exhibit a good activity.

Example E-4

Action Against *Plasmopara viticola* on Vines

Vine seedlings at the 4- to 5-leaf stage are sprayed to drip point with an aqueous spray mixture (0.02% active ingredient) prepared from a wettable powder formulation of the test compound and infected 24 hours later with a sporangia suspension of the fungus. The fungus infestation is evaluated 6 days after infection, during which period 95 to 100% relative humidity and a temperature of 20° are maintained.

Compounds from the Tables exhibit a good activity.

Example E-5

Action Against *Colletotrichum lagenarium* on Cucumbers

After a cultivation period of 2 weeks, cucumber plants are sprayed with a spray mixture (0.002% concentration) prepared from a wettable powder formulation of the test compound. Two days later, the plants are infected with a spore suspension ($1.5 \times 10^5$ spores/ml) of the fungus and incubated for 36 hours at 23° C. and high humidity. Incubation is then continued at normal humidity and about 22° C. The fungus infestation that has occurred is evaluated 8 days after infection.

Compounds from the Tables exhibit a good activity.

Example E-6

Residual-protective Action Against *Venturia inaegualis* on Apples

Apple cuttings with 10 to 20 cm long fresh shoots are sprayed to drip point with an aqueous spray mixture (0.02% active ingredient) prepared from a wettable powder formulation of the test compound, and infected 24 hours later with a conidia suspension of the fungus. The plants are incubated for 5 days at 90 to 100% relative humidity and placed in a greenhouse for a further 10 days at 20 to 24°. The fungus infestation is evaluated 12 days after infection.

Compounds from the Tables exhibit a good activity.

Example E-7

Action Against *Erysiphe graminis* on Barley a) Residual-protective Action

Barley plants about 8 cm in height are sprayed to drip point with an aqueous spray mixture (0.02% active ingredient) prepared from a wettable powder formulation of the test compound and dusted 3 to 4 hours later with conidia of the fungus. The infected plants are placed in a greenhouse at 22°. The fungus infestation is evaluated 12 days after infection.

Compounds from the Tables exhibit a good activity.

b) Systemic Action

Barley plants about 8 cm in height are watered with an aqueous spray mixture (0.002% active ingredient, based on the volume of the soil) prepared from a wettable powder formulation of the test compound. Care is taken that the spray mixture does not come into contact with the parts of the plants above the soil. The plants are dusted 48 hours later with conidia of the fungus. The infected plants are placed in a greenhouse at 22°. The fungus infestation is evaluated 12 days after infection.

Compounds from the Tables exhibit a good activity.

Example E-8

Action Against *Podosphaera leucotricha* on Apple Shoots

Apple cuttings with approximately 15 cm long fresh shoots are sprayed with a spray mixture (0.06% active ingredient). The treated plants are infected 24 hours later with a conidia suspension of the fungus and are placed in a controlled environment chamber at 70% relative humidity and 20° C. The fungus infestation is evaluated 12 days after infection.

Compounds from the Tables exhibit a good activity.

Biological Examples

B. Insecticidal Action

Example E-9

Action Against *Aphis craccivora*

Pea seedlings are infested with *Aphis craccivora*, subsequently sprayed with a spray mixture comprising 100 ppm of the test compound and then incubated at 20°. 3 and 6 days later the percentage reduction in population (% activity) is determined by comparing the number of dead aphids on the treated plants with that on untreated plants.

Compounds of the Tables exhibit a good activity in this test, that is to say a mortality rate of more than 80%.

Example E-10

Action Against *Diabrotica balteata*

Maize seedlings are sprayed with an aqueous emulsion spray mixture comprising 100 ppm of the test compound. After the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants.

Compounds of the Tables exhibit good activity in this test.

Example E-11

Action Against *Heliothis virescens*

Young soybean plants are sprayed with an aqueous emulsion spray mixture comprising 100 ppm of test compound.

After the spray-coating has dried, the plants are populated with 10 caterpillars of *Heliothis virescens* in the first stage and then placed in a plastics container. 6 days later, the percentage reduction in population and the percentage reduction in feeding damage (% activity) are determined by comparing the number of dead caterpillars and the feeding damage on the treated plants with that on untreated plants.

Compounds of the Tables exhibit good activity in this test.

Example E-12

Action Against *Spodoptera littoralis*

Young soybean plants are sprayed with an aqueous emulsion spray mixture comprising 100 ppm of test compound. After the spray-coating has dried, the plants are populated with 10 caterpillars of *Spodoptera littoralis* in the third stage and then placed in a plastics container. 3 days later, the percentage reduction in population and the percentage reduction in feeding damage (% activity) are determined by comparing the number of dead caterpillars and the feeding damage on the treated plants with that on untreated plants,.

Compounds of the Tables exhibit good activity in this test.

E-13

Action Against *Nilaparvata lugens*

Rice plants are treated with an aqueous emulsion spray mixture comprising 100 ppm of the test compound. After the spray-coating has dried, the rice plants are populated with cicada larvae in the 2nd and 3rd stages. The evaluation is carried out 21 days later. The percentage reduction in population (% activity) is determined by comparing the number of surviving cicadas on the treated plants with that on the untreated plants.

The compounds of the Tables exhibit an activity exceeding 90%.

B-14

Action Against *Plutella xylostella* Caterpillars

Young cabbage plants are sprayed with an aqueous emulsion spray mixture comprising 100 ppm of test compound. After the spray-coating has dried, the cabbage plants are populated with 10 caterpillars of *Plutella xylostella* in the third stage and placed in a plastics container. The evaluation is carried out 3 days later. The percentage reduction in population and the percentage reduction in feeding damage (% activity) are determined by comparing the number of dead caterpillars and the feeding damage on the treated plants with that on the untreated plants.

Compounds from the Tables exhibit a good activity.

Example E-15

Action Against *Musca domestica*

A sugar cube is so treated with a solution of the test compound that, after drying overnight, the concentration of test compound in the sugar is 250 ppm. The treated cube is placed on an aluminium dish together with a wet cotton wool swab and 10 adult Musca domestica of an OP-resistant strain, covered with a glass beaker and incubated at 25° C. The mortality rate is determined 24 hours later.

Compounds from the Tables exhibit a good activity.

BIOLOGICAL EXAMPLES

C. Acaricidal Action

E-16

Action Against *Tetranychus urticae*

Young bean plants are populated with a mixed population of *Tetranychus urticae* and sprayed one day later with an aqueous emulsion spray mixture comprising 400 ppm of test compound. The plants are then incubated for 6 days at 25° C. and subsequently evaluated. The percentage reduction in population (% activity) is determined by comparing the number of dead eggs, larvae and adults on the untreated plants with that on the untreated plants.

Compounds from the Tables exhibit a good activity.

E-17

Action Against a Mixed Population of *Tetranychus cinnabarinus* Series of Dilutions Dwarf beans are populated at the 2-leaf stage with a mixed population (eggs, larvae/nymphs, adults) of an OP-tolerant *Tetranychus cinnabarinus* strain. 24 hours after infestation, the products are applied to the plants in concentrations of 200, 100, 50 mg a.i./l in an automatic spray cabin. The substances are formulated and diluted to the corresponding concentrations with water. The test is evaluated for percentage mortality of eggs, larvae/nymphs and adults 2 and 7 days after the application. Compounds of the Tables exhibit over 70% mortality in dilutions up to 50 mg a.i./litre.

E-18

Action Against *Boophilus microplus*

Fully replete adult tick females are affixed to a PVC sheet, covered with a cotton wool swab, and 10 ml of an aqueous test solution comprising 125 ppm of test compound are poured on. The cotton wool swab is removed and the ticks are incubated for 4 weeks until oviposition has taken place. The action is demonstrated either as mortality or sterility in the females, or as ovicidal action in the eggs.

What is claimed is:

1. A compound of formula I

I 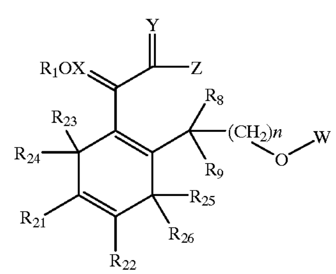 wherein:

X is CH or N;

Y is O, S, S=O or $NR_5$;

Z is $OR_2$, $SR_2$ or $N(R_3)R_4$;

n is 0, 1, 2, 3, 4 or 5; or

Y and Z together form a 5- to 7-membered ring having 2 or 3 hetero atoms O and/or N that is unsubstituted or mono- or poly-substituted by $C_1$–$C_4$alkyl, halo-$C_1$–$C_4$alkyl, halogen, =O or by cyclopropyl;

W is an aldimino or ketimino group selected from the group consisting of group a)

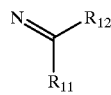

wherein
- $R_{11}$ and $R_{12}$ are each independently of the other hydrogen, cyano, $C_1$–$C_{12}$alkyl, halo-$C_1$–$C_{12}$alkyl, $C_2$–$C_{12}$alkenyl, $C_2$–$C_{12}$alkynyl, $C_3$–$C_6$cycloalkyl, cyclopropylmethyl, $C_1$–$C_4$alkoxy, $C_2$–$C_{12}$alkoxyalkyl, $C_1$–$C_4$alkoxycarbonyl, aminocarbonyl, $C_1$–$C_4$alkylaminocarbonyl, bis($C_1$–$C_4$alkyl)aminocarbonyl, ureidocarbonyl, $C_1$–$C_4$alkylthio, $C_2$–$C_5$alkylthioalkyl; an unsubstituted or up to penta-substituted ring having a maximum of 15 ring carbon atoms that may be multi-membered and has from 0 to 3 hetero atoms N, O and/or S, it being possible for the ring to be bonded by a bridge having a maximum of 4 chain atoms and that may be linear or branched and may contain CO, oxygen or sulfur; or
- $R_{11}$ and $R_{12}$ together with the common carbon atom are an unsubstituted or up to penta-substituted ring having a maximum of 15 ring carbon atoms that may be multi-membered and has from 0 to 3 hetero atoms N, O and/or S;
- the possible substituents of all of those groups mentioned for $R_{11}$ and $R_{12}$ individually or together being selected from $C_1$–$C_4$alkyl, $C_2$–$C_4$alkenyl, $C_2$–$C_4$alkynyl, $C_1$–$C_4$alkoxy, $C_1$–$C_4$alkylthio, $C_1$–$C_4$haloalkyl, $C_2$–$C_4$haloalkenyl, $C_2$–$C_4$haloalkynyl, $C_1$–$C_4$haloalkoxy, halogen, cyano, cyano-$C_1$–$C_2$alkyl, cyano-$C_1$–$C_2$alkoxy, oxo, thioxo, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxy-$C_1$–$C_4$alkyl, $C_1$–$C_4$alkylcarbonyl, $C_1$–$C_4$haloalkylcarbonyl, $C_1$–$C_4$alkoxycarbonyl, $C_1$–$C_4$haloalkoxycarbonyl, aminocarbonyl, $C_1$–$C_4$alkyl-aminocarbonyl, bis($C_1$–$C_4$alkylamino)carbonyl, arylaminocarbonyl, arylaminothiocarbonyl, $C_1$–$C_4$haloalkylcarbonyloxy, $C_1$–$C_4$alkylcarbonyloxy, $C_1$–$C_4$alkoxycarbonyloxy, aminocarbonyloxy, $C_1$–$C_4$alkylaminocarbonyloxy, bis($C_1$–$C_4$alkylamino)carbonyloxy, arylaminocarbonyloxy, arylaminothiocarbonyloxy, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl, phenyl, benzyl, phenoxy, phenylthio, benzyloxy and benzylthio;
  - it being possible for the aromatic groups to carry a maximum of 5 further substituents selected from halogen, $C_1$–$C_4$alkyl, $C_1$–$C_4$alkoxy, $C_1$–$C_4$haloalkyl, $C_1$–$C_4$haloalkoxy, CN and $NO_2$, and it being possible for two adjacent substituents of the maximum of 5 substituents to form an aliphatic bridge having a maximum of 5 members, which bridge has from 0 to 2 oxygen atoms and 0 or 1 carbonyl group and may be substituted a maximum of four times by halogen, $C_1$–$C_4$alkyl, $C_1$–$C_4$alkoxy and/or by a single phenyl group;

or wherein

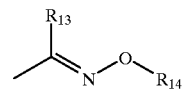

$R_{12}$ is a group e)
wherein:
- $R_{13}$ is hydrogen, cyano, $C_1$–$C_6$alkyl, $C_3$–$C_6$cycloalkyl, $C_1$–$C_6$alkoxycarbonyl, heteroaryl, heterocyclyl, naphthyl, $C_1$–$C_6$alkoxy, aryloxy, heteroaryloxy, $C_1$–$C_6$alkylamino, bis($C_1$–$C_6$alkyl)amino, arylamino or heteroarylamino, it being possible for all of the radicals mentioned other than cyano to be unsubstituted or substituted by alkyl, alkoxy, haloalkyl, haloalkoxy, alkylthio, alkylsulfenyl, alkylsulfinyl, halogen, nitro, cyano, aryl, aryloxy, heteroaryl or by heteroaryloxy,
- or a group f)

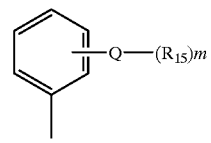

wherein
- $R_{15}$ is $C_1$–$C_6$alkyl, halo-$C_1$–$C_6$alkyl, $C_1$–$C_6$alkoxy, halo-$C_1$–$C_6$alkoxy, halogen, $C_3$–$C_6$cycloalkyl unsubstituted or substituted by from 1 to 5 halogen atoms, $C_2$–$C_6$alkenyl, halo-$C_2$–$C_6$alkenyl, optionally substituted $C_3$–$C_6$-alkynyl, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl)$_2$, $C_1$–$C_4$alkoxymethyl, $C_1$–$C_4$haloalkylcarbonyl, $C_1$–$C_4$alkylcarbonyl, $C_1$–$C_4$alkoxycarbonyl, aminocarbonyl, $C_1$–$C_4$alkylaminocarbonyl, bis($C_1$–$C_4$alkylamino)carbonyl, arylaminocarbonyl, arylaminothiocarbonyl, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkyl sulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$alkylcarbonyloxy, $C_1$–$C_4$alkoxycarbonyloxy, aminocarbonyloxy, $C_1$–$C_4$alkylaminocarbonyloxy, bis($C_1$–$C_4$alkylamino)carbonyloxy, arylaminocarbonyloxy, arylaminothiocarbonyloxy, aryl, heteroaryl or heterocyclyl;
- the aromatic groups in $R_{15}$ each independently of the others being unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy; tri($C_1$–$C_4$alkyl)silyl or di($C_1$–$C_4$alkyl)phenylsilyl;
- wherein when n is greater than 1 the $R_{15}$ radicals may be identical or different;
- Q is a direct bond, $C_1$–$C_8$alkylene, $C_2$–$C_6$alkenylene, $C_2$–$C_6$alkynylene, O, O($C_1$–$C_6$alkylene), ($C_1$–$C_6$alkylene)O, S(=O)p, S(=O)$_p$($C_1$–$C_6$alkylene) or ($C_1$–$C_6$alkylene)S(=O)$_p$;
- m is 0, 1, 2, 3, 4 or 5;
- p is 0, 1 or 2; and
- $R_{14}$ is hydrogen; $C_1$–$C_6$alkyl; $C_1$–$C_6$haloalkyl having from 1 to 15 halogen atoms; $C_1$–$C_4$-alkoxy- $C_1$–$C_2$alkyl; $C_2$–$C_4$alkenyl-$C_1$–$C_2$alkyl unsubstituted or substituted by from 1 to 3 halogen atoms; $C_2$–$C_4$alkynyl-$C_1$–$C_2$alkyl; $C_3$–$C_6$cycloalkyl unsubstituted or substituted by from 1 to 4 halogen atoms; $C_3$–$C_6$cycloalkyl-$C_1$–$C_4$alkyl unsubstituted or substituted by from 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl unsubstituted or substituted by halogen, $C_1$–$C_3$alkyl, $C_1$–$C_4$alkoxy, $C_1$–$C_4$haloalkyl, cyano, nitro and/or by $C_1$–$C_4$alkylenedioxy and wherein the phenyl group may be substituted by from 1 to 3 identical or different substituents; phenyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano; or pyridyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano;

$R_1$ is cyclopropyl, $C_1$–$C_6$alkyl or halo-$C_1$–$C_6$alkyl;

$R_2$ and $R_3$ are each independently of the other $C_1$–$C_6$alkyl or halo-$C_1$–$C_6$alkyl;

$R_4$ and $R_5$ are each independently of the other hydrogen, $C_1$–$C_6$alkyl or $C_1$–$C_6$alkoxy;

$R_8$ and $R_9$ are each independently of the other hydrogen or $C_1$–$C_3$alkyl; or $R_8$ and $R_9$ together are $C_2$–$C_6$alkenyl or $C_3$–$C_6$cycloalkyl;

$R_{21}$ and $R_{22}$ are each independently of the other hydrogen, halogen, $C_1$–$C_8$alkyl, $C_1$–$C_8$alkoxy or $C_1$–$C_8$alkylthio; and $R_{23}$, $R_{24}$, $R_{25}$ and $R_{26}$ are each independently of the others hydrogen, halogen, $C_1$–$C_8$alkyl or $C_1$–$C_8$alkoxy.

2. A compound according to claim 1 wherein:

$R_1$ is methyl;

$R_2$, $R_3$ and $R_5$ are each independently of the others $C_1$–$C_2$alkyl, and $R_4$ is hydrogen.

3. A compound according to claim 1 wherein:

X is N;

Y is O, S or S=O, preferably O;

Z is $OR_2$, $SR_2$ or $N(R_3)H$; and $R_2$ and $R_3$ are $C_1$–$C_2$alkyl.

4. A compound according to claim 1 wherein:

X is CH;

Y is O, S or S=O,

Z is $OR_2$; and $R_2$ is $C_1$–$C_2$alkyl.

5. A compound according to claim 1 wherein Y and Z together are a group

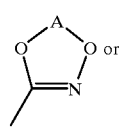

a)

-continued

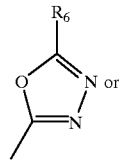

b)

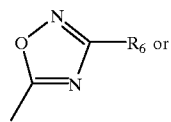

c)

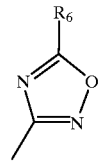

d)

wherein:

A is unsubstituted or methyl-substituted alkanediyl having from 1 to 3 carbon atoms; and $R_6$ is hydrogen, $C_1$–$C_3$alkyl, cyclopropyl or $CF_3$.

6. A compound according to claim 1 wherein:

$R_8$ and $R_9$ are hydrogen or methyl;

$R_{21}$ and $R_{22}$ are each independently of the other hydrogen, chlorine, bromine, $C_1$–$C_4$alkyl or $C_1$–$C_4$alkoxy;

$R_{23}$, $R_{24}$, $R_{25}$ and $R_{26}$ are hydrogen; and n is 0, 1 or 2.

7. A compound according to claim 6 wherein:

$R_8$ and $R_9$ are hydrogen;

$R_{21}$ and $R_{22}$ are each independently of the other hydrogen or methyl; and n is 0.

8. A compound according to claim 1 wherein: $R_{11}$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano; and $R_{12}$ is phenyl or pyridyl each unsubstituted or substituted.

9. A compound according to claim 8 wherein:

$R_{11}$ is $C_1$–$C_4$alkyl, cyclopropyl or cyano; and $R_{12}$ is phenyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, $C_2$–$C_4$alkenyl, $C_2$–$C_4$alkynyl, nitro and cyano; or pyridyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano.

10. A compound according to claim 1 wherein:

$R_{11}$ is hydrogen, $C_1$–$C_4$alkyl, halo-$C_1$–$C_4$alkyl, cyclopropyl, $C_1$–$C_4$alkoxymethyl, $C_1$–$C_4$alkoxy, $C_1$–$C_4$alkylthio or cyano; and $R_{12}$ is a group e)

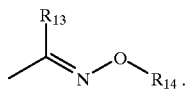

11. A compound according to claim 10 wherein:

$R_{13}$ is hydrogen, $C_1$–$C_6$alkyl, $C_3$–$C_6$cycloalkyl, cyano or a group f)

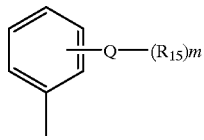

wherein $R_{15}$ is $C_1$–$C_6$alkyl, halo-$C_1$–$C_6$alkyl, cyclopropyl unsubstituted or substituted by from 1 to 5 chlorine atoms, $C_2$–$C_6$alkenyl unsubstituted or substituted by from 1 to 3 halogen atoms, or unsubstituted or substituted $C_3$–$C_6$alkynyl; also phenyl unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy; or pyridyl unsubstituted or mono- to tetra-substituted by $C_1$–$C_6$alkyl, halo-$C_1$–$C_6$alkyl, halogen, $C_1$–$C_6$alkoxy or by halo-$C_1$–$C_6$alkoxy;

Q is a direct bond, $C_1$–$C_4$alkylene, O, O($C_1$–$C_4$alkylene) or ($C_1$–$C_4$alkylene)O, m is 0, 1 or 2; and $R_{14}$ is hydrogen; $C_1$–$C_6$alkyl; $C_1$–$C_6$haloalkyl having from 1 to 15 halogen atoms; $C_1$–$C_4$-alkoxy-$C_1$–$C_2$alkyl; $C_2$–$C_4$alkenyl-$C_1$–$C_2$alkyl unsubstituted or substituted by from 1 to 3 halogen atoms; $C_2$–$C_4$alkynyl-$C_1$–$C_2$alkyl; $C_3$–$C_6$-cycloalkyl unsubstituted or substituted by from 1 to 4 halogen atoms; $C_3$–$C_6$cycloalkyl-$C_1$–$C_4$alkyl unsubstituted or substituted by from 1 to 4 halogen atoms; cyano-$C_1$–$C_4$alkyl; $C_1$–$C_4$alkoxycarbonyl-$C_1$–$C_4$alkyl; phenyl-$C_1$–$C_3$alkyl unsubstituted or substituted by halogen, $C_1$–$C_3$alkyl, $C_1$–$C_4$alkoxy, $C_1$–$C_4$haloalkyl, cyano, nitro and/or by $C_1$–$C_4$alkylenedioxy wherein the phenyl group may be substituted by from 1 to 3 identical or different substituents; phenyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano; or pyridyl unsubstituted or substituted by one or two substituents, which may be the same or different, selected from $C_1$–$C_4$alkyl, $C_1$–$C_4$alkoxy, halogen, $C_1$–$C_2$haloalkyl having from 1 to 3 halogen atoms, nitro and cyano.

12. A compound according to claim 1 wherein:

$R_{11}$ is methyl;

$R_{12}$ is a group e)

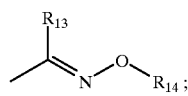

$R_{13}$ is a group f)

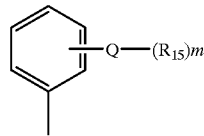

wherein $R_{15}$ is $C_1$–$C_6$alkyl, halo-$C_1$–$C_6$alkyl, $C_1$–$C_6$alkoxy, halo-$C_1$–$C_6$alkoxy, halogen, $C_3$–$C_6$-cycloalkyl unsubstituted or substituted by from 1 to 5 halogen atoms, $C_2$–$C_6$alkenyl, halo-$C_2$–$C_6$alkenyl, $C_3$–$C_6$alkynyl, cyano, cyano-$C_1$–$C_2$alkyl, cyano-$C_1$–$C_2$alkoxy, OH, $NO_2$, SCN, thiocyanomethyl, $Si(CH_3)_3$, $NH_2$, $NH(C_1$–$C_4$alkyl), $N(C_1$–$C_4$alkyl$)_2$, $C_1$–$C_4$alkoxymethyl, $C_1$–$C_4$haloalkylcarbonyl $C_1$–$C_4$alkylcarbonyl, $C_1$–$C_4$alkoxycarbonyl, aminocarbonyl, $C_1$–$C_4$alkylaminocarbonyl, bis($C_1$–$C_4$alkylamino)carbonyl, arylaminocarbonyl, arylaminothiocarbonyl, $C_1$–$C_4$alkoximinomethyl, —$CSNH_2$, —SH, $C_1$–$C_4$alkylthiomethyl, $C_2$–$C_4$alkenyloxy, $C_2$–$C_4$alkynyloxy, $C_2$–$C_4$haloalkenyloxy, $C_1$–$C_4$alkylsulfinylmethyl, $C_1$–$C_4$alkylsulfonylmethyl, phenylsulfinylmethyl, phenylsulfonylmethyl, trifluoromethylsulfonyl, $C_3$–$C_6$cycloalkyl, $C_1$–$C_4$haloalkylcarbonyloxy, $C_1$–$C_4$-alkylcarbonyloxy, $C_1$–$C_4$alkoxycarbonyloxy, aminocarbonyloxy, $C_1$–$C_4$alkylaminocarbonyloxy, bis($C_1$–$C_4$alkylamino)carbonyloxy, arylaminocarbonyloxy, arylaminothiocarbonyloxy, aryl, heteroaryl or heterocyclyl; wherein the aromatic groups in $R_{15}$ are each independently of the other unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy;

Q is a direct bond, $C_1$–$C_4$alkylene, $C_2$–$C_4$alkenylene, $C_2$–$C_4$alkynylene, O, O($C_1$–$C_2$alkylene) or ($C_1$–$C_2$alkylene)O;

m is 0 or 1; and $R_{14}$ is methyl, ethyl or propargyl.

13. A compound according to claim 10 wherein:

$R_{13}$ is heteroaryl or heterocyclyl, which are each independently of the other unsubstituted or mono- to penta-substituted by $C_1$–$C_6$alkyl, halo-$C_1$–$C_6$alkyl, halogen, $C_1$–$C_6$alkoxy or by halo-$C_1$–$C_6$alkoxy.

14. A compound according to claim 13 wherein:

$R_{13}$ is pyridyl, pyrimidinyl, imidazolyl, thiazolyl or pyrrolyl each unsubstituted or mono- to tri-substituted by methyl, halo-$C_1$–$C_2$alkyl, $C_1$–$C_2$alkoxy, halo-$C_1$–$C_2$alkoxy or by halogen.

15. A compound according to claim 2 wherein:

at least one of $R_2$, $R_3$ and $R_5$ is methyl.

16. A compound according to claim 3 wherein Y is O.

17. A compound according to claim 3 wherein Z is $OR_2$ or $SR_2$.

18. A compound according to claim 3 wherein $R_2$ and $R_3$ are methyl.

19. A compound according to claim 4 wherein Y is O.

20. A compound according to claim 4 wherein $R_2$ is methyl.

21. A compound according to claim 5 wherein A is unsubstituted or methyl-substituted dimethylene.

22. A process for the preparation of a compound of formula I according to claim 1, which comprises reacting a compound of formula II with a compound of formula III

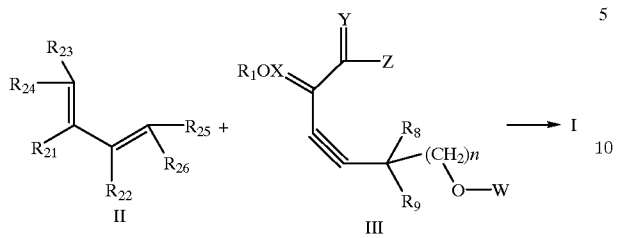

wherein n, X, Y, Z, $R_1$, $R_8$, $R_9$, W and $R_{21}$ to $R_{26}$ are as defined for formula I.

23. A compound of formula IV

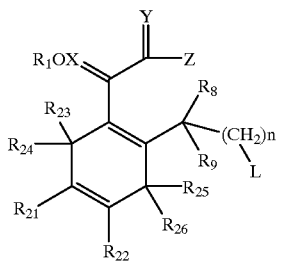

wherein n, X, Y, Z, $R_1$, $R_8$, $R_9$ and $R_{21}$ to $R_{26}$ are as defined for formula I according to claim 1 and L is a leaving group.

24. A compound of formula XII

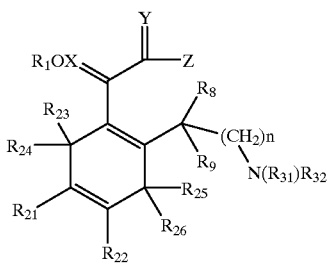

wherein n, X, Y, Z, $R_1$, $R_8$, $R_9$ and $R_{21}$ to $R_{26}$ are as defined for formula I according to claim 1 and wherein $R_{31}$ and $R_{32}$ are each independently of the other $C_1$–$C_6$alkyl, $C_1$–$C_6$alkenyl, $C_1$–$C_6$alkoxyalkyl, $C_3$–$C_6$cycloalkyl or unsubstituted or substituted benzyl, or $R_{31}$ and $R_{32}$ together with the nitrogen atom are an unsubstituted or substituted 6- or 7-membered ring that may have a further hetero atom O, S or N in addition to the nitrogen atom.

25. A compound of formula XIV

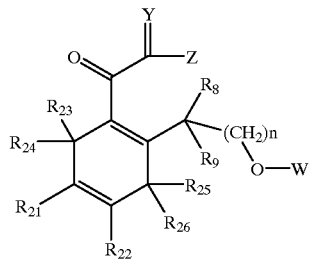

wherein n, Y, Z, W, $R_8$, $R_9$ and $R_{21}$ to $R_{26}$ are as defined for formula I according to claim 1.

26. A process for the preparation of a compound of formula XIV which comprises reacting a compound of formula II with a compound of formula XIII

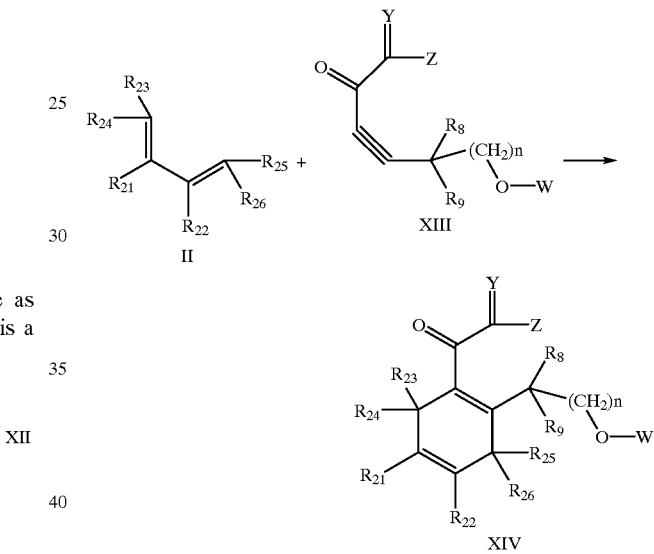

wherein n, Y, Z, $R_8$, $R_9$, W and $R_{21}$ to $R_{26}$ are as defined for formula I according to claim 1.

27. A composition for controlling pests, comprising as active ingredient an effective amount of a compound according to claim 1 together with a suitable carrier.

28. A method for the control and prevention of pests, which comprises applying a compound according to claim 1 to the pests or to the locus thereof.

29. A method according to claim 28, wherein the pests are phytopathogenic fungi.

30. A method according to claim 28, wherein the pests are insects or Acarina.

31. A method according to claim 28, wherein seed is treated.

* * * * *